(12) United States Patent
King et al.

(10) Patent No.: US 8,586,575 B1
(45) Date of Patent: *Nov. 19, 2013

(54) ABUSE DETERRENT AND ANTI-DOSE DUMPING PHARMACEUTICAL SALTS USEFUL FOR THE TREATMENT OF ATTENTION DEFICIT/HYPERACTIVITY DISORDER

(75) Inventors: Clifford Riley King, Hendersonville, NC (US); Stephen G. D'Ambrosio, Etowah, NC (US); David W. Bristol, Mills River, NC (US)

(73) Assignee: Pisgah Laboratories, Inc., Pisgah Forest, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/443,643

(22) Filed: Apr. 10, 2012

Related U.S. Application Data

(62) Division of application No. 12/846,936, filed on Jul. 30, 2010.

(51) Int. Cl.
| | |
|---|---|
| *A01N 43/00* | (2006.01) |
| *A01N 43/46* | (2006.01) |
| *A61K 31/55* | (2006.01) |
| *A61K 31/445* | (2006.01) |
| *A01N 43/08* | (2006.01) |
| *A61K 31/34* | (2006.01) |
| *A01N 33/02* | (2006.01) |
| *A61K 31/135* | (2006.01) |
| *C07D 223/18* | (2006.01) |
| *C07D 211/34* | (2006.01) |
| *C07D 307/77* | (2006.01) |
| *C07D 307/93* | (2006.01) |
| *C07C 211/00* | (2006.01) |

(52) U.S. Cl.
USPC ........... 514/217; 514/315; 514/468; 514/646; 546/238; 564/336; 540/592; 549/456

(58) Field of Classification Search
USPC .................. 514/217, 315, 468, 646; 540/592; 546/238; 549/456; 564/336
See application file for complete search history.

(56) References Cited

U.S. PATENT DOCUMENTS

| | | | | |
|---|---|---|---|---|
| 3,326,896 | A * | 6/1967 | Holstius | 540/592 |
| 7,718,649 | B1 | 5/2010 | King et al. | |
| 8,039,461 | B1 * | 10/2011 | Audia et al. | 514/217 |
| 2003/0229122 | A1 * | 12/2003 | Wiig et al. | 514/317 |
| 2005/0158382 | A1 | 7/2005 | Cruz et al. | |
| 2009/0259039 | A1 | 10/2009 | Bristol et al. | |

OTHER PUBLICATIONS

Remington: The Science and Practice of Pharmacy, 2005, Lippincott Williams & Wilkins, 21st ed., pp. 184-185.*

* cited by examiner

*Primary Examiner* — Sarah Pihonak
(74) *Attorney, Agent, or Firm* — Joseph T. Guy; Perkins Law Firm

(57) ABSTRACT

A pharmaceutical composition comprising a drug substance consisting essentially of a pharmaceutically acceptable organic acid addition salt of an amine containing pharmaceutically active compound wherein the amine containing pharmaceutical active compound is selected from the group consisting of racemic or single isomer ritalinic acid or phenethylamine derivatives and the drug substance has a physical form selected from amorphous and polymorphic.

9 Claims, 109 Drawing Sheets

ABUSE DETERRENT AND ANTI-DOSE DUMPING PHARMACEUTICAL SALTS USEFUL FOR THE TREATMENT OF ATTENTION DEFICIT/HYPERACTIVITY DISORDER

CROSS REFERENCE TO RELATED APPLICATIONS

This application is a divisional application of pending U.S. patent application Ser. No. 12/846,936 filed Jul. 30, 2010 which is incorporated herein by reference. This application is related to U.S. patent application Ser. Nos. 11/805,225 filed May 22, 2007; 11/973,252 filed Oct. 5, 2007; 12/080,514 filed Apr. 3, 2008; 12/080,513 filed Apr. 3, 2008; 12/080,531 filed Apr. 3, 2008; 11/595,379 filed Nov. 10, 2006 now U.S. Pat. No. 7,718,649 issued May 18, 2010; 11/843,690 filed Aug. 23, 2007; 11/928,592 filed Oct. 30, 2007; 11/932,336 filed Oct. 31, 2007; 12/423,641 filed Apr. 14, 2009 and 12/537,664 filed Aug. 7, 2009 each of which is incorporated herein by reference.

BACKGROUND OF THE INVENTION

The present invention is related to pharmaceutical compositions which are particularly suitable for treating Attention Deficit/Hyperactivity Disorder (ADHD, also known as ADD, both terms may be used interchangeably herein). More particularly, the present invention is related to pharmaceutical compositions, particularly comprising racemic or single isomer ritalinic acid or phenethylamine derivatives, such as methylphenidate or amphetamine, which can be rendered less susceptible to abuse or dose dumping and which can be tailored to achieve specific lipophilic and hydrophilic properties.

Shire is a prominent pharmaceutical company engaged in marketing medication for the treatment of Attention Deficit/Hyperactivity Disorder (ADHD). In a "Shire News" informational newsletter published on the internet entitled, "Results from a European Caregiver Survey Highlight the Impact of Attention Deficit Hyperactivity Disorder (ADHD) on the Child and the Family", the following excerpt from the section "About ADHD" is included below as a primer on ADHD. "ADHD is one of the most common psychiatric disorders in children and adolescents. Worldwide prevalence of ADHD is estimated at 5.3 percent (with large variability), according to a comprehensive systematic review of this topic published in 2007 in the American Journal of Psychiatry. In the United States, approximately 7.8 percent of all school-aged children, or about 4.4 million children aged 4 to 17 years, have been diagnosed with ADHD at some point in their lives, according to the Centers for Disease Control and Prevention (CDC). The disorder is also estimated to affect 4.4 percent of US adults aged 18 to 44 based on results from the National Comorbidity Survey Replication. When this percentage is extrapolated to the full US population aged 18 and over, approximately 9.8 million adults are believed to have ADHD. ADHD is a psychiatric behavioral disorder that manifests as a persistent pattern of inattention and/or hyperactivity-impulsivity that is more frequent and severe than is typically observed in individuals at a comparable level of development. The specific etiology of ADHD is unknown and there is no single diagnostic test for this syndrome. Adequate diagnosis requires the use of medical and special psychological, educational and social resources, utilizing diagnostic criteria such as *Diagnostic and Statistical Manual of Mental Disorders-IV (DSM-IV-TR) or International Classification of Diseases* 10 (ICD-10). Although there is no "cure" for ADHD, there are accepted treatments that specifically target its symptoms. Standard treatments include educational approaches, psychological, or behavioral modification, and medication."

The treatment of ADHD as manifested in adults and children is a disease with known treatment regimens. An overview of the symptoms, signs, diagnosis, prognosis, treatment and therapeutic agents applicable to these learning and developmental disorders can be found in The Merck Manual $18^{th}$ Edition, ©2006, published by Merck Research Laboratories, pp. 2483-2486. Two drugs are principally used to treat these conditions: methylphenidate and dextro-amphetamine. The dosing regimen generally consists of first titrating the patient with immediate release (IR) dosage forms to effect the desired change while minimizing adverse effects followed by switching to an extended release (ER) formulation once the patient's response to the drug is understood. Both dextro-amphetamine and methylphenidate, in either IR or ER formulations, are stimulants and prone to abuse, misuse and diversion.

The abuse, misuse and diversion of controlled substances is discussed at length in U.S. patent application Ser. Nos. 11/805,225 [Bristol et al.], and 11/973,252 [King, et al.] and 12/423,641 [King et al.] wherein included are technical approaches to imparting anti-abuse and abuse deterrent features to controlled substances. The abuse of dextro-amphetamine and methylphenidate, both of which are controlled substances, is widespread. These drugs are readily prescribed and consequently, their common availability or access by diversion has made them comparatively easy targets for those people intent on abuse or misuse of the drug. The challenge to the pharmaceutical industry and to medical professionals is to provide these medications to patients in genuine need of the drug's therapeutic benefits while restricting or eliminating the ability to abuse the drug.

In the case of dextro-amphetamine, New River Pharmaceuticals has risen to the abuse deterrent/misuse/diversion challenge by preparing a prodrug form of dextro-amphetamine. New River's U.S. Pat. No. 7,105,486 B2 (Mickle et al.), the disclosure of which is incorporated herein by reference, describes the covalent attachment of L-lysine to the drug substance, amphetamine, to provide compounds and compositions exhibiting abuse-resistant properties and which are useful for the treatment of disorders including attention deficit hyperactivity disorder (ADHD), attention deficit disorder (ADD), narcolepsy and obesity. The drug product incorporating the prodrug delivers an abuse deterrent feature through chemical means which would require some expertise to defeat—and only through chemical transformation. Unfortunately, the prodrug approach, in general, requires significant R&D resources to tailor each prodrug to a host of regulatory specifications before market approval can be granted by the FDA. Consequently, the prodrug approach is costly, time-intensive and does not provide a universal, platform solution to imparting abuse deterrent properties to the medically necessary amine-containing controlled substances. The invention described herein encompasses a platform approach to imparting abuse deterrent properties at the molecular level through unique salt forms of the opioid alkaloids.

Not surprisingly, the abuse, misuse and diversion of (dextro)-amphetamine and methylphenidate (racemic and single isomer) is due to the psychoactive effect these drugs exhibit which is similar to cocaine. In "The Chemistry of Mind-Altering Drugs, History, Pharmacology, and Cultural Context", by Daniel M. Perrine, ©1996, published by the American Chemical Society, p. 196-198, the authors report on a study conclusively demonstrating methylphenidate and cocaine acted on the same part of the brain. Similarly, on page 193 the authors report that the final psychotic toxicity of amphetamines is "essentially identical to that found with cocaine". While these drugs provide necessary medical treatment, their abuse serves no valued purpose to society. Consequently, the challenge is to provide these drugs, as drug substances and in dosage forms (drug products) which are not easily abused or misused and thereby diminish the motive for diversion.

In addition to the scientific and technical challenges faced by drug substance and product manufacturers, the United States government recognizes the severe detrimental consequences drug abuse has on the Nation and has taken action, principally through the Food and Drug Administration (FDA), in an effort to mitigate drug abuse. A summary of the FDA's intent, philosophy and actions is found in the Federal Register, Volume 74, Number 74, Monday Apr. 20, 2009, pages 17967-17970 as it relates to their Risk Evaluation and Mitigation Strategies (REMS) program for opioid-based drug products. However, a REMS program requirement may be required by all drug product manufacturers to ascertain the risk/benefit to (controversial) drug products as authorized by the Food and Drug Administration Amendments Act of 2007. Beyond cited opioids in the FDA's Federal Registry entry, all controlled substances including those of the present invention will likely be subject to a REMS requirement. A top level overview of the REMS initiative, presented by the FDA's top administrators, is available on-line. As the effort to fight drug abuse increases, the terminology employed to address the topic is evolving. In previous applications by the present inventors, "anti-abuse" was employed as a term to describe properties imparted to drug substances and drug products as a result of design engineering to these substances and products, features which inhibit their use in a manner for which they were not intended. As the terminology has evolved within administrative law, the term "abuse-deterrent" is more often employed. Within the context of this disclosure, no limitation is implied through the use of either term and both are engendered to be interpreted in the broadest sense. However, for completeness and to provide a broader understanding of the invention herein, the United States Food and Drug Administration in their January 2010 issuance of Guidance for Industry: Assessment of Abuse Potential of Drugs, it is stated: "Currently, the concept of abuse deterrence is viewed as the introduction of some limits or impediments to abuse, as opposed to the outright elimination of abuse."

The Government Accounting Office (GAO) in a publication entitled, "Prescription Drugs, OxyContin Abuse and Diversion and Efforts to Address the Problem", (GAO-04-110) in the "Recommendation for Executive Action", page 42, stated: "To improve efforts to prevent or identify the abuse and diversion of schedule II controlled substances, we recommend that the Commissioner of Food and Drugs ensure that FDA's risk management plan guidance encourages pharmaceutical manufacturers that submit new drug applications for these substances to include plans that contain a strategy for monitoring the use of these drugs and identifying potential abuse and diversion problems." It is well known that the amphetamines and methylphenidate are intentionally abused and diverted for illicit purpose.

Clearly there remains a need to address the abuse, misuse and diversion of schedule II controlled substances (both the active pharmaceutical ingredient and for the formulated dosage product). A host of technical requirements must be met in addition to the regulatory administrative requirements to meet society's needs. Beyond technical requirements, today's pharmaceutical marketplace requires inventions be consistent with the prevailing politics and policy of the federal government. The administrative controls being placed on the stakeholders involved in the commercial use of controlled substances are burdensome. The stakeholders include the drug manufacturer, distributor, the prescriber (physician and other medical personnel), dispenser (pharmacist) and the patient. Such burdensome administrative controls such as health provider certifications and the like may have the unintentional outcome of restricting necessary medications to those patients legitimately in need of the controlled substance, such as those substances of the present invention.

There has been a long felt need for pharmaceuticals, pharmaceutical systems, and methods of predictably altering pharmaceuticals to achieve the goals set forth above. Pharmaceuticals, pharmaceutical systems, and methods of predictably altering pharmaceuticals which are less susceptible to abuse, and particularly dose dumping, are provided herein. It is an object of the invention is to provide a beneficial technical solution which does not overwhelm the healthcare system and addresses an entire product/therapeutic family to curb prescriber and dispenser confusion.

SUMMARY OF THE INVENTION

It is an object of the invention is to provide a beneficial technical solution to drug abuse which does not overwhelm the healthcare system and which addresses an entire product/therapeutic family to curb prescriber and dispenser confusion.

It is an object of the invention to provide organic acid addition salts of racemic and single-isomer methylphenidate and amphetamine exhibiting abuse deterrent properties including anti-dose dumping characteristics.

A particular advantage of the invention is the ability to establish a patient's therapeutic treatment for ADD/ADHD with immediate release dosage products and then exchanging the patient's treatment to a dosage formulation exhibiting abuse deterrent properties.

A particular advantage of the present invention is the ability to provide medical professionals, or prescribers, the ability to prescribe an abuse deterrent formulation for the therapeutic treatment of patients with a propensity toward drug abuse.

One embodiment of the present invention is to provide a means for fulfilling a United States Food and Drug Administration mandate to all stakeholders in the manufacture, prescribing, dispensing and to the recipient patient to curb drug abuse and to demonstrate compliance with the FDA's statutorily driven REMS program.

An embodiment of the present invention is the ability to provide a business franchise or enterprise solution for the manufacture, distribution, prescription and fulfillment of medically necessary drug products of a given therapeutic category and which exhibit abuse deterrent properties.

An advantage of the invention is the ability to provide a franchise/enterprise regulatory compliant business solution for the provision of amine-containing controlled substances while fulfilling a medical need exhibiting abuse deterrent properties.

An advantage of the present invention is the ability to provide drug substances within a therapeutic family of drug products which exhibit abuse deterrent properties.

It is a feature of the present invention to provide methylphenidate organic acid addition salts and amphetamine organic acid addition salts possessing abuse-deterrent properties which are useful for the treatment of ADD or ADHD.

It is an object of the present invention to employ abuse deterrent technology to drug substances which are currently unapproved yet which could be rendered sufficiently safe that they could serve a legitimate medical need.

It is an object of the present invention to provide the organic acid addition salt of cocaine exhibiting abuse deterrent features and useful for the treatment of ADHD.

It is an object of the present invention to provide organic acid addition salts of amine containing compounds wherein brain receptor selectivity is unaltered by the abuse deterrent feature.

It is yet another object of the present invention to provide an organic acid moiety which, when reacted with an amine, provides a non-toxic, drug delivery system. Furthermore, the organic acid moiety is, by design, engineering and through chemical derivatization adjusted to predictably alter its hydrophilic or lipophilic balance to aid as a drug delivery system.

A particular advantage of the present invention is that the organic acid moiety can be chemically derivatized, by reaction with an amine, to alter the hydrophilic or lipophilic balance of the resulting organic acid addition salt.

Another advantage of the present invention is that the organic acid moiety can be chemically modified to selectively impart a desired dissolution performance feature of salts formed between the organic acid moiety and amine-containing active pharmaceutical ingredients.

In yet another advantage of the present invention the organic acid moiety can be selected to enhance or increase the lipophilicity of an amine-containing active pharmaceutical ingredient upon salt formation with the organic acid moiety, wherein the moiety contains hydrophobic substitution.

It is another object of the invention to enhance or increase the hydrophilicity of an amine-containing active pharmaceutical ingredient upon salt formation with an organic acid moiety, the moiety containing hydrophilic substitution.

It is another object of the invention to increase the resistance of an amine-containing organic acid addition salt to dissolution in low pH environments, particularly in the human gastrointestinal tract.

It is another object of the present invention to provide controlled release of the amine-containing active pharmaceutical ingredient from its organic acid addition salt by selection of the organic acid component wherein the hydrophilic-lipophilic balance of the salt and its response to pH have been altered by chemical design of the organic acid component.

The present invention includes modifications to the ortho-hydroxy organic acid components of the invention to increase its hydrophilicity and that of subsequent salts formed by reaction with amine-containing active pharmaceutical ingredients. Such modifications include but are not limited to attaching polar, hydrophilic groups to the organic acid moiety. Particularly preferred polar groups are selected from the group consisting of ethers, esters, alcohols, oligomeric ethers derived from alkylene oxides, polyoxyalkylenes, and the like.

The present invention includes modifications to the ortho-hydroxy organic acids to increase the lipophilicity and that of subsequent salts formed by reaction with amine-containing active pharmaceutical ingredients. Such modifications include but are not limited to attaching non-polar, lipophilic groups to the organic acid moiety. Particularly preferred non-polar groups are selected from the group consisting of linear and branched alkyl, aryl, alkyl/aryl groups and the like.

A particular feature of the present invention is the ability to provide organic acid derivatives incorporating a surfactant moiety as a dissolution profile modifier which are capable of forming salts with amine-containing active pharmaceutical compounds.

Yet another aspect of the invention is to chemically attach to the organic acid component a substituent possessing surfactant exhibiting anionic, cationic and neutral surfactant properties.

Yet another object of the present invention is the ability to provide controlled release of an amine-containing active pharmaceutical ingredient from its organic acid addition salt. This is accomplished by selection of the organic acid component wherein the hydrophilic-lipophilic balance of the salt, its response to pH, and its dissolution properties imparted through the dissolution profile modifier of the organic acid component have been altered by design.

A particular feature of the present invention is the ability to optimize, adjust or otherwise tune the dissolution properties of organic acid addition salts of amine containing active pharmaceutical ingredients by selection of properties of the salt and the organic acid component as a delivery mechanism utilizing: the selection of: a) the organic acid family, b) the stoichiometry available in salt formation such as 2:1 or 1:1, c) the amorphous or polymorphic form of the salt and d) substitution upon the organic acid component to adjust its: 1) hydrophilic-lipophilic balance, 2) sensitivity to pH, and 3) surfactant properties. Each of these factors allows for the design and engineering of dissolution properties of amine-containing active pharmaceutical ingredients.

A feature of the present invention is the ability to optimize an in vitro and in vivo dissolution profile of an amine-containing active pharmaceutical ingredients at the molecular level by:

a) preparation of its bis-functional acid salt;
b) selection of a preferred stoichiometric ratio of the bis-functional acid salt intermediate compared to amine-containing active pharmaceutical ingredient and to amine-containing hydrophilic (or conversely, lipophilic) components used to form the salt;
c) evaluation and optimization of the stoichiometry ratio to optionally produce an amorphous or polymorphic salt;
d) evaluation and optimization of the stoichiometry ratio to produce the preferred dissolution profile; based on a) through c) above; and
e) an iterative evaluation and optimization of the hydrophilic (or lipophilic) component to identify a preferred molecular weight range to yield the desired dissolution profile.

An aspect of the present invention is the preparation of a bis-functional salt wherein at least one functionality portion of the salt is used to deliver a physiologically active and/or psychoactive alkaloid and/or amine-containing active pharmaceutical ingredient; another functionality of the salt is to provide the delivery mechanism of the alkaloid and/or active pharmaceutical ingredient.

It is yet another aspect of the invention to provide a process methodology suitable for preparing a mixed organic acid addition salt of amine-containing active pharmaceutical ingredients and an essentially inactive amine component, the mixed organic acid addition salt arising from the stoichiometric displacement of one essentially inactive amine component of a bis-substituted organic acid.

It is another object of the present invention to employ xinafoate salts of amine containing active pharmaceutical ingredients in formulated drug products in order to deliver the active pharmaceutical ingredient to the intestinal tract by retarding the rate of release in the stomach and enhance the stability of low pH sensitive drugs. In addition, a combination of pamoate and xinafoate salts of a given amine containing controlled substance would provide for a tunable and targeted release profile in a dosage form.

These and other features of the invention are provided in a pharmaceutical composition comprising a drug substance consisting essentially of a pharmaceutically acceptable organic acid addition salt of an amine containing pharmaceutically active compound wherein the amine containing pharmaceutical active compound is selected from the group consisting of racemic or single isomer ritalinic acid or phenethylamine derivatives, particularly methylphenidate and amphetamine, and the drug substance has a physical form selected from amorphous and polymorphic.

Yet another embodiment is provided in a pharmaceutical composition comprising a drug substance consisting essentially of A-B-C wherein A is an amine containing pharmaceutically active compound; C is an amine which can be the same as A, and B is a bidentate linking group used to ionically or covalently link A and C, and defined by the formula:

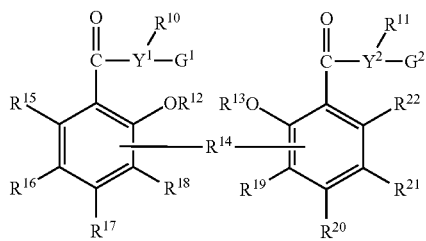

wherein $Y^1$ and $Y^2$ are independently selected from nitrogen, oxygen and sulfur;
$G^1$ and $G^2$ independently represent ionically or covalently bound groups;
$R^{19}$ and $R^{11}$ are present when necessary to satisfy the valence of $Y^1$ and $Y^2$, respectively, and are independently selected from hydrogen and an alkyl of 1-6 carbons; aryl of 6-12 carbons, alkylacyl of 1-8 carbons or arylacyl 7-15 carbons;
$R^{12}$ and $R^{13}$ are independently selected from hydrogen, alkyl or 1-6 carbons, alkylacyl of 1-8 carbons or arylacyl of 7-15 carbons;
$R^{14}$ will replace one of $R^{15}$, $R^{16}$, $R^{17}$ or $R^{18}$ and one of $R^{19}$, $R^{20}$, $R^{21}$ or $R^{22}$ and is an alkyl or branched alkyl of 1-10 carbons, aryl, arylalkyl of 7-15 carbons and wherein $R^{14}$ may include at least one optically active carbon; and
$R^{15}$, $R^{16}$, $R^{17}$, $R^{18}$, $R^{19}$, $R^{20}$, $R^{21}$ and $R^{22}$, are independently selected from hydrogen, alkyl of 1-6 carbons, and wherein adjacent groups may be taken together to form a cyclic alkyl or cyclic aryl moiety Yet another embodiment is provided in a drug substance consisting essentially of a pharmaceutically acceptable organic acid addition salt of an amine containing pharmaceutically active compound wherein the amine containing pharmaceutical active compound is selected from the group consisting of racemic or single isomer ritalinic acid or phenethylamine derivatives, particularly methylphenidate and amphetamine, and the drug substance has a physical form selected from amorphous and polymorphic and wherein the drug substance is useful for the treatment of a therapeutic ailment administration and the drug substance exhibits anti-abuse properties when employed in non-therapeutic administration.

Yet another embodiment is provided in a drug substance consisting essentially of A-B-C wherein A is a pharmaceutically active compound; C is a dissolution modifying amine and B is a bidentate linking group used to ionically or covalently link A and C, and defined by the formula:

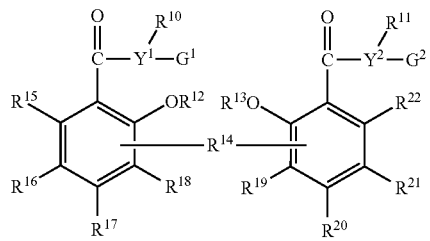

wherein $Y^1$ and $Y^2$ are independently selected from nitrogen, oxygen and sulfur;
$G^1$ and $G^2$ independently represent ionically or covalently bound groups;
$R^{10}$ and $R^{11}$ are present when necessary to satisfy the valence of $Y^1$ and $Y^2$, respectively, and are independently selected from hydrogen and an alkyl of 1-6 carbons; aryl of 6-12 carbons, alkylacyl of 1-8 carbons or arylacyl 7-15 carbons;
$R^{12}$ and $R^{13}$ are independently selected from hydrogen, alkyl or 1-6 carbons, alkylacyl of 1-8 carbons or arylacyl of 7-15 carbons;
$R^{14}$ will replace one of $R^{15}$, $R^{16}$, $R^{17}$ or $R^{18}$ and one of $R^{19}$, $R^{20}$, $R^{21}$ or $R^{22}$ and is an alkyl or branched alkyl of 1-10 carbons, aryl, arylalkyl of 7-15 carbons and wherein $R^{14}$ may include at least one optically active carbon; and
$R^{15}$, $R^{16}$, $R^{17}$, $R^{18}$, $R^{19}$, $R^{20}$, $R^{21}$ and $R^{22}$, are independently selected from hydrogen, alkyl of 1-6 carbons, and wherein adjacent groups may be taken together to form a cyclic alkyl or cyclic aryl moiety; and
wherein said drug substance is useful for the treatment of a therapeutic ailment administration and exhibits anti-abuse properties when employed in non-therapeutic administration.

Yet another embodiment is provided in a method for mitigating dose dumping comprising:
providing a drug product comprising a pharmaceutically acceptable organic acid addition salt of an amine containing pharmaceutically active compound wherein the amine containing pharmaceutically active compound is selected from the group consisting of racemic or single isomer ritalinic acid or phenethylamine derivatives, particularly methylphenidate and amphetamine, and the drug substance has a physical form selected from amorphous and polymorphic wherein the drug substance meets at least one condition in 0.1 N HCl selected from the group consisting of: no more than 35% of the pharmaceutically active compound is released at 30 minutes with 5 wt % ethanol in 0.1 N HCl;
the percentage of pharmaceutically active compound released with at least 5 wt % ethanol in 0.1 N HCl is no more than a percentage of active pharmaceutically active compound released in said 0.1 N HCl without ethanol; and the percentage of drug substance released with 40 wt % ethanol in 0.1 N HCl does not exceed 60% while the percentage of pharmaceutically active compound released under the conditions selected from water, 0.1 N HCl, 5 wt % ethanol in 0.1 N HCl and 20 wt % ethanol in 0.1 N HCl does not exceed the pharmaceutically active compound released with 40 wt % ethanol in 0.1 N HCl. It is particularly preferred that no more than about 35% of the active pharmaceutical be released over an extended time, such as at least 45 minutes.

Yet another embodiment is provided in a drug product not susceptible to dose dumping wherein the drug product comprises a drug substance wherein the drug substance is a pharmaceutically acceptable organic acid salt of an amine containing pharmaceutically active compound selected from the group consisting of racemic or single isomer ritalinic acid or phenethylamine derivatives, particularly, methylphenidate and amphetamine, and said drug substance meets at least one condition in 0.1 N HCl selected from the group consisting of: no more than 35% of the drug substance is released at 30 minutes with 5 wt % ethanol in said 0.1 N HCl; the percentage of drug substance released with at least 5 wt % ethanol in said 0.1 N HCl is no more than a percentage of drug substance released in said 0.1 N HCl without ethanol; and the percentage of drug substance released with 40 wt % ethanol in 0.1 N HCl does not exceed 60% while the percentage of drug substance released under the conditions selected from water, 0.1 N HCl, 5 wt % ethanol in 0.1 N HCl and 20 wt % ethanol in 0.1 N HCl does not exceed the drug substance released with 40 wt % ethanol in 0.1 N HCl. It is particularly preferred that no more than about 35% of the active pharmaceutical be released over an extended time, such as at least 45 minutes.

Yet another embodiment is provided in a method for mitigating dose dumping comprising:
providing a drug product comprising a drug substance consisting essentially of A-B-C wherein A is d-methylphenidate; C is an amine and B is a bidentate linking group used to ionically or covalently link A and C, and defined by the formula:

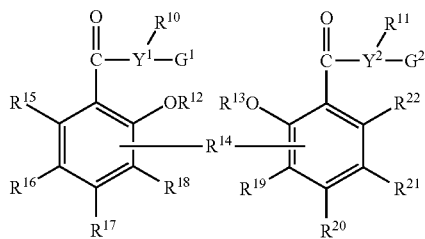

wherein $Y^1$ and $Y^2$ are independently selected from nitrogen, oxygen and sulfur;
$G^1$ and $G^2$ independently represent ionically or covalently bound groups;
$R^{10}$ and $R^{11}$ are present when necessary to satisfy the valence of $Y^1$ and $Y^2$, respectively, and are independently selected from hydrogen and an alkyl of 1-6 carbons; aryl of 6-12 carbons, alkylacyl of 1-8 carbons or arylacyl 7-15 carbons;
$R^{12}$ and $R^{13}$ are independently selected from hydrogen, alkyl or 1-6 carbons, alkylacyl of 1-8 carbons or arylacyl of 7-15 carbons;
$R^{14}$ will replace one of $R^{15}$, $R^{16}$, $R^{17}$ or $R^{18}$ and one of $R^{19}$, $R^{20}$, $R^{21}$ or $R^{22}$ and is an alkyl or branched alkyl of 1-10 carbons, aryl, arylalkyl of 7-15 carbons and wherein $R^{14}$ may include at least one optically active carbon; and
$R^{15}$, $R^{16}$, $R^{17}$, $R^{18}$, $R^{19}$, $R^{20}$, $R^{21}$ and $R^{22}$, are independently selected from hydrogen, alkyl of 1-6 carbons, and wherein adjacent groups may be taken together to form a cyclic alkyl or cyclic aryl moiety; and wherein said drug substance meets at least one condition in 0.1 N HCl selected from the group consisting of: no more than 35% of drug substance is released at 30 minutes with 5 wt % ethanol in 0.1 N HCl; the percentage of drug substance with at least 5 wt % ethanol in 0.1 N HCl is no more than a percentage of drug substance in 0.1 N HCl without ethanol; and the percentage of drug substance released with 40 wt % ethanol in 0.1 N HCl does not exceed 60% while the percentage of drug substance released under the conditions selected from water, 0.1 N HCl, 5 wt % ethanol in 0.1 N HCl and 20 wt % ethanol in 0.1 N HCl does not exceed the drug substance released with 40 wt % ethanol in 0.1 N HCl.

Yet another embodiment is provided in a drug product not susceptible to dose dumping wherein the drug product comprises a drug substance consisting essentially of A-B-C wherein A is d-methylphenidate; C is an amine and B is a bidentate linking group used to ionically or covalently link A and C, and defined by the formula:

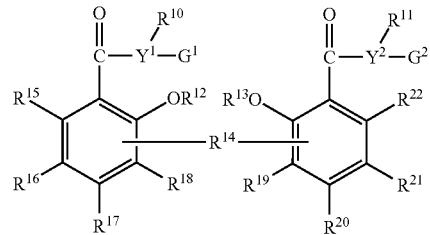

wherein $Y^1$ and $Y^2$ are independently selected from nitrogen, oxygen and sulfur;
$G^1$ and $G^2$ independently represent ionically or covalently bound groups;
$R^{10}$ and $R^{11}$ are present when necessary to satisfy the valence of $Y^1$ and $Y^2$, respectively, and are independently selected from hydrogen and an alkyl of 1-6 carbons; aryl of 6-12 carbons, alkylacyl of 1-8 carbons or arylacyl 7-15 carbons;
$R^{12}$ and $R^{13}$ are independently selected from hydrogen, alkyl or 1-6 carbons, alkylacyl of 1-8 carbons or arylacyl of 7-15 carbons;
$R^{14}$ will replace one of $R^{15}$, $R^{16}$, $R^{17}$ or $R^{18}$ and one of $R^{19}$, $R^{20}$, $R^{21}$ or $R^{22}$ and is an alkyl or branched alkyl of 1-10 carbons, aryl, arylalkyl of 7-15 carbons and wherein $R^{14}$ may include at least one optically active carbon; and
$R^{15}$, $R^{16}$, $R^{17}$, $R^{18}$, $R^{19}$, $R^{20}$, $R^{21}$ and $R^{22}$, are independently selected from hydrogen, alkyl of 1-6 carbons, and wherein adjacent groups may be taken together to form a cyclic alkyl or cyclic aryl moiety; and said drug substance meets at least one condition in 0.1 N HCl selected from the group consisting of no more than 35% of the drug substance is released at 30 minutes with 5 wt % ethanol in 0.1 N HCl; the percentage of drug substance with at least 5 wt % ethanol in said 0.1 N HCl is no more than a percentage of drug substance released in said 0.1 N HCl without ethanol; and the percentage of drug substance released with 40 wt % ethanol in 0.1 N HCl does not exceed 60% while the percentage of drug substance released under the conditions selected from water, 0.1 N HCl, 5 wt % ethanol in 0.1 N HCl and 20 wt % ethanol in 0.1 N HCl does not exceed the drug substance released with 40 wt % ethanol in 0.1 N HCl.

Yet another embodiment is provided in a method for forming a drug substance consisting essentially of A-B-C wherein A is a pharmaceutically active compound; C is an amine and B is a bidentate linking group used to ionically or covalently link A and C, and comprising:

mixing at least two moles of said pharmaceutically active compound or said amine with a mole of said bidentate linking group defined by the formula:

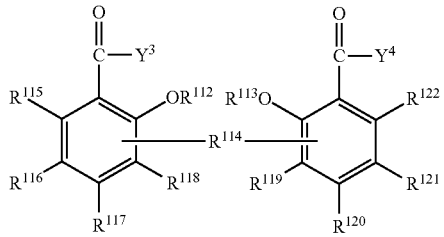

wherein $Y^3$ and $Y^4$ are independently selected from groups capable of being displaced by at least one of said pharmaceutically active compound and said amine;

$R^{112}$ and $R^{113}$ are independently selected from hydrogen, alkyl of 1-6 carbons, alkylacyl of 1-8 carbons or arylacyl of 7-15 carbons;

$R^{114}$ will replace one of $R^{115}$, $R^{116}$, $R^{117}$ or $R^{118}$ and one of $R^{119}$, $R^{120}$, $R^{121}$ or $R^{122}$ and is an alkyl or branched alkyl of 1-10 carbons, aryl, arylalkyl of 7-15 carbons and wherein $R^{114}$ may include at least one optically active carbon; and $R^{115}$, $R^{116}$, $R^{117}$, $R^{118}$, $R^{119}$, $R^{120}$, $R^{121}$ and $R^{122}$, are independently selected from hydrogen, alkyl of 1-6 carbons, and wherein adjacent groups may be taken together to form a cyclic alkyl or cyclic aryl moiety; thereby forming a conjugate; and mixing 0.9 to 1.1 moles of other amine or said pharmaceutically active compound with the conjugate thereby forming A-B-C.

Yet another embodiment is provided in a method for forming a drug substance consisting essentially of A-B-C wherein A is a pharmaceutically active compound; C is an amine and B is a bidentate linking group used to ionically or covalently link A and C, and defined by the formula:

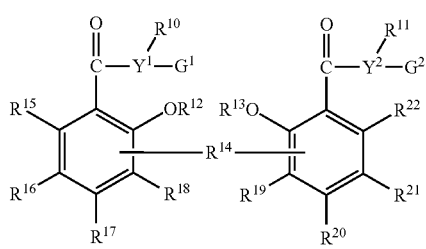

wherein $Y^1$ and $Y^2$ are independently selected from nitrogen, oxygen and sulfur;

$G^1$ and $G^2$ independently represent ionically or covalently bound groups;

$R^{10}$ and $R^{11}$ are present when necessary to satisfy the valence of $Y^1$ and $Y^2$, respectively, and are independently selected from hydrogen and an alkyl of 1-6 carbons; aryl of 6-12 carbons, alkylacyl of 1-8 carbons or arylacyl 7-15 carbons; alkali earth metals, ammonium, alkyl ammonium with 1-20 carbons and esters with 1-20 carbons;

$R^{12}$ and $R^{13}$ are independently selected from hydrogen, alkyl or 1-6 carbons, alkylacyl of 1-8 carbons or arylacyl of 7-15 carbons;

$R^{14}$ will replace one of $R^{15}$, $R^{16}$, $R^{17}$ or $R^{18}$ and one of $R^{19}$, $R^{20}$, $R^{21}$ or $R^{22}$ and is an alkyl or branched alkyl of 1-10 carbons, aryl, arylalkyl of 7-15 carbons and wherein $R^{14}$ may include at least one optically active carbon; and $R^{15}$, $R^{16}$, $R^{17}$, $R^{18}$, $R^{19}$, $R^{20}$, $R^{21}$ and $R^{22}$, are independently selected from hydrogen, alkyl of 1-6 carbons, and wherein adjacent groups may be taken together to form a cyclic alkyl or cyclic aryl moiety; comprising:

mixing at least 0.9 moles and no more than 1.1 moles of one of said pharmaceutically active compound or said amine with a mole of a bidentate linking group defined by

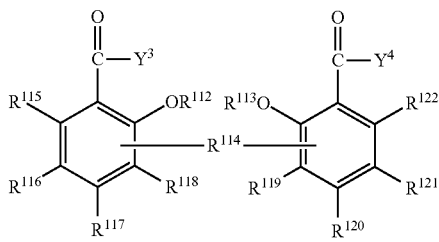

wherein $Y^3$ and $Y^4$ are independently selected from groups with capable of being displaced by at least one of said pharmaceutically active compound and said amine;

$R^{112}$ and $R^{113}$ are independently selected from hydrogen, alkyl or 1-6 carbons, alkylacyl of 1-8 carbons or arylacyl of 7-15 carbons;

$R^{114}$ will replace one of $R^{115}$, $R^{116}$, $R^{117}$ or $R^{118}$ and one of $R^{119}$, $R^{120}$, $R^{121}$ or $R^{122}$ and is an alkyl or branched alkyl of 1-10 carbons, aryl, arylalkyl of 7-15 carbons and wherein $R^{114}$ may include at least one optically active carbon; and $R^{115}$, $R^{116}$, $R^{117}$, $R^{118}$, $R^{119}$, $R^{120}$, $R^{121}$ and $R^{122}$, are independently selected from hydrogen, alkyl of 1-6 carbons, and wherein adjacent groups may be taken together to form a cyclic alkyl or cyclic aryl moiety;

thereby forming a conjugate; and mixing at least 0.9 moles and no more than 1.1 moles of other of said amine or said pharmaceutically active compound with a mole of said conjugate thereby forming said A-B-C.

Yet another embodiment is provided in a pharmaceutical composition comprising:

a first drug substance consisting essentially of a pharmaceutically acceptable organic acid addition salt of a first amine containing pharmaceutically active compound wherein the first amine containing pharmaceutical active compound is selected from the group consisting of racemic or single isomer ritalinic acid or phenethylamine derivatives, particularly methylphenidate and amphetamine, and the drug substance has a physical form selected from amorphous and polymorphic with a first percent dissolution at a pH of 1 at 60 minutes at ambient temperature; and a second drug substance consisting essentially of a salt of a second amine containing pharmaceutically active compound with a second percent dissolution at a pH of 1 at 60 minutes at ambient temperature.

Yet another embodiment is provided in a pharmaceutical composition comprising:

a first drug substance consisting essentially of a first pharmaceutically acceptable organic acid addition salt of a first amine containing pharmaceutically active compound; and a second drug substance consisting essentially of A-B-C wherein A is a second pharmaceutically active compound, C is an amine and B used to ionically or covalently link A and C, and is defined by the following structure:

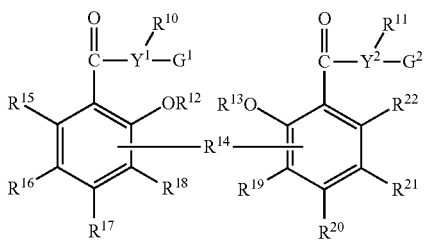

wherein $Y^1$ and $Y^2$ are independently selected from nitrogen, oxygen and sulfur;
$G^1$ and $G^2$ independently represent ionically or covalently bound groups;
$R^{10}$ and $R^{11}$ are present when necessary to satisfy the valence of $Y^1$ and $Y^2$, respectively, and are independently selected from hydrogen and an alkyl of 1-6 carbons; aryl of 6-12 carbons, alkylacyl of 1-8 carbons or arylacyl 7-15 carbons;
$R^{12}$ and $R^{13}$ are independently selected from hydrogen, alkyl or 1-6 carbons, alkylacyl of 1-8 carbons or arylacyl of 7-15 carbons;
$R^{14}$ will replace one of $R^{15}$, $R^{16}$, $R^{17}$ or $R^{18}$ and one of $R^{19}$, $R^{20}$, $R^{21}$ or $R^{22}$ and is an alkyl or branched alkyl of 1-10 carbons, aryl, arylalkyl of 7-15 carbons and wherein $R^{14}$ may include at least one optically active carbon; and
$R^{15}$, $R^{16}$, $R^{17}$, $R^{18}$, $R^{19}$, $R^{20}$, $R^{21}$ and $R^{22}$, are independently selected from hydrogen, alkyl of 1-6 carbons, and wherein adjacent groups may be taken together to form a cyclic alkyl or cyclic aryl moiety.

Yet another embodiment is provided in a method for treating Attention Deficit/Hyperactivity Disorder comprising the steps of:
determining a suitable dosage of a drug substance for a patient and a drug substance release profile;
providing at least one drug product comprising said suitable dosage of said drug substance and said drug substance release profile wherein said drug substance is selected from the group consisting of:
a pharmaceutically acceptable organic acid addition salt of a first amine containing pharmaceutically active compound wherein said first amine containing pharmaceutical active compound is selected from the group consisting of racemic or single isomer ritalinic acid or phenethylamine derivatives, particularly methylphenidate and amphetamine, and said drug substance has a physical form selected from amorphous and polymorphic; and
A-B-C wherein A is a second amine containing pharmaceutically active compound; C is an amine and B is a bidentate linking group used to ionically or covalently link A and C, and is defined by the formula:

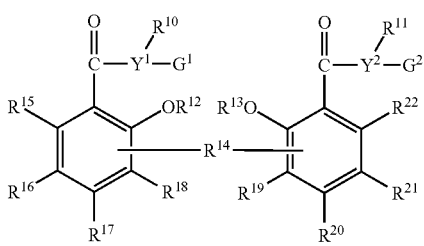

wherein $Y^1$ and $Y^2$ are independently selected from nitrogen, oxygen and sulfur;
$G^1$ and $G^2$ independently represent ionically or covalently bound groups;
$R^{10}$ and $R^{11}$ are present when necessary to satisfy the valence of $Y^1$ and $Y^2$, respectively, and are independently selected from hydrogen and an alkyl of 1-6 carbons; aryl of 6-12 carbons, alkylacyl of 1-8 carbons or arylacyl 7-15 carbons;
$R^{12}$ and $R^{13}$ are independently selected from hydrogen, alkyl or 1-6 carbons, alkylacyl of 1-8 carbons or arylacyl of 7-15 carbons;
$R^{14}$ will replace one of $R^{15}$, $R^{16}$, $R^{17}$ or $R^{18}$ and one of $R^{19}$, $R^{20}$, $R^{21}$ or $R^{22}$ and is an alkyl or branched alkyl of 1-10 carbons, aryl, arylalkyl of 7-15 carbons and wherein $R^{14}$ may include at least one optically active carbon; and
$R^{15}$, $R^{16}$, $R^{17}$, $R^{18}$, $R^{19}$, $R^{20}$, $R^{21}$ and $R^{22}$, are independently selected from hydrogen, alkyl of 1-6 carbons, and wherein adjacent groups may be taken together to form a cyclic alkyl or cyclic aryl moiety;
medicating said patient with said drug substance thereby providing a medicated patient; determining a degree of physiological/psychological disorder for said medicated patient; and
providing at least one second drug product comprising a second suitable dosage and a second drug release profile wherein said drug product comprises said at least one drug substance.

Yet another embodiment is provided in a method of administering an active pharmaceutical comprising:
providing a drug product comprising a drug substance in a dose suitable for achieving a therapeutic dose of drug substance in a predetermined time wherein the therapeutic dose is not exceeded by ingestion of alcohol at biological pH and the drug substance is selected from the group consisting of:
a pharmaceutically acceptable organic acid addition salt of a first amine containing pharmaceutically active compound wherein said first amine containing pharmaceutical active compound is selected from the group consisting of racemic or single isomer ritalinic acid or phenethylamine derivatives, particularly methylphenidate and amphetamine, and said drug substance has a physical form selected from amorphous and polymorphic; and
A-B-C wherein A is a second amine containing pharmaceutically active compound; C is an amine and B is a bidentate linking group used to link A and C, and is defined by the formula:

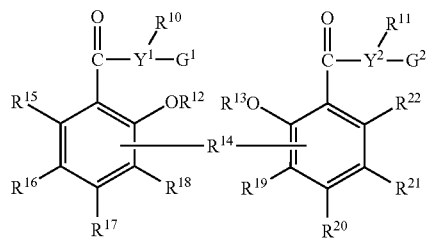

wherein $Y^1$ and $Y^2$ are independently selected from nitrogen, oxygen and sulfur;
$G^1$ and $G^2$ independently represent ionically or covalently bound groups; $R^{10}$ and $R^{11}$ are present when necessary to satisfy the valence of $Y^1$ and $Y^2$, respectively, and are independently selected from hydrogen and an alkyl of 1-6 carbons; aryl of 6-12 carbons, alkylacyl of 1-8 carbons or arylacyl 7-15 carbons;
$R^{12}$ and $R^{13}$ are independently selected from hydrogen, alkyl or 1-6 carbons, alkylacyl of 1-8 carbons or arylacyl of 7-15 carbons;

$R^{14}$ will replace one of $R^{15}$, $R^{16}$, $R^{17}$ or $R^{18}$ and one of $R^{19}$, $R^{20}$, $R^{21}$ or $R^{22}$ and is an alkyl or branched alkyl of 1-10 carbons, aryl, arylalkyl of 7-15 carbons and wherein $R^{14}$ may include at least one optically active carbon; and $R^{15}$, $R^{16}$, $R^{17}$, $R^{18}$, $R^{19}$, $R^{20}$, $R^{21}$ and $R^{22}$, are independently selected from hydrogen, alkyl of 1-6 carbons, and wherein adjacent groups may be taken together to form a cyclic alkyl or cyclic aryl moiety.

Yet another embodiment is provided in a drug system comprising:

a first drug substance comprising a first amine containing pharmaceutically active compound with an immediate release profile to reach a therapeutic level; and a second drug product comprising a second drug substance selected from the group consisting of:

a pharmaceutically acceptable organic acid addition salt of a second amine containing pharmaceutically active compound wherein said second amine containing pharmaceutical active compound is selected from the group consisting of:

methylphenidate and amphetamine wherein said drug substance has a physical form selected from amorphous and polymorphic; and A-B-C wherein A is a third amine containing pharmaceutically active compound; C is an amine and B is a bidentate linking group used to ionically or covalently link A and C, and is defined by the formula:

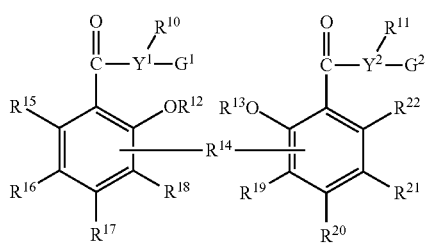

wherein $Y^1$ and $Y^2$ are independently selected from nitrogen, oxygen and sulfur;

$G^1$ and $G^2$ independently represent ionically or covalently bound groups;

$R^{10}$ and $R^{11}$ are present when necessary to satisfy the valence of $Y^1$ and $Y^2$, respectively, and are independently selected from hydrogen and an alkyl of 1-6 carbons; aryl of 6-12 carbons, alkylacyl of 1-8 carbons or arylacyl 7-15 carbons;

$R^{12}$ and $R^{13}$ are independently selected from hydrogen, alkyl or 1-6 carbons, alkylacyl of 1-8 carbons or arylacyl of 7-15 carbons;

$R^{14}$ will replace one of $R^{15}$, $R^{16}$, $R^{17}$ or $R^{18}$ and one of $R^{19}$, $R^{20}$, $R^{21}$ or $R^{22}$ and is an alkyl or branched alkyl of 1-10 carbons, aryl, arylalkyl of 7-15 carbons and wherein $R^{14}$ may include at least one optically active carbon; and $R^{15}$, $R^{16}$, $R^{17}$, $R^{18}$, $R^{19}$, $R^{20}$, $R^{21}$ and $R^{22}$, are independently selected from hydrogen, alkyl of 1-6 carbons, and wherein adjacent groups may be taken together to form a cyclic alkyl or cyclic aryl moiety;

wherein said second drug substance has a dissolution release profile suitable for maintaining said therapeutic level from 1-24 hours.

Yet another embodiment is provided in a method for treating Attention Deficit/Hyperactivity Disorder comprising:

prescribing a first drug product comprising a first drug substance at a first dose to reach a first therapeutic level of the first drug substance wherein the first drug substance comprises a first amine containing pharmaceutically active compound with an immediate release profile;

monitoring results of the first dose to determine second dose;

prescribing a second drug product comprising the first drug substance at the second dose to reach a second therapeutic level wherein the second drug substance comprises the first amine containing pharmaceutically active compound with the immediate release profile;

monitoring results of the second dose to confirm suitability of the second dose;

prescribing a third drug product comprising a second drug substance wherein the second drug substance has a dissolution release profile suitable for maintaining the therapeutic level and the second drug substance is selected from the group consisting of:

a pharmaceutically acceptable organic acid addition salt of a second amine containing pharmaceutically active compound wherein the amine containing pharmaceutical active compound is selected from the group consisting of methylphenidate and amphetamine and said drug substance has a physical form selected from amorphous and polymorphic; and A-B-C wherein A is a third amine containing pharmaceutically active compound; C is an amine and B is a bidentate linking group used to ionically or covalently link A and C, and is defined by the formula:

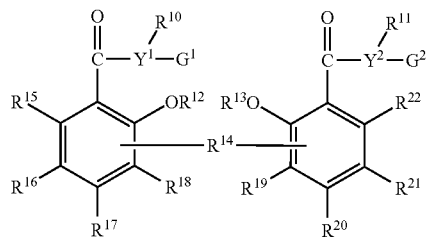

wherein $Y^1$ and $Y^2$ are independently selected from nitrogen, oxygen and sulfur;

$G^1$ and $G^2$ independently represent ionically or covalently bound groups;

$R^{10}$ and $R^{11}$ are present when necessary to satisfy the valence of $Y^1$ and $Y^2$, respectively, and are independently selected from hydrogen and an alkyl of 1-6 carbons; aryl of 6-12 carbons, alkylacyl of 1-8 carbons or arylacyl 7-15 carbons;

$R^{12}$ and $R^{13}$ are independently selected from hydrogen, alkyl or 1-6 carbons, alkylacyl of 1-8 carbons or arylacyl of 7-15 carbons;

$R^{14}$ will replace one of $R^{15}$, $R^{16}$, $R^{17}$ or $R^{18}$ and one of $R^{19}$, $R^{20}$, $R^{21}$ or $R^{22}$ and is an alkyl or branched alkyl of 1-10 carbons, aryl, arylalkyl of 7-15 carbons and wherein $R^{14}$ may include at least one optically active carbon; and $R^{15}$, $R^{16}$, $R^{17}$, $R^{18}$, $R^{19}$, $R^{20}$, $R^{21}$ and $R^{22}$, are independently selected from hydrogen, alkyl of 1-6 carbons, and wherein adjacent groups may be taken together to form a cyclic alkyl or cyclic aryl moiety.

Yet another embodiment is provided in a method for forming an improved drug system with an optimized bioavailability comprising the steps of:

forming a drug substance consisting essentially of A-B-C wherein A is an amine containing pharmaceutically active compound; C is a first dissolution modifying amine and B is a bidentate linking group used to ionically or covalently link A and C, and is defined by the formula:

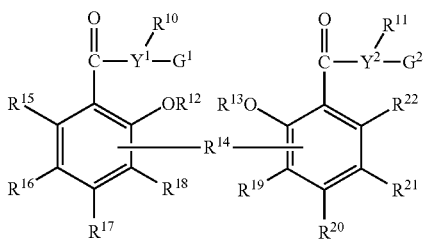

wherein $Y^1$ and $Y^2$ are independently selected from nitrogen, oxygen and sulfur;
$G^1$ and $G^2$ independently represent ionically or covalently bound groups;
$R^{10}$ and $R^{11}$ are present when necessary to satisfy the valence of $Y^1$ and $Y^2$, respectively, and are independently selected from hydrogen and an alkyl of 1-6 carbons; aryl of 6-12 carbons, alkylacyl of 1-8 carbons or arylacyl 7-15 carbons;
$R^{12}$ and $R^{13}$ are independently selected from hydrogen, alkyl or 1-6 carbons, alkylacyl of 1-8 carbons or arylacyl of 7-15 carbons;
$R^{14}$ will replace one of $R^{15}$, $R^{16}$, $R^{17}$ or $R^{18}$ and one of $R^{19}$, $R^{20}$, $R^{21}$ or $R^{22}$ and is an alkyl or branched alkyl of 1-10 carbons, aryl, arylalkyl of 7-15 carbons and wherein $R^{14}$ may include at least one optically active carbon; and
$R^{15}$, $R^{16}$, $R^{17}$, $R^{18}$, $R^{19}$, $R^{20}$, $R^{21}$ and $R^{22}$, are independently selected from hydrogen, alkyl of 1-6 carbons, and wherein adjacent groups may be taken together to form a cyclic alkyl or cyclic aryl moiety;
measuring a dissolution profile at pH intervals representing gastric, intestinal and aqueous conditions;
comparing said dissolution profile with a predetermined standard;
forming a second drug substance consisting essentially of A-B-C' wherein A is said amine containing pharmaceutically active compound; C' is a second dissolution modifying amine and B is said bidentate linking group wherein said second dissolution modifying amine has a different hydrophilicity than said first dissolution modifying amine.

DETAILED DESCRIPTION OF THE INVENTION

Figure 1:
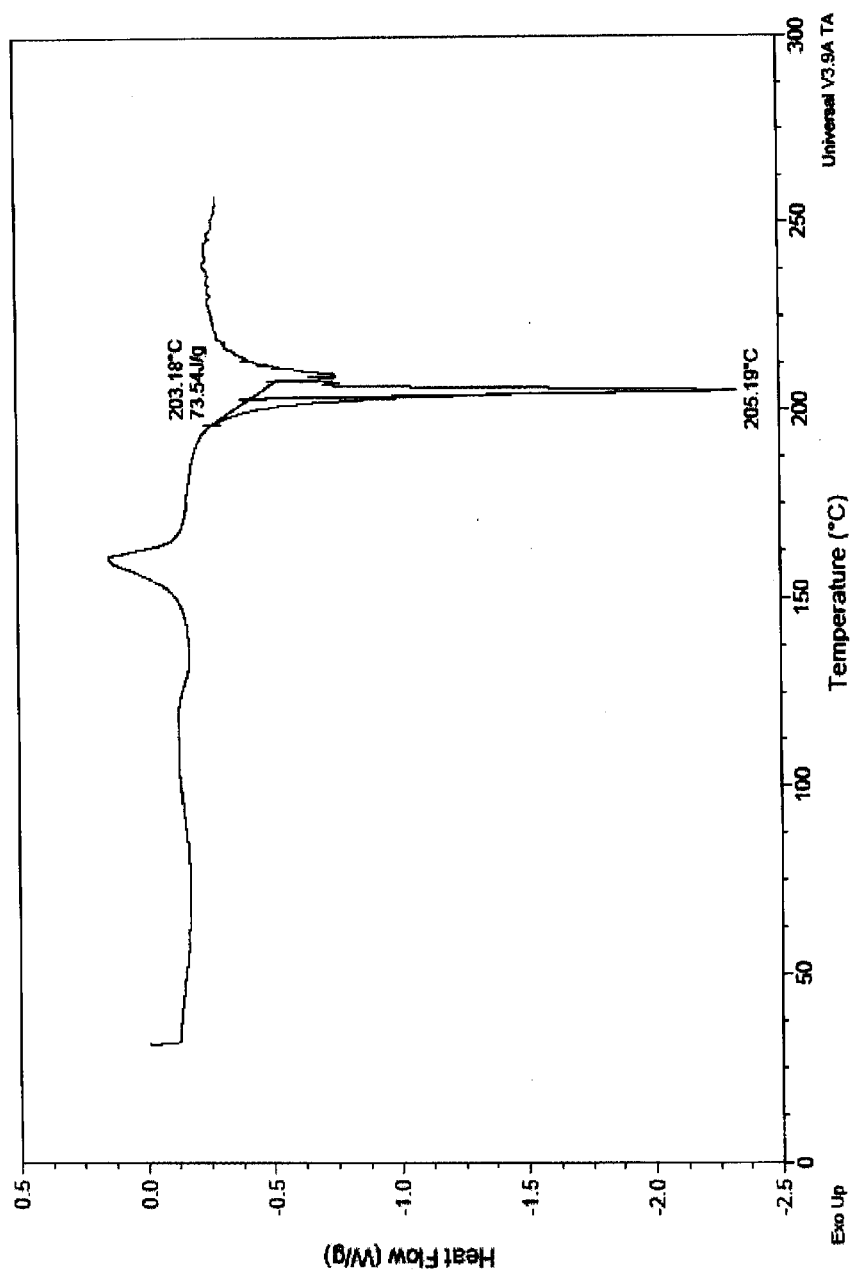
FIG. 1 is the differential scanning calorimetry (DSC) thermogram of amorphous racemic-methylphenidate pamoate.

The present invention is directed to improved pharmaceuticals, particularly, for use in treating AD(H)D. The improved pharmaceuticals are abuse-deterrent, especially, with regards to abuse via alcohol enhanced dose dumping. The improved pharmaceuticals provide for an improved system of administration and an enhanced ability to design drug substances for optimized bioavailability through systematic dissolution profile alteration with selected hydrophilic and lipophilic properties.

The invention will be described with reference to figures which are an integral, non-limiting, component of the specification.

The present invention provides compounds which are useful in the legitimate and medically necessary treatment of ADD/ADHD. More specifically, the present invention provides for the isolation, identification and characterization of unique physical forms of organic acid addition salts of racemic or single isomer derivatives of ritalinic acid or phenethylamine derivatives, and particularly methylphenidate and dextro-amphetamine, where their use in treating ADD/ADHD is enhanced by rendering them abuse-deterrent. Furthermore, the present invention provides for the ability to adjust the hydrophilic and lipophilic character of amine containing drug substances thereby allowing the drug designer to engineer a pre-determined dissolution profile of the drug substance. The advantages are provided through the synthetic ability to manipulate and prepare drug substances with a myriad of substitutions. The present invention therefore provides a highly desirable technical solution to a complex pharmaceutical need and a government mandated program.

The inventive drug substances, and drug product comprising the drug substances, are organic addition salts of an amine containing active pharmaceutical compound. In a particularly preferred embodiment the amine containing active pharmaceutical compound is selected from the group consisting of racemic or single isomer ritalinic acid or phenethylamine derivatives, particularly amphetamine and methylphenidate wherein the drug substance is in a physical form selected from amorphous and polymorphic.

The phenethylamine derivatives are defined by the structure:

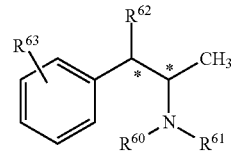

wherein $R^{60}$ and $R^{61}$ are independently selected from hydrogen, alkyl of 1-15 carbons, cycloaliphatic and aromatic;
$R^{62}$ is selected from selected from hydrogen, alkyl of 1-15 carbons, cycloaliphatic and aromatic, benzyl and acetyl;

$R^{63}$ is selected from alkyl of 1-15 carbons, halogen, alkoxy of 1-5 carbons, benzyl, carbonyl and carboxyl; and

* indicates an R or S carbon. Dextro-amphetamine is defined as $R^{60}$, $R^{61}$, $R^{62}$, and $R^{63}$ each being hydrogen and the remaining chiral center has an absolute stereochemistry of S.

The ritalinic acid derivatives are defined by the structure:

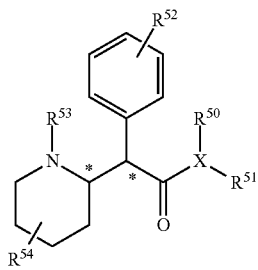

wherein X is selected from O, N and S;

$R^{50}$ is selected from hydrogen, alkyl of 1-15 carbons, cycloaliphatic and aromatic;

$R^{51}$ when necessary to balance the valence of X is selected from hydrogen, alkyl of 1-15 carbons, cycloaliphatic and aromatic;

$R^{53}$ is selected from selected from hydrogen, alkyl of 1-15 carbons, cycloaliphatic and aromatic, benzyl and acetyl;

$R^{52}$ and $R^{54}$ are independently selected from alkyl of 1-15 carbons, halogen, alkoxy of 1-5 carbons, benzyl, carbonyl and carboxyl; and

* indicates an R or S carbon. d-methylphenidate is defined by X being oxygen; $R^{50}$ not being necessary; $R^{51}$ is methyl; $R^{52}$, $R^{53}$ and $R^{54}$ are hydrogen and both stereochemical centers have an absolute configuration of R.

Where appropriate, optical isomers are specified herein by their chirality in accordance with standard nomenclature using the terms dextro-, or d-, for dextrorotatory; levo-, or l, for levorotatory and racemic-, for mixed optical isomers. Also employed herein are the designations R and S which represent a stereochemical center's absolute configuration.

The organic acid is described herein as either the acid or the linking group with the understanding that the acid moiety reacts with an amine to form an ionic chemical bond. Throughout the specification the organic acid is represented, for convenience, as —COXR'R", or an equivalent, wherein X, R' and R" are further defined or as —COY'R'"—, or the equivalent, wherein Y' and R'" are further defined and the vacant valency indicates a bond to a subsequent group. These definitions are used interchangeably for convenience of discussion.

An embodiment of the organic acid is defined by the following Structures A through H wherein Structure A represents the general family of compounds embodied within the invention. Structure B represents the subset of salicylic acid and its derivatives. Structures C, D and E are regio-isomeric variations of Compound A wherein two adjacent substituents on Compound A form a fused aryl ring (i.e. $R^1+R^2$; $R^2+R^3$; and $R^3+R^4$). Structures F, G and H represent a further subcategory of dimer-like compounds derived from Structure A. In Structure F, dimerization has occurred through $R^4$ of two Structure A compounds with both possessing fused-aryl ring systems formed via $R^2+R^3$. In Structure G, dimerization has again occurred through $R^4$ of two Structure A compounds; however both Structure A residues possess fused-aryl ring systems formed via $R^1+R^2$.

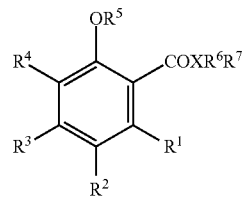

Structure A

Wherein $R^1$-$R^4$ are independently selected from H, alkyl or substituted alkyl of 1-6 carbons, adjacent groups may be taken together to form a cyclic alkyl or cyclic aryl moiety; $R^5$ represents H, alkyl, alkylacyl or arylacyl; $R^6$ and $R^7$ are independently selected from H, alkyl of 1-6 carbons, aryl of 6-12 carbons, alkylacyl or arylacyl analogues sufficient to satisfy the valence of X (e.g. to provide a mixed anhydride or carbamate); X is selected from nitrogen, oxygen or sulfur, and when X=O, $R^6$+$R^7$ may represent an alkali earth cation, ammonium or together form a heterocyclic ammonium moiety;

Particularly preferred organic acids include Structures B through E.

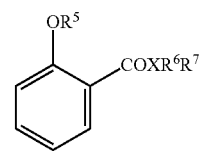

Structure B wherein $R^5$, $R^6$, $R^7$ and X remain as defined above for Structure A;

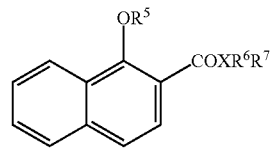

Structure C wherein X, $R^5$, $R^6$ and $R^7$ remain as defined above for Structure A and more preferably X is O;

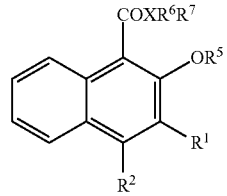

Structure D wherein X, $R^1$, $R^2$, $R^5$, $R^6$ and $R^7$ remain as defined above for Structure A and more preferably X is O; $R^1$ and $R^2$ are hydrogen;

Structure E

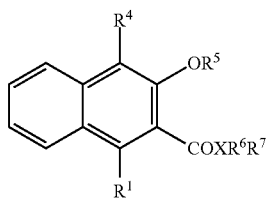

wherein X, $R^1$, $R^4$, $R^5$, $R^6$ and $R^7$ remain as defined above for Structure A and more preferably X is O, $R^1$ and $R^4$ are hydrogen;

Structure F

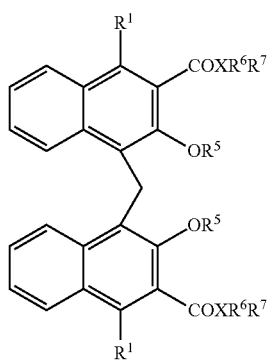

wherein X, $R^1$, $R^5$, $R^6$ and $R^7$ are independently defined as above for Structure A and more preferably at least one X is O and at least one $R^1$ is hydrogen; and Structure G

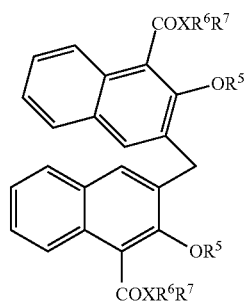

wherein X, $R^5$, $R^6$ and $R^7$ are independently defined as above for Structure A and more preferably X is O and $R^5$ is hydrogen.

Pamoic acid, or a synthetic equivalent of pamoic acid, is the preferred embodiment. Pamoic acid has a formula corresponding to Structure F wherein X is O; $R^1$, $R^5$, $R^6$ and $R^7$ are hydrogen.

A synthetic equivalent of pamoic acid is a material that provides the structural moiety independent of its particular salt, ester, or amide form and that upon pH adjustment yields pamoate functionality suitable for reaction, optionally with one or two equivalents of an amine-containing active pharmaceutical ingredient to form a pamoate salt. Examples of synthetic equivalents of pamoic acid capable of manipulation to produce pamoate salts include but are not limited to, disodium pamoate, mono-alkali pamoate, di-ammonium pamoate and derivatives (e.g. di-triethylammonium pamoate), di-potassium pamoate, lower molecular weight di-alkyl and/or di-aryl amine pamoate, lower molecular weight di-alkyl and/or di-aryl esters of pamoic acid, and lower molecular weight di-alkylacyl and/or di-arylacyl O-esters of pamoic acid, i.e. those alkylacyl and arylacyl esters formed using the hydroxyl moiety of pamoic acid and not the carboxylic acid functional group. The descriptor phrase "lower molecular weight" used herein means the indicated moiety has a molecular mass contribution within the pamoate derivative of less than about 200 amu.

For clarity, the use of lower molecular weight di-alkyl or di-aryl amine pamoate allows for the exchange of higher molecular weight amines, or a drug's free base, to be exchanged for the lower molecular weight amine component during the salt formation reaction. Similarly, the use of lower molecular weight di-alkylacyl and/or di-arylacyl pamoates allow for their conversion through ester hydrolysis to the pamoic/pamoate moiety followed by reaction with the desired drug free base.

A particularly preferred bis-functional, or bidentate, organic acid linking group is defined by Structure H:

Structure H

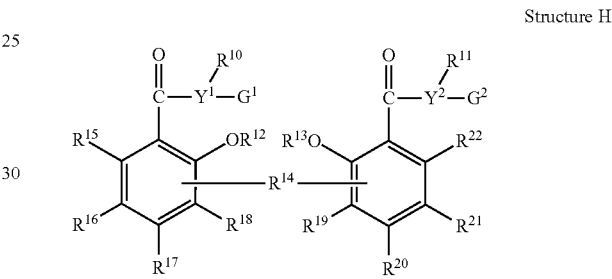

wherein $Y^1$ and $Y^2$ are independently selected from nitrogen, oxygen and sulfur;
$R^{10}$ and $R^{11}$ are present when necessary to satisfy the valence of $Y^1$ and $Y^2$, respectively, and are independently selected from hydrogen; an alkyl of 1-6 carbons; aryl of 6-12 carbons, alkylacyl of 1-8 carbons or arylacyl 7-15 carbons;
$G^1$ and $G^2$ independently represent ionically or covalently bound groups;
$R^{12}$ and $R^{13}$ are independently selected from hydrogen, alkyl or 1-6 carbons, alkylacyl of 1-8 carbons or arylacyl of 7-15 carbons;
$R^{14}$ will replace one of $R^{15}$, $R^{16}$, $R^{17}$ or $R^{18}$ and one of $R^{19}$, $R^{20}$, $R^{21}$ or $R^{22}$ and is an alkyl or branched alkyl of 1-10 carbons, aryl, arylalkyl of 7-15 carbons and wherein $R^{14}$ may include at least one optically active carbon; and
$R^{15}$, $R^{16}$, $R^{17}$, $R^{18}$, $R^{19}$, $R^{20}$, $R^{21}$ and $R^{22}$, are independently selected from hydrogen, alkyl of 1-6 carbons, and wherein adjacent groups may be taken together to form a cyclic alkyl or cyclic aryl moiety.

A particular advantage of bis-functional organic acids includes the ability to attach separate amines to the organic acid at $Y^1$ and $Y^2$ (as the amine salt of the bis-carboxylic acid). Two identical pharmaceutically active compounds can be employed. For convenience of discussion these are referred to herein as 2:1 compounds designating two pharmaceutically active compounds per one bis-organic acid. Similarly, one of the organic acid groups may remain as the acid while the other forms a salt with a pharmaceutically active compound. For convenience of discussion these are referred to herein as 1:1 compounds. In another embodiment one compound attached to the bis-functional organic acid may be a pharmaceutically active compound with the other being an amine. For convenience these are referred to herein as 1:1:1 compounds. When a bis-organic acid, such as represented by Structure H is utilized with an amine, the amine is preferably a pharmacophore or a dissolution modifying amine, both of which are more specifically described below.

Additional pharmaceutically active compounds which can be incorporated with the present invention include those selected from the group consisting of acetaminophen, caffeine, acetorphine, acetylmethadol, allylprodine, alphacetylmethadol, bufotenine, dextromoramide, diethyltryptamine, etorphine, heroin, ibogaine, ketobemidone, lysergic acid diethylamide, mescaline, methaqualone, 3,4-methylenedioxyamphetamine, 3,4-methylenedioxymethamphetamine, N-ethyl-1-phenylcyclohexylamine, peyote, 1-(1-phenylcyclohexyl)pyrrolidine, psilocybin, psilocin, 1-{1-(2-thienyl) cyclohexyl}-piperidine, alphaprodine, anileridine, cocaine, dextropropoxyphene, diphenoxylate, ethylmorphine, glutethimide, hydrocodone, hydromorphone, levo-alpha-acetylmethadol, levorphanol, meperidine, methadone, morphine, opium, oxycodone, oxymorphone, poppy straw, thebaine, amphetamine, methamphetamine, methylphenidate, phencyclidine, codeine, benzphetamine, ketamine, alprazolam, chlorodiazepoxide, clorazepate, diethylpropion, fenfluramine, flurazepam, halazepam, lorazepam, mazindol, mebutamate, midazolam, oxazepam, pemoline, pentazocine, phentermine, prazepam, quazepam, temazepam, triazolam, zolpidem, buprenorphine, imipramine, apomorphine, dihydrocodeine, codeinone, thebaine, morphothebaine, thebenine, metathebainone, phenyldihydrothebaine, thebainhydroquinone, flavothebanone, alpha-codeimethine, acetylmethylmorphol, methylmorphenol, 14-hydroxycodeinone, sinomenine, dihydrosinomenine, hasubanonine, nalbuphine, nalmefene, naloxone, naltrexone, noscapine, oripavine and imipramine.

Particularly preferred pharmaceutically active compounds are selected from the group consisting of methylphenidate, d-methylphenidate, amphetamine, dextro-amphetamine, hydrocodone, morphine, oxycodone, hydromorphone, oxymorphone, methadone, 14-hydroxycodeinone, phentermine, imipramine, codeine, naloxone, naltrexone, oripavine and thebaine.

In a preferred embodiment of the invention, at least one equivalent of the amine containing drug substance is reacted per mole of disodium organic acid salt to yield the drug substance. Occasionally, the charge neutral amine species can be combined with organic acid in a solvent (e.g. DMF) to yield the desired salt. Preferably, 2:1, 1:1, or mixtures thereof, equivalents of amine per mole of organic acids are prepared. Typically, an aqueous acidic solution of the amine containing drug substance is combined with a basic solution of organic acid or disodium salt of the organic acid. Occasionally, the neutral species for each reactant can be combined to form the desired salt. In either case, the acid/base reaction ensues and the insoluble organic acid salt precipitates from the aqueous solution. Optionally, the salt can be purified, dried and milled to obtain a drug substance ready for formulation into the desired delivery format.

The drug product formulated with the drug substances then possesses the targeted delivery characteristics of the drug substance and the potential for abuse of either the drug substance and/or drug product is eliminated or greatly reduced when abuse is attempted via the mucosal membranes or by injection.

In one embodiment an amine containing pharmacophore can be utilized as a substituent on the organic acid. Particularly preferred pharmacophores include those selected from the group consisting of prostaglandins, benzyl derivatives; benzhydryl derivatives, phenethylamines; phenylpropylamines, arylacetic acids, arylpropionic acids, arylethylenes, monocyclic aromatic compounds, polycyclic aromatic compounds, steroids, tetracyclines, acyclic compounds, five-membered heterocycles, six-membered heterocycles, derivatives of morphine, derivatives of morphinan, derivatives of benzomorphan, phenylpiperidine, five-membered heterocycles fused to one benzene ring, six membered heterocycles fused to one benzene ring, benzodiazepines, phenothizaines, dibenzopyrans, acridines, thioxanthenes, dibenzaepines, dihydrobenzaepines, dibenzazepines, dibenzoxepines, dibenzodiazepines, dibenzothiazepines, beta-lactam antibiotics, purines and pyrimidines.

In addition, synthetic methodology can be employed which allows for the isolation of the organic acid moiety uniquely substituted with the active pharmaceutical ingredient and a dissolution modifying agent in a one-to-one ratio. The ability to isolate the single component from the potentially-formed statistical reaction mixture allowed for the evaluation and comparison of the impact of hydrophilic and lipophilic dissolution modifying agents compared to the organic acid salt containing only the active ingredient.

Stearylamine is particularly suitable for demonstrating the introduction of lipophilic character to a molecule and a low molecular weight polyethylene oxide (EO)/polypropylene oxide (PO) polymer possessing amino functionality is particularly suitable for demonstrating introduction of hydrophilic character. The oleophilic nature of the stearylamine contrasted sharply to the hydrophilic, hydrogen bonding capability of the EO/PO polymer. Particularly preferred amines for demonstrating hydrophilic character are selected from the commercially available, amine containing Jeffamine® product line. Detailed information about the Jeffamine® series of polymers is found online.

Imipramine pamoate derivatives are particularly suitable for demonstrating the utility of the invention with regards to incorporation of hydrophobic and hydrophilic enhancements.

Particularly preferred dissolution modifying amines are those considered to be approved excipients by the United States Food and Drug Administration, and/or are Generally Recognized as Safe (GRAS) listed, and/or used as food additives for oral consumption. More particularly, preferred dissolution modifying amines are those selected from the group consisting of primary amines, secondary amines, tertiary amines and quaternary amines and more particularly selected from the group consisting of aliphatic primary amines with 1-30 carbons; secondary amines with 1-30 carbons; branched alkyl amines with 1-30 carbons and cyclic aliphatic amines with 1-30 carbons.

A particularly preferred dissolution modifying amine is defined by the formula:

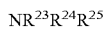

$NR^{23}R^{24}R^{25}$ and $R^{23}$, $R^{24}$ and $R^{25}$ are independently selected hydrogen, alkyl of 1-60 carbons; cyclic alkyl of 3-22 carbons; polyoxyalkylene with 1-5 carbons per oxyalkylene monomeric unit or polyoxyarylene with 8-12 carbons per oxyarylene monomeric unit. In one embodiment at least one of $R^{23}$, $R^{24}$ or $R^{25}$ is not hydrogen. More preferably at least one of $R^{23}$, $R^{24}$ or $R^{25}$ comprises a polymerized monomeric unit selected from the group consisting of ethylene oxide, propylene oxide, butylene oxide and styrene oxide. In another embodiment at least one of the groups $R^{23}$, $R^{24}$ or $R^{25}$ comprises a random or block copolymer comprising at least one of polymerized oxyalkylene monomeric units or polymerized oxyarylene monomeric units also referred to in the art as polyetheramines. In another embodiment at least one of $R^{23}$, $R^{24}$ or $R^{25}$ comprises polymerized monomeric units selected from the group consisting of ethylene oxide, propylene oxide, butylene oxide and styrene oxide. In another embodiment at least one of $R^{23}$, $R^{24}$ or $R^{25}$ is defined by the formula:

$$—(R^{26}—O)_w—(R^{27}—O)_v—R^{28}$$

wherein $R^{26}$ and $R^{27}$ are independently selected from alkyl of 1-5 carbons and aryl of 8-12 carbons;
$R^{28}$ is an alkyl of 1-5 carbons; and
w and v are integers independently selected to have a ratio of from 1:20 to 20:1 and the molecular weight is at least 200 to no more than 3000. Yet another embodiment is defined by the formula:

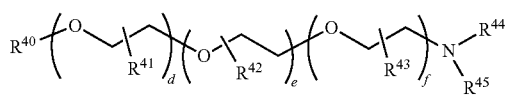

wherein $R^{40}$, $R^{41}$, $R^{42}$ and $R^{43}$ are independently selected from hydrogen, alkyl of 1-6 carbons, aryl or 6-10 carbons, or arylalkyl of 7-11 carbons,
d, e and f are integers with each integer independently selected from 0 to no more than 20 with the proviso that at least one integer selected from d, e and f is at least 1; and
$R^{44}$ and $R^{45}$ are independently selected from hydrogen, alkyl of 1-6 carbons, aryl or 6-10 carbons, or arylalkyl of 7-11 carbons and

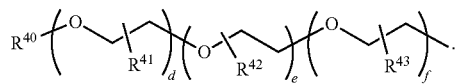

In another embodiment at least one of $R^{40}$, $R^{41}$, $R^{42}$ and $R^{43}$ is selected from hydrogen, methyl, ethyl and phenyl. A particularly preferred embodiment is defined by the formula:

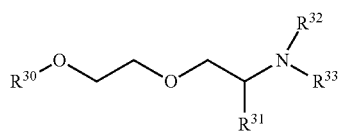

wherein:
$R^{30}$ and $R^{31}$ are independently selected from an alkyl of 1-5 carbons and most preferably methyl;
$R^{32}$ and $R^{33}$ are independently selected from hydrogen and $R^{30}$—(O—$CH_2CH_2)_x(OCH_2CHR^{31})_y$—; and
x and y are integers independently selected to have a ratio of from 1:20 to 20:1 and said dissolution modifying amine has a molecular weight of at least 200 to no more than 3000.

Particularly preferred dissolution modifying amines are selected from the group consisting of: JEFFAMINE® XTJ-505 (M-600); JEFFAMINE® XTJ-506 (M-1000); JEFFAMINE® M-2005; JEFFAMINE® M2070; JEFFAMINE® D-230; JEFFAMINE® D-400; JEFFAMINE® D-2000; JEFFAMINE® D-4000 (XTJ-510); JEFFAMINE® HK-511; JEFFAMINE® ED-600 (XTJ-500); JEFFAMINE® ED-900 (XTJ-501); JEFFAMINE® ED-2003 (XTJ-502); JEFFAMINE® EDR-148 (XTJ-504); JEFFAMINE® EDR-176 (XTJ-590); JEFFAMINE® T-403; JEFFAMINE® T-3000 (XTJ-509); JEFFAMINE® T-5000; JEFFAMINE® SD-231 (XTJ-584); JEFFAMINE® SD-401 (XTJ-585); JEFFAMINE® SD-2001 (XTJ-576); JEFFAMINE® ST-404 (XTJ-586); JEFFAMINE® XTJ-435; JEFFAMINE® XTJ-436; JEFFAMINE® XTJ-566 and JEFFAMINE® XTJ-568. More preferably the dissolution modifying amine is selected from the group consisting of: JEFFAMINE® XTJ-505 (M-600); JEFFAMINE® XTJ-506 (M-1000); JEFFAMINE® M-2005 and JEFFAMINE® M2070.

Particularly preferred materials are defined by the structure:

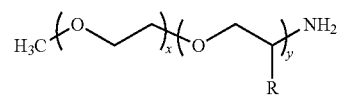

wherein R, X and Y are provided in Table 1.

TABLE 1

| Commercial Name | R | Y/X | Approximate MW |
|---|---|---|---|
| JEFFAMINE ® XTJ-505 (M-600) | Methyl | 9:1 | 600 |
| JEFFAMINE ® XTJ-506 (M-1000) | Methyl | 3:19 | 1,000 |
| JEFFAMINE ® M-2005 | Methyl | 29:6 | 2,000 |
| JEFFAMINE ® M2070 | Methyl | 10:31 | 2,000 |

The most preferred amines are octadecylamine (stearylamine) and polyoxyalkylene amine (Jeffamine XTJ-505®) as representing a range of hydrophobic to hydrophilic amines, respectively.

In another embodiment the dissolution modifying amine is selected from the group consisting of methyl amine; ethyl amine; propyl amine; butyl amine; pentyl amine; hexyl amine; octyl amine; nonyl amine; decyl amine; undecyl amine; octadecyl amine; hexadecyl amine; di-dodecyl amine; dimethyl amine, diethyl amine; dipropyl amine; dibutyl amine; dipentyl amine; dihexyl amine; dicyclohexyl amine; diheptyl amine; dioctyl amine; didecyl amine; dioctadecyl amine; didodecyl amine; cyclohexyl amine; 2,3-dimethyl-1-cyclohexylamine; piperidine; morpholine; pyrrolidine; aniline; anisidine; rosin amine, dehydroabietyl amine; dihydroabietyl amine; hydroabietyl amine; adamantyl amine; isonipecotamide; polyoxyalkylenemonoamine wherein each oxyalkylene independently comprise 1-5 carbons; polyoxyalkylenediamine wherein each oxyalkylene independently comprise 1-5 carbons; polyoxyalkylenetriamine wherein each oxyalkylene independently comprise 1-5 carbons; 3,3'-diamino-N-methyl-dipropylamine; polyethylene imine; ethylene diamine; hexamethylene diamine; cyclohexyl-diamines; 1,3-pentadiamine; 1,12-dodecanediamine; 3-dimethylaminopropylamine; 4,7,10-trioxa-1,13-tridecanediamine; diethylene triamine; 3,3-diamino-N-methyl-dipropylamine; tris(2-aminoethyl)amine; tridecylamine; pentadecylamine; hexadecylamine; heptadecylamine; octadecylamine; monodecylamine; eicosylamine; heneicosylamine; docosylamine; tricosylamine; tetracosylamine; pentacosylamine; hexacosylamine; laurylamine; myristylamine; palmitylamine; stearoamine; arachidylamine; behenylamine; lignocerylamine; lauroleylamine; myristoleylamine; palmitoleyamine; gadoleylamine; erucylamine; ricinoleylamine; linoleylamine; linolenylamine; eleostearoamine; arachidonylamine; clupanodylamine; di-dodecylamine; di-tridecylamine; di-pentadecylamine; di-hexadecylamine; di-heptadecylamine; di-octadecylamine; di-monodecylamine; di-eicosylamine; di-heneicosaneamine; di-docosylamine; di-tricosylamine; di-tetracosylamine; di-pentacosylamine; di-hexacosylamine; di-laurylamine; di-myristylamine;

di-palmitylamine; di-stearoamine; di-arachidylamine; di-behenylamine; di-lignocerylamine; di-lauroleylamine; di-myristoleylamine; di-palmitoleyamine; di-gadoleylamine; di-erucylamine; di-ricinoleylamine; di-linoleylamine; di-linolenylamine; di-eleostearoamine; di-arachidonylamine; and di-clupanodylamine; tri-dodecylamine; tri-tridecylamine; tri-pentadecylamine; tri-hexadecylamine; tri-heptadecylamine; tri-octadecylamine; tri-monodecylamine; tri-eicosylamine; tri-heneicosylamine; tri-docosylamine; tri-tricosylamine; tri-tetracosylamine; tri-pentacosylamine; tri-hexacosylamine; tri-laurylamine; tri-myristylamine; tri-palmitylamine; tri-stearylamine; tri-arachidylamine; tri-behenylamine; tri-lignocerylamine; tri-lauroleylamine; tri-myristoleylamine; tri-palmitoleyamine; tri-gadoleylamine; tri-erucylamine; tri-ricinoleylamine; tri-linoleylamine; tri-linolenylamine; tri-eleostearylamine; tri-arachidonylamine; tri-clupanodylamine; meglumine and amino-glucose.

A particularly preferred dissolution modifying amine is selected from the group consisting of n-propyl amine; iso-propyl amine; n-butyl amine, iso-butyl amine; s-butyl amine; t-butyl amine; n-pentyl amine, iso-pentyl amine, t-pentyl amine; n-hexyl amine, iso-hexyl amine, t-hexyl amine; n-octyl amine, iso-octyl amine, t-octyl amine; n-nonyl amine, iso-nonyl amine, t-nonyl amine; n-decyl amine; branched decyl amine; n-undecyl amine, branched undecyl amine; n-octadecyl amine, branched octadecyl amine; n-hexadecyl amine, branched hexadecyl amine; n-dodecyl amine, branched dodecyl amine; dimethyl amine, diethyl amine; di-n-propyl amine; di-isopropyl amine; di-n-butyl amine, di-isobutyl amine, di-t-butyl amine; di-n-pentyl amine; di-isopentyl amine; di-t-pentyl amine; di-n-hexyl amine, di-iso-hexyl amine; di-t-hexyl amine; di-n-cyclohexyl amine; di-iso-cyclohexyl amine; di-t-cyclohexyl amine; di-n-heptyl amine; di-iso-heptyl amine; di-t-heptyl amine; di-n-octyl amine, di-isooctyl amine; di-t-octyl amine; di-n-decyl amine; di-iso-decyl amine; di-t-decyl amine; di-n-octadecyl amine; diisooctadecyl amine; di-t-octadecyl amine; di-n-dodecyl amine; di-isododecyl amine; di-t-dodecyl amine; tri-n-propyl; tri-isopropyl amine; tri-n-butyl amine; tri-isobutyl amine; tri-t-butyl amine; tri-n-pentyl amine; tri-iso-pentyl amine, tri-t-pentyl amine; tri-n-hexyl amine, tri-isohexyl amine; tri-t-hexyl amine; tri-cyclohexyl amine; tri-n-heptyl amine; tri-iso-heptyl amine and tri-t-heptyl amine.

Amino alcohol precursors are particularly preferred amines. The amino alcohol precursors include any compound that contains at least one alcohol functional group and at least one amine functional group. The preferred classes of amino alcohols are monoalkanol amines and dialkanol amines and can include trialkanol amines and combinations thereof. Examples of amino alcohols include ethanolamine; 3-amino-1,2-propanediol; serinol; 2-amino-2-methyl-1,3-propanediol; tris(hydroxymethyl)-aminomethane; 1-amino-1-deoxy-D-sorbitol; diethanolamine; diisopropanolamine; N-methyl-N,N-diethanolamine; triethanolamine; and N,N,N',N'-tetrakis (2-hydroxypropyl) ethylenediamine and combinations thereof.

The organic acid component to the salt forming process also imparts a drug delivery performance feature for selective absorption. It has been reported by Bristol et al. that the organic acid addition salts are essentially insoluble in the mucosal membranes. However, if the Active Pharmaceutical Ingredient (API) organic acid addition salt is subjected to the gastrointestinal tract where it encounters low pH conditions, the active ingredient is released. In this regard, the selective release is accomplished by pH conditions. Conversely, the use of organic acid addition salts may also be used to selectively deliver amine-containing drug substances wherein the driving force is not a pH change, but an alteration of the hydrophilic/lipophilic balance of the amine-containing API. An analogy to this concept is represented by the work reported by Acura Pharmaceuticals and Collegium.

In regard to Collegium's effort to impart abuse deterrent properties to controlled substances, an abuse-deterrent pharmaceutical composition is described in United States Patent Application Publication Number US 2004/0052731 A1 [Hirsh et al.], the disclosure of which is incorporated herein by reference in its entirety. The publication indicates the intention to alter the lipophilicity of an opioid drug substance by complexation with oleophilic metal salts such as zinc stearate. It is suggested that the "likelihood of improper administration of drugs, especially drugs such as opioids" would be due to the increase in lipophilicity imparted to the opioid by the complexation with said metal salts.

In U.S. Pat. No. 7,201,920 B2 [Kumar et al.] assigned to Acura Pharmaceuticals, the disclosure of which is incorporated herein in its entirety, the inventors describe a formulation technique to prepare abuse deterrent dosage forms of opioid analgesics by employing a polyethylene oxide polymer to form a matrix.

In regard to Acura's work, the gel forming tendency of the hydrophilic polyethylene oxide polymer was selected essentially to perform as a desiccant. The opioid is formulated with the polymer and any attempt to abuse the drug by snorting would yield a globular gel in the mucosal membranes of the nose and thus deny the "high" sought by the abuser. In contrast, Collegium reports forming a complex with the opioid using an alkyl substituted metal, such as zinc stearate. The resulting complex increases the hydrophobicity of the otherwise water soluble opioid. As drug abusers attempt to snort the hydrophobic opioid complex, it allegedly does not provide the desired result to the abuser. For both Acura and Collegium the approach was to provide a selective drug release profile to thwart drug abuse by using a chemical drug delivery mechanism; Acura used a formulation technique while Collegium modified the API properties. Both methods however are fundamentally dependent upon altering the hydrophilic/lipophilic balance of the opioid and to allow its release only when used for legitimate purposes. With Acura's approach, the hydrophilic nature of the opioid, or amine containing drug substance, is competitively defeated by adding the highly hydrophilic polyethylene oxide polymer. With Collegium's approach, the hydrophilic nature of the opioid is reduced by adding an oleophilic residue via complexation chemistry through a metal ion.

One aspect of the invention herein is to utilize organic acid addition salts as a drug delivery platform at the molecular level. A drug delivery platform as used herein is defined as a means to deliver an active pharmaceutical ingredient according to "time, manner, and place", wherein:
  a) the time component impacts the pharmacokinetic release of the drug substance;
  b) the manner component relates to mechanism of release from the drug delivery system; and
  c) the place component refers to the location in the physiological system where release begins to occur and extends for the duration of the release.

Herein, drug delivery systems are described employing the bis-functionality of a bis-functional organic acid moiety to carry both the active pharmaceutical ingredient and a dissolution modifying component within the same molecule. To elaborate, the bis-functional organic acid moiety was reacted with an equivalent of amine-containing active pharmaceutical ingredient and with an equivalent of an amine-containing dissolution modifying agent. In this manner the bis-functional salts formed would be in a statistical distribution of potential compounds depending upon the comparative reactivities and molar ratios of amine-containing active pharmaceutical ingredient and amine-containing polymer component used to form the bis-functionalized salt. When an equivalent of each amine is used having equivalent reactivities, one would expect the statistical ratio of organic acid entities to encompass: 25 molar % bis-functional organic acid substituted only with active ingredient; 50 molar % bis-functional organic acid substituted with one each of the active ingredient and the dissolution modifying amine, and lastly, 25 molar % bis-functional organic acid substituted entirely with the dissolution modifying agent. This bulk mixture exhibits desired drug delivery properties and dissolution profiles otherwise unachievable.

The pH of the gastrointestinal tract essentially remains highly acidic with the exception of the lower colon which reaches pH 8; vaginal pH is typically around 5.8 and the nasal cavity is approximately pH 4.5. More generally, each of the mucosal membranes, particularly ocular, nasal, pulmonary, buccal, sublingual, gingival, rectal and vaginal, are receptive to drug absorption if release can occur. A feature of the present invention is the ability to provide drug substances with retarded release of the controlled substance, particularly amine-containing pamoate salt (or related salt family) in the pH range of about 4 to 9 which encompasses the physiological pH of the mucosa. These release properties were an unexpected finding recognized and observed after performing dissolution tests over a wide pH range on several unrelated compounds. The release properties and saturation solubility profiles are a means to evaluate a reasonable dosage application to the mucosa. The non-release of the drug in the 4 to 9 pH range negates absorption and prevents the physical act of abuse. For the amine-containing hydrochloride salts, an abuse mechanism remains operative since these salts do not exhibit the discriminating "on/off" switch of the present invention.

An experimental refinement of the dissolution tests was performed on several compounds to better represent the physiological conditions encountered during abuse attempts and to account for the saturation solubility factor. Further, control experiments were included in the experimental design to compare the organic acid addition salts of the current invention with the hydrochloride salts of identical amine-containing controlled substances. In some cases, model compounds were used to demonstrate the principles of the invention instead of using compounds legally designated as controlled substances. Side-by-side dissolution experiments on hydrochloride salts versus those of the present invention were conducted at three different pH conditions: a) a pH of about 1 to simulate gastric conditions, b) pH of about 4.5 to simulate mucosal membrane pH, and c) a pH of about 7 to evaluate a potential pH range of mucosal membranes and blood pH for purposes of simulating injection. In addition, the experimentation was designed to demonstrate the equivalence of the organic acid addition salts to the mineral acid salts if used by their intended route of oral administration route and hence the concentration effects were included in the study. For oral administration of a dosage form, the United States Pharmacopeia (USP) recommends the immediate release testing procedure on a unit dosage to be performed on a simulated stomach "solution" volume of 900 mL. Besides temperature, pH and concentration, the time factor was also evaluated under the presumption that an individual abusing a drug will want to obtain their anticipated physiological response within an hour or less.

Immediate release is defined as a drug substance wherein under simulated gastric conditions at least 85% is released within 30 minutes.

For the purposes of the present application, dose dumping is considered to be mitigation if under simulated gastric conditions, represented by 0.1 N HCl, any of the following conditions are met: a) no more than about 35% of an active pharmaceutical is released at 30 minutes with at least 5% ethanol present; b) the percentage of active pharmaceutical released with at least 5% ethanol present is no more than the percentage of active pharmaceutical released with no alcohol present; or c) the percentage of drug substance released with 40 wt % ethanol in 0.1 N HCl does not exceed 60% while the percentage of drug substance released under the conditions selected from water, 0.1 N HCl, 5 wt % ethanol in 0.1 N HCl and 20 wt % ethanol in 0.1 N HCl does not exceed the drug substance released with 40 wt % ethanol in 0.1 N HCl. It is particularly preferred that no more than about 35% of the active pharmaceutical be released over an extended time, such as at least 45 minutes.

The dissolution profiles are best understood by their organization into three broad categories. The first category consists of the existing, currently commercialized drug substances d-methylphenidate hydrochloride, racemic-methylphenidate hydrochloride and dextro-amphetamine sulfate. For each drug substance an intrinsic pH dependent dissolution profile and a corresponding dose dumping profile were performed. The second category contains drug substances prepared as their pamoate (which are representative of a bis-functional organic acid salt) and xinafoate salts. This second category is exemplified by the intrinsic and dose dumping profiles for a selection of amorphous and polymorphic forms of d-methylphenidate pamoate; d-methylphenidate xinafoate, racemic-methylphenidate pamoate, racemic-methylphenidate xinafoate, dextro-amphetamine pamoate and dextro-amphetamine xinafoate.

The third category of dissolution profiles is exemplified by controlled dissolution profiles of organic acid salts by: 1) selection of the stoichiometric proportions of the free-base drug substance to the bis-functional organic acid moiety such as 2:1 vs. 1:1 drug substance base:bis-functional organic acid moiety; 2) the effect arising from mixed bis-functional organic acid salts with a 1:1:1 ratio of drug substance base: bis-functional organic acid moiety:functional amine, and 3) the impact of matching the physical properties of a drug substance base with a functional amine, both coupled as a salt to the bis-functional organic acid moiety. This third category contains the intrinsic and dose dumping profiles demonstrated for a selection of amorphous and/or polymorphic forms of imipramine pamoate (1:1); imipramine triethylammonium pamoate (1:1:1); imipramine Jeffamine® pamoate (1:1:1); imipramine stearyl amine pamoate (1:1:1); hydrocodone Jeffamine® pamoate (1:1:1); hydrocodone stearyl amine pamoate (1:1:1); d-methylphenidate triethylammonium pamoate (1:1:1); and racemic-methylphenidate stearylamine pamoate (1:1:1).

Figure 98:
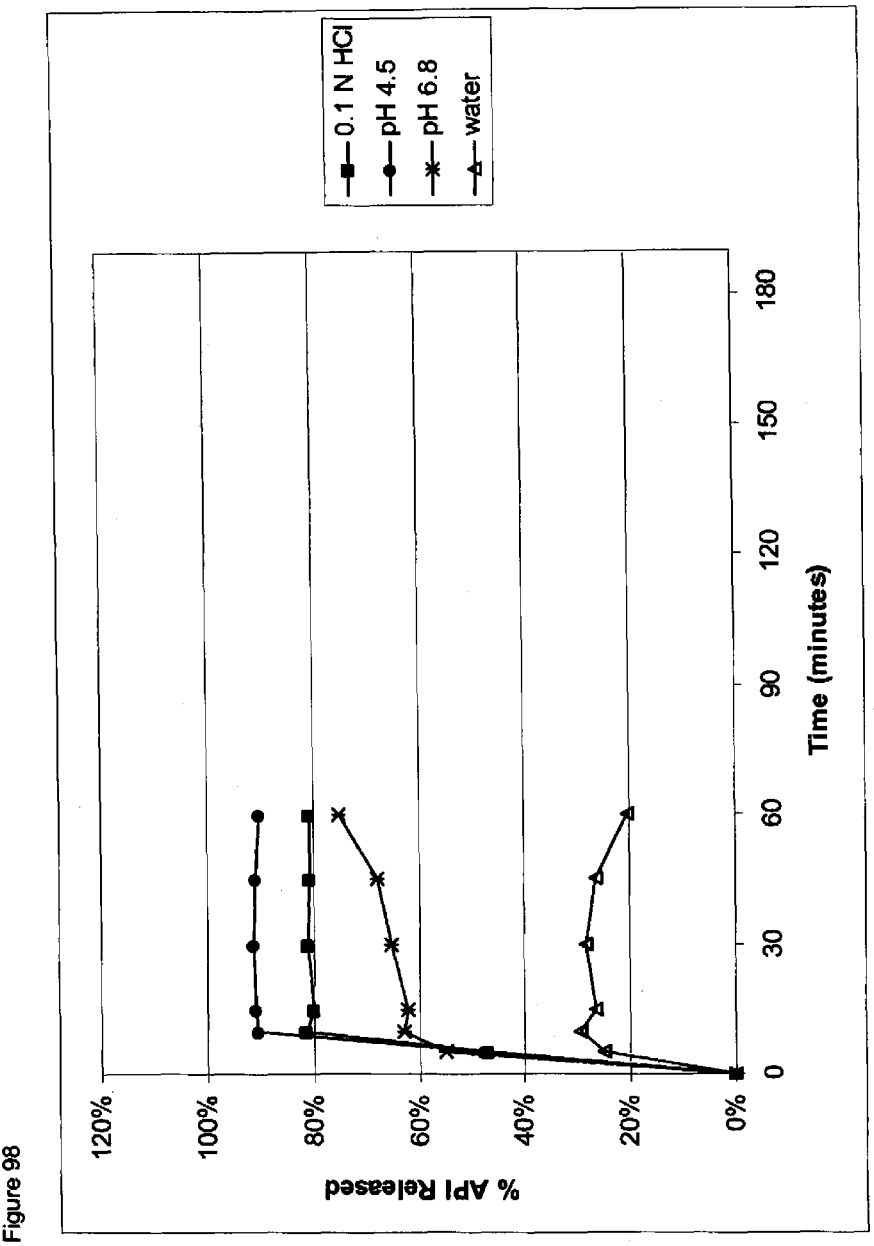
FIG. 98 is a graphical representation of the pH dependent dissolution profiles of d-methylphenidate hydrochloride.
Figure 99:
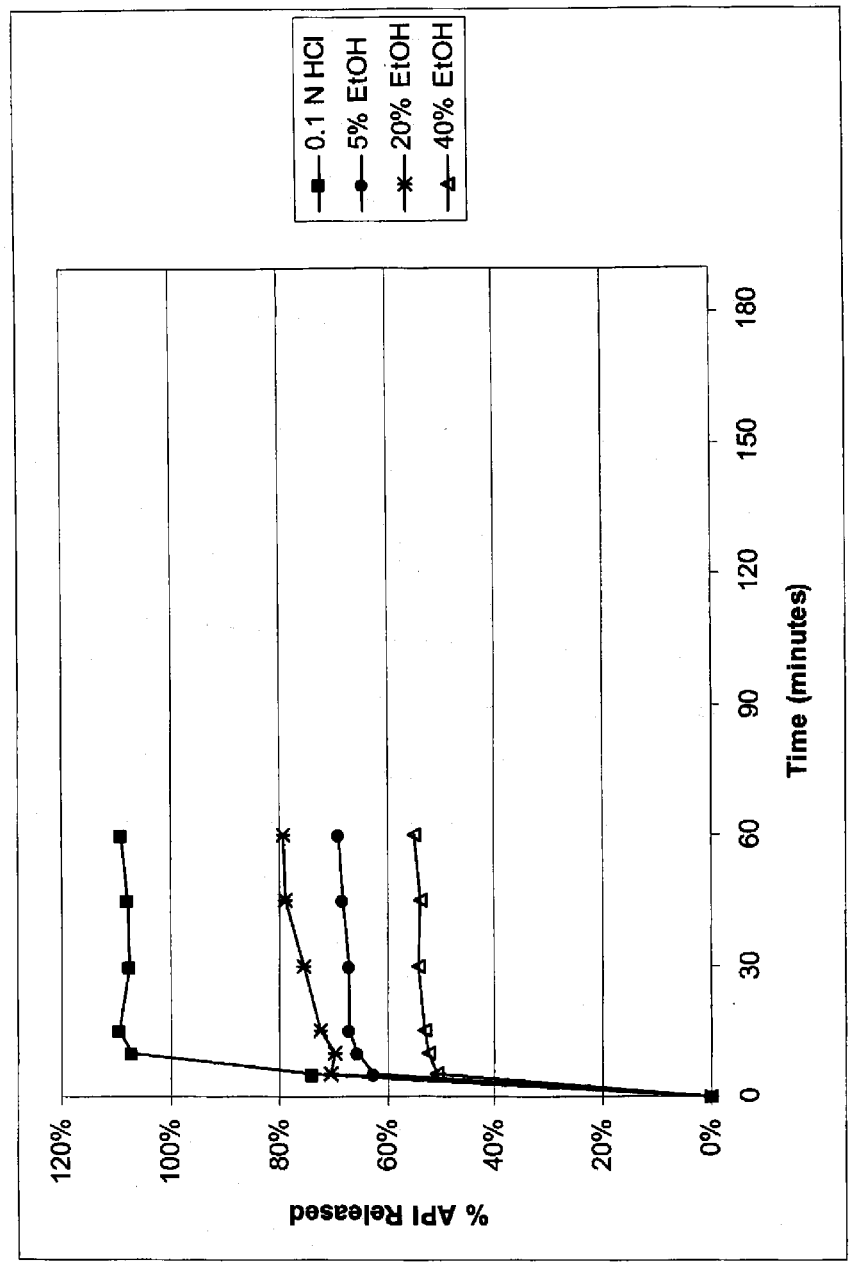
FIG. 99 is a graphical representation of the dissolution profiles of d-methylphenidate hydrochloride under acidic conditions as a function of ethanol concentration.
Figure 100:
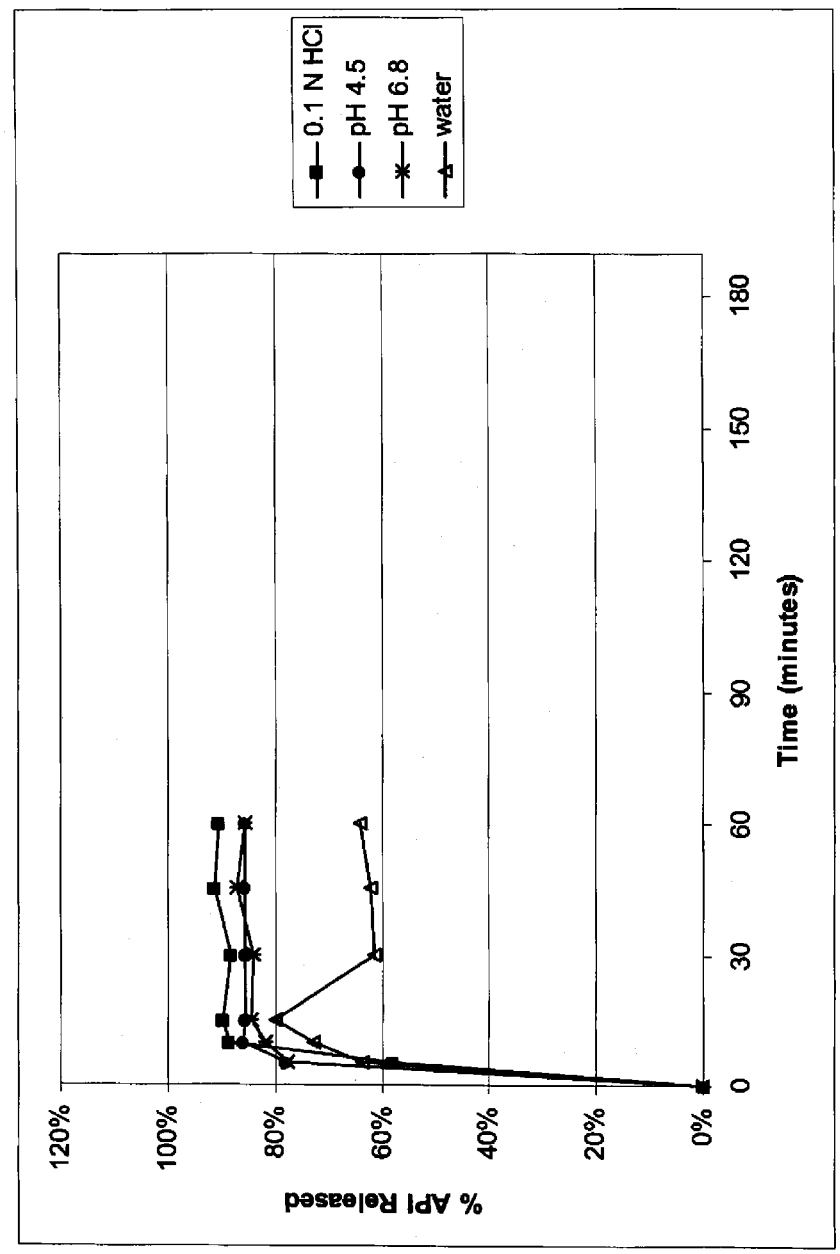
FIG. 100 is a graphical representation of the pH dependent dissolution profiles of racemic-methylphenidate hydrochloride.
Figure 101:
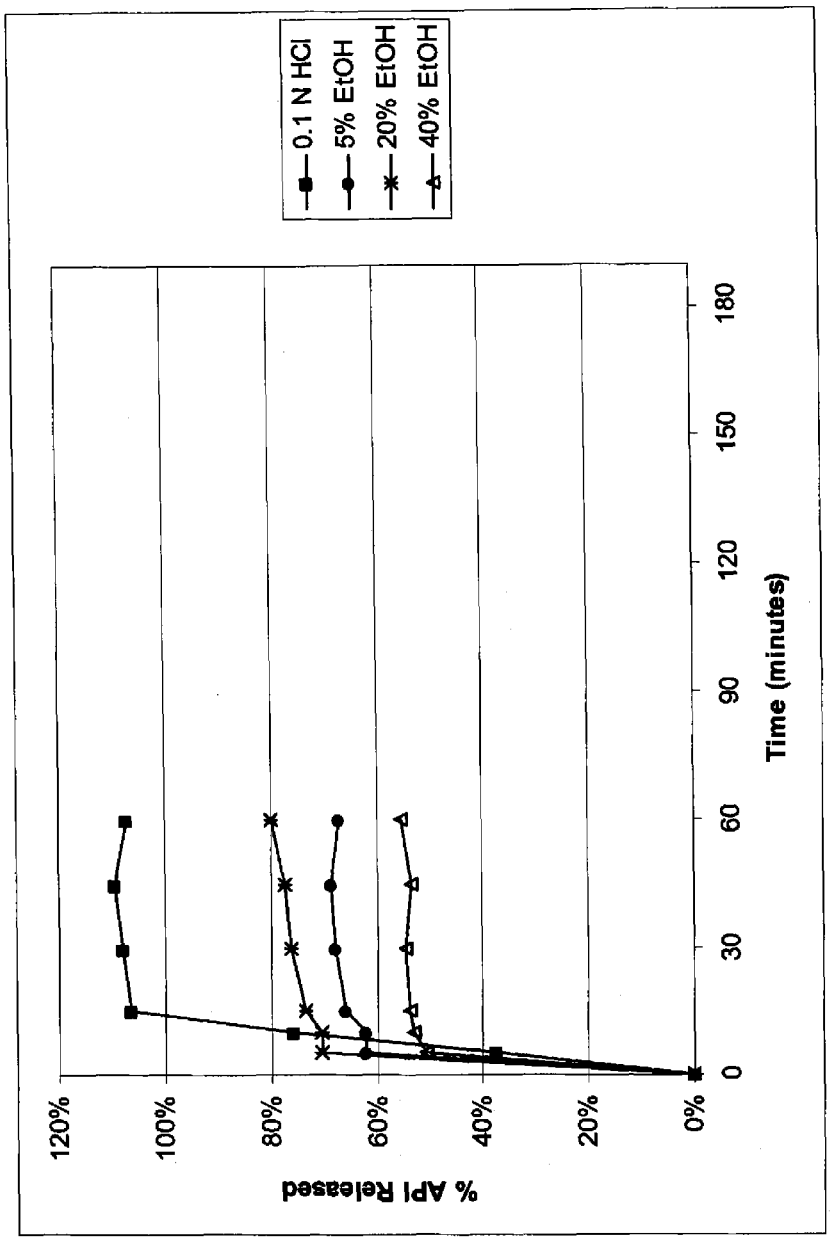
FIG. 101 is a graphical representation of the dissolution profiles of racemic-methylphenidate hydrochloride under acidic conditions as a function of ethanol concentration.
Figure 102:
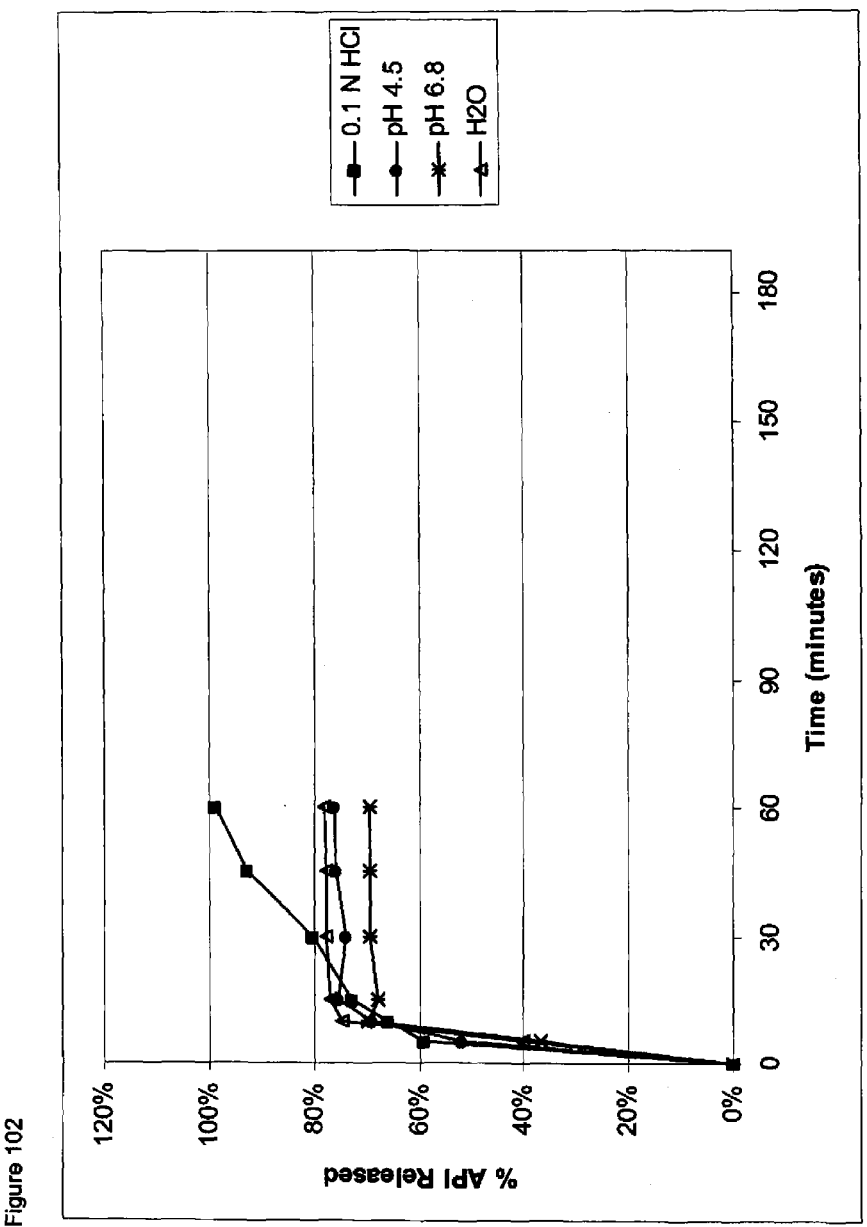
FIG. 102 is a graphical representation of the pH dependent dissolution profiles of dextro-amphetamine sulfate.
Figure 103:
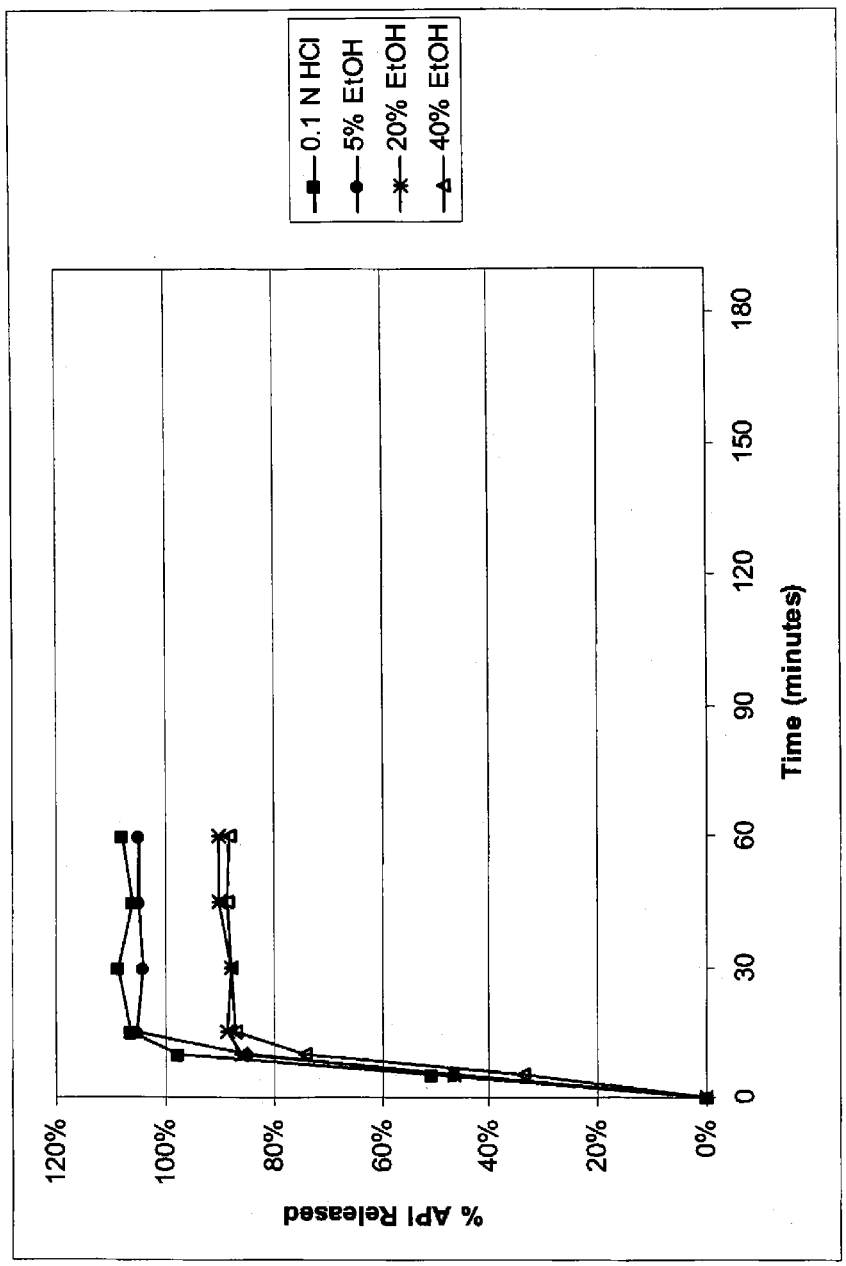
FIG. 103 is graphical representation of the dissolution profiles of dextro-amphetamine sulfate under acidic conditions as a function of ethanol concentration.

The intrinsic pH dissolution and dose dumping profiles of the first category provide the motivation for establishing a chemical methodology for imparting abuse-deterrent performance features to the active, drug substance moiety. Not surprisingly, drug product development has historically depended upon the incorporated drug substance to be freely water soluble as a condition of bioavailability. The active ingredients d-methylphenidate hydrochloride, racemic-methylphenidate hydrochloride and dextro-amphetamine sulfate are all freely soluble in water and their pH and dose dumping dissolution profiles confirm this observation. FIG. 98 is the dissolution profile and FIG. 99 the dose dumping profile for d-methylphenidate hydrochloride. FIG. 100 is the dissolution profile and FIG. 101 the dose dumping profile for racemic-methylphenidate hydrochloride. FIG. 102 is the dissolution profile and FIG. 103 is the dissolution profile for dextro-amphetamine sulfate. The results reflect the formulation difficulty in providing these drug substances in a form that is abuse deterrent. The active ingredient as the mineral acid salt is readily available under nearly any aqueous condition and the need to modify the drug substance's dissolution properties is apparent in order to provide an abuse deterrent feature. In recent years, this concept has been significantly challenged by advanced drug substances having poor water solubility and thus, a higher burden placed on the formulator to achieve the desired dissolution profile of the drug product as monitored by the dissolution profile behavior of the drug substance.

Figure 36:
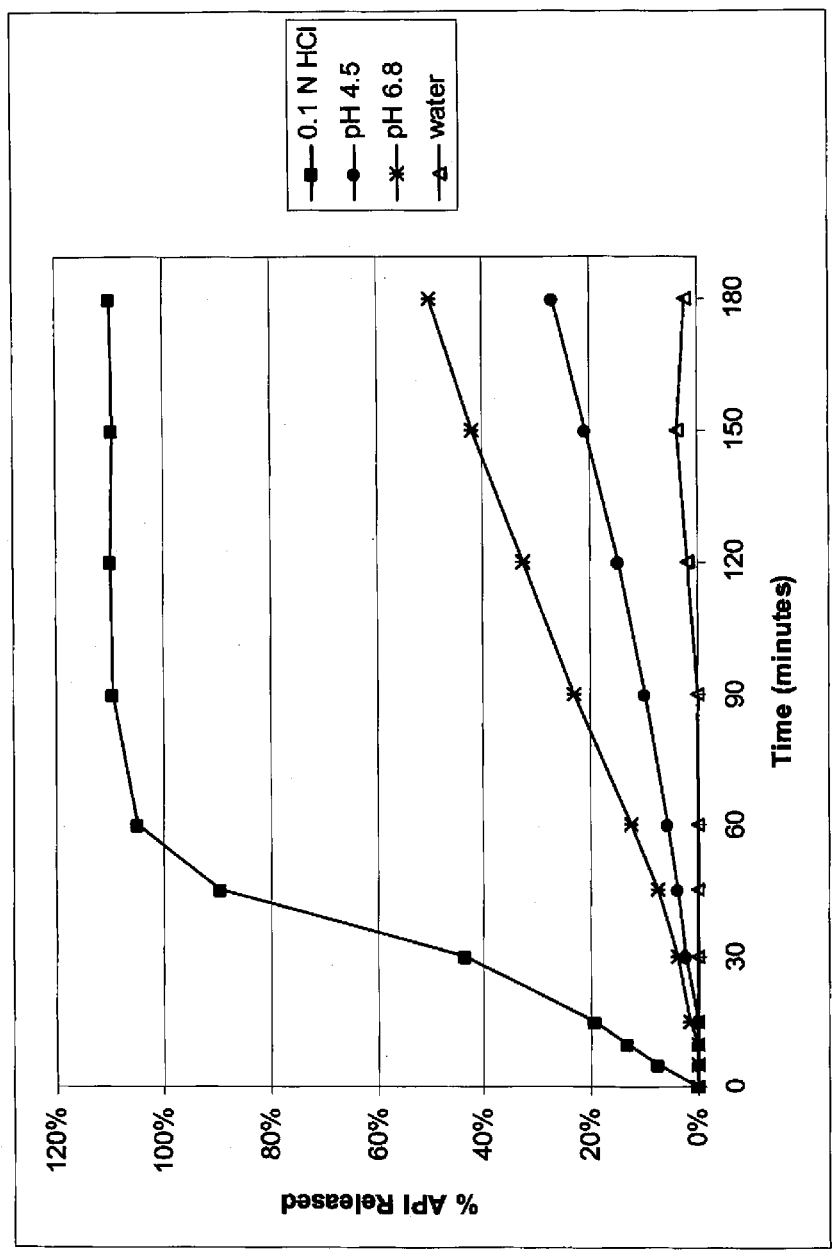
FIG. 36 is a graphical representation of the pH dependent dissolution profiles of amorphous d-methylphenidate pamoate.
Figure 37:
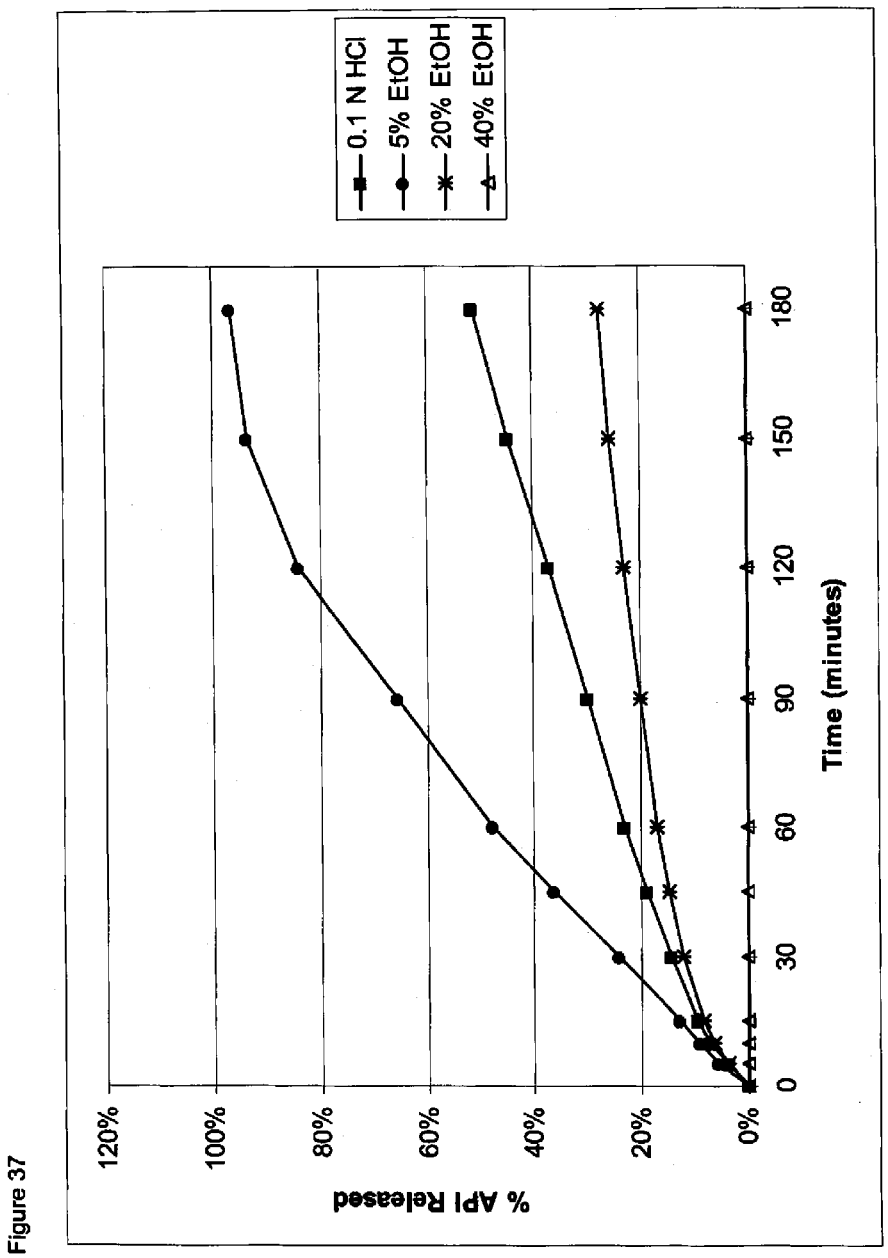
FIG. 37 is a graphical representation of the dissolution profiles of amorphous d-methylphenidate pamoate under acidic conditions as a function of ethanol concentration.

Exemplars within the second category establish the basis satisfying the need to impart abuse-deterrent features to the active, drug substance moieties. Without imposing limitation to the invention, the particular active, drug substance exemplars illustrated herein include d-methylphenidate, racemic-methylphenidate and dextro-amphetamine as their amorphous or polymorphic salts selected from the salt forming acid families of Formula H with pamoates (as 2:1, or 1:1:1 salts) or xinafoates being most preferred embodiments. For ease of comparison between amorphous or polymorphic forms of the same drug substance, both the intrinsic pH dissolution and dose dumping profiles of one physical form should be compared to the comparable profiles of a second form of the drug substance salt. Throughout this discussion this approach will be used in order to fully reveal the depth and breadth of the invention. For these paired comparisons, the following nomenclature is used when describing the intrinsic pH dissolution and dose dumping profiles. For a given drug substance evaluation, Figures A/B will mean Figure A is the intrinsic pH dissolution profile and Figure B is the corresponding dose dumping profile of the same drug substance. In this manner Figures A/B are readily compared with Figures C/D which may be a different polymorphic form of the same drug substance, or a different, but analogous drug substance. By way of example, amorphous and polymorphic d-methylphenidate pamoate are readily compared by comparing FIGS. 36/37 with FIGS. 34/35, respectively. The polymorphic form exhibits a desirable dose dumping profile particularly with the 40% ethanol condition leveling out at about 20% release of the active moiety. This result also indicates ethanol extraction of the active ingredient from a formulated drug product is impeded. The polymorphic form also exhibits a linear response under the 0.1 N HCl condition (simulated gastric condition) and is preferable to an immediate release response observed for the corresponding hydrochloride salt as shown in FIGS. 98/99. Further, and from analysis of these paired comparisons, the amorphous form of d-methylphenidate pamoate exhibits a slightly faster rate of release at the 0.1 N HCl condition, but "fails" the dose dumping test since the presence of 5% ethanol appears to accelerate the release of the drug substance at a rate faster than in the simulated gastric condition. From this analysis, polymorphic d-methylphenidate pamoate exhibits the properties desired for an abuse-deterrent drug substance suitable for incorporation into a formulated drug product.

Figure 28:
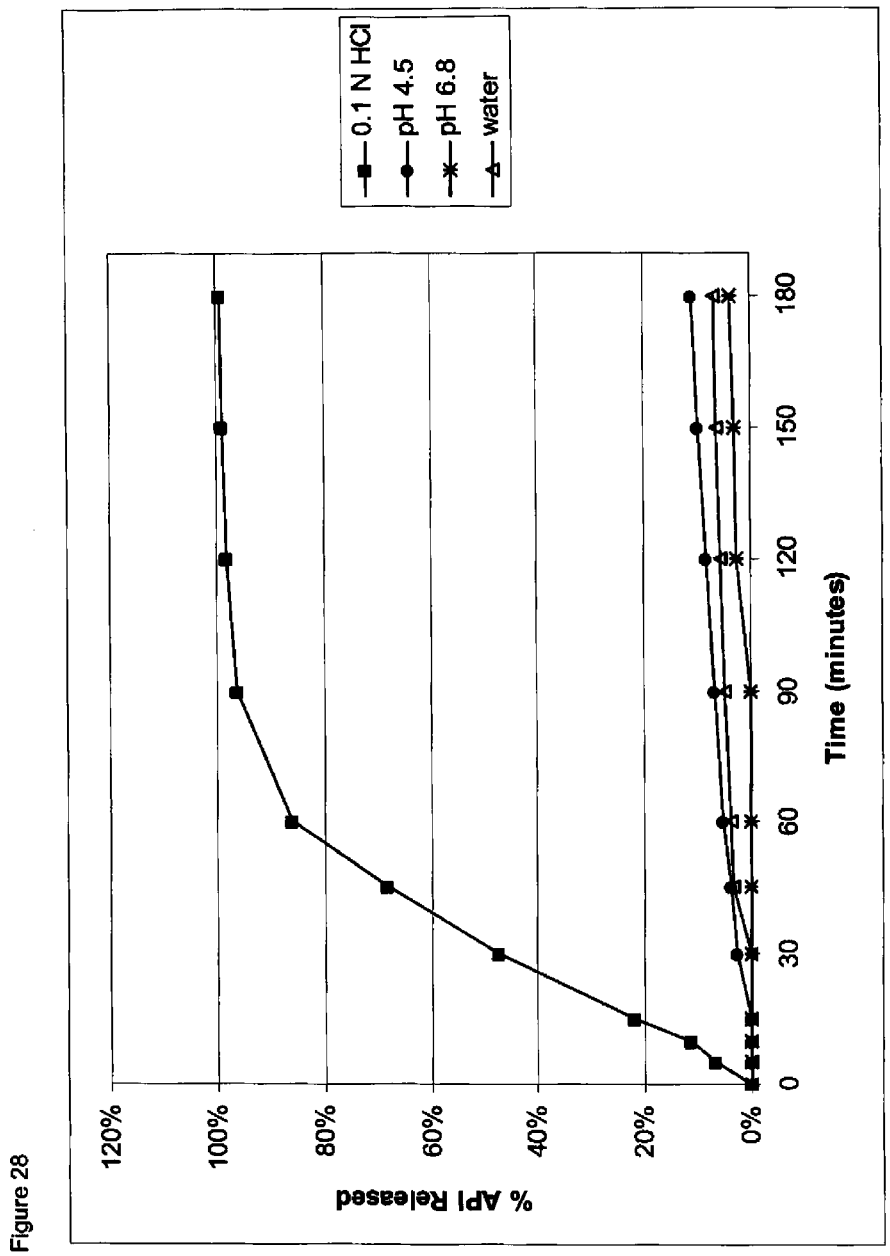
FIG. 28 is a graphical representation of the pH dependent dissolution profiles of amorphous racemic-methylphenidate pamoate.
Figure 29:
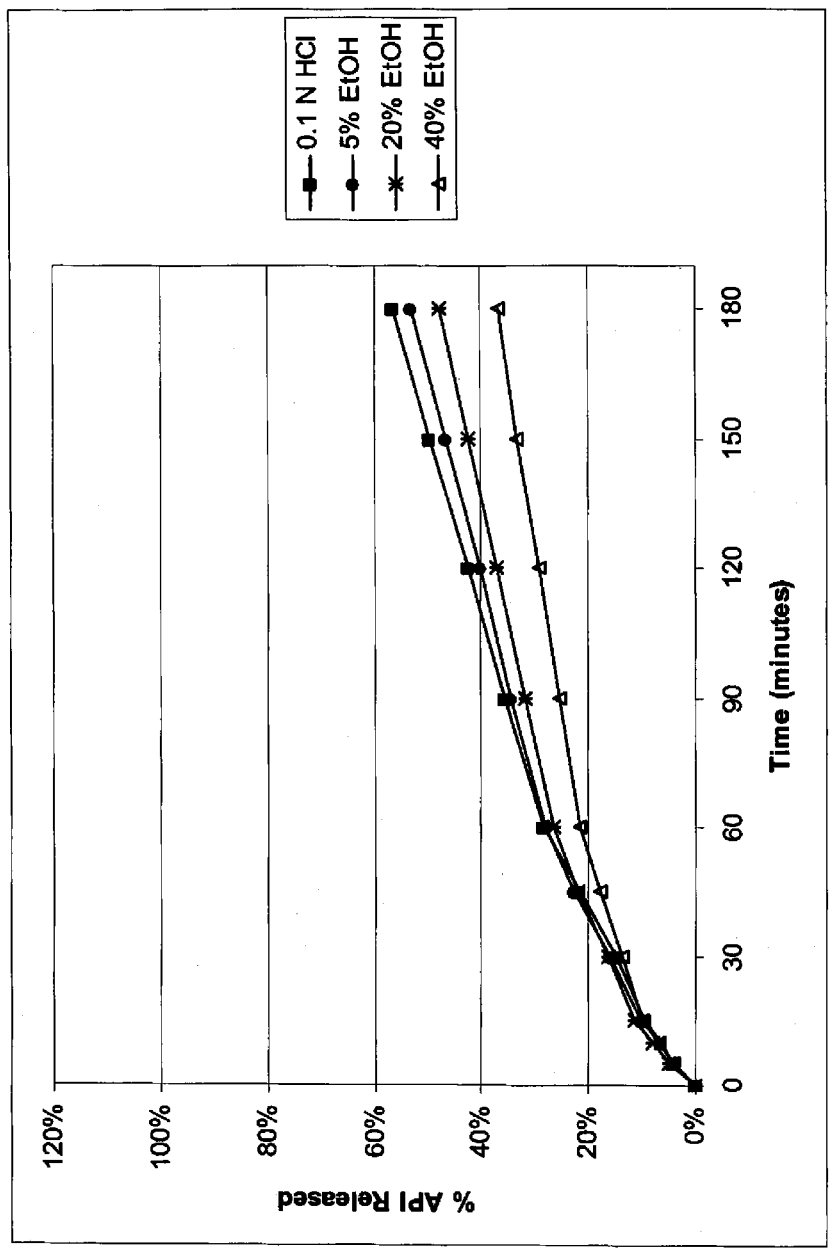
FIG. 29 is a graphical representation of the dissolution profiles of amorphous racemic-methylphenidate pamoate under acidic conditions as a function of ethanol concentration.
Figure 30:
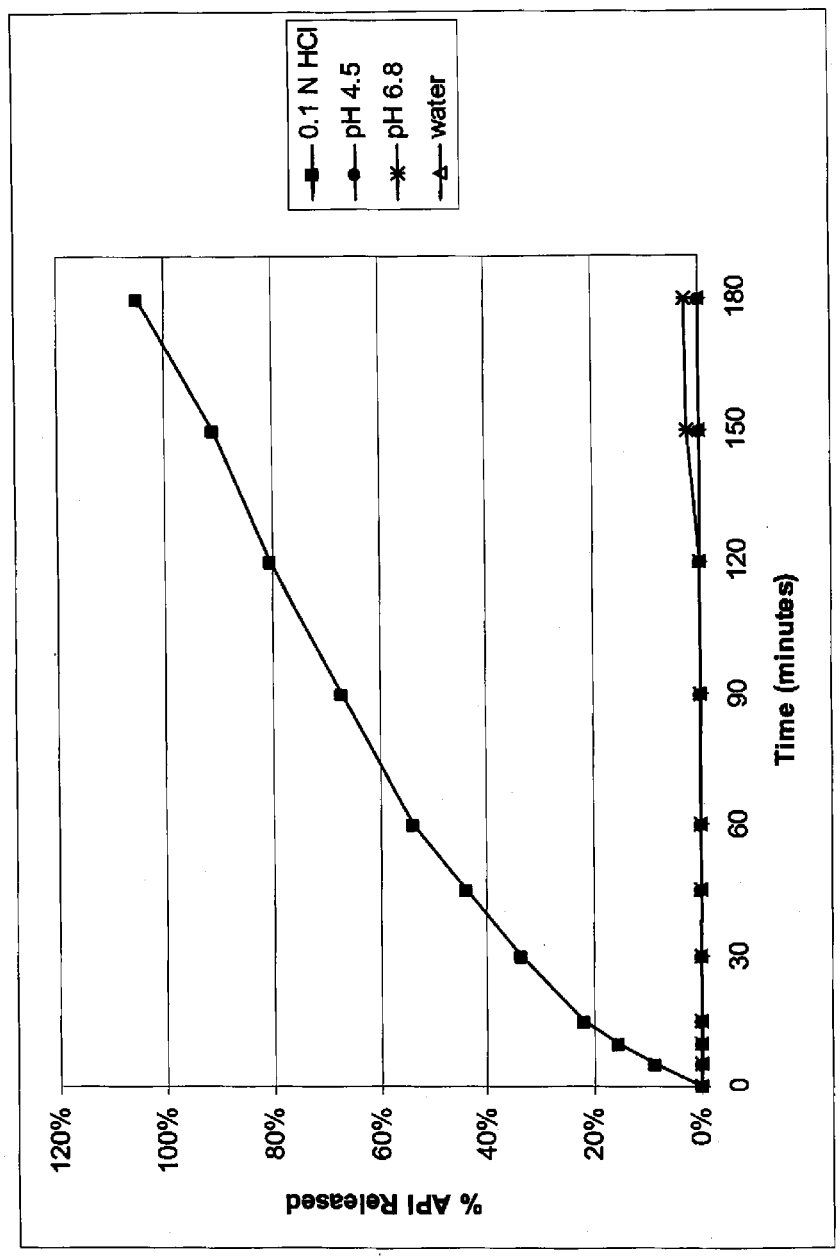
FIG. 30 is a graphical representation of the pH dependent dissolution profiles of polymorphic racemic-methylphenidate pamoate.
Figure 31:
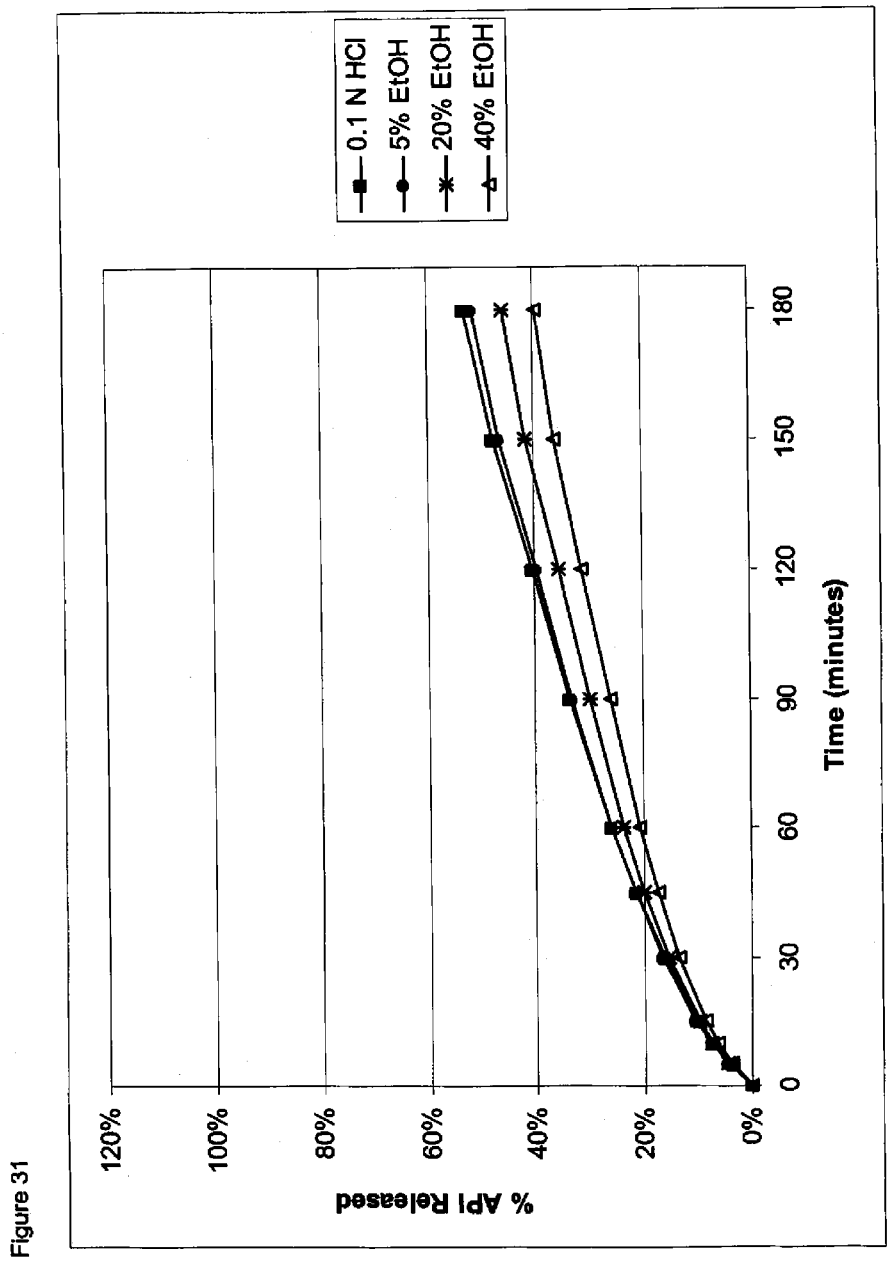
FIG. 31 is a graphical representation of the dissolution profiles of polymorphic racemic-methylphenidate pamoate under acidic conditions as a function of ethanol concentration.
Figure 34:
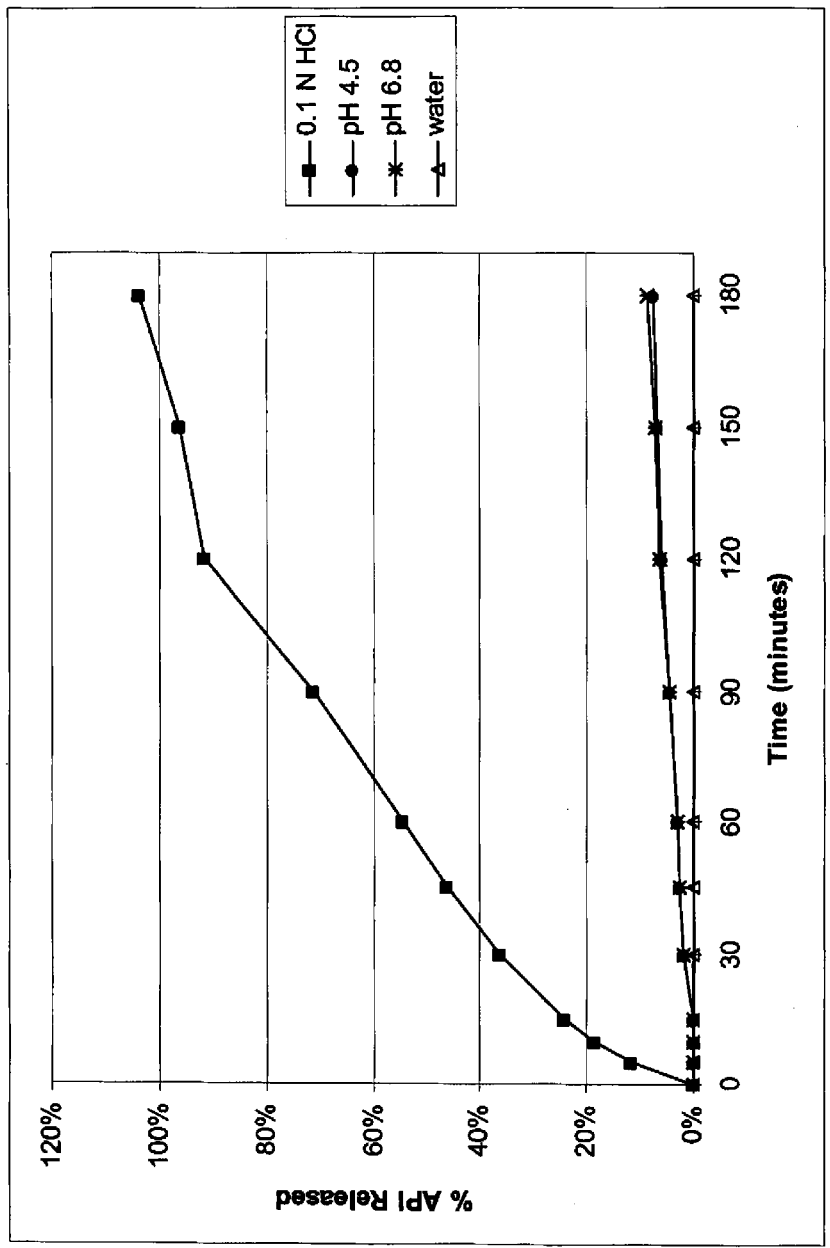
FIG. 34 is a graphical representation of the pH dependent dissolution profiles of polymorphic d-methylphenidate pamoate.
Figure 35:
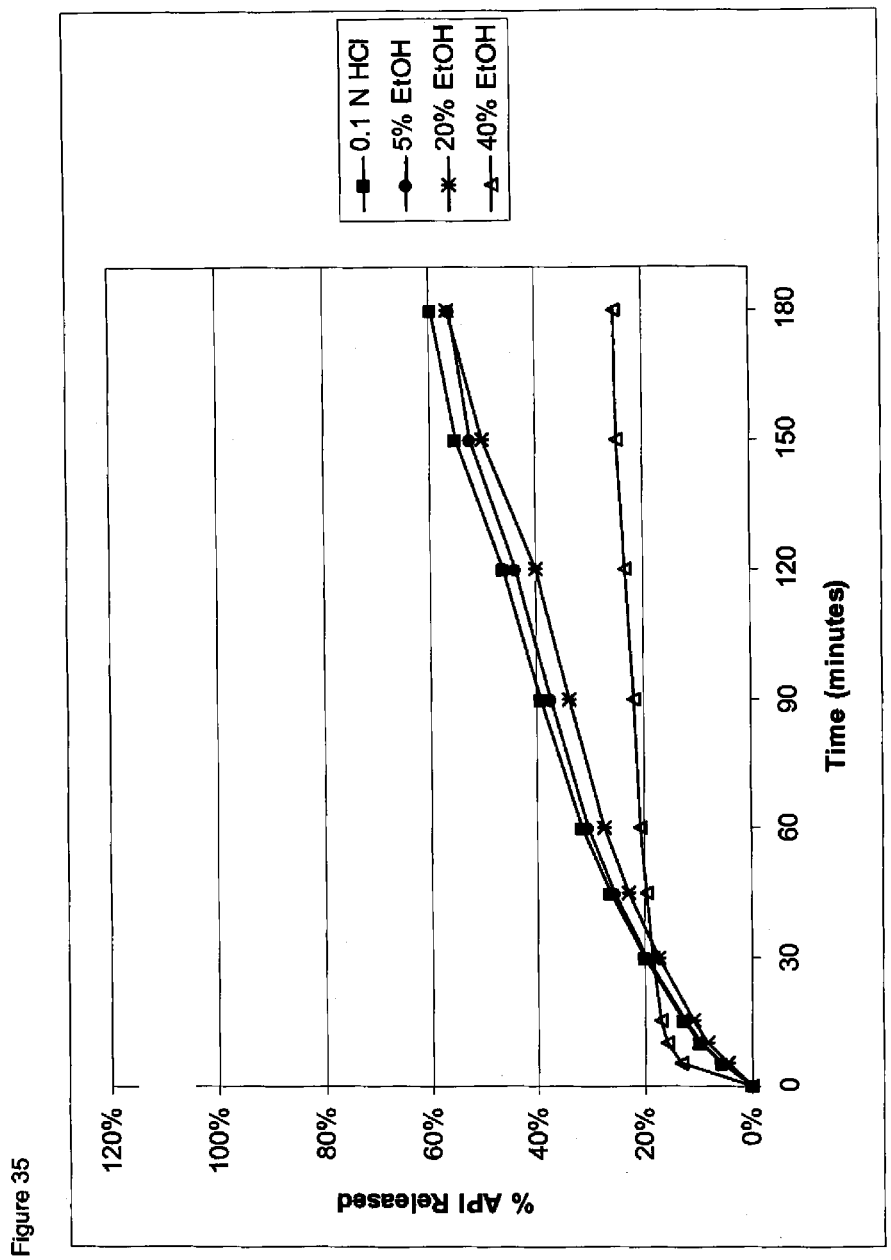
FIG. 35 is a graphical representation of the dissolution profiles of polymorphic d-methylphenidate pamoate under acidic conditions as a function of ethanol concentration.

The results from the d-methylphenidate pamoate polymorphic series can be compared with those from amorphous and polymorphic racemic-methylphenidate pamoate by examination of FIGS. 28/29 and FIGS. 30/31, respectively. The pH dissolution profiles of the amorphous racemic salt, FIG. 28, are quite similar to the profiles obtained for the polymorphic d-methylphenidate pamoate as shown in FIG. 34. The dose dumping profile for this amorphous form, FIG. 29, is quite similar to the polymorphic single isomer drug substance, as illustrated in FIG. 35. Similarly, the polymorphic racemic salt, FIGS. 30/31, exhibits pH dissolution and dose dumping profiles highly comparable to the single isomer, polymorphic d-methylphenidate pamoate, as seen in FIGS. 34/35. As a result of these comparisons for the methylphenidate pamoate series (single isomer vs. racemate vs. the available amorphous/polymorphic forms of each), the preferred abuse-deterrent compound is polymorphic d-methylphenidate pamoate.

Figure 38:
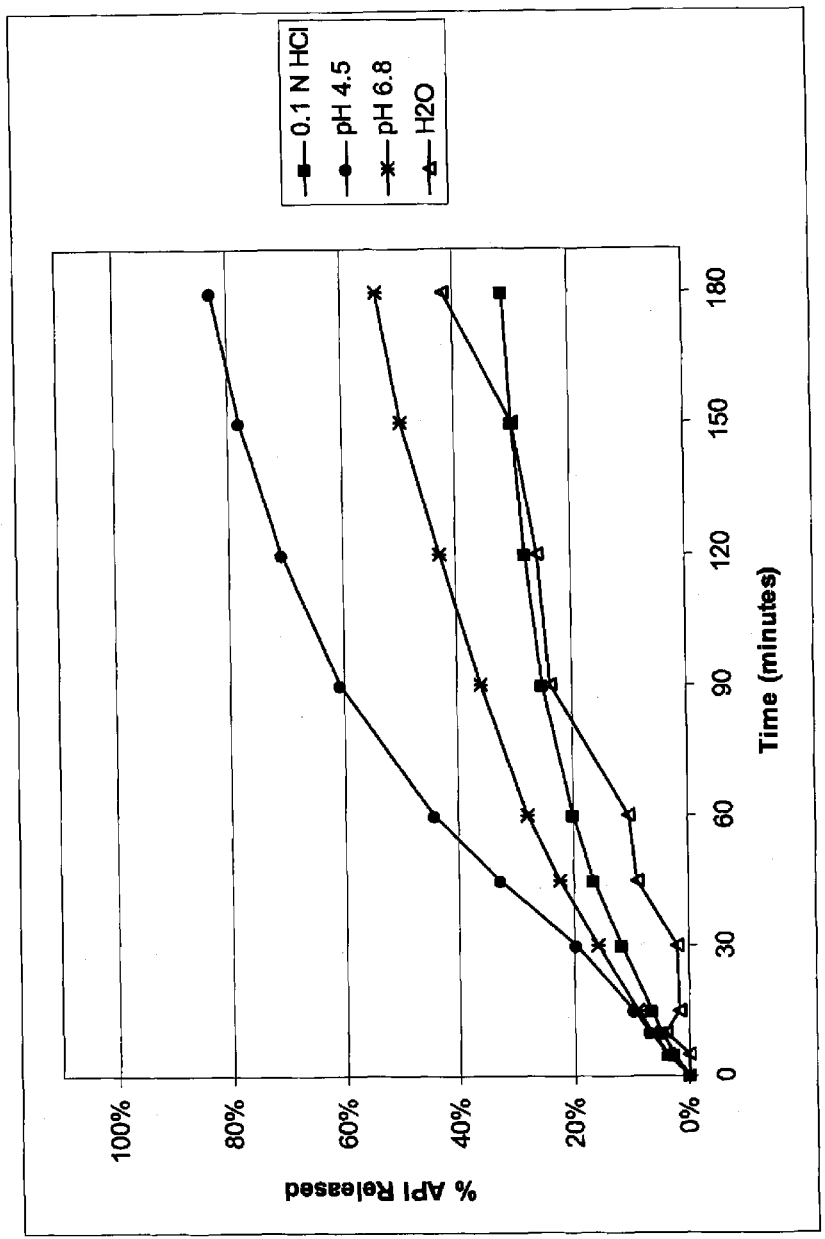
FIG. 38 is a graphical representation of the pH dependent dissolution profiles of amorphous d-methylphenidate xinafoate.
Figure 39:
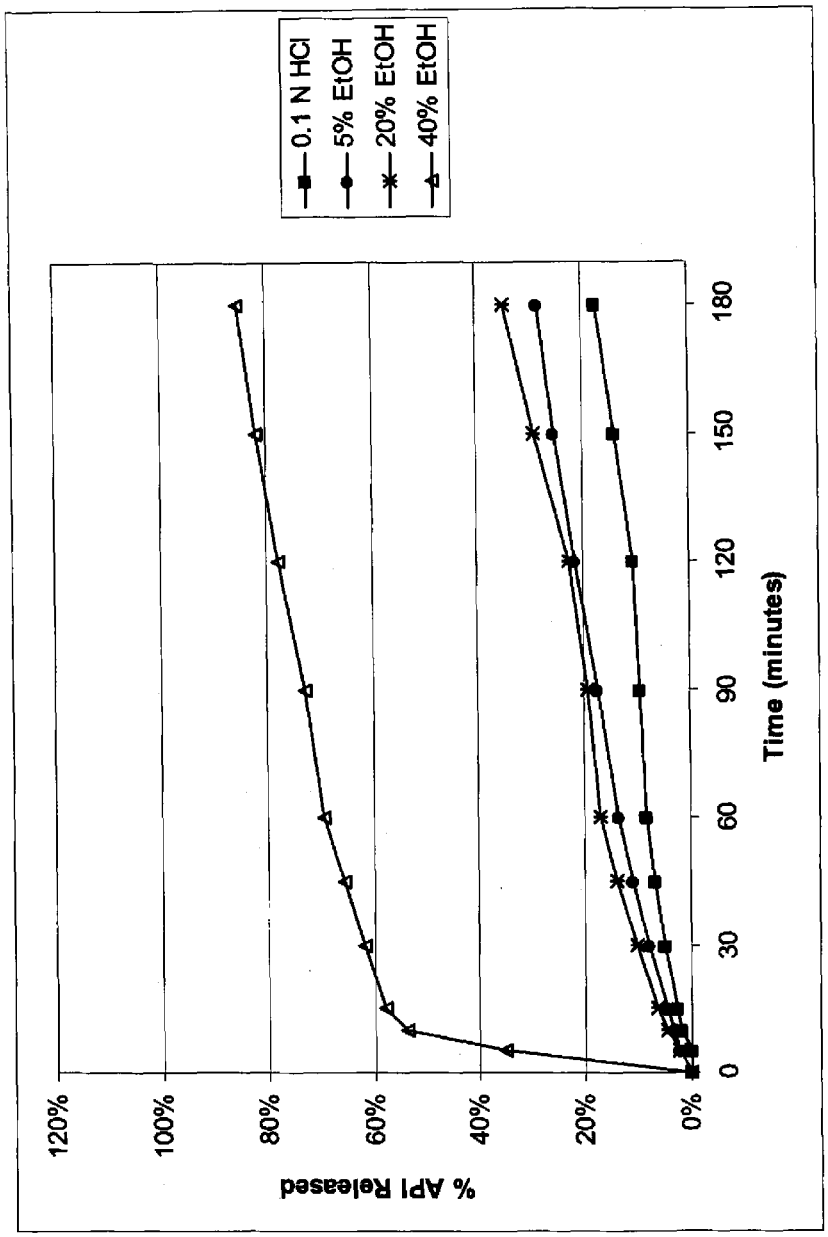
FIG. 39 is a graphical representation of the dissolution profiles of amorphous d-methylphenidate xinafoate under acidic conditions as a function of ethanol concentration.

Upon changing the salt forming family, anomalous, unexpected results are obtained for amorphous d-methylphenidate xinafoate as observed in FIGS. 38/39. First, the pH dissolution profile, FIG. 38, indicates a pH 4.5 condition provides a faster release rate than the 0.1 N HCl condition. Typically, the lower pH condition has been observed to yield the fastest release of the active ingredient from its organic acid addition salt contrary to this present finding. Indeed, the higher pH conditions accelerate the active's release with the 0.1 N HCl condition paralleling the release rate observed in water only. This unexpected finding would indicate d-methylphenidate xinafoate could pass from the stomach to the intestinal tract before being completely released. In contrast, when the drug substance was subjected to the dose dumping regimen, all conditions inhibited dose dumping except the 40% ethanol solution which enabled approximately 60% release of the active ingredient after about thirty minutes. This result indicates ethanol could promote dose dumping of the dosage and potentially, aid in the extraction of the active amine from a dosage form.

Figure 32:
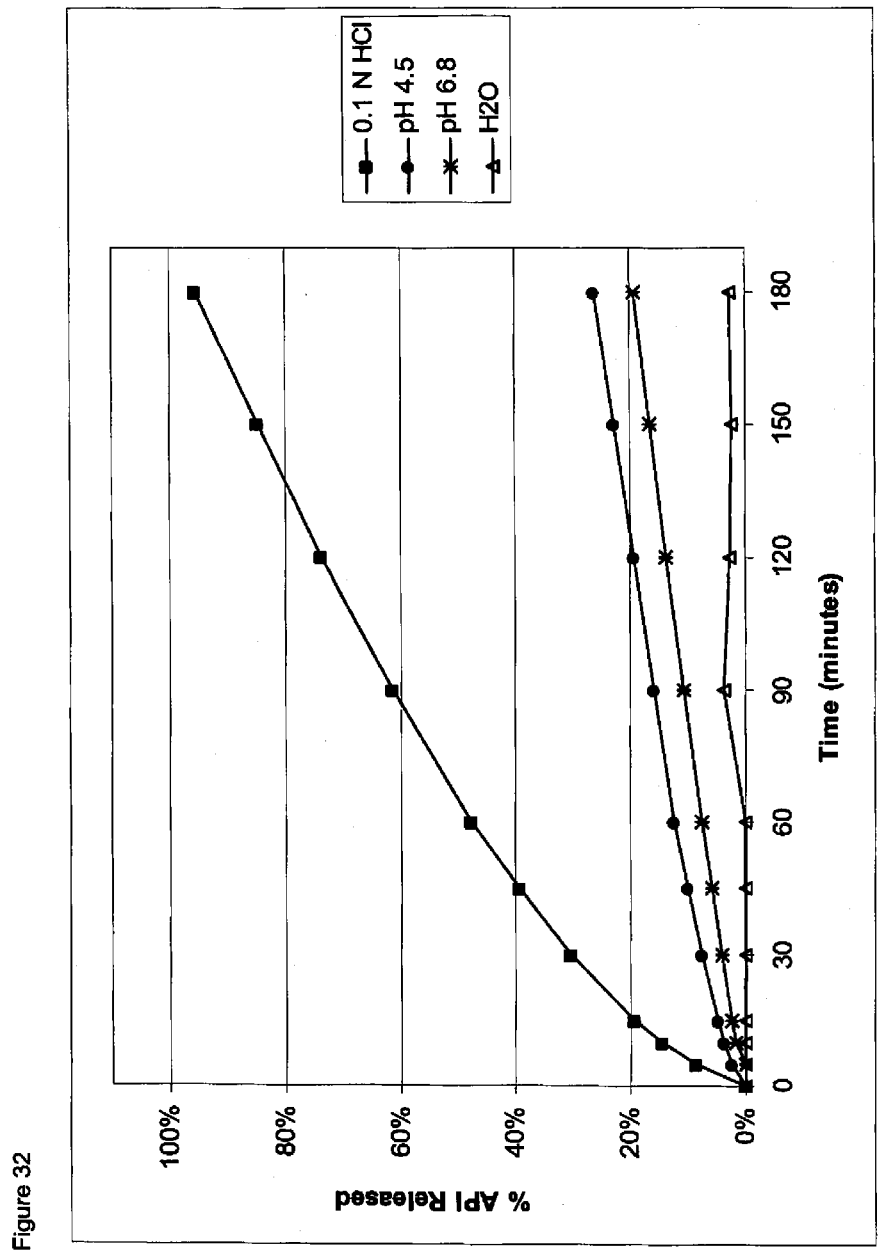
FIG. 32 is a graphic representation of the pH dependent dissolution profiles of polymorphic racemic-methylphenidate xinafoate.
Figure 33:
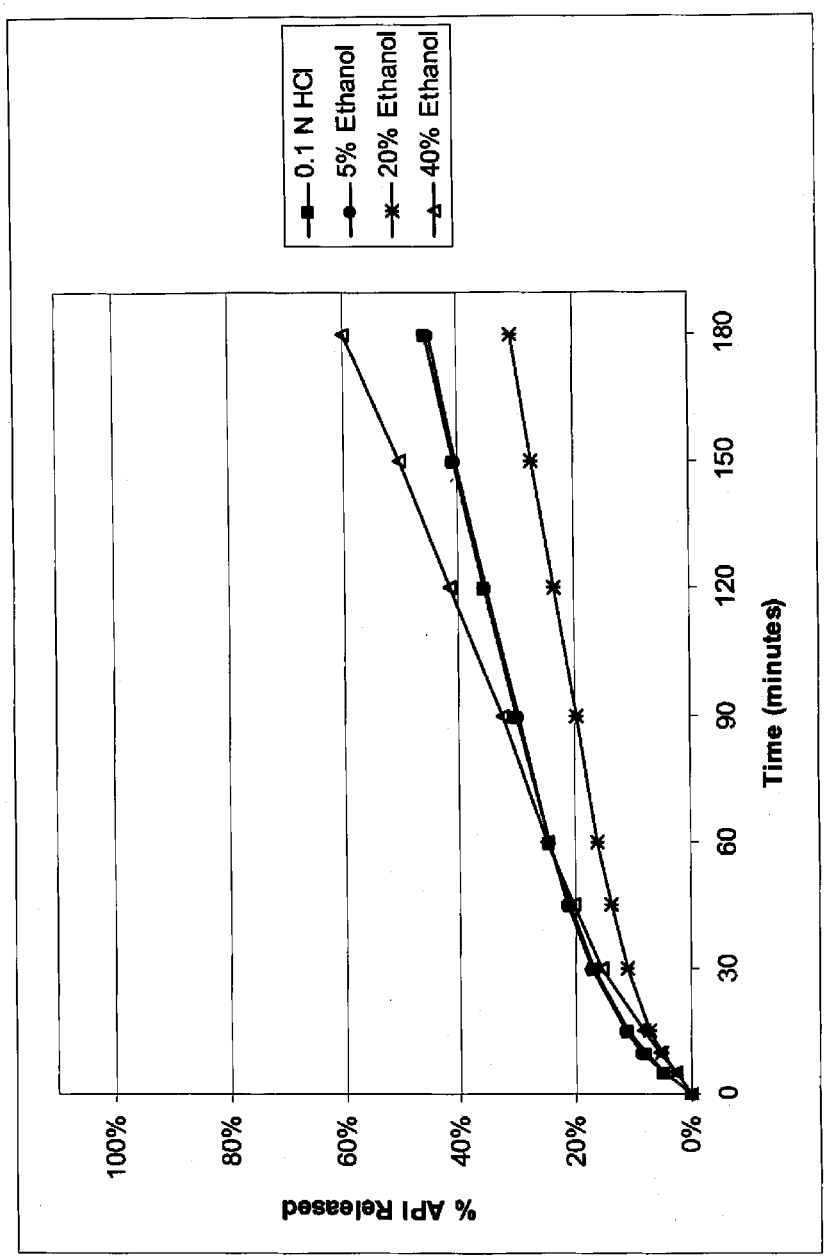
FIG. 33 is a graphical representation of the dissolution profiles of polymorphic racemic-methylphenidate xinafoate under acidic conditions as a function of ethanol concentration.

The amorphous, single isomer d-methylphenidate xinafoate (FIGS. 38/39) was compared with the polymorphic racemic methylphenidate xinafoate (FIGS. 32/33). A very favorable pH dissolution profile was obtained wherein for amorphous d-methylphenidate xinafoate (FIG. 38) the 0.1 N HCl condition provided a gradual linear release. For polymorphic racemic methylphenidate xinafoate, there was observed release suppression at the higher pH conditions (FIG. 32). The dose dumping profile was also quite favorable wherein less than twenty percent of the active was released after thirty minutes (at any condition) for polymorphic racemic methylphenidate xianfoate (FIG. 33). Only after about ninety minutes did the forty percent ethanol condition deviate from the 0.1 N HCl condition and exhibit any accelerated release (FIG. 33). Under practical abuse-deterrent considerations, a potential drug abuser intent on employing dose dumping to get "high" would be disappointed with a ninety minute delay.

To summarize, from the paired comparisons of the three categories: 1) single isomer vs. racemic-methylphenidate 2) their organic acid addition salt family (pamoate vs. xinafoate); and 3) the amorphous vs. polymorphic forms of each, a rank order was established for imparting abuse-deterrent features to methylphenidate. The most preferred embodiment is polymorphic d-methylphenidate pamoate, followed essentially equally by polymorphic racemic-methylphenidate pamoate and polymorphic racemic-methylphenidate xinafoate. A full consideration of physiological properties and FDA regulatory preference would further support the selection of polymorphic d-methylphenidate pamoate as the preferred drug substance form.

Figure 40:
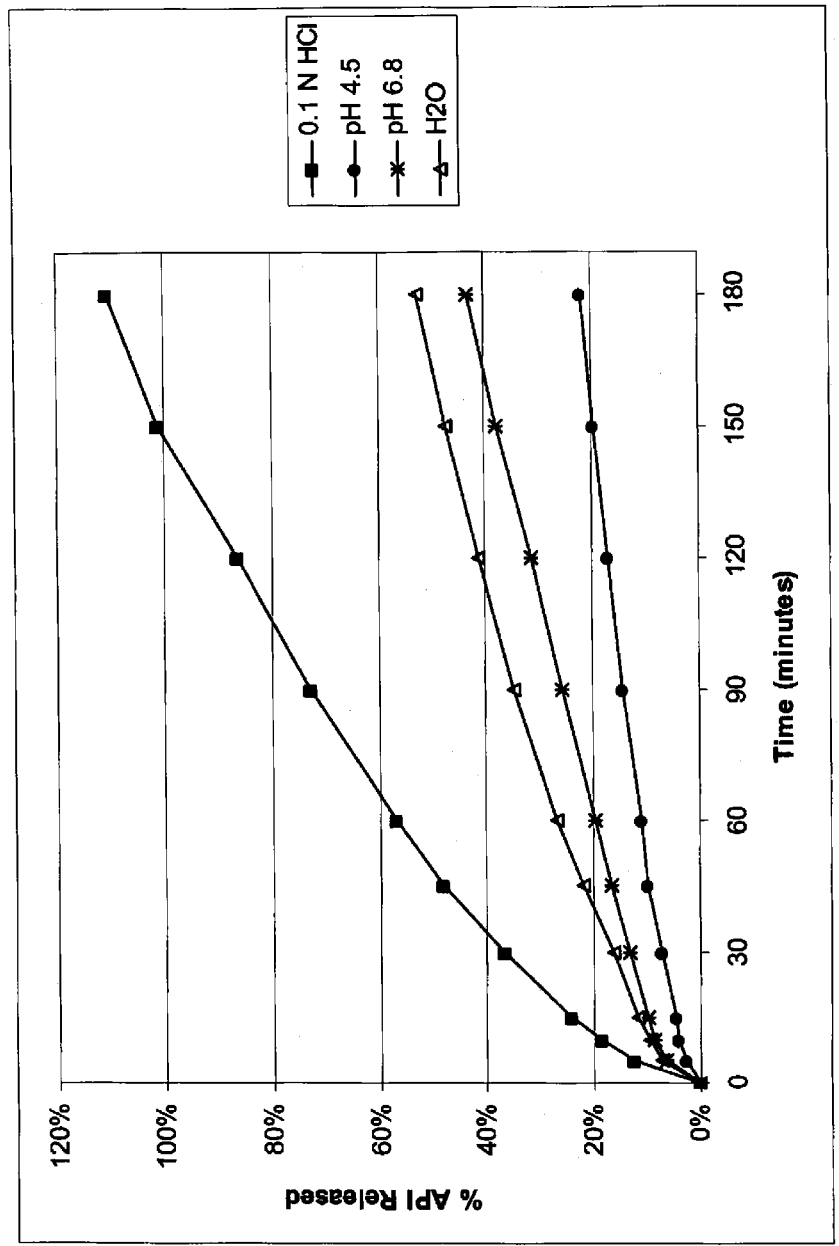
FIG. 40 is a graphical representation of the pH dependent dissolution profiles of polymorphic dextro-amphetamine pamoate.
Figure 41:
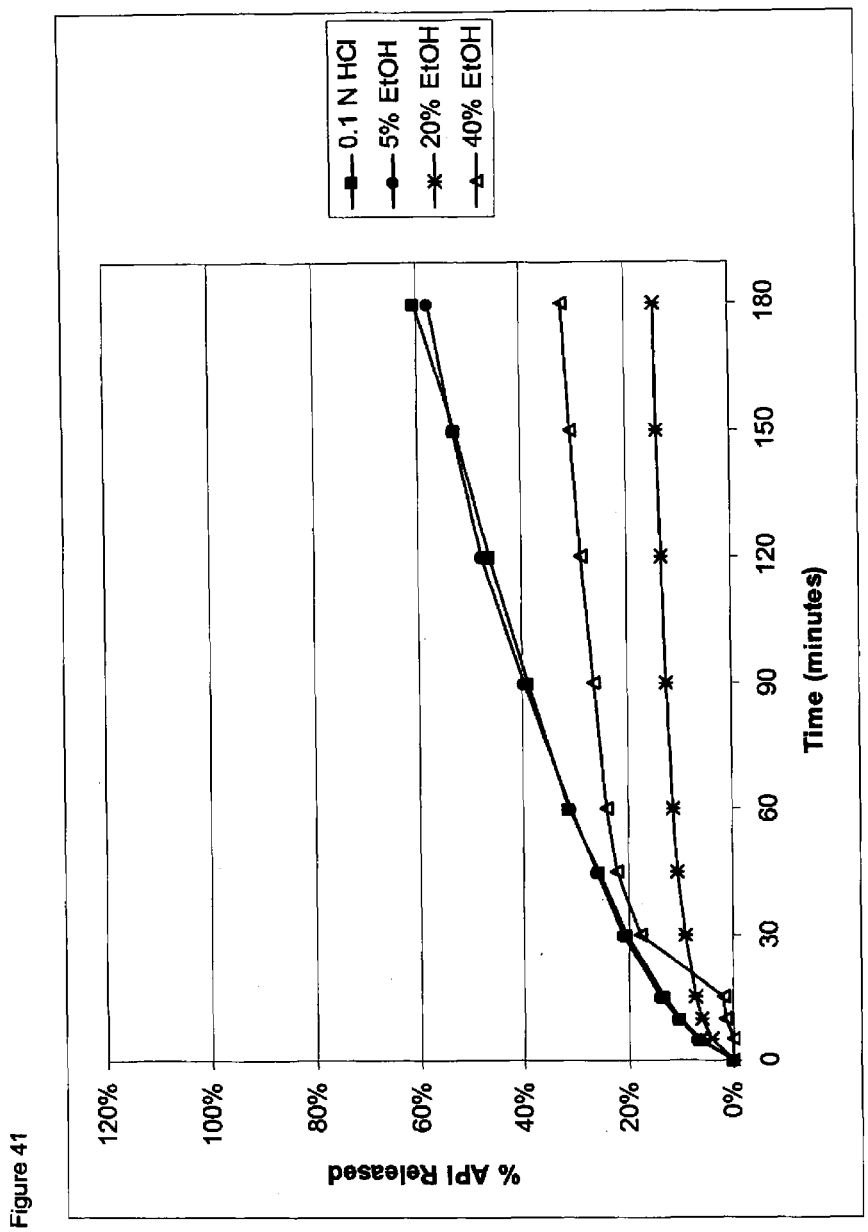
FIG. 41 is a graphical representation of the dissolution profiles of polymorphic dextro-amphetamine pamoate under acidic conditions as a function of ethanol concentration.
Figure 42:
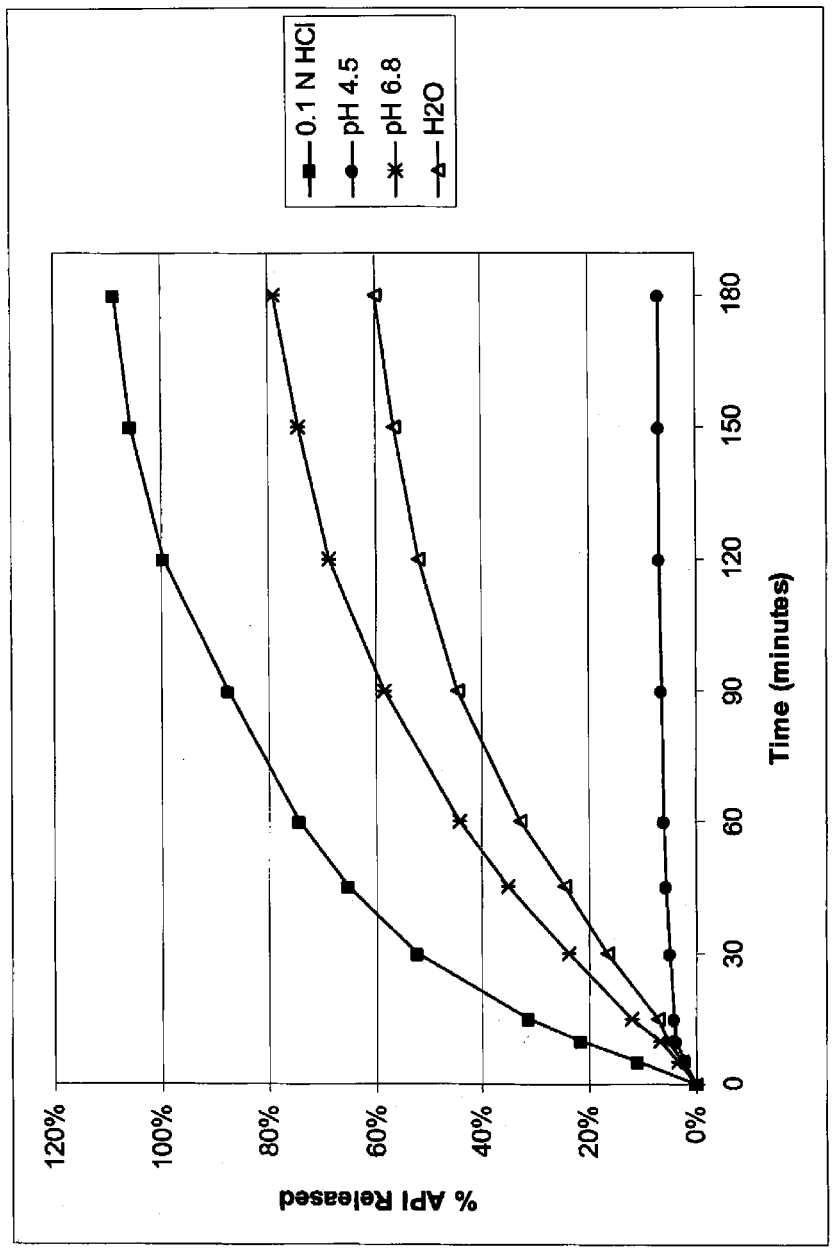
FIG. 42 is a graphical representation of the pH dependent dissolution profiles of amorphous dextro-amphetamine pamoate.
Figure 43:
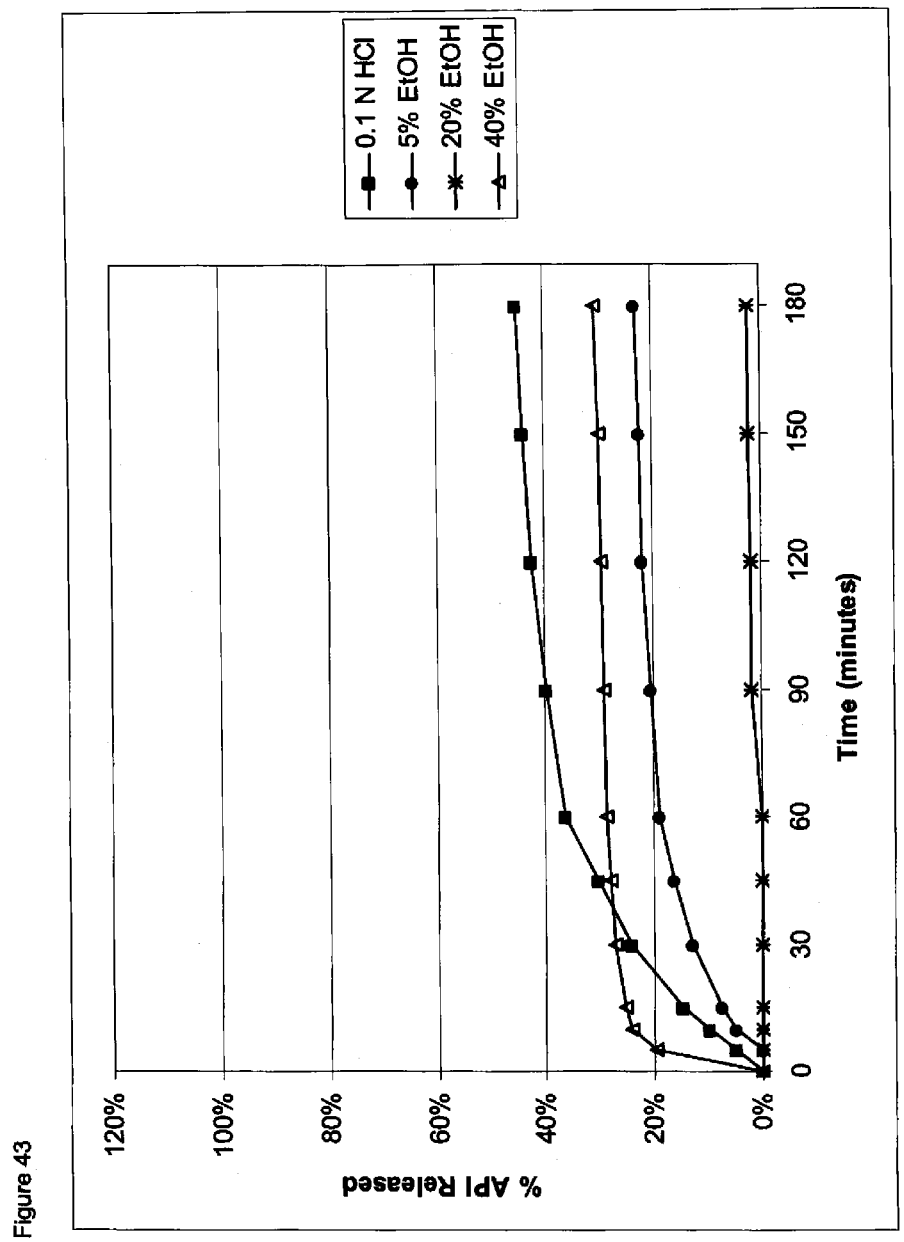
FIG. 43 is a graphical representation of the dissolution profiles of amorphous dextro-amphetamine pamoate under acidic conditions as a function of ethanol concentration.

Dextro-amphetamine is another important active ingredient in the arsenal to treat ADD or ADHD, yet this active ingredient is also quite susceptible to abuse. Analogous to the methylphenidate investigation above, the present invention demonstrated the use of organic acid addition salts to impart abuse-deterrent features to dextro-amphetamine. Here too, the organic acid addition salt family was compared with the available amorphous and polymorphic forms. Specifically, the pH dissolution and dose dumping profiles of amorphous dextro-amphetamine pamoate, as realized from the results presented in FIGS. 42/43, are compared with the polymorphic form of the drug substance as presented in FIGS. 40/41. Minor differences were observed in these paired comparisons and either amorphous or polymorphic forms of dextro-amphetamine pamoate exhibit excellent abuse-deterrent capability. In particular, each exhibits a linear release of the active ingredient at the 0.1 N HCl condition and an inhibition of dose dumping at all ethanol concentrations.

Figure 44:
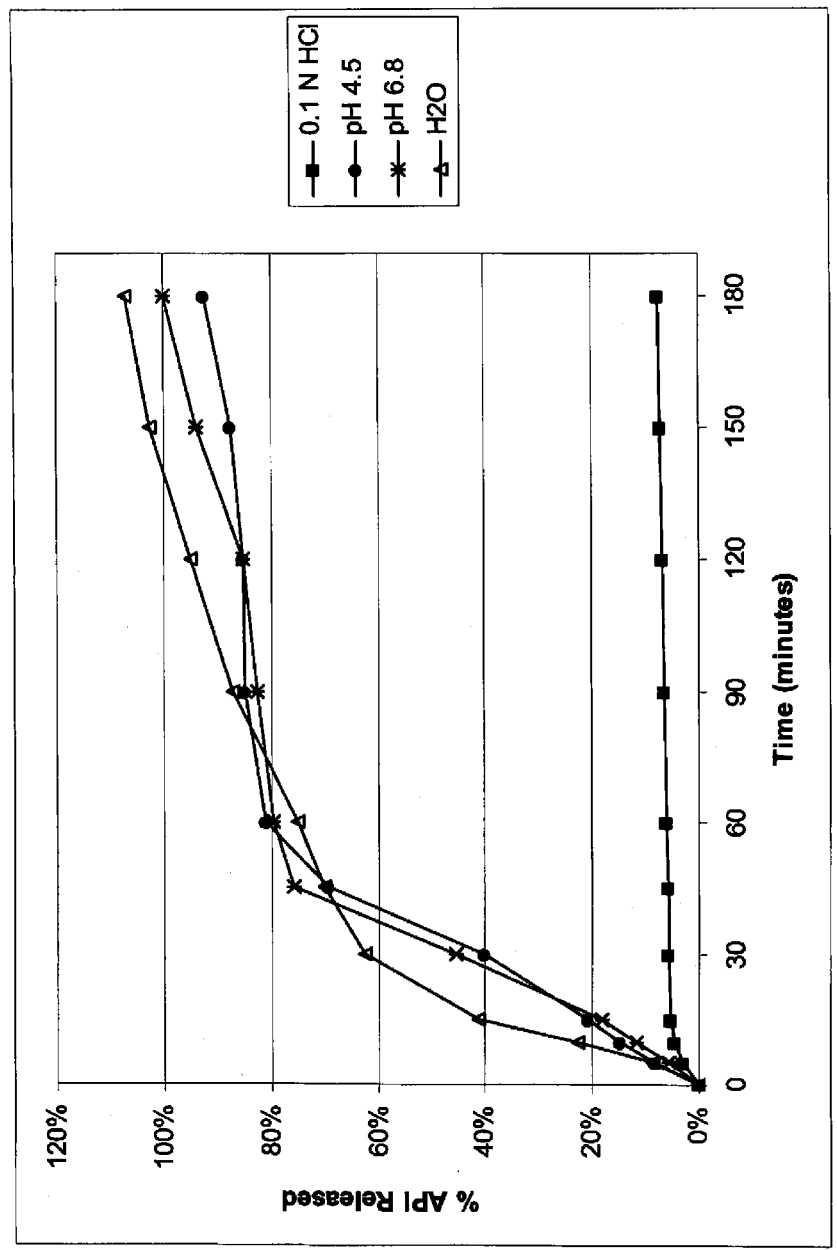
FIG. 44 is a graphical representation of the pH dependent dissolution profiles of polymorphic dextro-amphetamine xinafoate.
Figure 45:
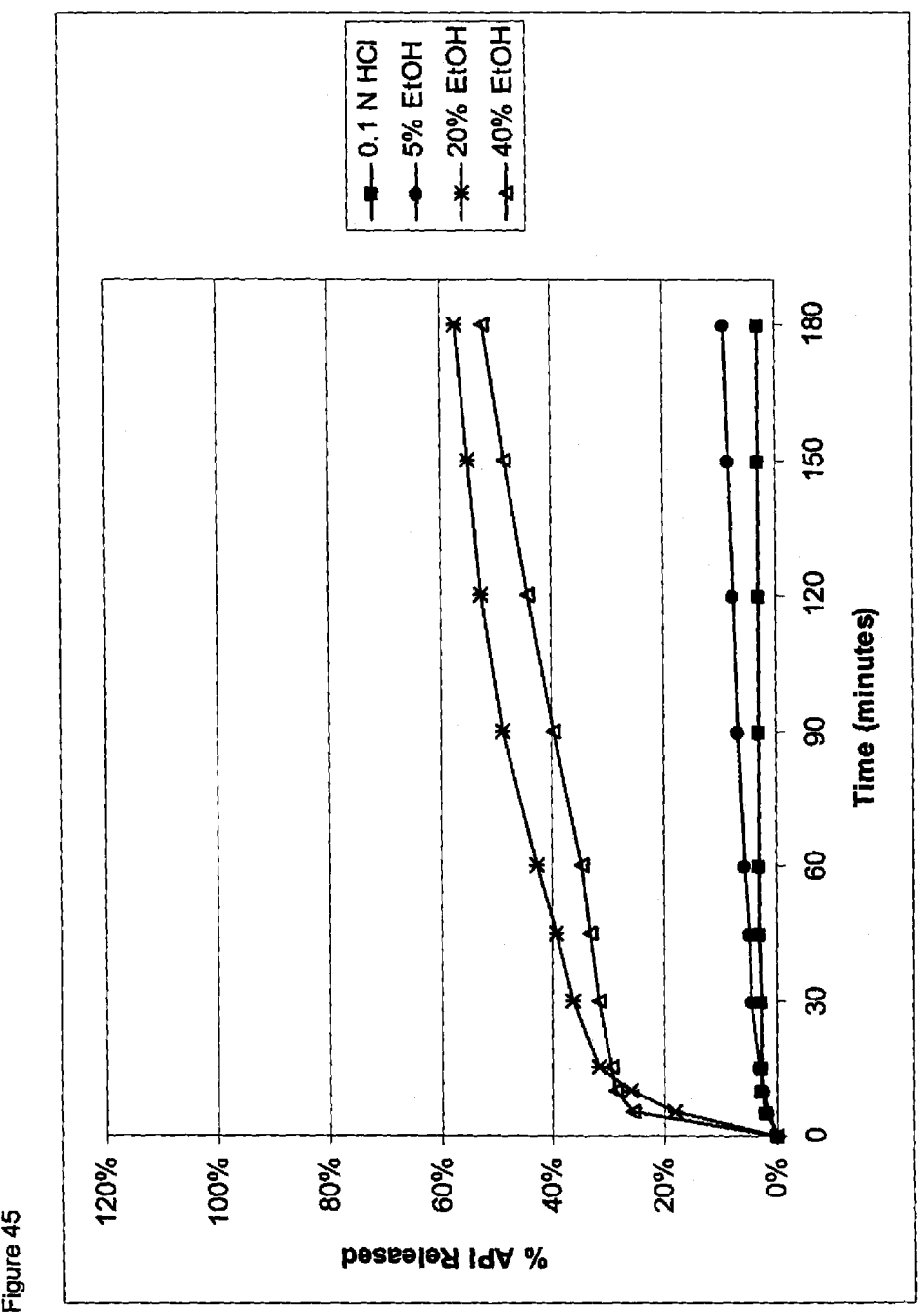
FIG. 45 is a graphical representation of the dissolution profiles of polymorphic dextro-amphetamine xinafoate under acidic conditions as a function of ethanol concentration.

Similar to the xinafoate salt of d-methylphenidate, polymorphic dextro-amphetamine xinafoate was subjected to the pH dissolution and dose dumping regimens with the results captured in FIGS. 44/45. Very unexpected results were obtained with this xinafoate salt wherein the 0.1 N HCl condition (the gastric condition) suppressed release of the active ingredient. Higher pH conditions (e.g. pH 4.5) provided for a restrained, but relatively quick release rate (approximately eighty percent release after sixty minutes). For dose dumping, the twenty and forty percent ethanol conditions led to about thirty-five percent release of the active after only thirty minutes compared to essentially no release of the active under the gastric condition. Clearly, an anomaly exists in the xinafoate's ability to impart predictable abuse deterrent features to an amine containing active ingredient. This emphasizes the unique ability of the pamoate salts to provide protection to the non-therapeutic use (i.e. abuse) of controlled substances. Interestingly, the faster release profiles of the xinafoate salts (at the higher pH conditions) provided a means for release of the active ingredient in the intestinal tract and avoided release in the low pH stomach. Hence, a combination of pamoate and xinafoate salts of a given amine containing controlled substance would provide for a tunable and targeted release profile in a dosage form and enhance the stability of low pH sensitive drugs.

Since the bis-functional organic salts, e.g. the pamoate salts, exhibited the preferential ability to impart abuse-deterrent features to amine containing controlled substances, further manipulation of the bis-functional organic moiety was accomplished while retaining salt formation with the amine-containing active ingredient. The di-basic functionality of the exemplary moiety set forth in Formula H allows formation of a mixed salt from two different amines, one of which is an active ingredient. Imipramine is exemplary for evaluating the depth and breadth of the invention's chemical aspects. Synthetically, the difficulty arises in preparing the desired mixed salt within one molecule and avoiding preparation of a statistical mixture of salts including the bis-functional moiety possessing two equivalents of amine active pharmaceutical ingredient and another bis-functional organic moiety consisting of salt formation with two equivalents of a second amine which functions as a dissolution modifier.

To achieve the desired synthetic goal of a mixed salt, two different synthetic methods were employed. One synthetic method entailed preparation of imipramine pamoate mono-triethylammonium salt by reaction of one equivalent of imipramine hydrochloride with di-triethylammonium pamoate. Subsequently, two other amines (stearylamine or Jeffamine®) could then react with imipramine pamoate mono-triethylammonium salt to form the desired 1:1:1 mixed salts. On a side note, if just the 1:1 salt of imipramine (free carboxylic acid group) is desired, mono-imipramine pamoate could also be prepared from deprotection of imipramine pamoate mono-triethylammonium salt or, in an entirely unrelated reaction, by reaction of 1:1 Tetronic® pamoate with imipramine pamoate (2:1). The second synthetic method entailed displacement of one of the imipramines of di-imipramine pamoate with one of the two other amines mentioned above (stearylamine or Jeffamine®).

Consequently, the analogues of mono-imipramine pamoate salts prepared as exemplars from the first synthetic method demonstrating the concept included: amorphous imipramine triethylammonium pamoate. Exemplars of the first synthetic method can also be applied to the d-methylphenidate pamoate series where d-methylphenidate pamoate mono-triethylammonium salt can be prepared from reaction of d-methylphenidate hydrochloride with di-triethylammonium pamoate.

The analogue pamoate salts prepared as exemplars from the second synthetic method demonstrating the concept included: amorphous imipramine Jeffamine® pamoate and polymorphic imipramine stearylamine pamoate.

Exemplars of the second synthetic method can also be applied to other analogous amine pamoates: 1) the racemic methylphenidate pamoate series where racemic methylphenidate pamoate (2:1) is reacted with one equivalent of stearylamine to provide polymorphic methylphenidate stearylamine pamoate (1:1:1), 2) the hydrocodone series where hydrocodone pamoate (2:1) is reacted with one equivalent of stearylamine to provide mostly amorphous hydrocodone stearylamine pamoate (1:1:1) and 3) the hydrocodone series where hydrocodone pamoate (2:1) is reacted with one equivalent of Jeffamine® to provide amorphous hydrocodone Jeffamine® pamoate (1:1:1). These will be expounded on later.

Figure 82:
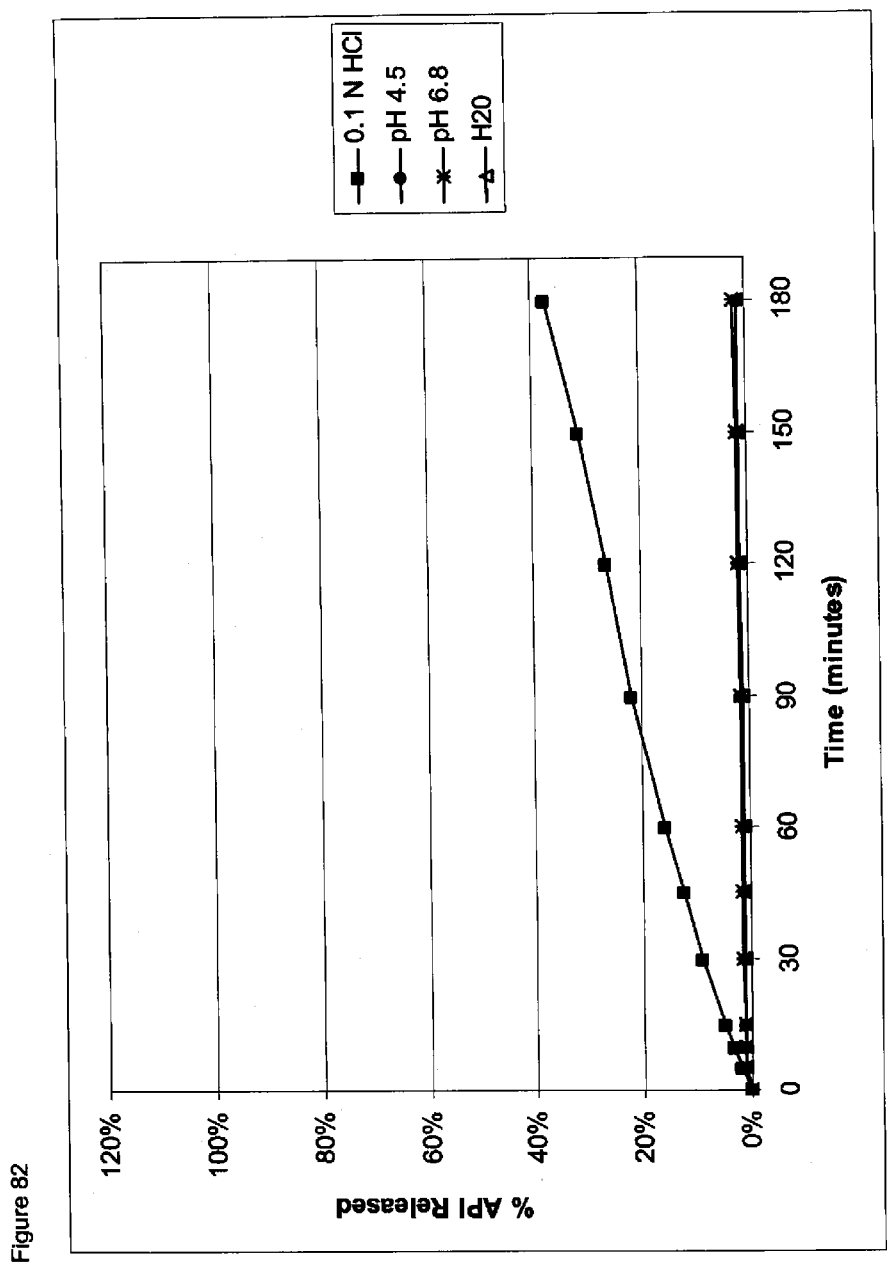
FIG. 82 is a graphical representation of the pH dependent dissolution profiles of amorphous imipramine pamoate, 1:1 salt.
Figure 83:
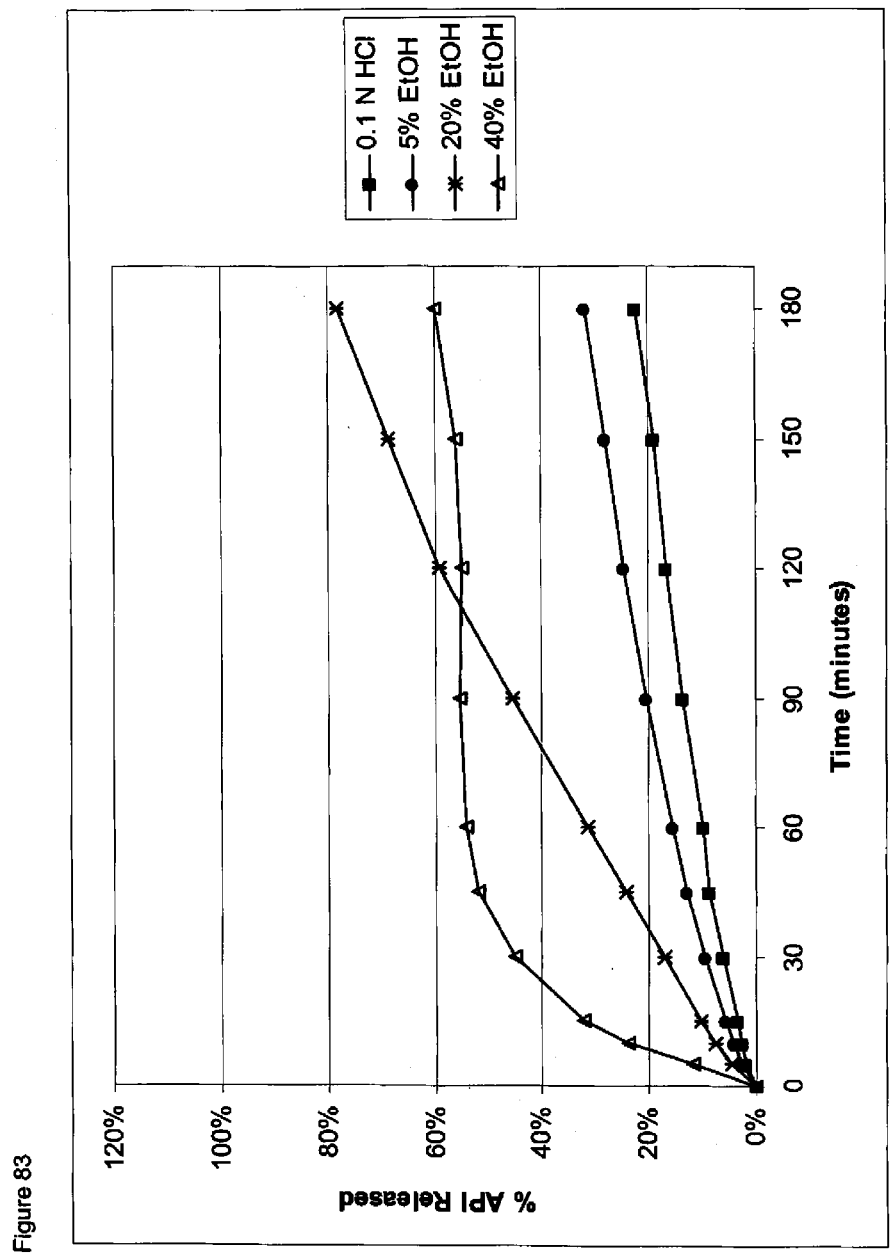
FIG. 83 is a graphical representation of the dissolution profiles of amorphous imipramine pamoate, 1:1 salt under acidic conditions as a function of ethanol concentration.
Figure 84:
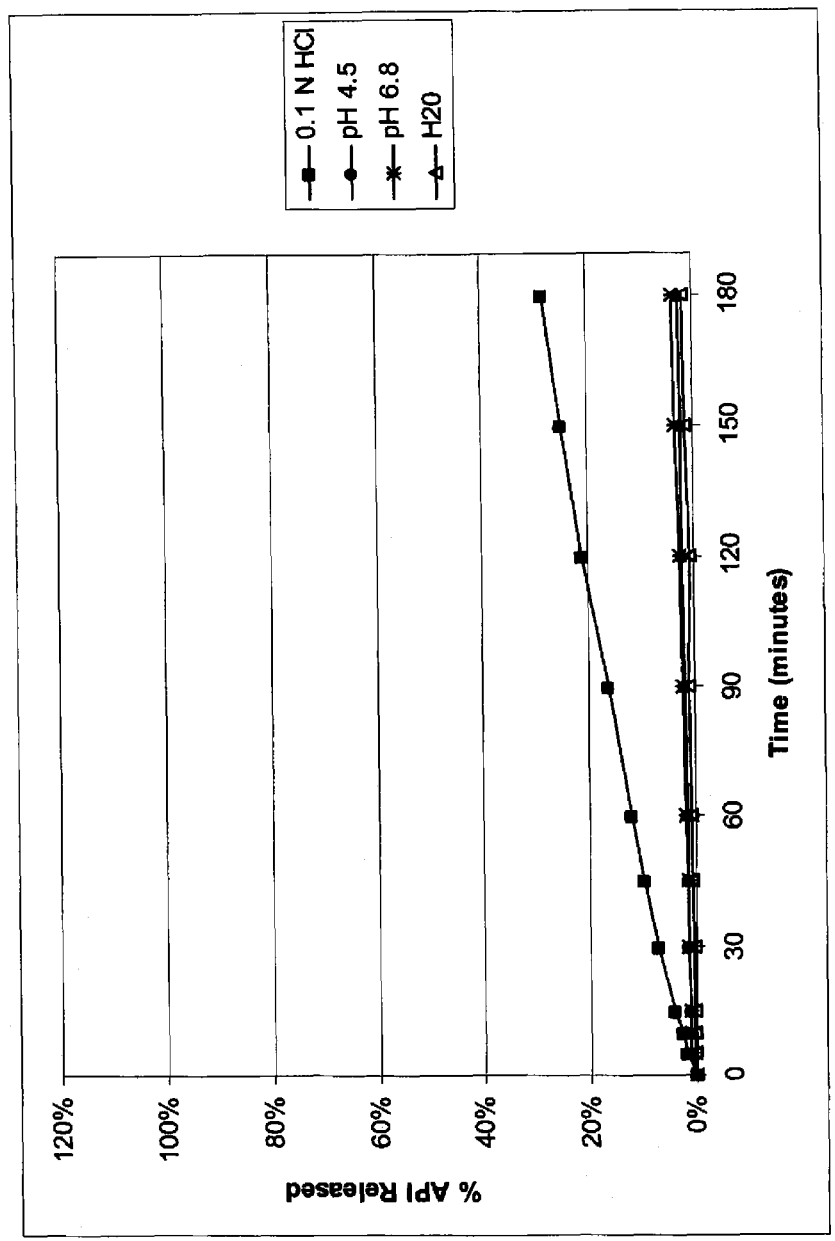
FIG. 84 is a graphical representation of the pH dependent dissolution profiles of amorphous imipramine mono-triethylammonium pamoate, 1:1:1 salt.
Figure 85:
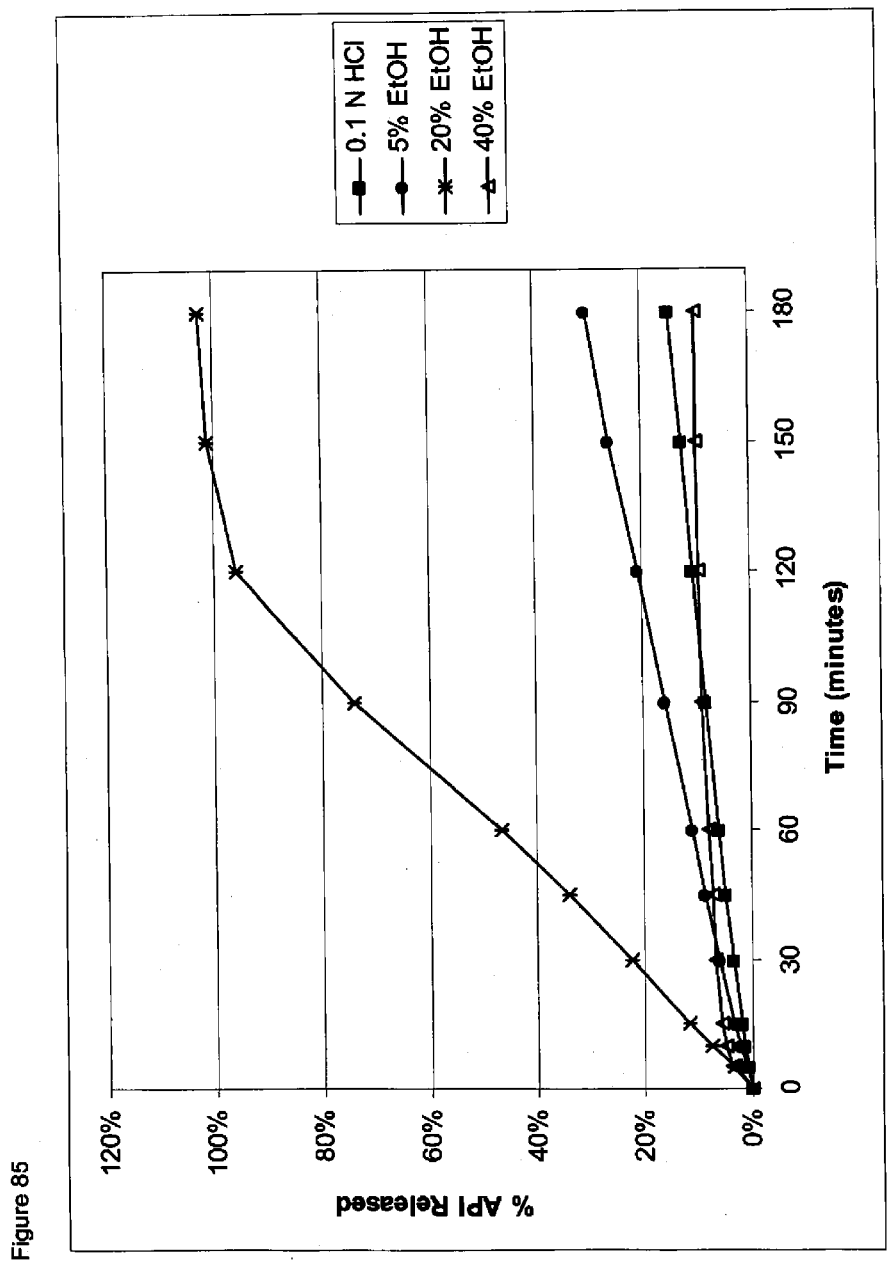
FIG. 85 is a graphical representation of the dissolution profiles of amorphous imipramine mono-triethylammonium pamoate, 1:1:1 salt under acidic conditions as a function of ethanol concentration.
Figure 86:
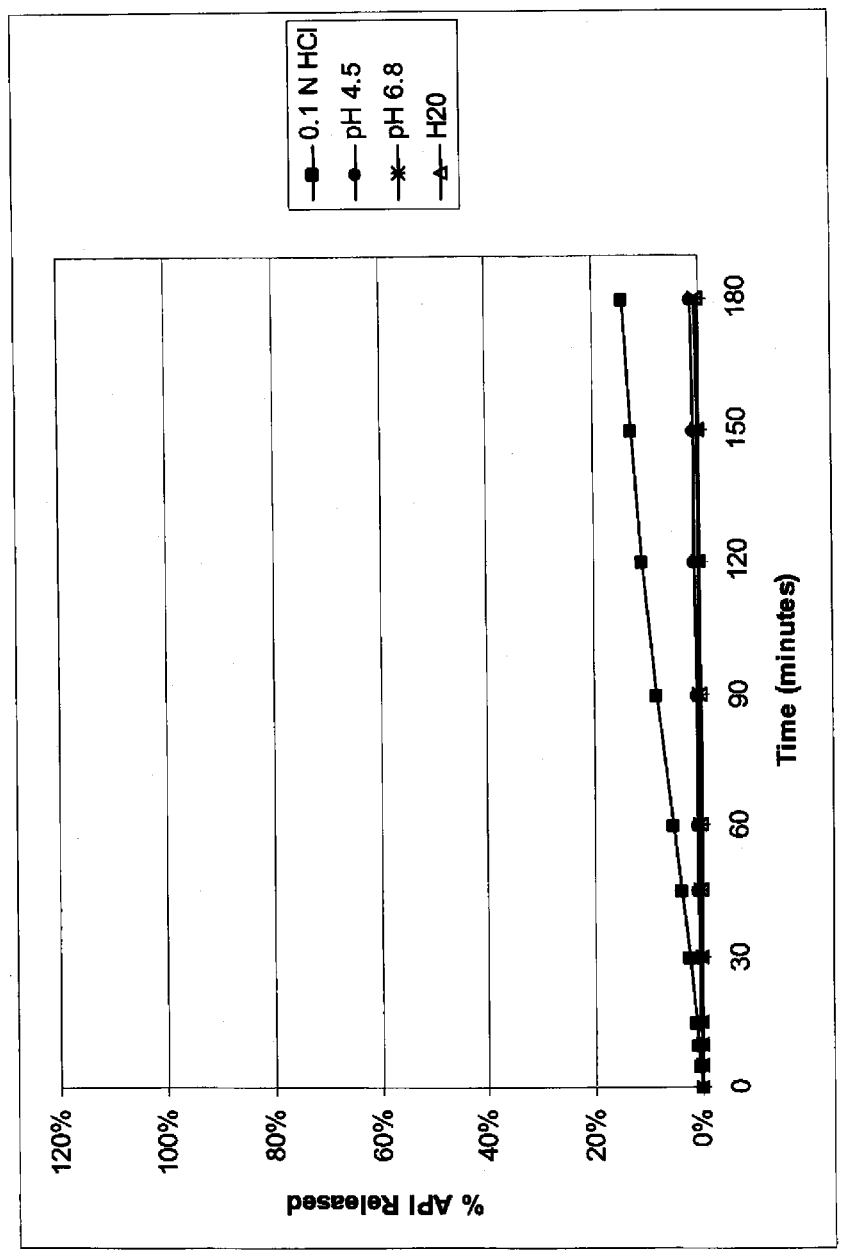
FIG. 86 is a graphical representation of the pH dependent dissolution profiles of polymorphic imipramine stearylamine pamoate, 1:1:1 salt.
Figure 87:
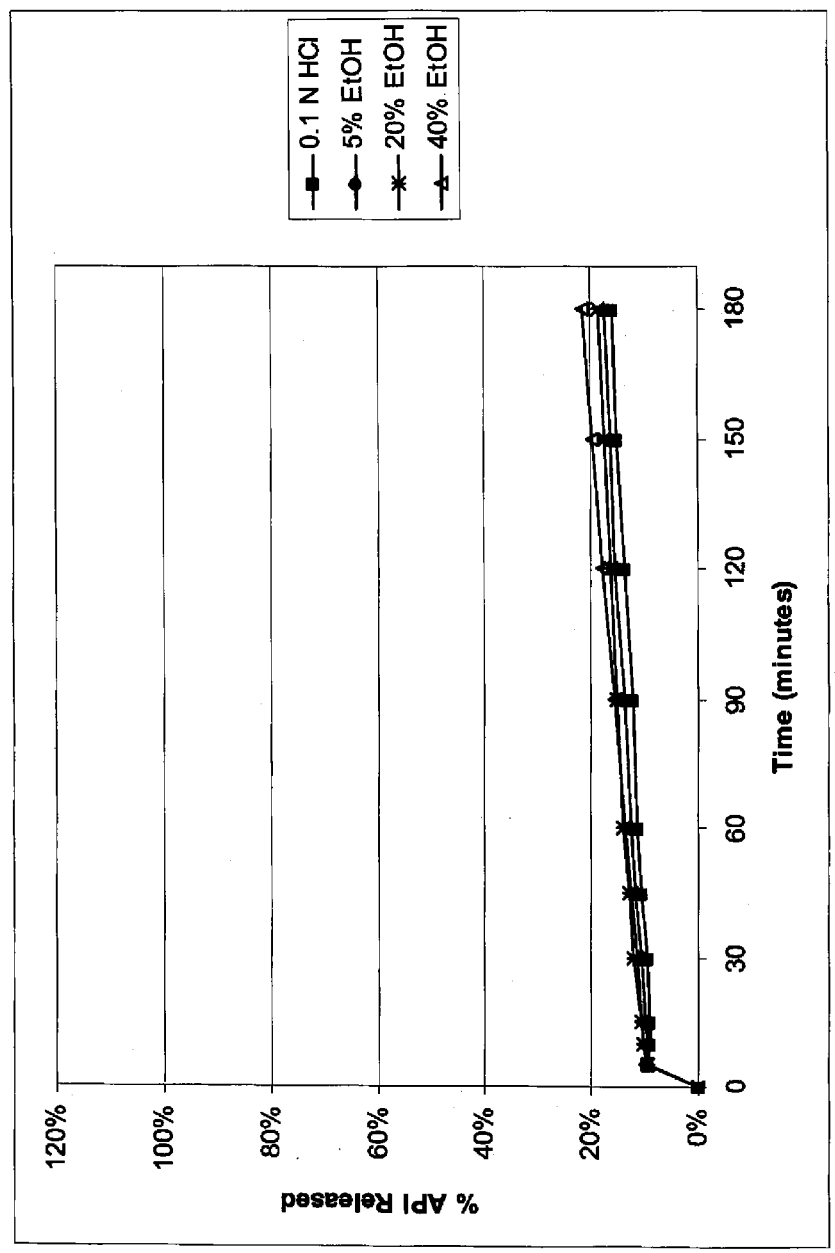
FIG. 87 is a graphical representation of the dissolution profiles of polymorphic imipramine stearylamine pamoate, 1:1:1 salt under acidic conditions as a function of ethanol concentration.
Figure 88:
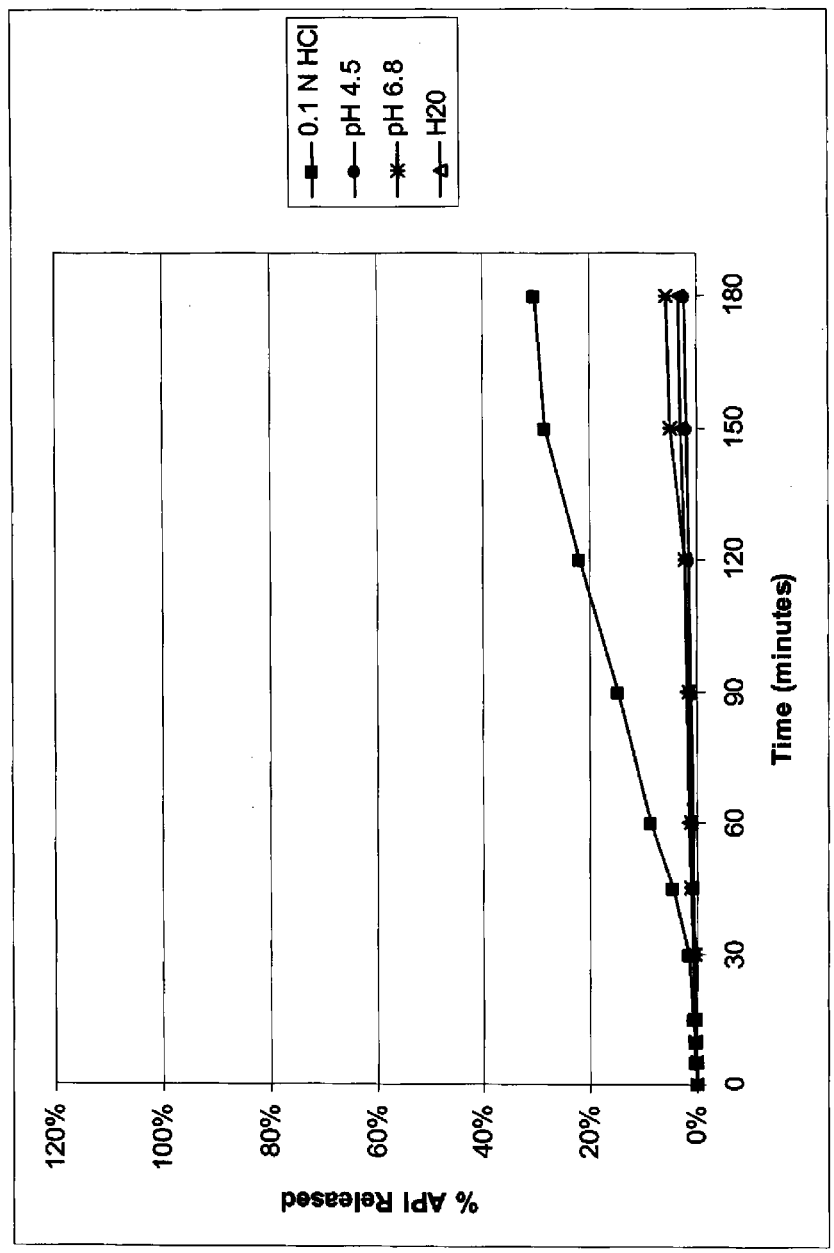
FIG. 88 is a graphical representation of the pH dependent dissolution profiles of amorphous imipramine Jeffamine® pamoate, 1:1:1 salt.
Figure 89:
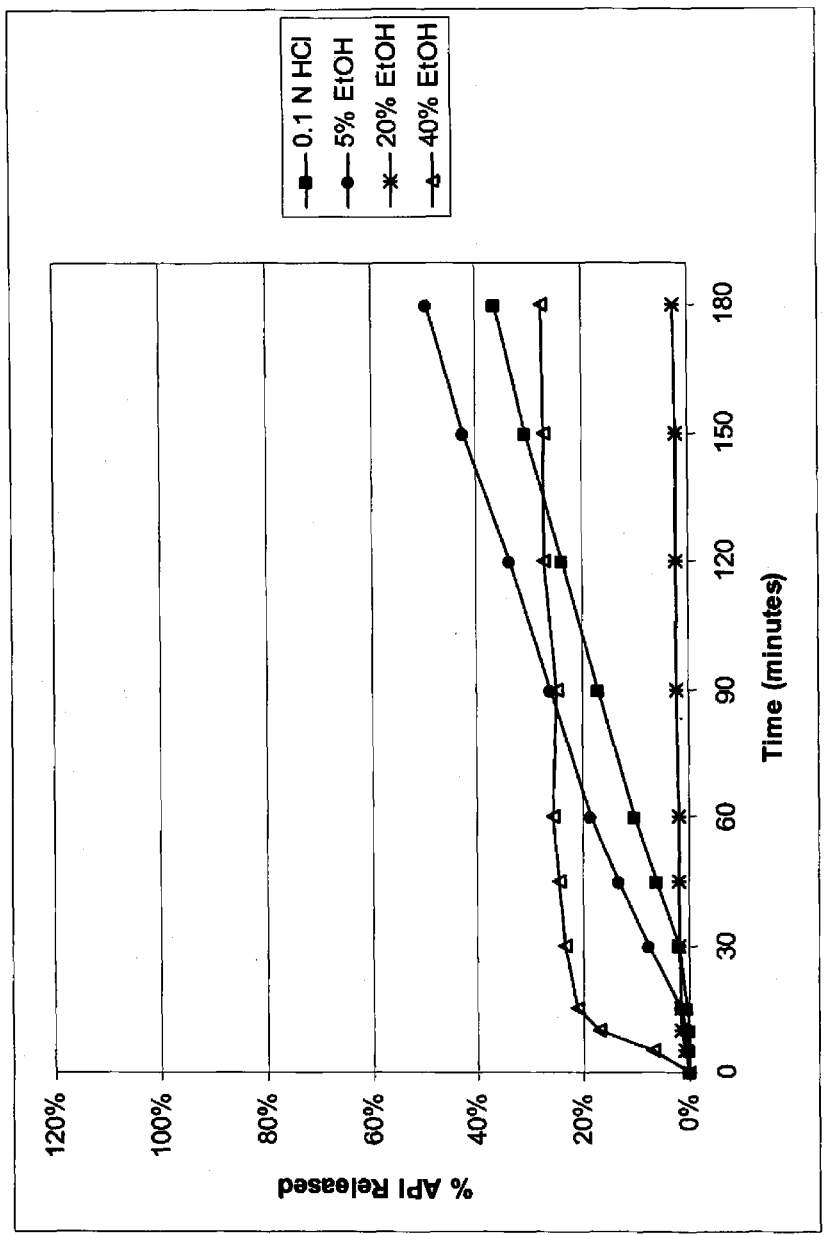
FIG. 89 is a graphical representation of the dissolution profiles of amorphous imipramine Jeffamine® pamoate, 1:1:1 salt under acidic conditions as a function of ethanol concentration.
Figure 108:
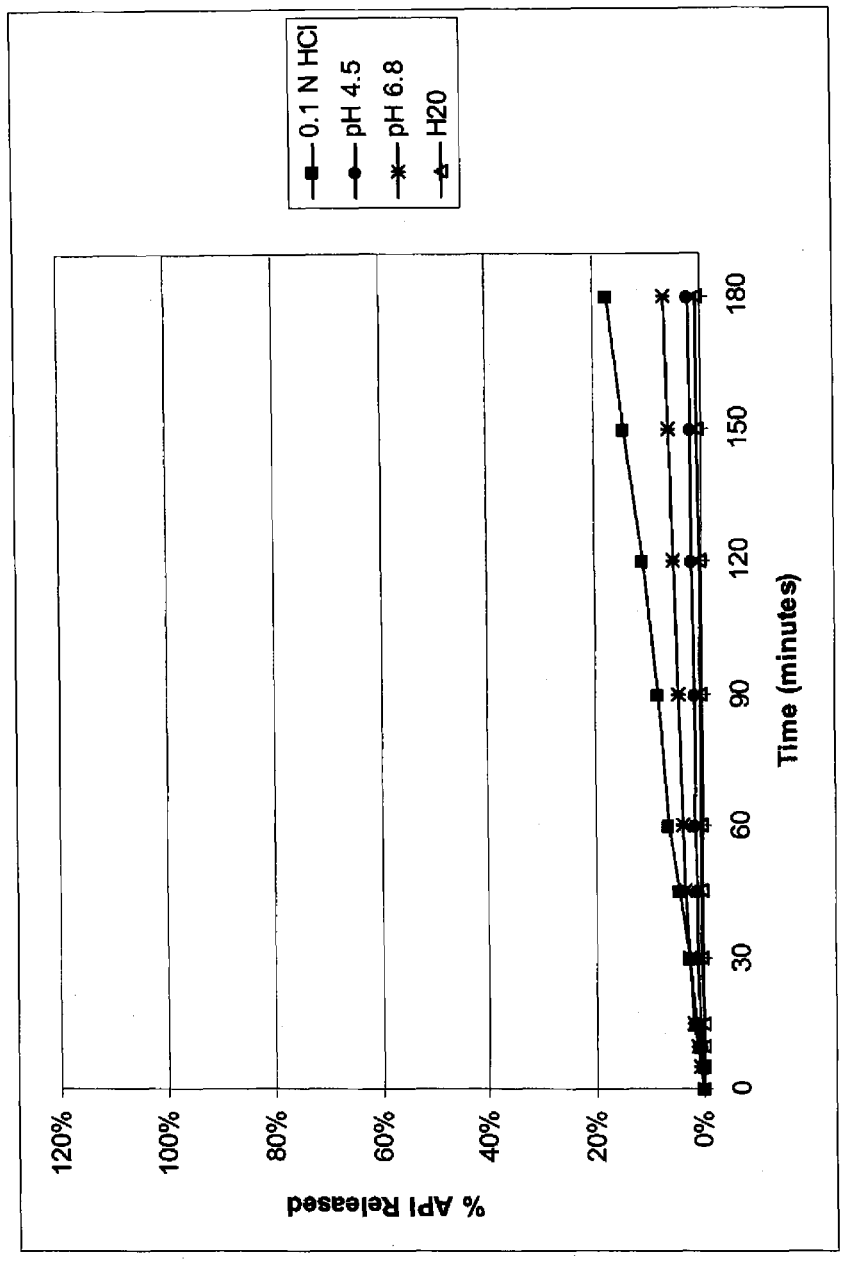
FIG. 108 is a graphical representation of the pH dependent dissolution profiles of polymorphic imipramine pamoate, 1:1 salt.
Figure 109:
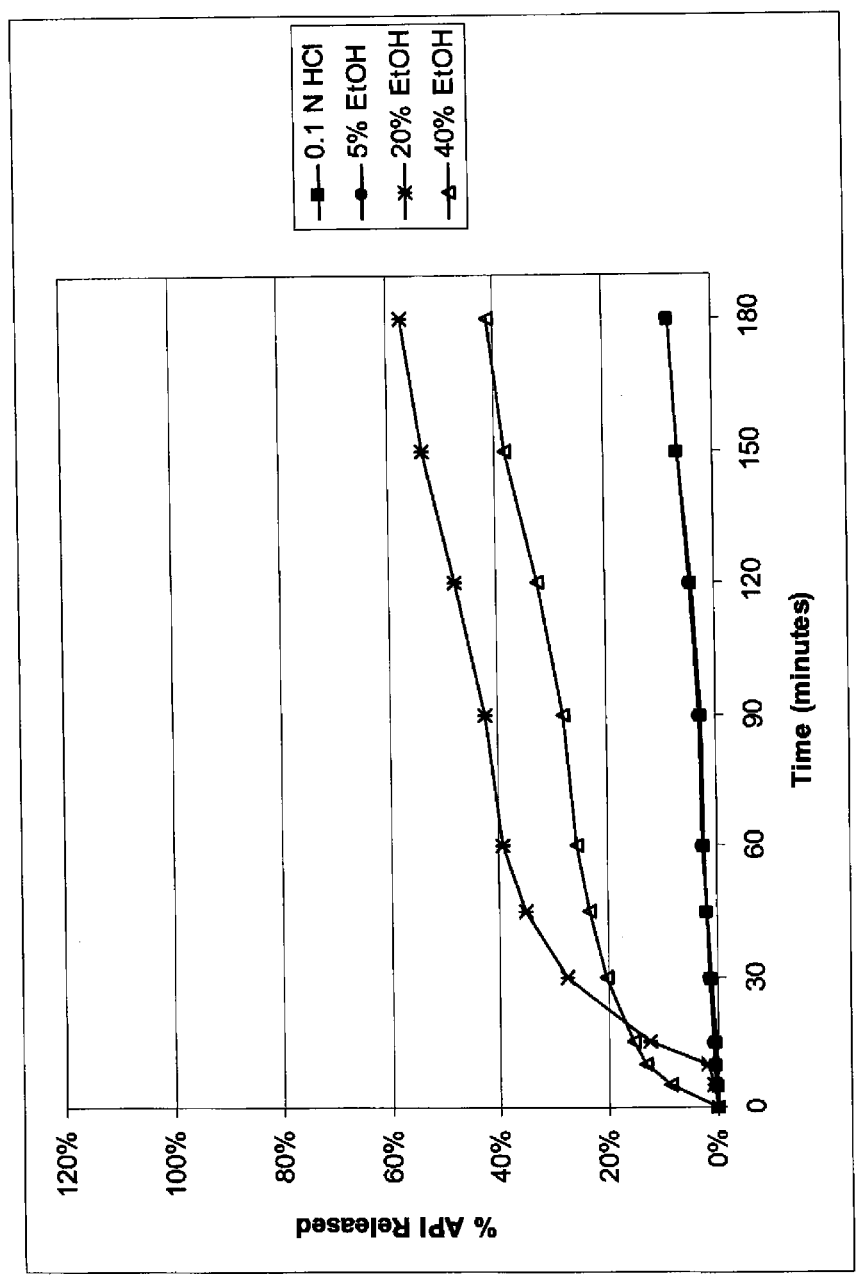
FIG. 109 is a graphical representation of the dissolution profiles of polymorphic imipramine pamoate, 1:1 salt under acidic conditions as a function of ethanol concentration.

Each of these compounds was analytically characterized and subjected to the pH and dose dumping dissolution regimens to determine their performance characteristics. The findings were contrary to the anticipated results. The free carboxyl group within the pamoic acid moiety is comparatively insoluble under lower pH conditions while incorporation of the triethylammonium salt would increase its solubility. Improving the hydrophilic character of the pamoic acid moiety by substitution with a polyoxyalkylene (Jeffamine) should also enhance the pamoate/pamoic acid moiety's solubility. In contrast, the hydrophobic stearylamine salt of the pamoate/pamoic acid moiety should markedly decrease the pamoate's solubility. Indeed, the most impact on the dissolution profile of this series of imipramine pamoate derivatives was observed after reacting other amines with mono-imipramine pamoate. For amorphous mono-imipramine pamoate, FIGS. 82/83, the pH dissolution profiles were highly retarded, but with a favorable slow release for the gastric condition. The dose dumping results indicated any presence of ethanol would accelerate release of the active ingredient from the salt form. Interestingly however, only the forty percent ethanol condition radically altered the active's release after a short time period with about fifty percent of the active available after thirty minutes. For the polymorphic mono-imipramine pamoate, FIGS. 108/109, the pH dissolution profiles were very similar to those found with the amorphous salt yet the 0.1 N HCl dissolution condition was diminished further. The polymorphic mono-imipramine pamoate salt was also found to be less responsive to dose dumping than its amorphous counterpart. The triethylammonium salt of mono-imipramine pamoate, FIGS. 84/85, exhibited a similar pH dissolution profile as the free acid, but the twenty percent ethanol condition accelerated release of the active. Still, only about twenty percent of the active was released after thirty minutes under this condition. Progressing to the Jeffamine® derivative, here again it was believed that the salt formation and the hydrophilic nature of the polyoxyalkylene would significantly enhance the dissolution performance while having little effect on dose dumping. The findings, FIGS. 88/89, did not support this presumption however; the pH dissolution profile was quite similar to the dissolution properties observed for the free acid and triethylammonium salts. In regard to dose dumping, the presence of ethanol accelerated the active's release from the salt, but likely not to the extent to satisfy someone intent on abusing the drug. For the supposed hydrophobic stearylamine derivative, FIGS. 86/87, the pH dissolution profile was highly retarded, and interestingly, the compound did not respond to ethanol in the dose dumping challenge. Clearly, this set of experiments led to implications concerning pamoate salts and their utility in abuse deterrence. With these derivatives, water soluble salt formers, such as triethylamine and Jeffamine® acted to retard the dissolution profiles contrary to current understandings and knowledge. Hence, a negative teaching was observed.

Figure 90:
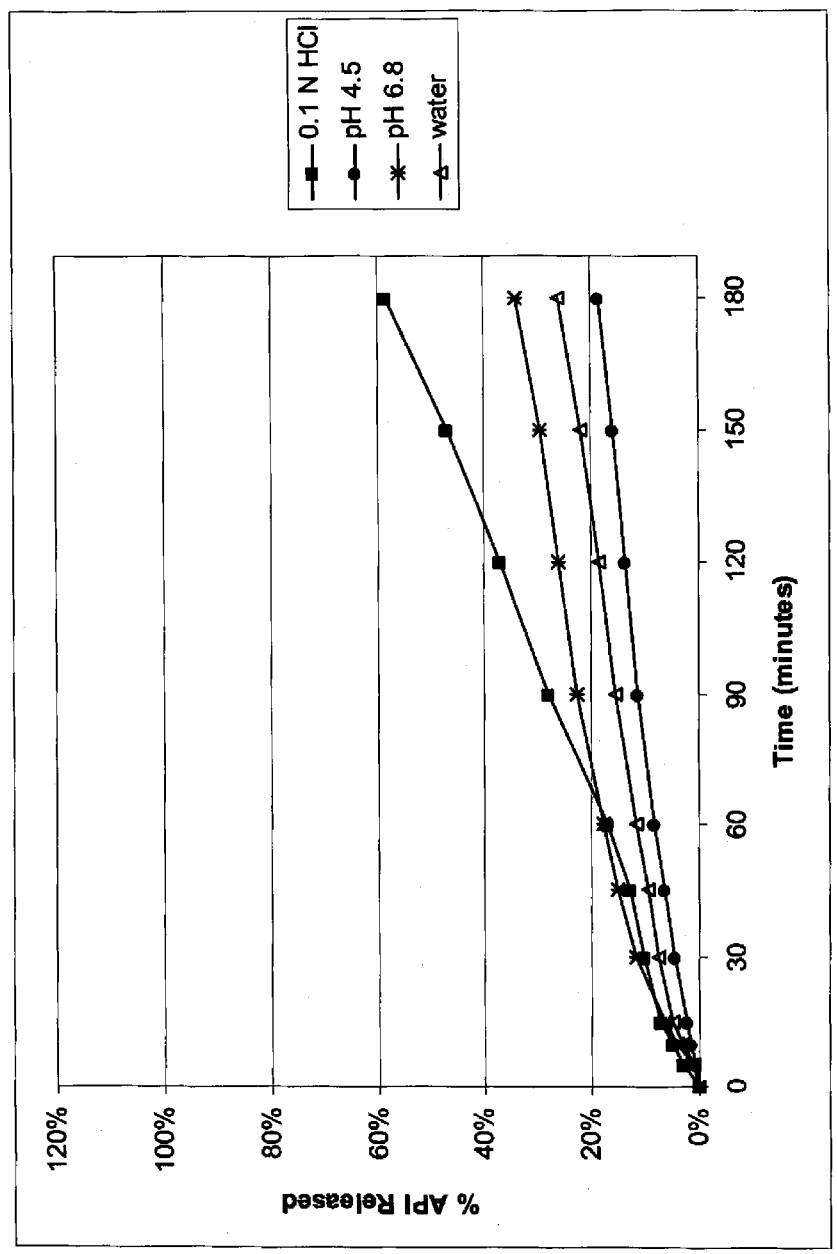
FIG. 90 is a graphical representation of the pH dependent dissolution profiles of amorphous hydrocodone stearylamine pamoate, 1:1:1 salt.
Figure 91:
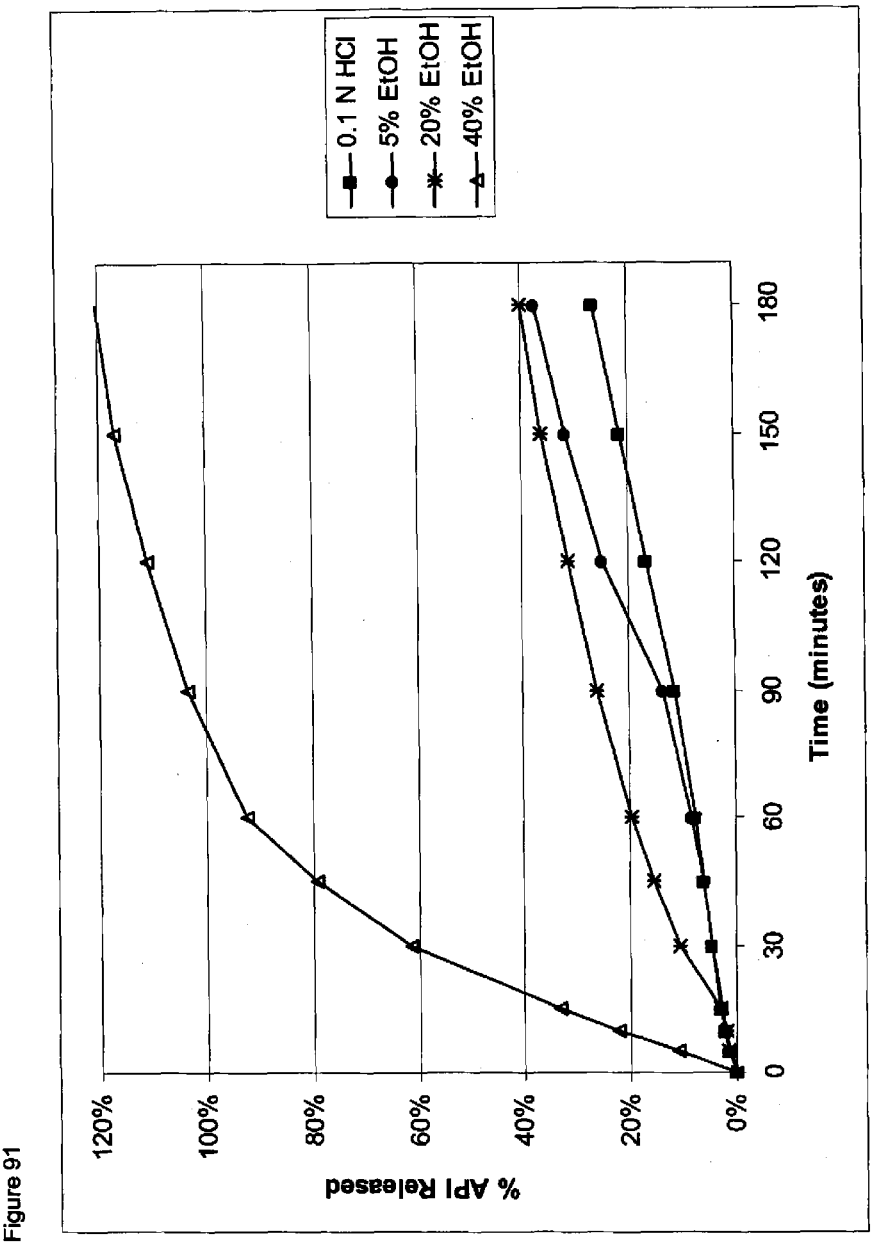
FIG. 91 is a graphical representation of the dissolution profiles of amorphous hydrocodone stearylamine pamoate, 1:1:1 salt under acidic conditions as a function of ethanol concentration.
Figure 92:
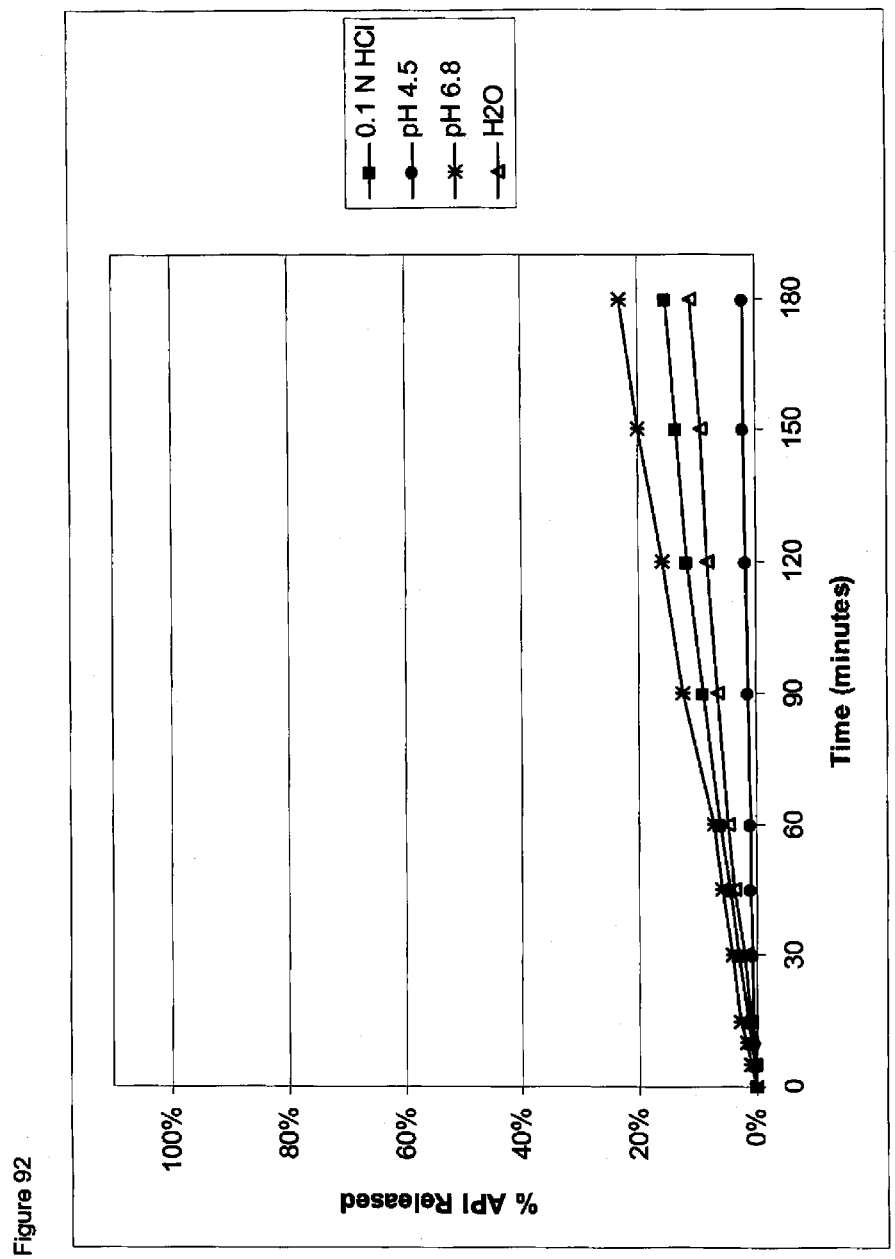
FIG. 92 is a graphical representation of the pH dependent dissolution profiles of amorphous hydrocodone Jeffamine® pamoate, 1:1:1 salt.
Figure 93:
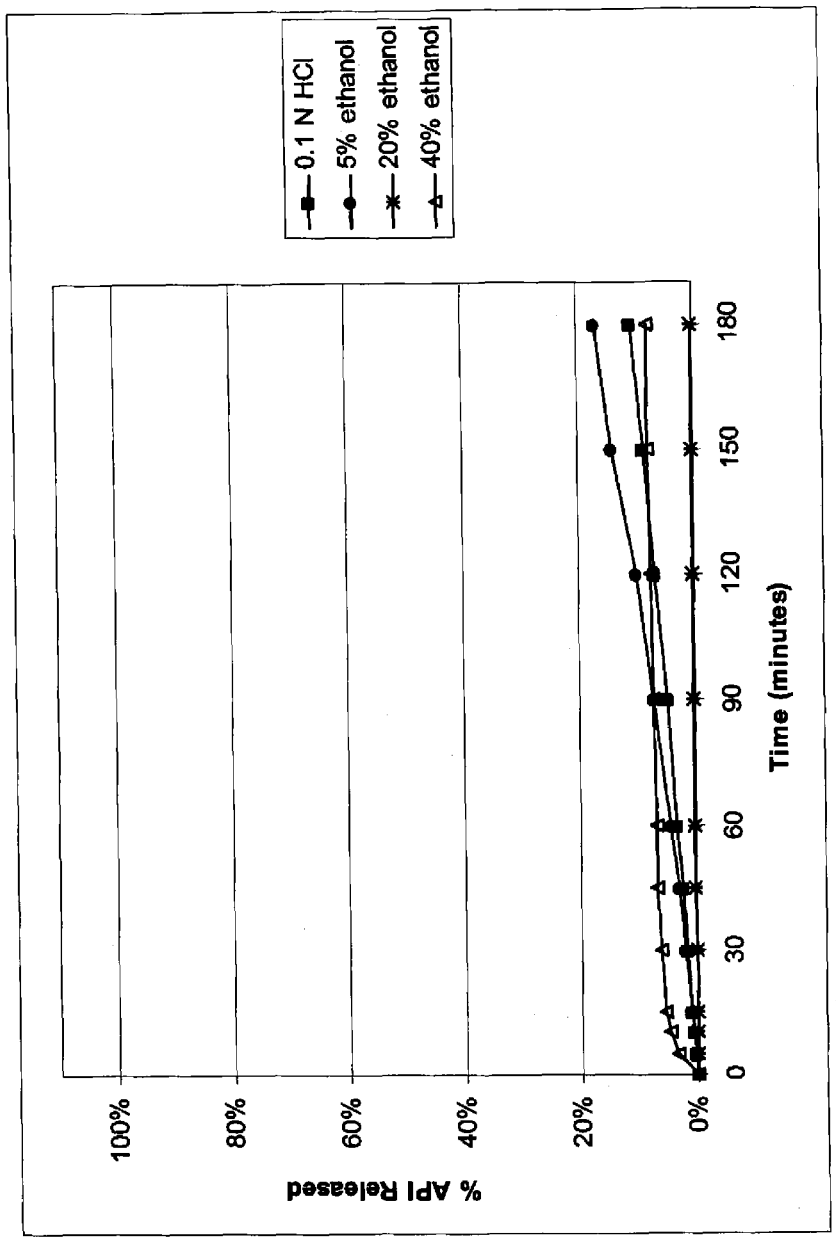
FIG. 93 is a graphical representation of the dissolution profiles of amorphous hydrocodone Jeffamine® pamoate, 1:1:1 salt under acidic conditions as a function of ethanol concentration.

To further explore this aspect of dissolution behavior as augmented by complex, mixed salts of active ingredients and salt inclusive dissolution profile modifiers, a similar set of analogues was prepared as mentioned earlier. Instead of imipramine, a different pharmacophore was employed in this case, namely, hydrocodone. Hence, amorphous hydrocodone Jeffamine® pamoate (1:1:1) and amorphous hydrocodone stearylamine pamoate (1:1:1) were prepared and their pH dissolution and dose dumping properties characterized. For amorphous hydrocodone Jeffamine® pamoate (1:1:1) salt, FIGS. 92/93, the pH and dose dumping dissolution profiles were slow and linear with very little active ingredient released under any condition. For the amorphous hydrocodone stearylamine pamoate (1:1:1) salt, FIGS. 90/91, a retarded, but faster pH dissolution profile was observed and the presence of forty percent ethanol in the dose dumping challenge indicated ethanol could be used to extract the active amine from the salt.

In comparing the effects of incorporating dissolution modifiers within the active ingredient/bis-functional organic acid salt to influence both pH dissolution and dose dumping profiles, the presence of water soluble enhancers attached to the pamoate moiety surprisingly do not function as expected, and the presence of an oleophilic component attached to the bis-functional moiety, such as stearylamine, yielded highly unexpected results. For imipramine stearylamine pamoate (1:1:1), the impact of stearylamine on dose dumping was profound by essentially stopping any suggestion of dose dumping. In contrast, for hydrocodone stearylamine pamoate (1:1:1), the stearylamine component accelerates dose dumping, particularly at the forty percent condition. The comparison between bis-functional organic acid derivatives and families of active ingredients with respect to their pH and dose dumping dissolution performance characteristics indicates a further design criterion. When employing a dissolution modifying agent as part of the bis-functional salt, the properties of the active ingredient must be properly matched with the dissolution agent in order to design/engineer a specific dissolution response.

Figure 78:
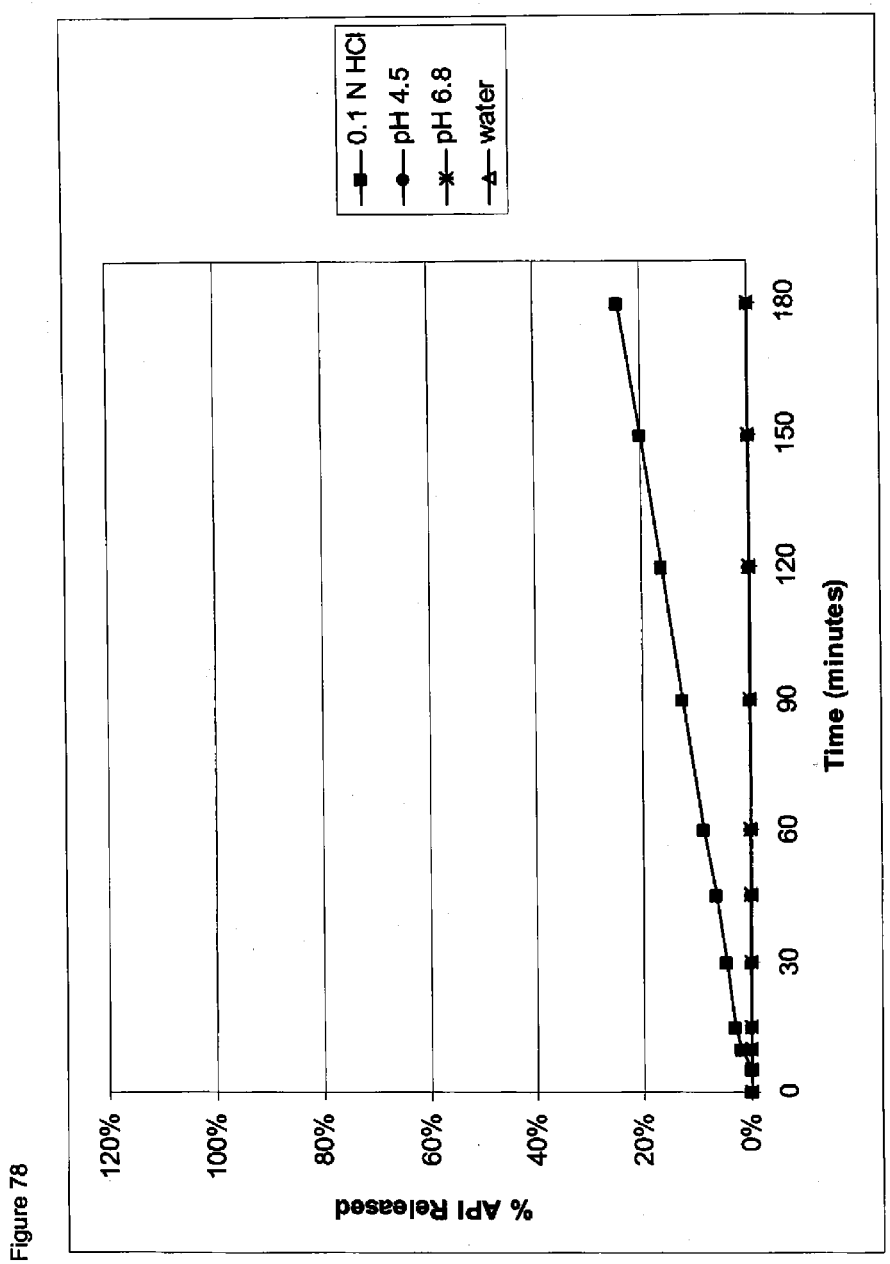
FIG. 78 is a graphical representation of the pH dependent dissolution profiles of polymorphic racemic-methylphenidate stearylamine pamoate, 1:1:1 salt.
Figure 79:
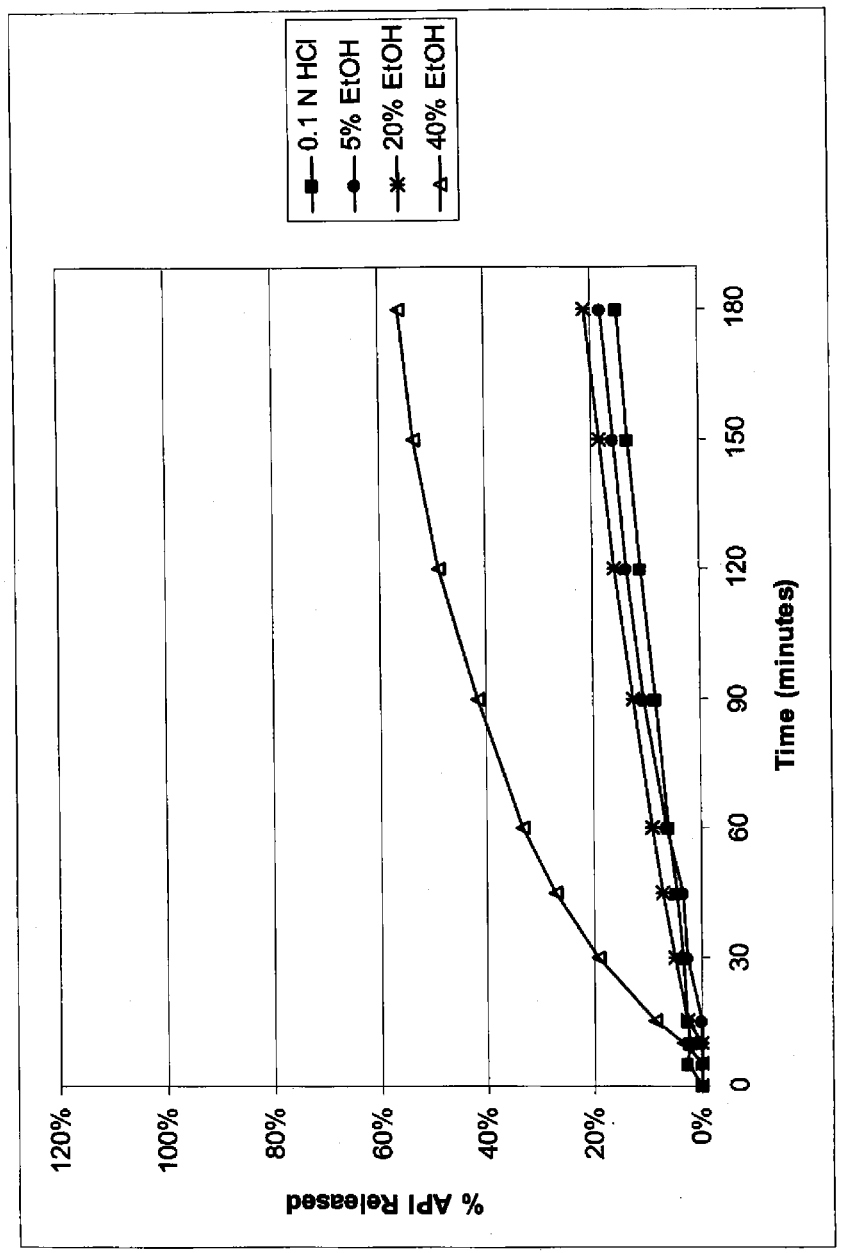
FIG. 79 is a graphical representation of the dissolution profiles of polymorphic racemic-methylphenidate stearylamine pamoate, 1:1:1 salt under acidic conditions as a function of ethanol concentration.

To refine this latter observation, the salt-inclusive dissolution modifier approach was applied to d-methylphenidate and racemic-methylphenidate. Consequently, amorphous d-methylphenidate triethylammonium pamoate (1:1:1) and polymorphic racemic-methylphenidate stearylamine pamoate (1:1:1) salts were prepared and evaluated for their pH and dose dumping dissolution characteristics. As was observed in FIGS. 80/81 the triethylammonium derivative exhibits superior performance characteristics. The d-methylphenidate component releases nicely from the salt at the gastric (0.1 N HCl condition) and is retarded under higher pH conditions. The lack of any significant dissolution under higher pH indicates the active ingredient would prove difficult to extract from the salt form in an effort to abuse the active component of the salt. Similarly, the triethylammonium salt behaves quite well under the dose-dumping dissolution challenge conditions and consequently, it does not appear to be susceptible to ethanol extraction. In comparison, the analogous stearylamine derivative, FIGS. 78/79, exhibits a highly retarded pH dissolution profile and an unfavorable dose dumping result only at the forty percent condition, but even then only after a significant period (i.e. sixty minutes).

Figure 80:
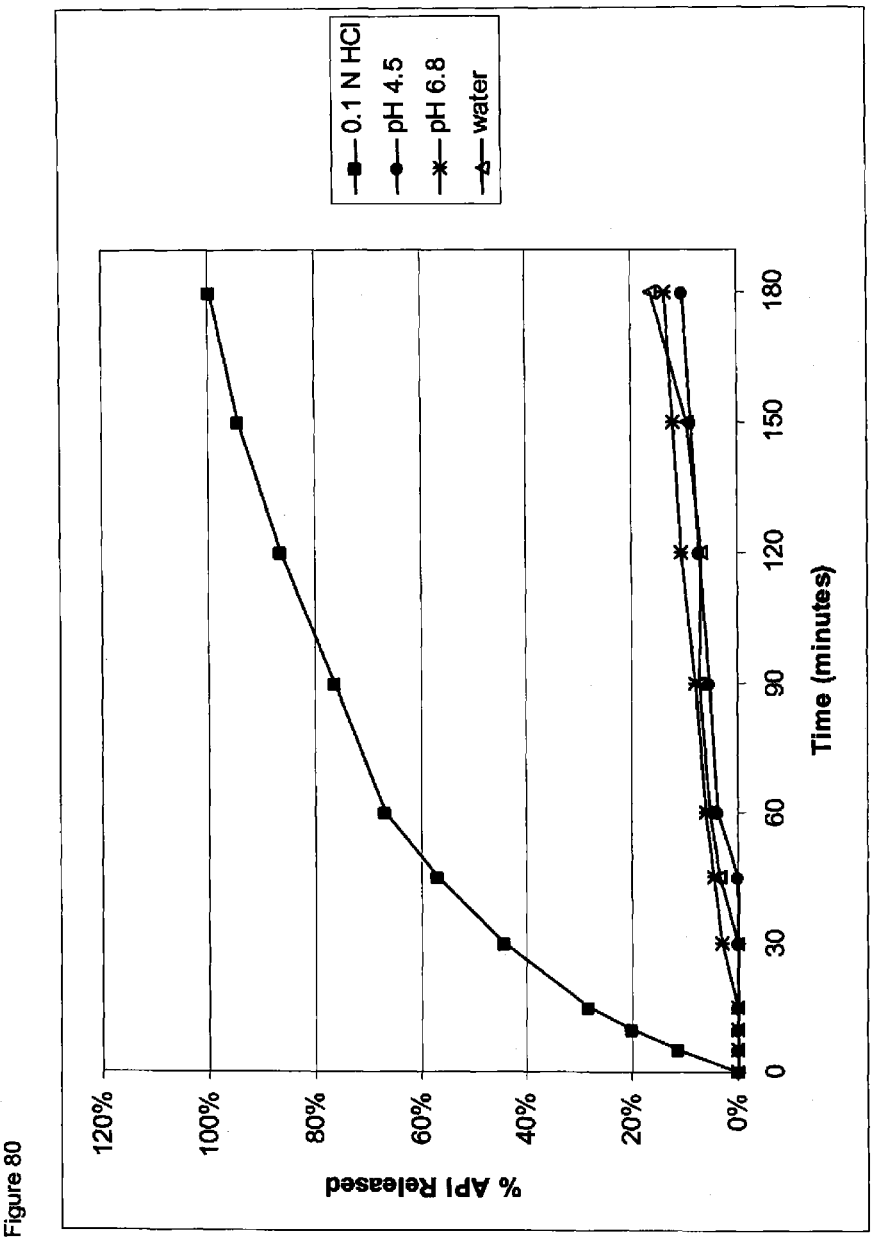
FIG. 80 is a graphical representation of the pH dependent dissolution profiles of amorphous d-methylphenidate mono-triethylammonium pamoate, 1:1:1 salt.
Figure 81:
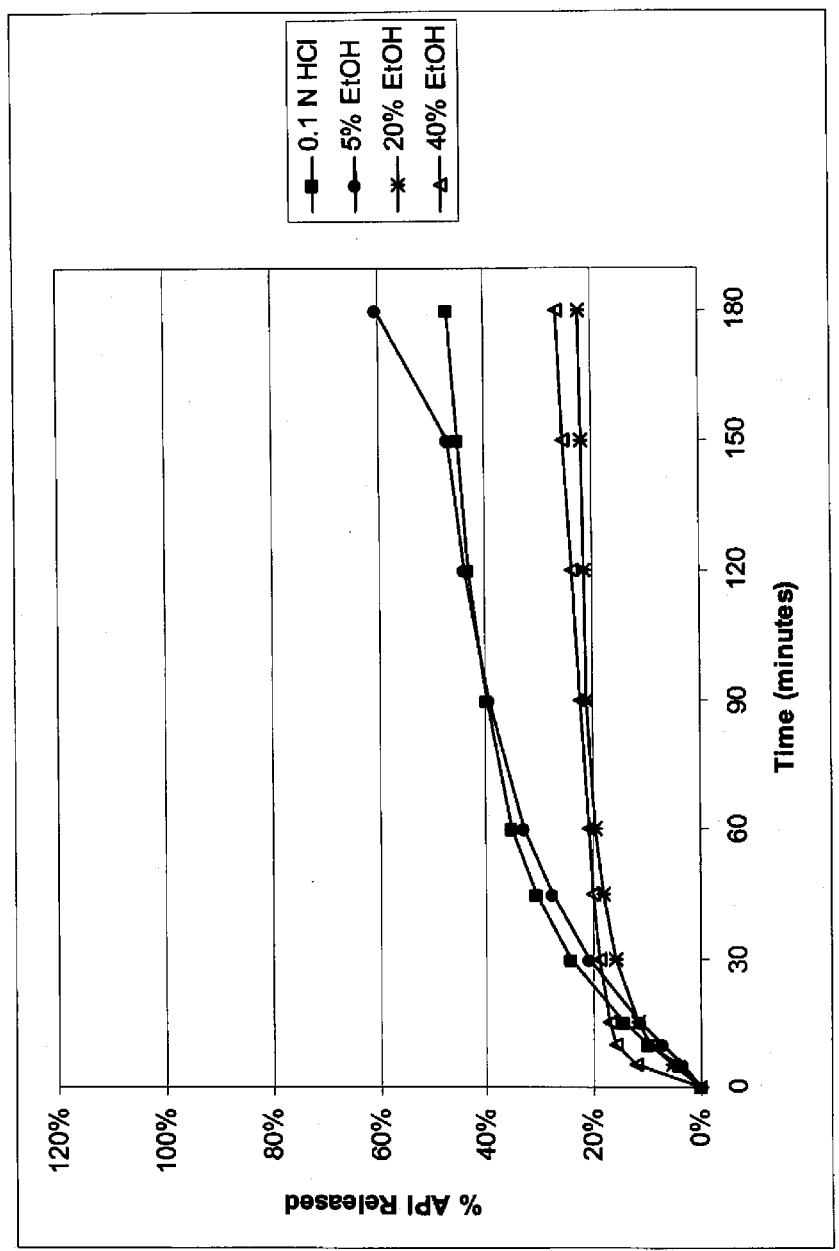
FIG. 81 is a graphical representation of the dissolution profiles of amorphous d-methylphenidate mono-triethylammonium pamoate, 1:1:1 salt under acidic conditions as a function of ethanol concentration.

According to the Merck Index, $14^{th}$ Edition, ©2006, methylphenidate hydrochloride, imipramine hydrochloride and hydrocodone hydrochloride are each freely soluble in water. Therefore, as the bis-functional organic acid salts (or the mixed salt analogues containing a salt-inclusive dissolution modifier) are subjected to the gastric condition of 0.1 N HCl, it would be reasonably expected that appreciable, if not complete dissolution, would occur due to in situ formation of the hydrochloride salt. Clearly, this does not occur by a straightforward acid/base chemical dissolution mechanism and the addition of salt-inclusive dissolution modifiers can be employed to accelerate or retard the pH and dose dumping dissolution profiles. In the specific instances herein, particularly with the AD(H)D drug methylphenidate, preferred embodiments for abuse-deterrent drug substance are distributed equally between polymorphic d-methylphenidate pamoate (2:1) salt (FIGS. 34/35) or amorphous d-methylphenidate triethylammonium pamoate (1:1:1) salt (FIGS. 80/81). Each exemplar provided a reasonable pH dissolution profile while not exhibiting any appreciable susceptibility to dose dumping in the presence of ethanol.

A particular aspect of the present invention is the ability to impart distinct properties to the drug substance. The drug product may have a single drug substance or a combination of drug substances. In one embodiment the drug product comprises a drug substance which exhibits rapid release and a drug substance which exhibits slow release. In particular, the drug product can comprise a rapid release drug substance and a slower release drug substance wherein each drug substance is abuse deterrent. The drug product can be formulated in different commercial presentations where, for example, one dosage presentation comprises a rapid release drug substance and another dosage presentation comprises a slow release drug substance. Alternatively, the drug product may comprise both the rapid release drug substance and the slow release drug substance for administration in a single dose.

The process of administering pharmaceuticals for AD(H)D patients involves the initial procedure for determining effective dose. A medical professional typically makes an initial determination of dose based on a quantitative, or qualitative analysis of the severity of the disorder and physical characteristics of the patient such as weight. A drug product is then prescribed wherein the drug product comprises a suitable drug substance, preferably, in a rapid release form. The severity of the disorder is then redetermined or the appearance of side effects is determined either qualitatively or by quantitative methods such as blood analysis for drug substance levels or side effects. If necessary, a subsequent drug product is prescribed, again in a rapid release formulation and the redetermination is repeated. This process is typically repeated until the medical professional considers the dose to be appropriate. Once an appropriate dose is determined, a drug product is prescribed wherein the appropriate drug substance is released with a slow release profile thereby maintaining the drug at the appropriate level for an extended period.

In the present invention a drug product can be prescribed and administered in a manner wherein proper administration provides a therapeutic effect and the function of the API is realized. With a different manner of administration (in other words, a non-therapeutic administration) the API does not enter the bloodstream in an amount sufficient to be active. To be effective the API must be bio-available. For the purposes of the present invention, one method of establishing a compound's bio-availability is by determining the percentage of weight API recovered from an aqueous solution at a pH representative of the method of administration described herein. For the purposes of the present invention a compound is considered to be abuse-deterrent when at least 85 wt % of the compound is recovered from an aqueous solution at a pH representative of the method of non-therapeutic administration. If, for example, 85 weight percent or more of a drug compound is recovered from a solution at a pH of 4-9, pH 7 for example, the material is considered to be bio-unavailable at a mucosal membrane and is considered non-permeable at the mucosal membrane and the compound exhibits prophylactic properties. If, for example, less than 85 weight percent of a drug compound is recovered from a solution at a pH of less than 4 (pH 1 for example), the material is considered to be effective and bio-available under oral administration and is considered permeable in, for example, the gastrointestinal tract due to the release of the API at the pH of the gastrointestinal tract.

A particularly preferred embodiment and method of administering the amine-containing pharmaceutically active compound is by oral dose. The oral dose is prepared by first preparing an organic acid addition salt of the active compound. The organic acid addition salt is then formulated into a dosage presentation to provide an oral dose drug product. The formulated product containing the drug substance is also composed of ingredients (excipients) optionally selected from the group, but not limited to, binders, fillers, flow enhancers, surfactants, disintegrants, buffers, and the like; these are typically employed in the art and found in the "Handbook of Pharmaceutical Excipients", Rowe, Sheskey and Owen (Editors), Fifth Edition, 2006, Pharmaceutical Press (publishers). When the oral dose is ingested, the organic salt dissociates under physiological conditions. The organic acid portion of the amine-containing organic acid addition salt forms the insoluble (organic) acid while the active compound is liberated and becomes bio-available. Efforts to directly isolate the active compound from the oral dose would be thwarted as described herein.

A common technique for de-formulating drug products, particularly for illicit use, is to isolate the active ingredient by organic phase extraction and separation from an aqueous environment. The technology disclosed herein interrupts this extraction process.

In an embodiment of the present invention, the controlled substance is an amine-containing organic acid addition salt which does not release in the pH window of about 4 to about 9. At a pH of less than about 4, the subject organic salts become protonated with the concomitant precipitation or gelling of the organic acid. At pH greater than about 9, the addition salt is soluble yet it is quite difficult to effect separation of the organic acid component and the active amine by organic solvent extraction.

The drug substances of the present invention are prepared by either a sequential reaction wherein amines (or amine salts) are added sequentially to a bis-functional organic acid (or organic acid salt) or by a displacement reaction wherein a bis-functional organic acid derivative is reacted with amines and one amine is displaced thereby forming a mixed amine (salt) compound.

By way of example, the initial reaction is at least one amine containing compound with a bis-functional organic acid defined by:

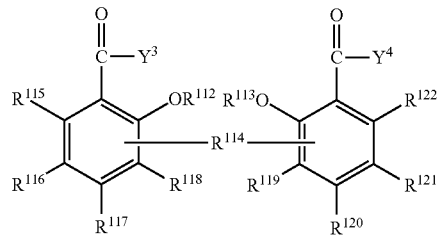

wherein $Y^3$ and $Y^4$ are carboxylate salts or lower molecular weight esters independently selected from groups capable of displacement with at least one of said pharmaceutically active compound and said amine to form the drug substance salt or mixed salt (when an amine dissolution modifier is employed); $R^{112}$ and $R^{113}$ are independently selected from hydrogen, alkyl of 1-6 carbons, alkylacyl of 1-8 carbons or arylacyl of 7-15 carbons;

$R^{114}$ will replace one of $R^{115}$, $R^{116}$, $R^{117}$ or $R^{118}$ and one of $R^{119}$, $R^{120}$, $R^{121}$ or $R^{122}$ and is an alkyl or branched alkyl of 1-10 carbons, aryl, arylalkyl of 7-15 carbons and wherein $R^{114}$ may include at least one optically active carbon; and $R^{115}$, $R^{116}$, $R^{117}$, $R^{118}$, $R^{119}$, $R^{120}$, $R^{121}$ and $R^{122}$, are independently selected from hydrogen, alkyl of 1-6 carbons, and wherein adjacent groups may be taken together to form a cyclic alkyl or cyclic aryl moiety. In one embodiment the reaction employs about a mole of amine per mole of the bis-functional organic acid derivative thereby forming a 1:1 conjugate. More preferably, the amine and bis-functional acid are in a molar ratio of about 0.9 to 1.1. In another embodiment an excess of amine is added, or at least about 2 moles of amine per mole of bis-functional organic acid, to form a 2:1 compound. In either case a second amine is added whereby either the second group on the bis-functional organic acid derivative is reacted, for the 1:1 conjugate, or a previously reacted amine is displaced. The first amine or second amine can be a pharmaceutically active compound or a dissolution modifying amine.

Throughout the specification terms of art such as alkyl, aryl, alkylaryl, cyclic alkyl, cyclic aryl, alkylacyl, arylacyl, benzyl, acetyl and similar terms are intended to refer to unsubstituted or substituted moieties.

EXPERIMENTAL METHODS

Differential Scanning Calorimetry (DSC)

Samples were evaluated using a Differential Scanning calorimeter from TA Instruments (DSC 2010). Prior to analysis of samples, a single-point calibration of the TA Instruments DSC 2010 Differential Scanning calorimeter (DSC 2010) with the element indium as calibration standard (156.6±0.25° C.) was completed.

Infrared Spectroscopy (FTIR)

IR Spectra were obtained in a KBr disc using a Perkin Elmer Spectrum BX Fourier Transform Infrared Spectrophotometer. For materials existing as oils, spectra were obtained neat (NaCl).

Powder X-Ray Diffraction (PXRD)

Powder X-Ray diffraction patterns were acquired on a Scintag XDS2000 powder diffractometer using a copper source and a germanium detector. Polymorphic materials are defined herein as having at least one polymorph which is distinguishable by powder x-ray diffraction.

HPLC

HPLC analyses were performed on a Waters 2695 HPLC system equipped with a Waters 2996 photo diode array detector.

$^1$H NMR Spectroscopy $^1$H NMR spectra were obtained on at least a 300 MHz Varian Gemini 2000 spectrometer. Spectra were referenced to solvent (DMSO-$d_6$) or to tetramethylsilane (TMS; δ=0.00 ppm).

Example 1

Synthesis of Racemic-Methylphenidate Free Base

To a 200 mL beaker was charged 10.0 g (37.1 mmol) racemic-methylphenidate hydrochloride and 135 mL water. About 3.39 g (96.8 mmol) ammonium hydroxide was then added to bring the pH to approximately 9 upon which an oily semi-solid formed. The product was extracted with three 100 mL portions of ethyl acetate, the combined organic layers dried over sodium sulfate, filtered and concentrated under reduced pressure at about 40° C. to provide 8.2 g of a clear, colorless viscous oil (95% yield). The IR spectrum of the oil was consistent with the intended product.

Example 2

Synthesis of Amorphous Racemic-Methylphenidate Pamoate, (2:1) Salt

Figure 2:
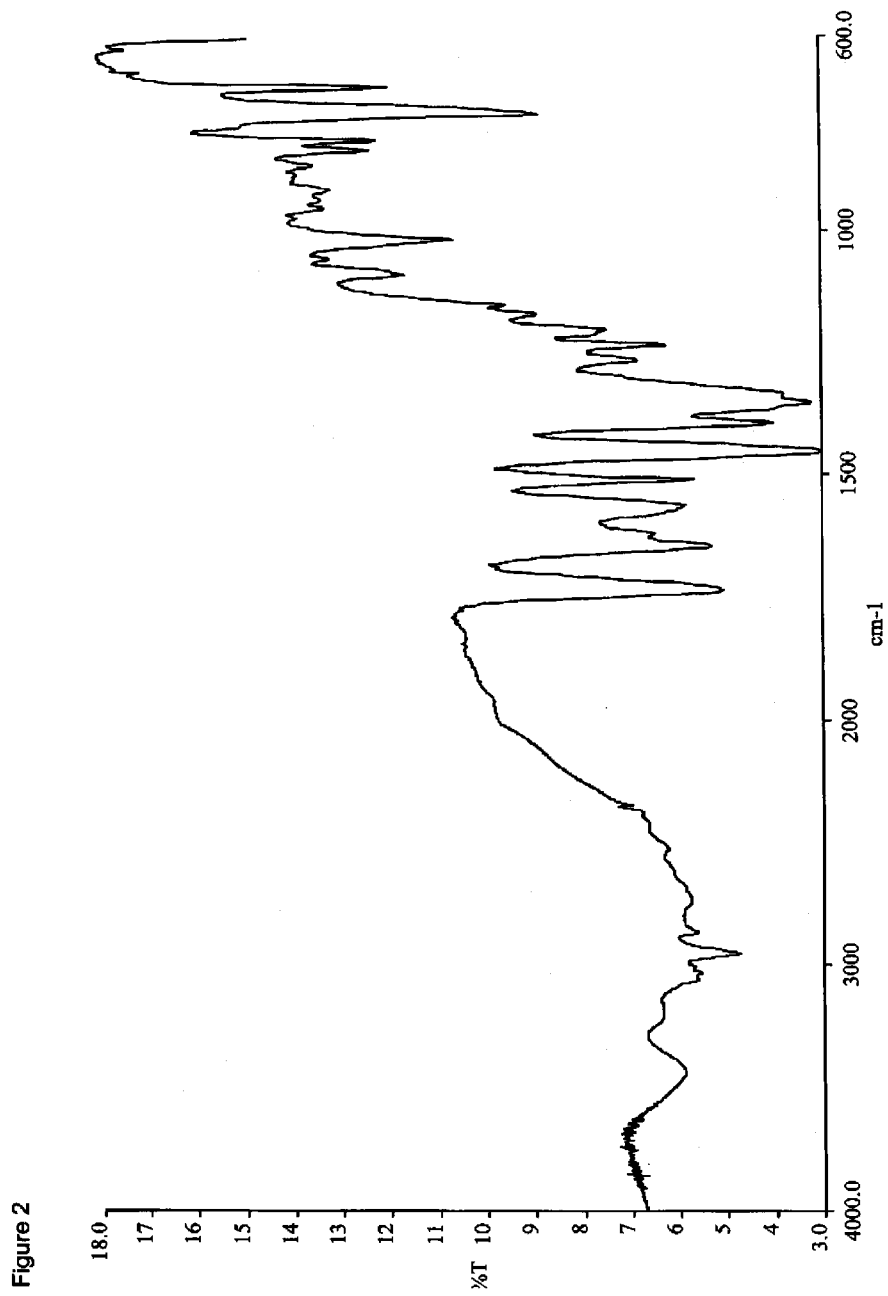
FIG. 2 is the Fourier Transform Infrared (FTIR) spectrum of amorphous racemic-methylphenidate pamoate.
Figure 3:
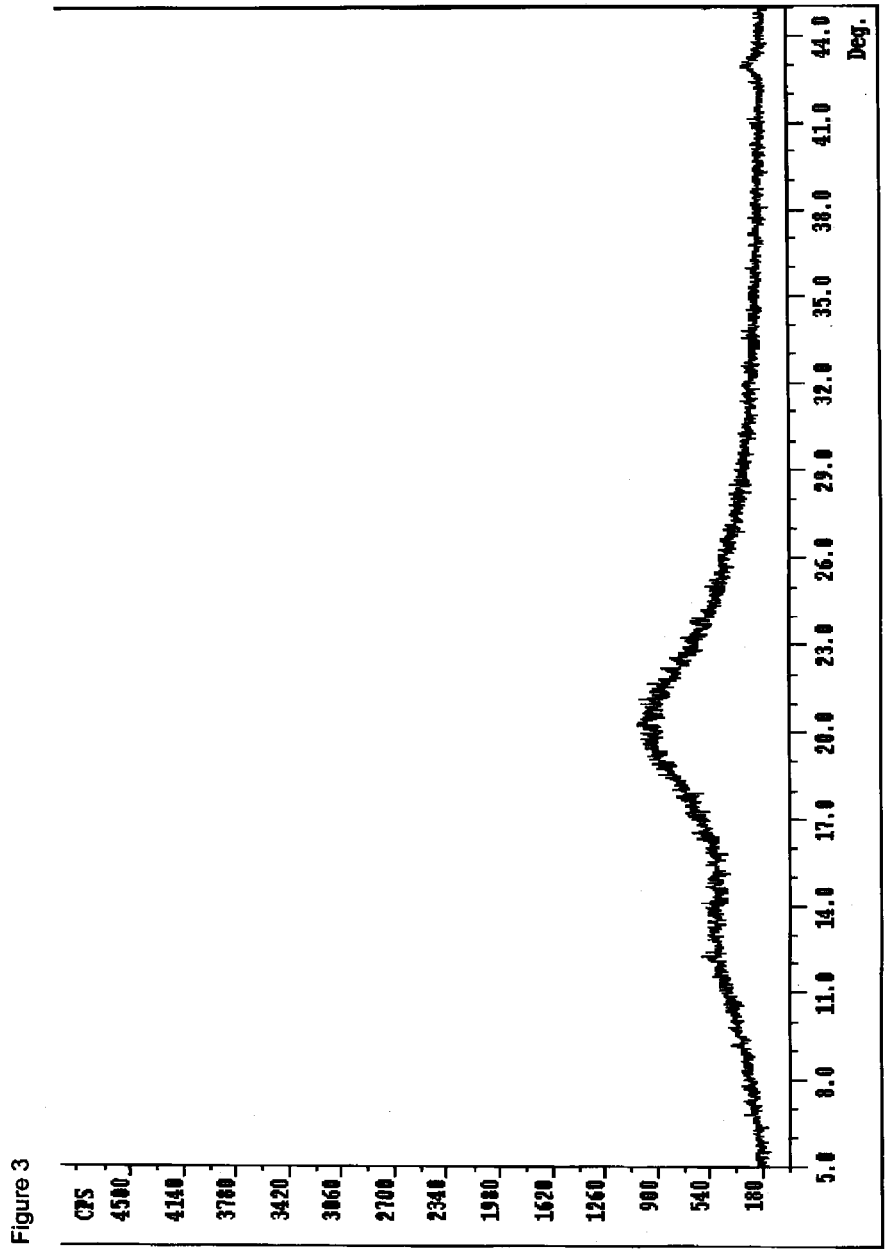
FIG. 3 is the powder X-ray diffraction (PXRD) diffractogram of amorphous racemic-methylphenidate pamoate.

To a 100 mL round bottom flask equipped with a magnetic stir bar, thermowell and nitrogen inlet was charged about 1.65 g (3.7 mmol) disodium pamoate (3.2% moisture) and 25 mL water. The pH was adjusted to 9-9.5 (pH paper) using 0.1 N sodium hydroxide. A solution of 2.0 g (7.4 mmol) racemic-methylphenidate hydrochloride in 37 mL water was prepared (pH 4-4.5 (pH paper)) and added to the above disodium pamoate solution over three minutes. As the resulting solution became a thick slurry; 20 mL more water was added and stirred at ambient temperature for 1.5 hours. The solids were collected by filtration (medium fritted glass filter) and dried under vacuum overnight at ambient temperature to provide 2.81 g (89%) of an off-white solid (1.42% water) which was analyzed by DSC, FTIR (FIG. 2), and PXRD (FIG. 3). PXRD analysis indicated the drug substance to be amorphous and HPLC analysis indicated a 1.8/1 ratio of methylphenidate/pamoate. The NMR results were consistent with the assigned structure. The DSC is provided in FIG. 1 wherein an endothermic phase change of at least 70 J/gram is observed at greater than 200° C.

Example 3

Synthesis of Polymorphic Racemic-Methylphenidate Pamoate, (2:1) Salt

Figure 4:
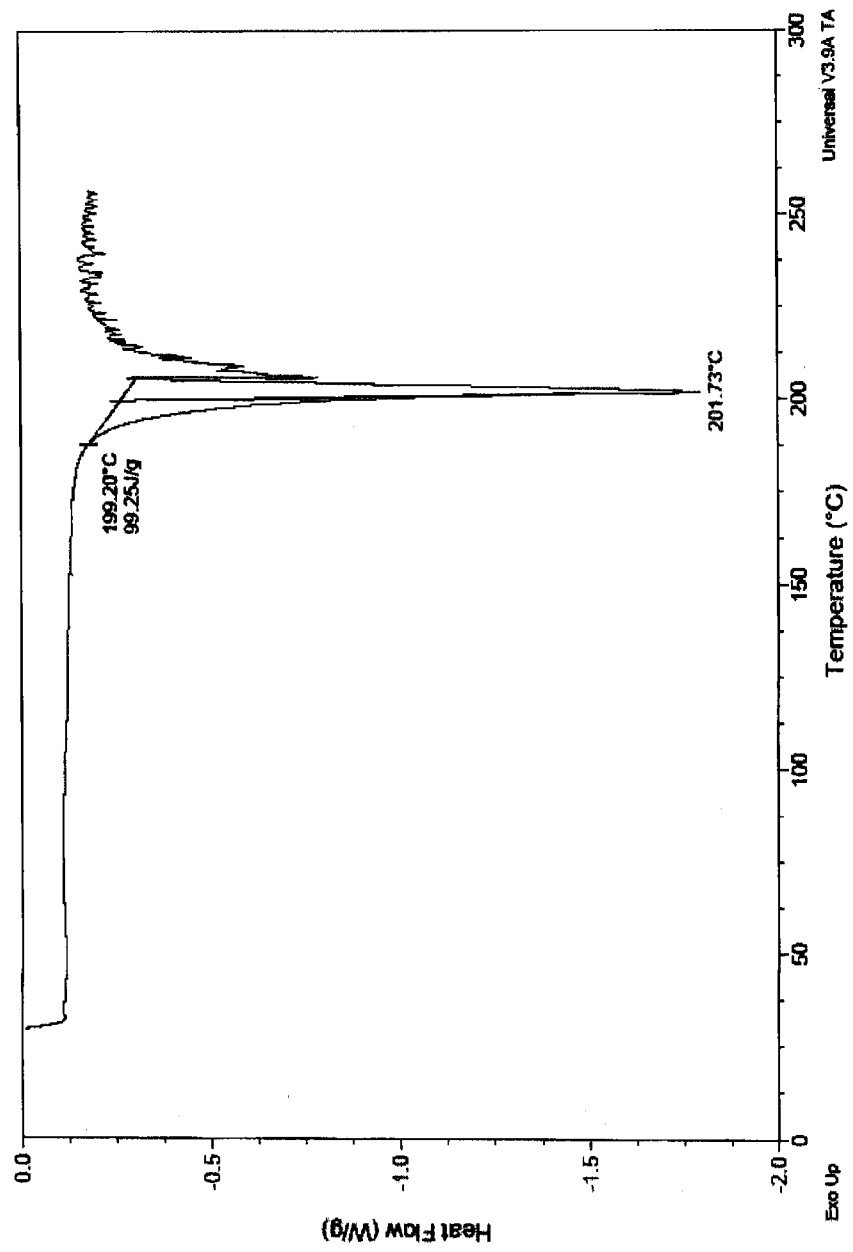
FIG. 4 is the differential scanning calorimetry (DSC) thermogram of polymorphic racemic-methylphenidate pamoate.

To a 100 mL one neck round bottom flask equipped with a magnetic stir bar, thermowell and nitrogen inlet was charged 2.20 g (9.43 mmol) racemic-methylphenidate. As solvent, 17 mL dimethylformamide (DMF) was then added which produced a clear colorless solution. Pamoic acid (1.83 g; 4.71 mmol; 0.36% moisture) was subsequently added over thirty seconds which produced a clear yellow solution. The solution was stirred under nitrogen for 3 hours at ambient temperature followed by filtration through a medium fritted glass filter to remove any particulates. The filtrate was transferred to a 250 mL one-neck round bottom flask and 54 g isopropanol was added over one minute. The solution was concentrated under reduced pressure at 100° C. to yield 4.2 g of a residue which was subsequently triturated in 24 g isopropanol and the yellow solids collected by filtration (medium fritted glass filter). The product was dried overnight under vacuum at ambient temperature to provide 3.7 g (92%) of a yellow solid (0.36% water) which was analyzed by DSC, FTIR (FIG. 5), and PXRD (FIG. 6). An HPLC analysis indicated a 1.8/1 ratio of methylphenidate/pamoate which was corroborated by NMR. The PXRD analysis indicated the drug substance salt was crystalline. The DSC is provided in FIG. 4 wherein an endotherm of at least 75 J/gram is illustrated above 200° C.

Example 4

Synthesis of Polymorphic Racemic-Methylphenidate Xinafoate

Figure 7:
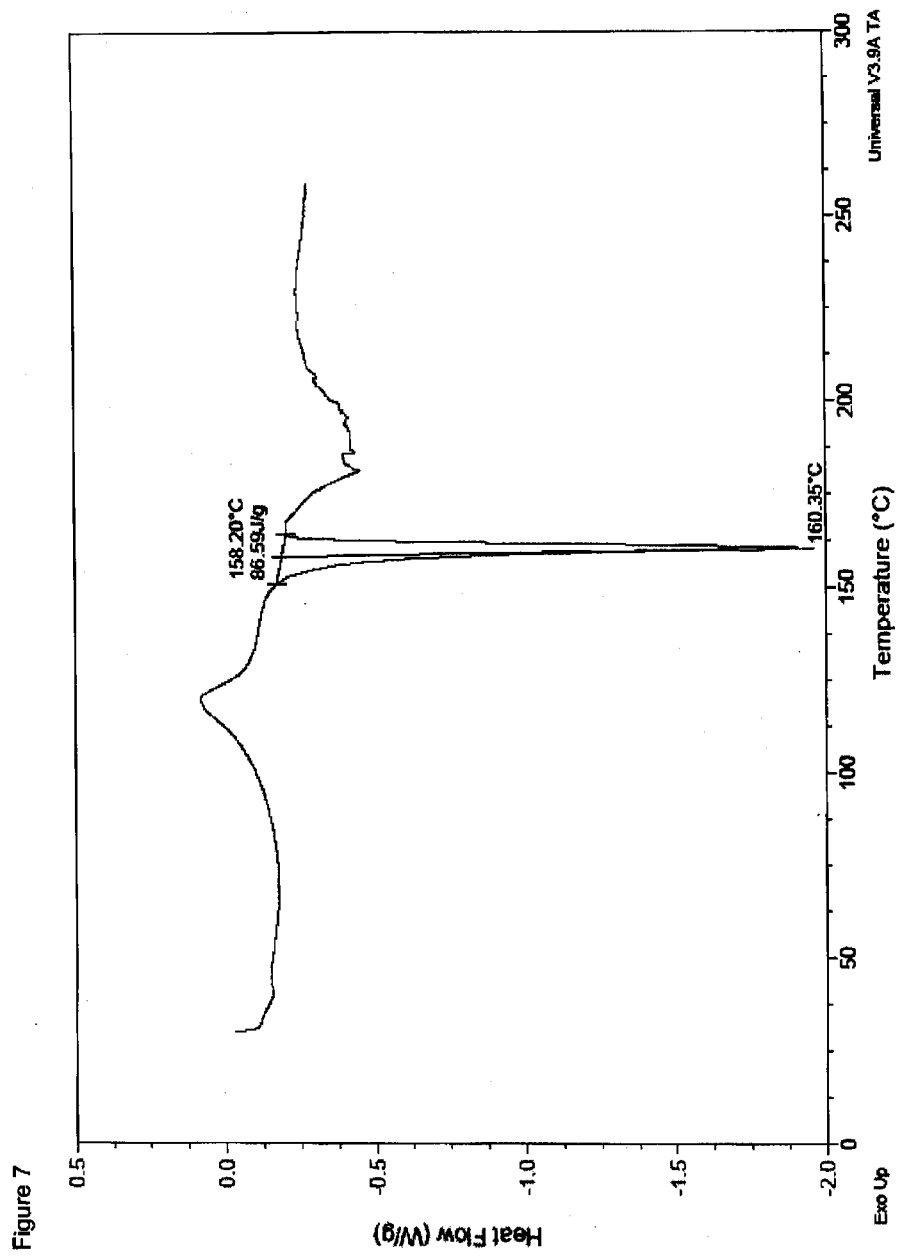
FIG. 7 is the differential scanning calorimetry (DSC) thermogram of polymorphic racemic-methylphenidate xinafoate.

To a 100 mL round bottom flask equipped with a magnetic stir bar, thermowell and nitrogen inlet was charged 1.39 g (7.4 mmol) BON acid (beta-oxy-naphthoic acid) and 13 mL water. Solid sodium hydroxide (0.296 g; 7.4 mmol) was added and the solution heated to 50° C. to dissolve all solids. After cooling to ambient temperature, the pH was adjusted to 9.5 with 0.1 N sodium hydroxide. A solution of 2.0 g (7.4 mmol) racemic-methylphenidate hydrochloride in 37 mL water was prepared (pH 4-4.5; pH paper) and added to the above BON acid solution at ambient temperature upon which a sticky gum formed. More water was added (20 mL) to facilitate stirring. The aqueous mixture was carefully decanted away from the gum, more water added to the residue, the mixture stirred for 5 minutes, again the water decanted away from the gum, and the residue dried under vacuum to provide 1.5 g (48%) of a tan crunchy solid (2.09% moisture) which was analyzed by DSC, FTIR (FIG. 8), and PXRD (FIG. 9). HPLC analysis confirmed the 1:1 stoichiometric relationship between methylphenidate and the BON acid moiety (xinafoate) and PXRD indicated the product to be crystalline. The DSC is provided in FIG. 7 wherein an endotherm of at least 75 J/gram is illustrated above 155° C.

Example 5

Synthesis of d-Methylphenidate Free Base

To a 200 mL beaker was charged 10.0 g (37.1 mmol) racemic-methylphenidate hydrochloride and 135 mL water. Ammonium hydroxide (3.40 g; 96.8 mmol) was then added to bring the pH to approximately 9 upon which an oily semi-solid formed. The product was extracted with three 100 mL portions of ethyl acetate, the combined organic layers were dried over sodium sulfate, filtered and concentrated under reduce pressure at 40° C. to provide 8.5 g of a clear, colorless viscous oil (98% yield). The free base was characterized by FTIR and found to be consistent with the anticipated structure Example 6

Synthesis of Amorphous d-Methylphenidate Pamoate, (2:1) Salt

Figure 10:
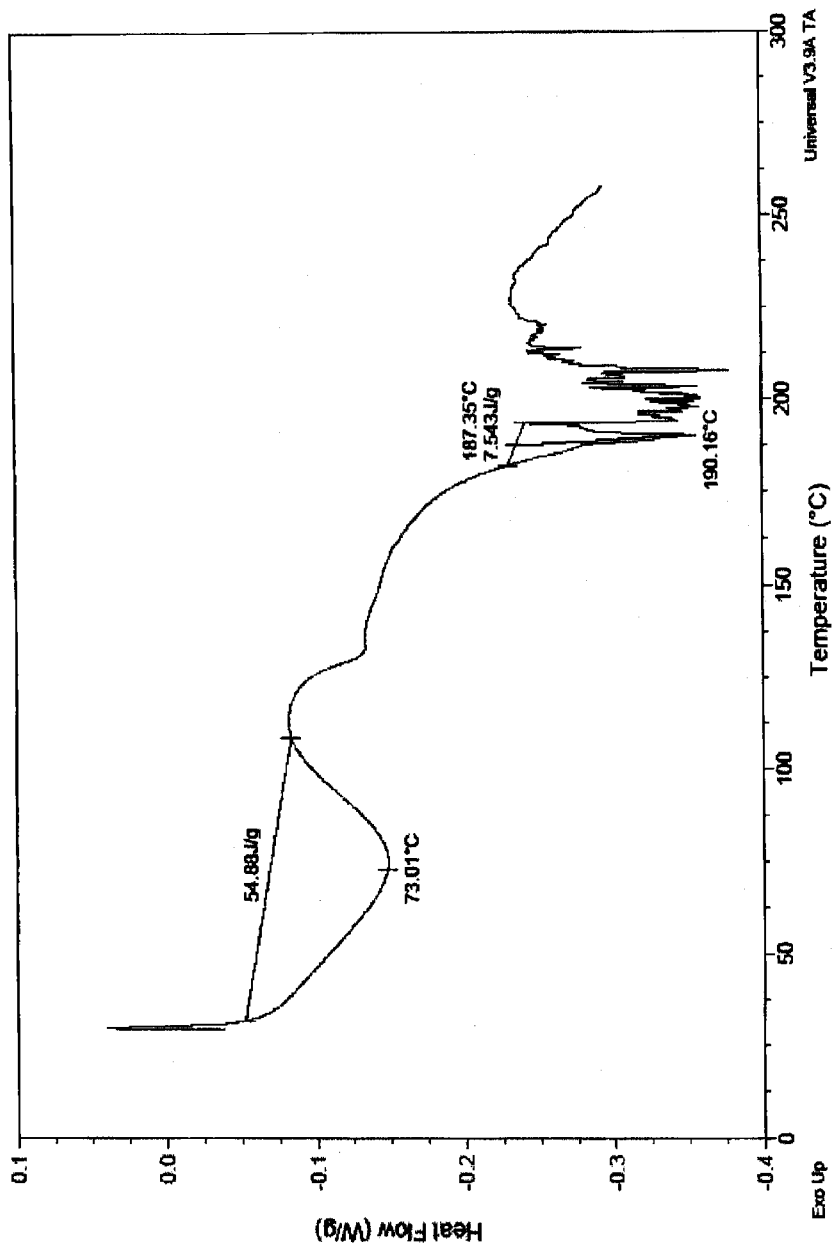
FIG. 10 is the differential scanning calorimetry (DSC) thermogram of amorphous d-methylphenidate pamoate.

To a 250 mL round bottom flask equipped with a magnetic stir bar, thermowell and nitrogen inlet was charged 1.65 g (3.7 mmol) disodium pamoate (3.16% moisture) and 22 mL water. The pH of the solution was adjusted to 9-9.5 (pH paper) with 0.1 N sodium hydroxide. A solution of 2.0 g (7.4 mmol) d-methylphenidate hydrochloride in 37 mL water was prepared (pH 4-4.5; pH paper) and added over two minutes to the disodium pamoate solution. As the resulting mixture became a thick slurry; 37 mL more water was added and stirring continued overnight at ambient temperature. The solids were collected by filtration (medium fritted glass filter) and dried under vacuum overnight at ambient temperature to provide 2.7 g (85%) of an off-white solid (1.44% water) which was analyzed by DSC (FIG. 10), FTIR (FIG. 11), and PXRD (FIG. 12). PXRD analysis confirmed the product to be amorphous. HPLC analysis indicated a 1.9/1 ratio of d-methylphenidate/pamoate. The DSC is provided in FIG. 10 wherein an endothermic phase change of at least 45 J/gram is observed at greater than 70° C. and an endothermic phase change of at least 30 J/gram at greater than 180° C. is observed.

Example 7

Synthesis of Polymorphic d-Methylphenidate Pamoate, (2:1) Salt

Figure 13:
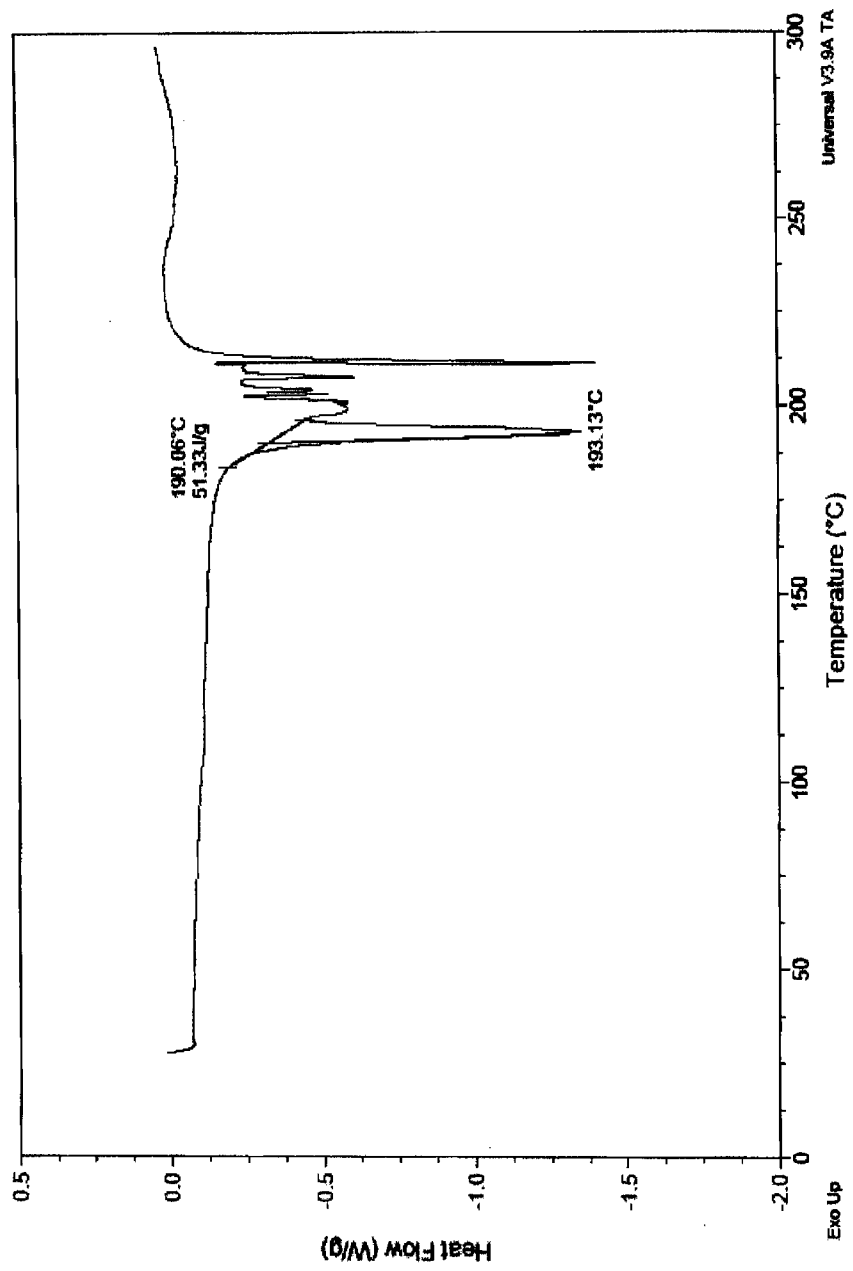
FIG. 13 is the differential scanning calorimetry (DSC) thermogram of polymorphic d-methylphenidate pamoate.

To a 100 mL round bottom flask equipped with a magnetic stir bar, thermowell and nitrogen inlet was charged 0.41 g (0.925 mmol) disodium pamoate (3.16% moisture) and 10 mL water. A solution of 0.5 g (1.85 mmol) d-methylphenidate hydrochloride in 10 mL water was prepared and added to the above disodium pamoate solution over a thirty minute period under a nitrogen atmosphere. The solution was then heated from ambient temperature to 95° C. and held on temperature for 5 hours under nitrogen upon which the solids turned to a yellow gum. Heating was ceased and the mixture allowed to slowly cool back to ambient temperature overnight and continuously under a nitrogen atmosphere. The solids were collected by filtration (medium fritted glass filter) and dried overnight under vacuum at ambient temperature to provide 0.7 g (89%) of a yellow solid (0.51% water) which was analyzed by DSC, HPLC, FTIR (FIG. 14), and PXRD (FIG. 15). PXRD showed the product to be crystalline. HPLC showed a 1.7/1 ratio of d-methylphenidate/pamoate. The DSC is provided in FIG. 13 wherein an endothermic phase change of at least 35 J/gram is observed at greater than 185° C.

Example 8

Synthesis of Amorphous d-Methylphenidate Xinafoate

Figure 16:
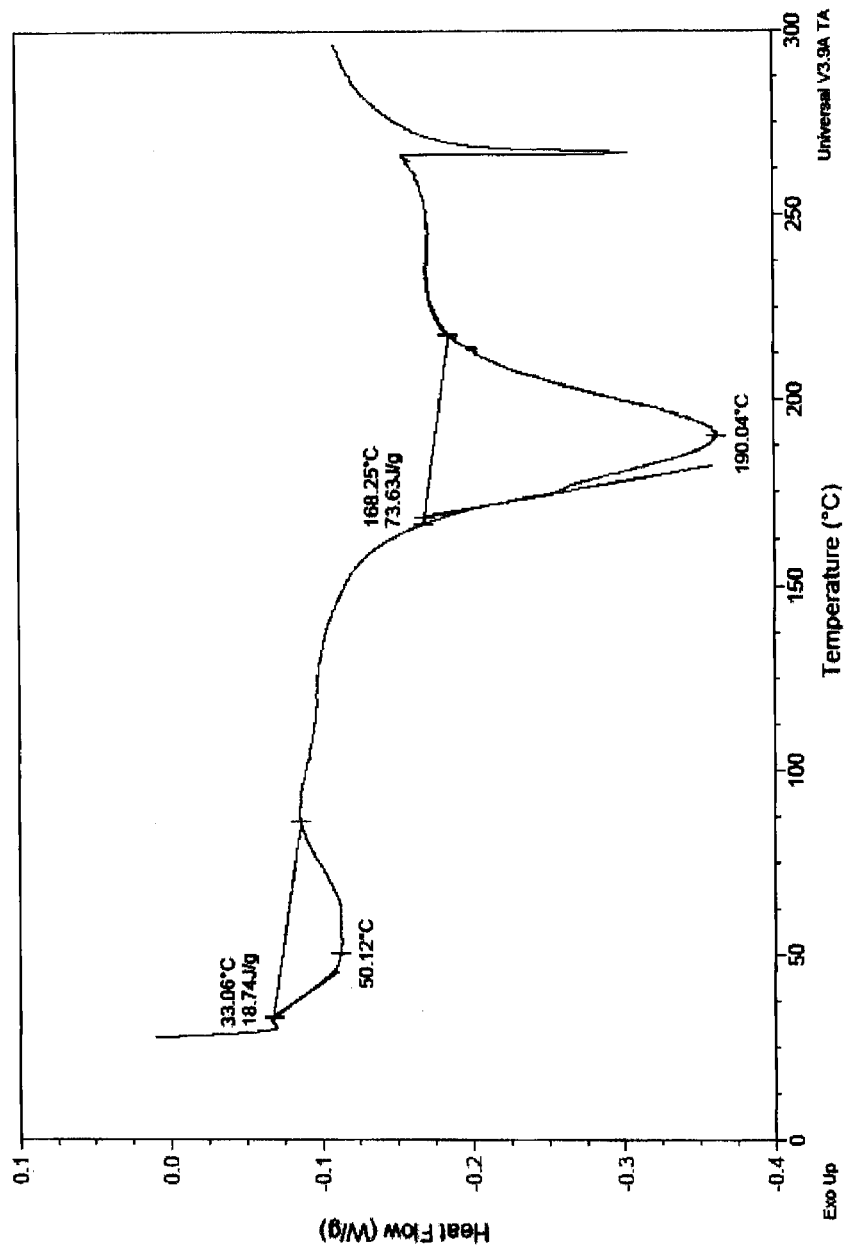
FIG. 16 is the differential scanning calorimetry (DSC) thermogram of amorphous d-methylphenidate xinafoate.

To a 100 mL round bottom flask equipped with a magnetic stir bar, thermowell and nitrogen inlet was charged 0.695 g (3.7 mmol) BON Acid (beta-oxy-naphthoic acid) and 10 mL water. Solid sodium hydroxide (0.148 g; 3.7 mmol) was added and the solution heated to 50° C. to dissolve all solids. After cooling to ambient temperature, the pH was adjusted to 9-9.5 with 0.1 N sodium hydroxide. A solution of 1.0 g (3.7 mmol) d-methylphenidate hydrochloride in 20 mL water was prepared (pH 4-4.5) and added to the above BON Acid solution at ambient temperature over 15 minutes upon which a sticky gum formed. The mixture was heated to 95° C. for 3 hours under a nitrogen atmosphere with oil formation apparent. After the hold period, the mixture was cooled to ambient temperature and the aqueous liquid was carefully decanted from the gum. More water added to the gum, stirring continued for 5 minutes, and again, the mixture was decanted. The residual gum was dried under vacuum to provide 1.0 g (64%) of a light yellow solid which was mostly brittle yet retained a small portion of the gummy solid, (2.8% moisture). The solid was analyzed by DSC, HPLC, FTIR (FIG. 17), and PXRD (FIG. 18). The PXRD analysis confirmed the drug substance was amorphous and an HPLC analysis confirmed the 1:1 stoichiometric relationship of d-methylphenidate and xinafoate moiety. The DSC is provided in FIG. 16 wherein an endothermic phase change of at least 10 J/gram is observed at greater than 45° C. and an endothermic phase change of at least 50 J/gram at greater than 160° C. is observed.

Example 9

Synthesis of Dextro-Amphetamine Free Base

To a 200 mL beaker equipped with a magnetic stir bar was charged 5.0 g (13.6 mmol) dextro-amphetamine sulfate and 50 mL water to dissolve the solid. Ammonium hydroxide (2.5 g; 70.7 mmol) was then added and the solution remained clear and colorless. The solution was subsequently extracted with three 50 mL portions of ethyl acetate and the combined organic layers were dried over sodium sulfate, filtered and concentrated under vacuum at 50° C. to provide 3.4 g (92%) of a clear colorless oil. The FTIR spectrum of the free base was consistent with the intended structure.

Example 10

Synthesis of Amorphous Dextro-Amphetamine Pamoate, (2:1) Salt

Figure 19:
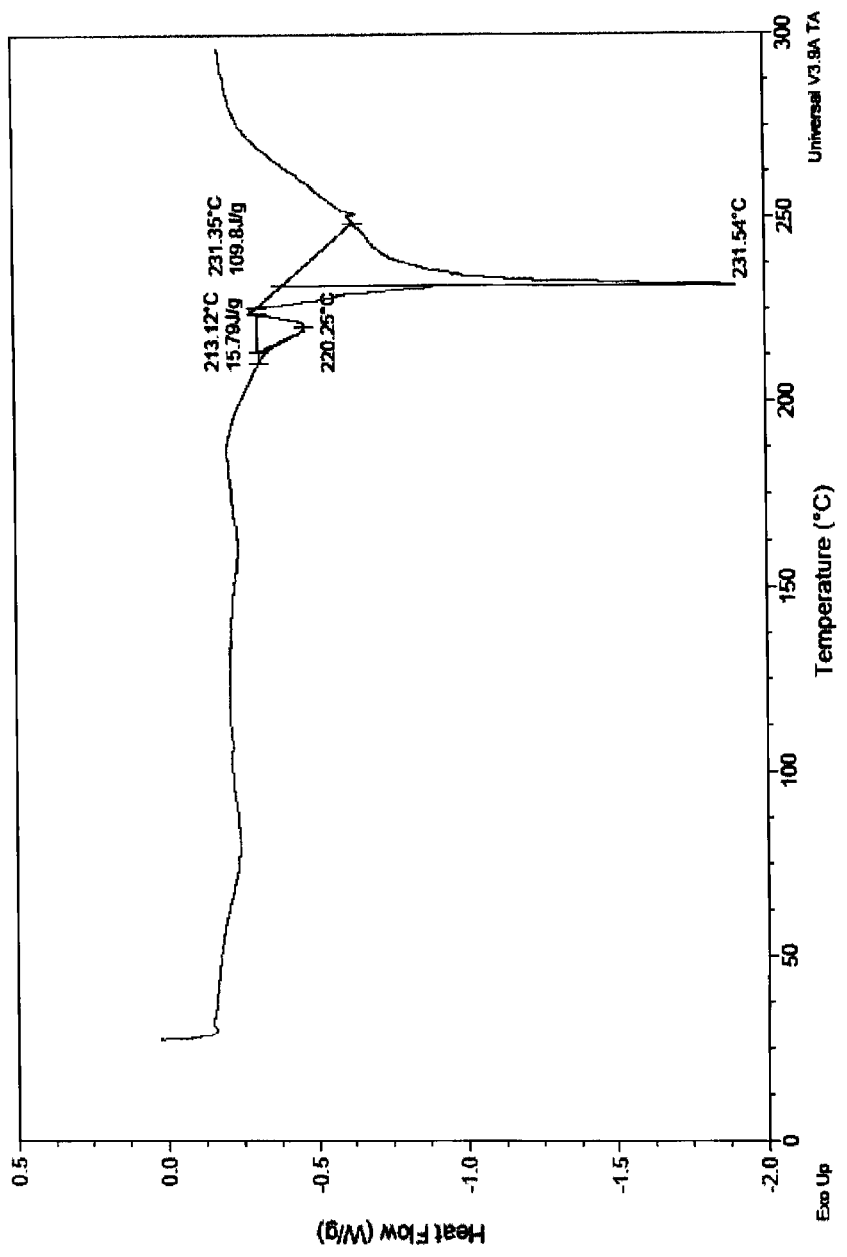
FIG. 19 is the differential scanning calorimetry (DSC) thermogram of amorphous dextro-amphetamine pamoate.

To a 10 mL round bottom flask equipped with a magnetic stir bar, thermowell and nitrogen inlet was charged 1.65 g (3.7 mmol) disodium pamoate (3.16% moisture) and 22 mL water. The pH was adjusted to 9-9.5 with 0.4 g of 0.1 N sodium hydroxide. A solution of dextro-amphetamine hydrochloride in water was prepared (pH 4-4.5) by mixing 1.0 g (7.4 mmol) dextro-amphetamine (free base from Example 9), 2.3 mL water and 1 equivalent (about 7.4 mL of 1N hydrochloric acid) to achieve a pH of about 4. The dextro-amphetamine hydrochloride solution was added to the above disodium pamoate solution over one minute under a slow stream of nitrogen. Solids formed initially but then turned to an intractable sticky gum. The aqueous mixture was carefully decanted, more water added to the residual gum, and stirring resumed for 5 minutes. The water was again decanted and the residual gum dried under vacuum to provide 1.6 g (67%) of a shiny tan crunchy solid (2.8% water) which was analyzed by DSC, HPLC, FTIR (FIG. 20), and PXRD (FIG. 21). PXRD analysis indicated the drug substance to be amorphous. HPLC analysis indicated a 1.7/1 ratio of dextro-amphetamine/pamoate. The DSC is provided in FIG. 19 wherein an endothermic phase change of at least 10 J/gram is observed at greater than 200° C. and an endothermic phase change of at least 75 J/gram at greater than 220° C. is observed.

Example 11

Synthesis of Polymorphic Dextro-Amphetamine Pamoate, (2:1) Salt

Figure 22:
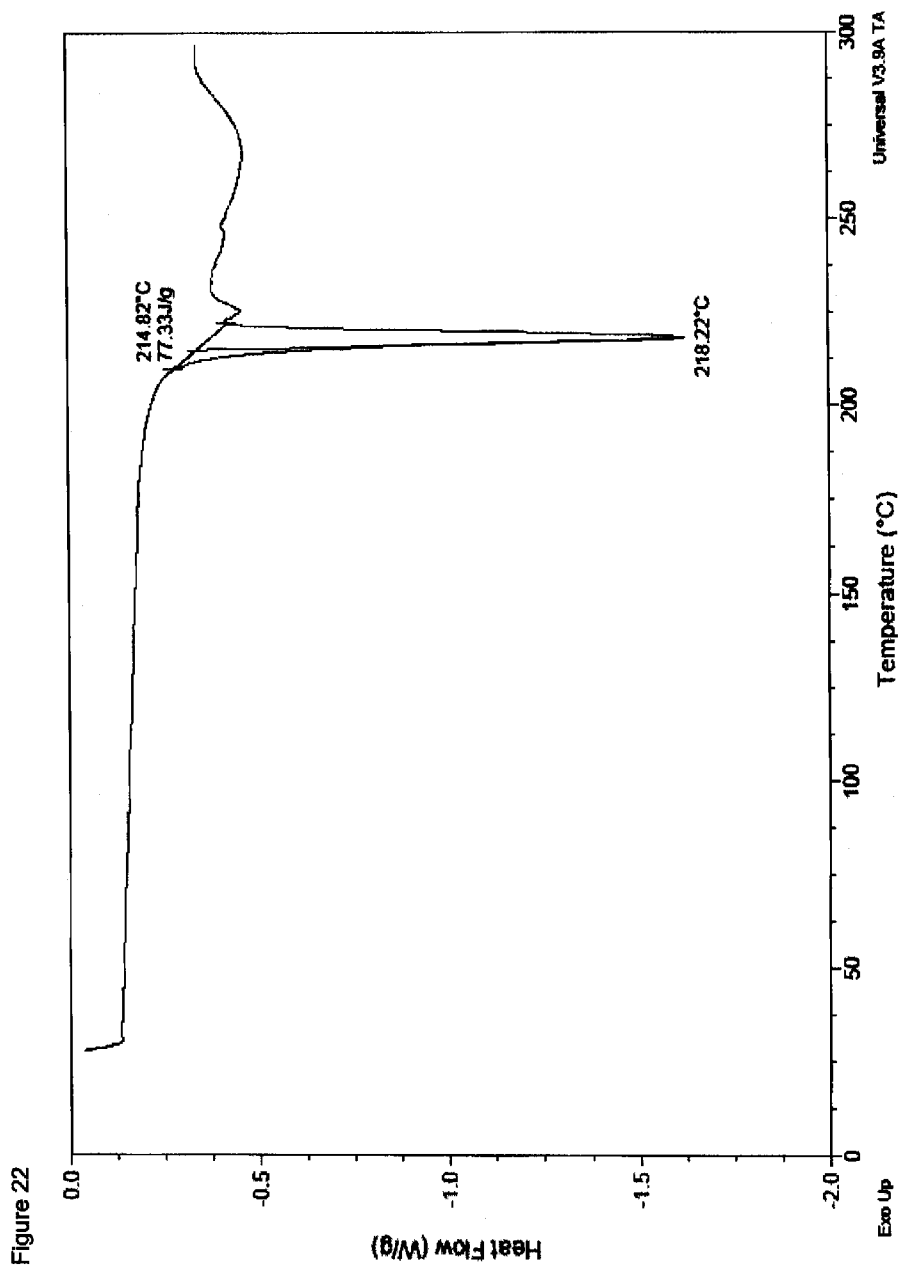
FIG. 22 is the differential scanning calorimetry (DSC) thermogram of polymorphic dextro-amphetamine pamoate.

To a 100 mL round bottom flask equipped with a magnetic stir bar, thermowell and nitrogen inlet was charged 3.32 g (7.74 mmol) disodium pamoate and 40 mL water. A solution of dextro-amphetamine hydrochloride in 40 mL water was prepared in situ by mixing 2.0 g (14.8 mmol) dextro-amphetamine free base, with the water charge and 1 equivalent (14.8 mL) hydrochloric acid (1 N). The dextro-amphetamine hydrochloride was subsequently added to the above disodium pamoate solution over 40 minutes under a slow stream of nitrogen. Free-flowing solids formed upon addition but then later turned to a partial gum. The solution was then heated from ambient temperature to about 46° C. over 50 minutes, then to 70° C. over the next 20 minutes and finally to 88-92° C. over the next 30 minutes and held at this temperature for an additional 2 hours under nitrogen upon which the solids turned to a yellow gummy solid. Heating was ceased and the mixture allowed to slowly cool to ambient temperature over the next 1.5 hours while remaining under a nitrogen atmosphere. Upon cooling, the solid became free flowing and were collected by filtration through a medium fritted funnel, washed with a small portion of water and dried under vacuum to provide 4.38 g (90%) of a yellow solid (0.29% water) which was analyzed by DSC, FTIR (FIG. 23), and PXRD (FIG. 24). The PXRD diffractogram was consistent with a drug substance having polymorphic character. The HPLC chromatogram indicated a 1.8/1 ratio of dextro-amphetamine/pamoate. The DSC is provided in FIG. 22 wherein an endothermic phase change of at least 60 J/gram is observed at greater than 200° C.

Example 12

Synthesis of Polymorphic Dextro-Amphetamine Xinafoate

Figure 25:
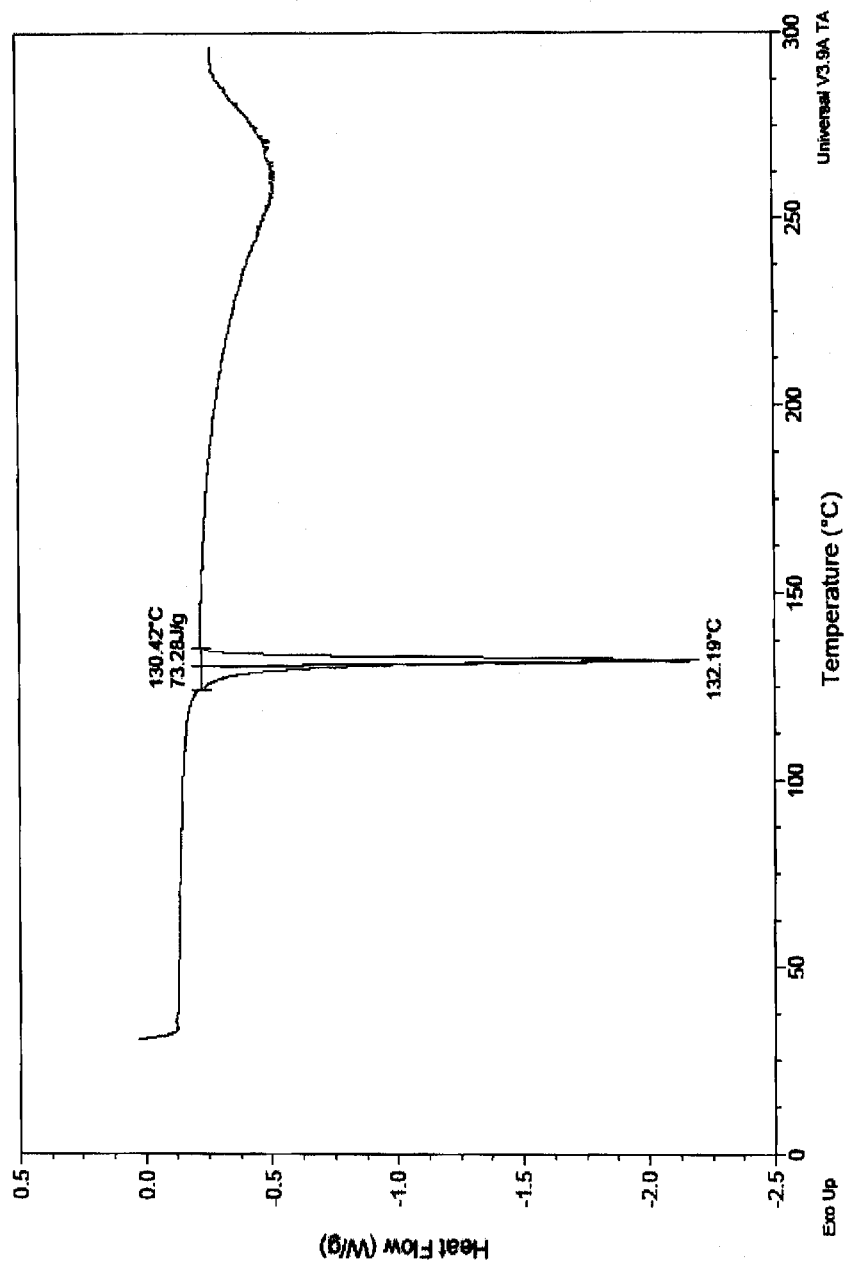
FIG. 25 is the differential scanning calorimetry (DSC) thermogram of polymorphic dextro-amphetamine xinafoate.

To a 100 mL round bottom flask equipped with a magnetic stir bar, thermowell and nitrogen inlet was charged 1.39 g (7.4 mmol) BON Acid (beta-oxy-naphthoic acid) and 13 mL water. Solid sodium hydroxide (0.296 g; 7.4 mmol) was added and the solution heated to 50° C. to dissolve all solids. After cooling to ambient temperature, the pH was adjusted to 9-9.5 with 0.1 N sodium hydroxide. A solution of dextro-amphetamine hydrochloride in water was prepared by mixing 1.0 g (7.4 mmol) dextro-amphetamine free base, 20 mL water and 1 equivalent (about 7.4 mL) hydrochloric acid (1 N). The dextro-amphetamine hydrochloride was added to the above disodium pamoate solution over 5 minutes under a slow stream of nitrogen with a sticky gum initially forming. The solution was stirred for 1 hour during which time the gum turned to a solid. The solids were collected by filtration (medium fritted glass filter), washed with water and dried overnight under vacuum at ambient temperature to provide 1.3 g (54%) of a light-yellow solid (0.06% water) which was analyzed by DSC, FTIR (FIG. 26), and PXRD (FIG. 27). The PXRD diffractogram indicated the polymorphic character of the isolated drug substance. The HPLC chromatogram indicated the 1:1 stoichiometric relationship of dextro-amphetamine and BON Acid (xinafoate) components. The DSC is provided in FIG. 25 wherein an endothermic phase change of at least 60 J/gram is observed at greater than 125° C.

Example 13

Figure 46:
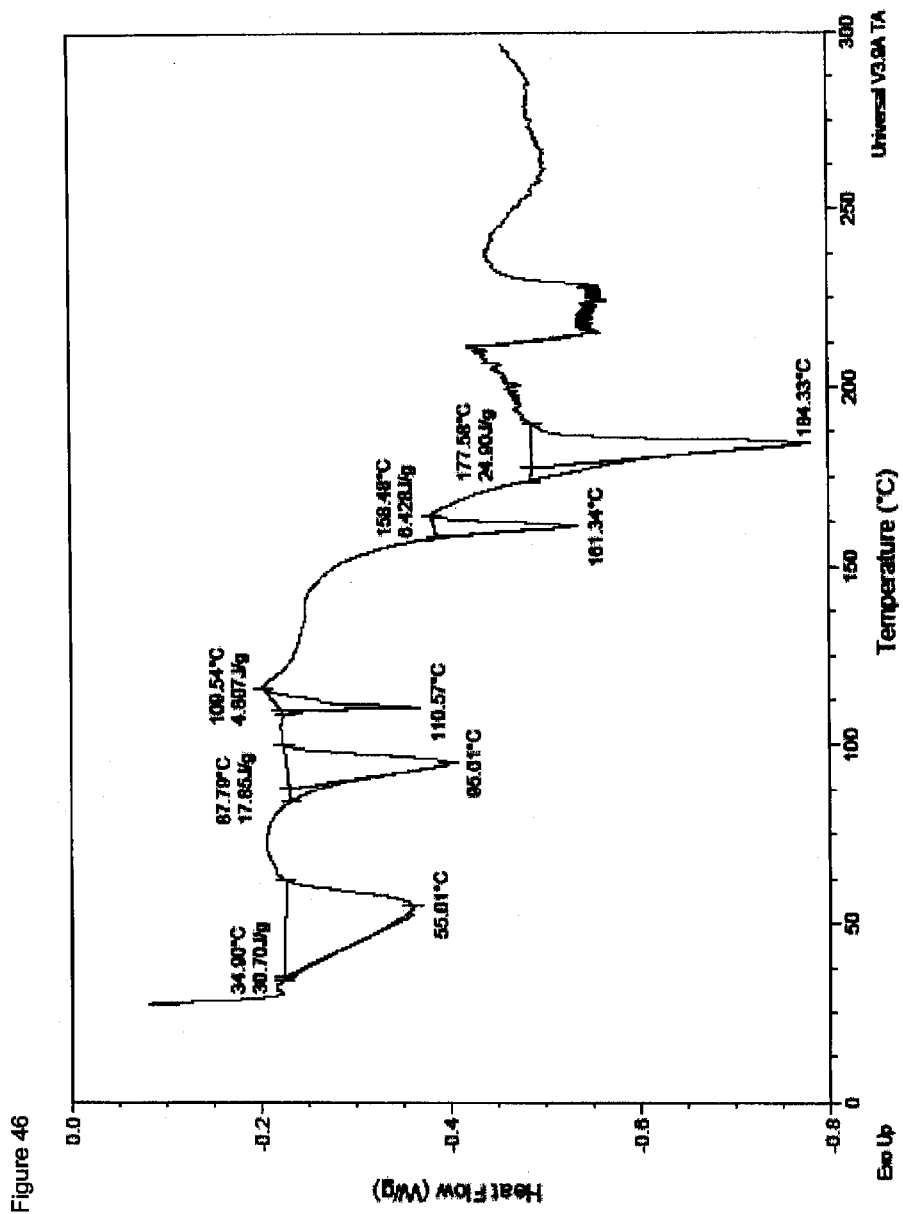
FIG. 46 is the differential scanning calorimetry (DSC) thermogram of polymorphic racemic-methylphenidate stearylamine pamoate, 1:1:1 salt.
Figure 47:
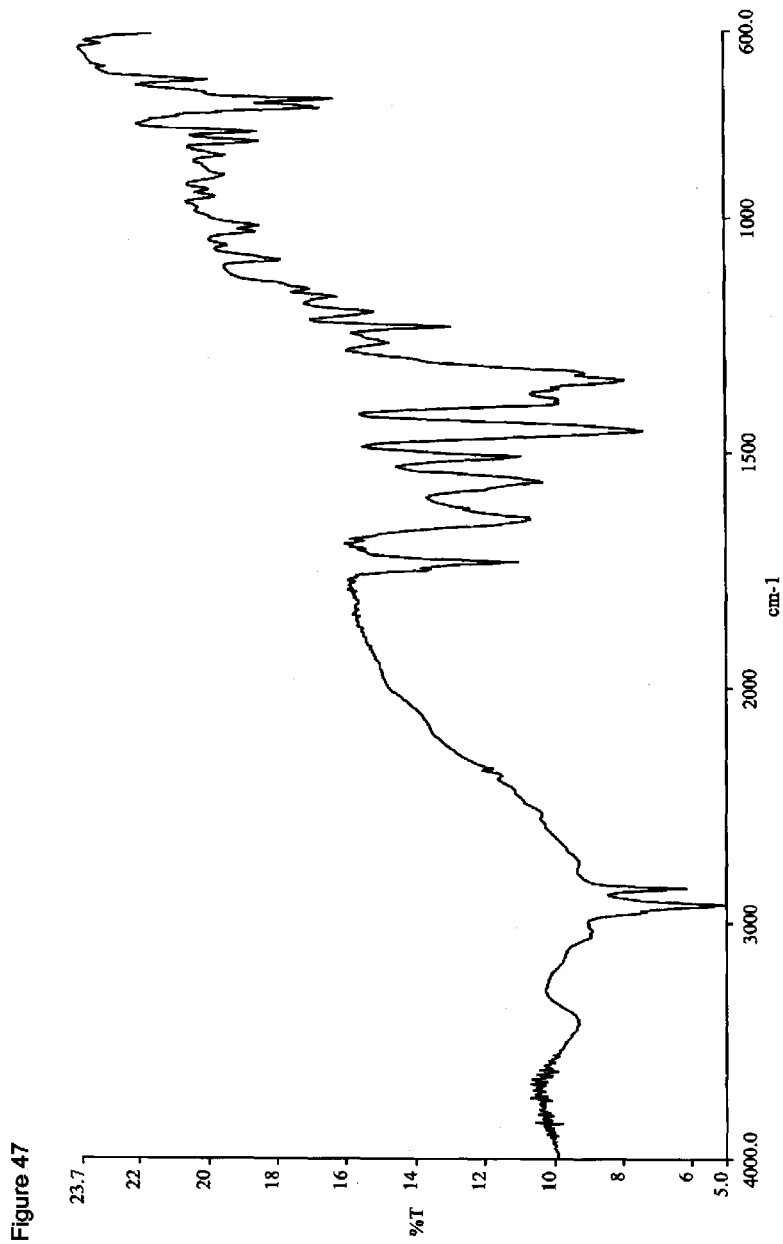
FIG. 47 is the Fourier Transform Infrared (FTIR) spectrum of polymorphic racemic-methylphenidate stearylamine pamoate, 1:1:1 salt.

Synthesis of Polymorphic Racemic-Methylphenidate Stearylamine Pamoate, (1:1:1) Salt To a 100 mL round-bottom flask equipped with a magnetic stir bar and addition funnel was charged 0.8 g (0.936 mmol) methylphenidate pamoate, (2:1) salt and 20 g toluene to form a suspension. A solution of 252.3 mg (0.936 mmol) octadecylamine in 20 g toluene was prepared and added dropwise to the above suspension over 30 minutes. The suspension was stirred overnight and the solids collected by filtration through a medium fritted filter. The product was dried under vacuum to provide 700 mg (84%) of an off-white solid (2.0% water) which was characterized by DSC, FTIR (FIG. 47), PXRD (FIG. 48), $^1$H NMR (FIG. 49), and HPLC. The PXRD diffractogram indicated the drug substance to be crystalline. The relative ratio of methylphenidate/pamoate was determined to be 0.9/1 by HPLC and the structure corroborated by $^1$H NMR with the relative ratio of stearylamine/pamoate as ~1/1. The filtrate from the above work-up was concentrated at reduced pressure and dried under vacuum to give 220 mg of a yellow residue which was by FTIR consistent with authentic methylphenidate free base. The DSC scan is provided in FIG. 46 wherein illustrated is an endothermic phase change of at least 15 J/g at a temperature above 50° C.; an endothermic phase change of at least 10 J/g at a temperature of above 90° C.; an endothermic phase change of at least 2 J/g at a temperature above 105° C.; an endothermic phase change of at least 4 J/g at above 155° C. and an endothermic phase change of at least 20 J/g above 180° C.

Example 14

Synthesis of Amorphous d-Methylphenidate Mono-Triethylammonium Pamoate, (1:1:1) Salt To a 100 mL round-bottom flask equipped with a magnetic stir bar and addition funnel was charged 722.1 mg (1.85 mmol) pamoic acid, 20 mL water and 423.0 mg (4.18 mmol) triethylamine. A solution of 0.5 g (1.85 mmol) d-methylphenidate hydrochloride in 20 mL water was added to the above solution over 3 hours with formation of a gum.

Figure 50:
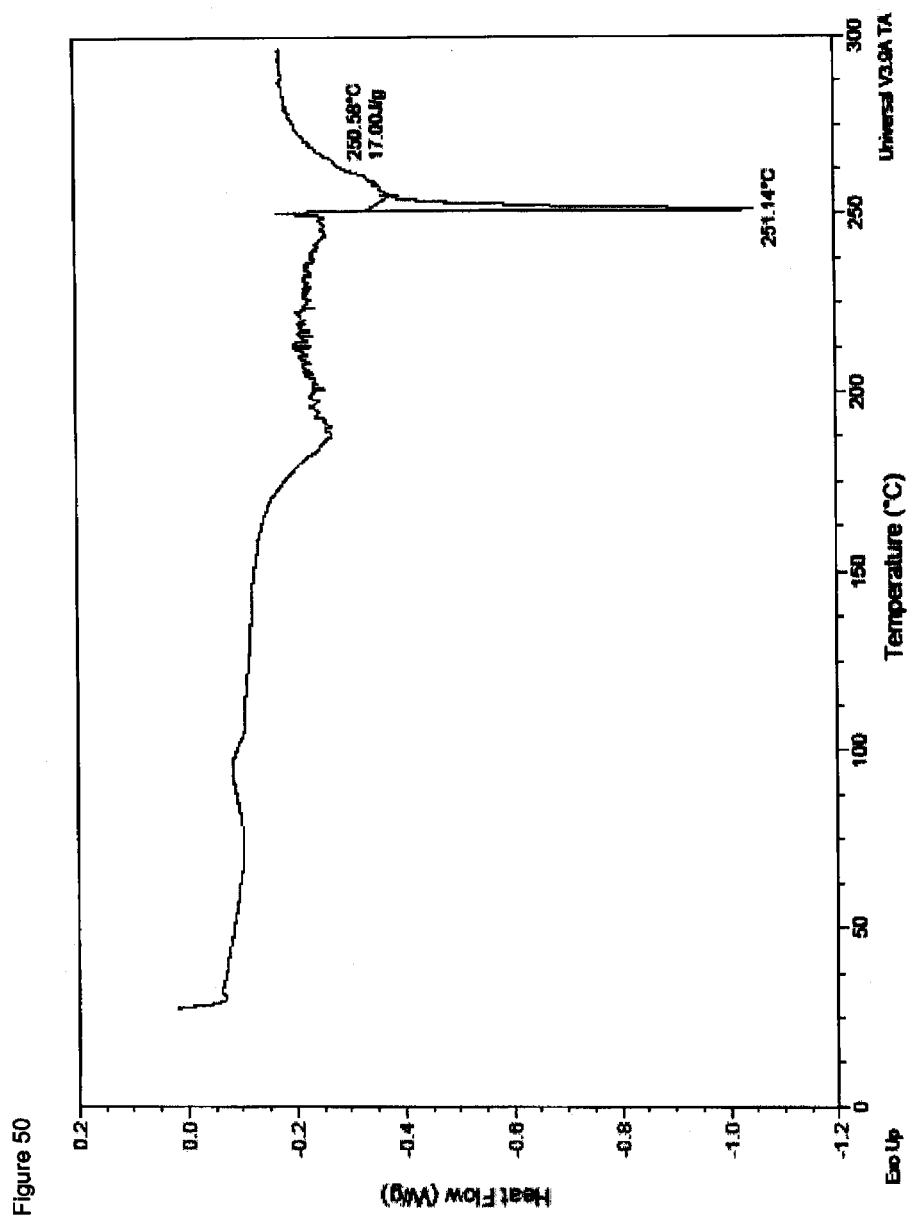
FIG. 50 is the differential scanning calorimetry (DSC) thermogram of amorphous d-methylphenidate mono-triethylammonium pamoate, 1:1:1 salt.

The water was carefully decanted and the residual gum dried under vacuum to provide 0.9 g (67%) of a tan solid (3.47% water) which was characterized by DSC, FTIR (FIG. 51), PXRD (FIG. 52), $^1$H NMR (FIG. 53), and HPLC. The PXRD diffractogram indicated the isolated drug substance was amorphous. The relative ratio of d-methylphenidate to pamoate was determined to be 1.0/1 by HPLC analysis and further corroborated by the relative ratio of triethylammonium ion to pamoate moiety as ~1/1 as determined by $^1$H NMR. The DSC is provided in FIG. 50 wherein illustrated is an endothermic phase change of at least 12 J/g at a temperature above 240° C.

Example 15

Synthesis of Amorphous Imipramine Pamoate, 1:1 Salt

To a 500 mL round bottom flask equipped with a magnetic stir bar was charged 3.0 g (3.9 mmol) imipramine pamoate mono-triethylammonium salt (as was prepared in Example 16) and 90 g acetone to produce a cloudy yellow solution. Hydrochloric acid solution (1.1 equivalents, 0.1 N HCl; 42.6 mL) was subsequently added at once to the solution and the combined mixture stirred for an additional 30 minutes whereupon the solution gradually became progressively cloudier. The solution was filtered through a medium fritted filter (removing ~80 mg of yellow pamoic acid) and the resulting clear filtrate was concentrated under reduce pressure at 40° C. until all volatile solvent was removed leaving solids and an aqueous layer. The water was carefully decanted and the solids washed with more water and again, the water was decanted. The remaining solids were slurried in acetone (50 g) and more pamoic acid (~0.4 g) was collected by filtration. The slightly turbid filtrate was refiltered again to provide a clear yellow solution which was concentrated under reduce pressure at 40° C. to remove ~90% of the acetone. The resulting turbid solution was filtered one more time as above and the clear solution again quickly concentrated under reduced pressure at 40° C. The resulting solids were dried under vacuum to provide 1.57 g (60%) of a tan yellow solid (2.0% water) which was characterized by DSC (FIG. 54), FTIR (FIG. 55), PXRD (FIG. 56)$^1$H NMR (FIG. 57), and HPLC. The PXRD diffractogram indicated the material was amorphous. The HPLC chromatogram and $^1$H NMR spectrum were both consistent with the stoichiometric ratio for the drug substance as ~1/1 imipramine/pamoate. $^1$H NMR also showed approximately 0.47 equivalents acetone included in the material.

Example 16

Synthesis of Amorphous Imipramine Pamoate Mono-Triethylammonium, (1:1:1) Salt

Figure 58:
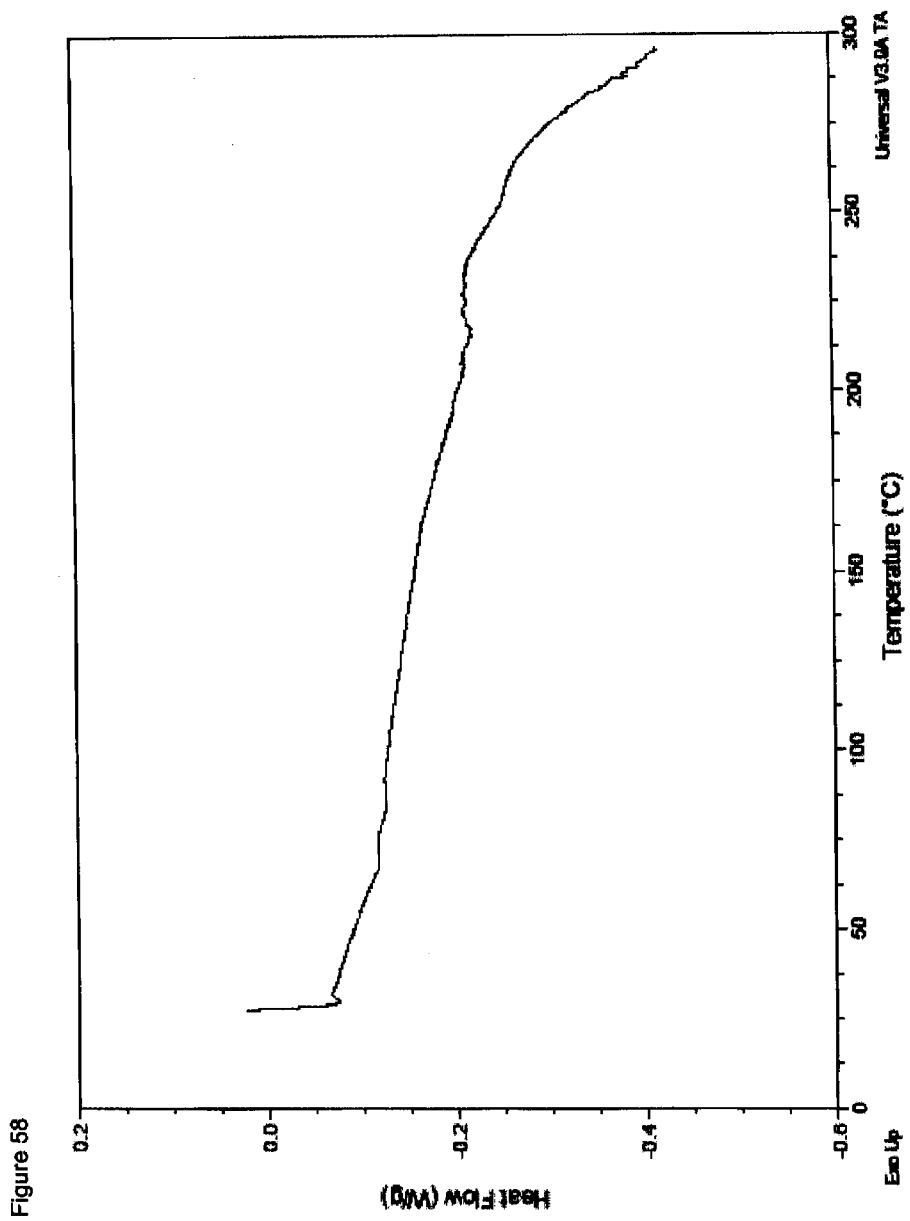
FIG. 58 is the differential scanning calorimetry (DSC) thermogram of amorphous imipramine mono-triethylammonium pamoate, 1:1:1 salt.
Figure 59:
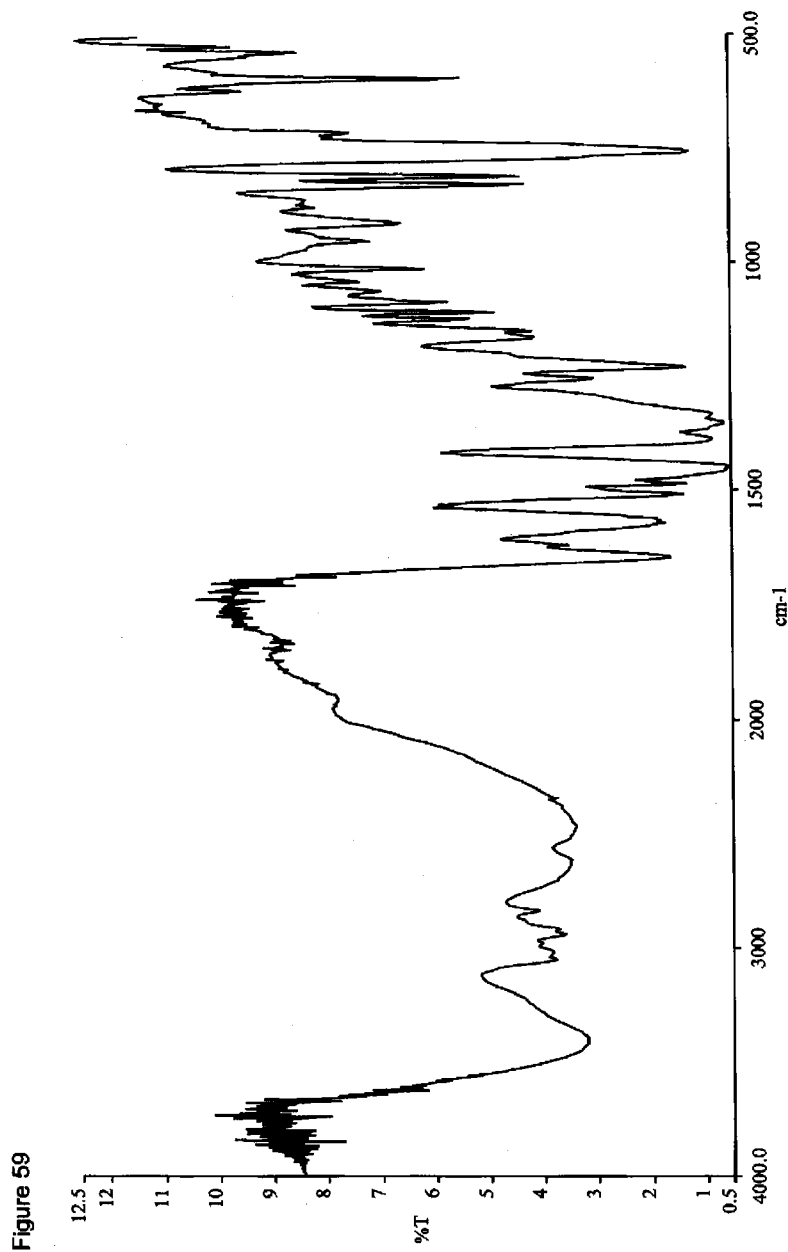
FIG. 59 is the Fourier Transform Infrared (FTIR) spectrum of amorphous imipramine mono-triethylammonium pamoate, 1:1:1 salt.
Figure 60:
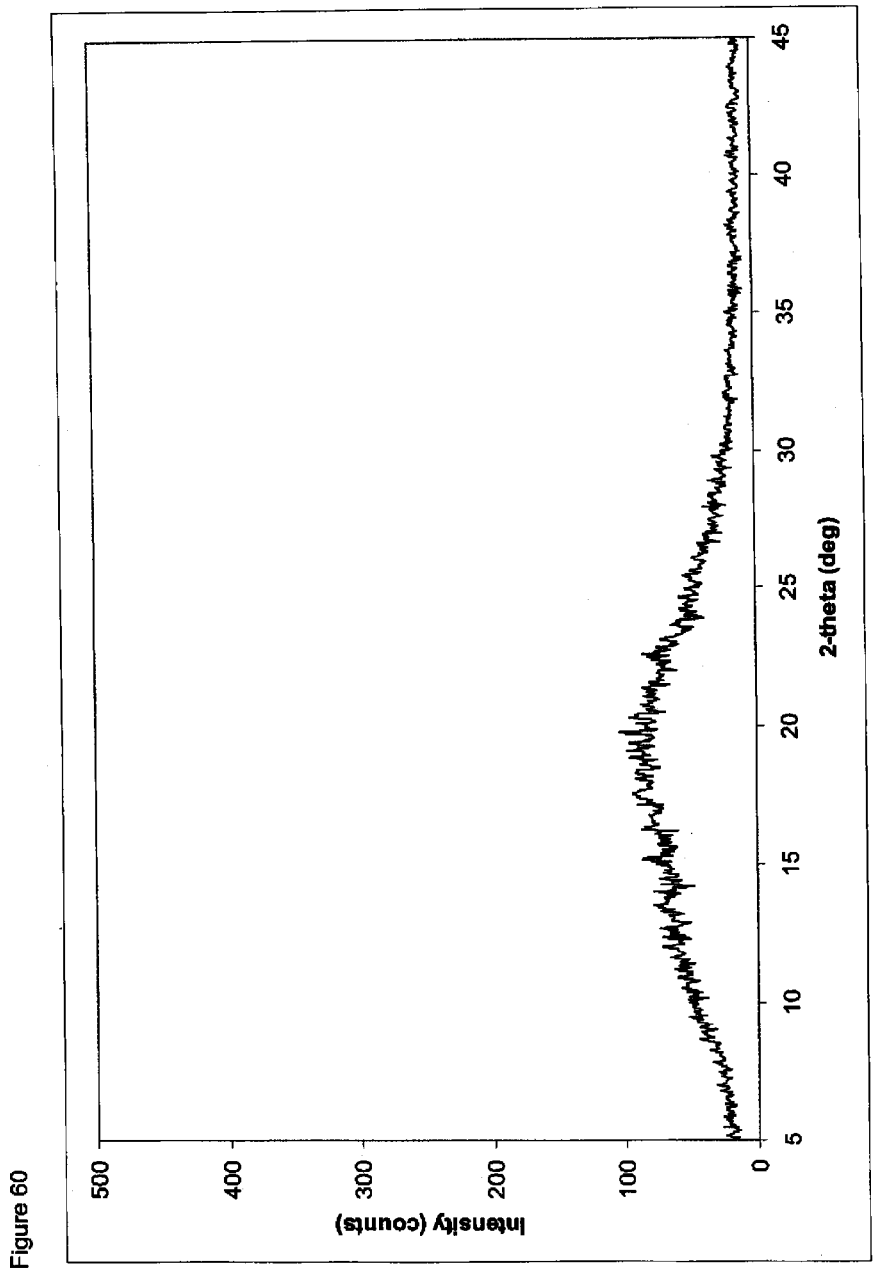
FIG. 60 is the powder X-ray diffraction (PXRD) diffractogram of amorphous imipramine mono-triethylammonium pamoate, 1:1:1 salt.
Figure 61:
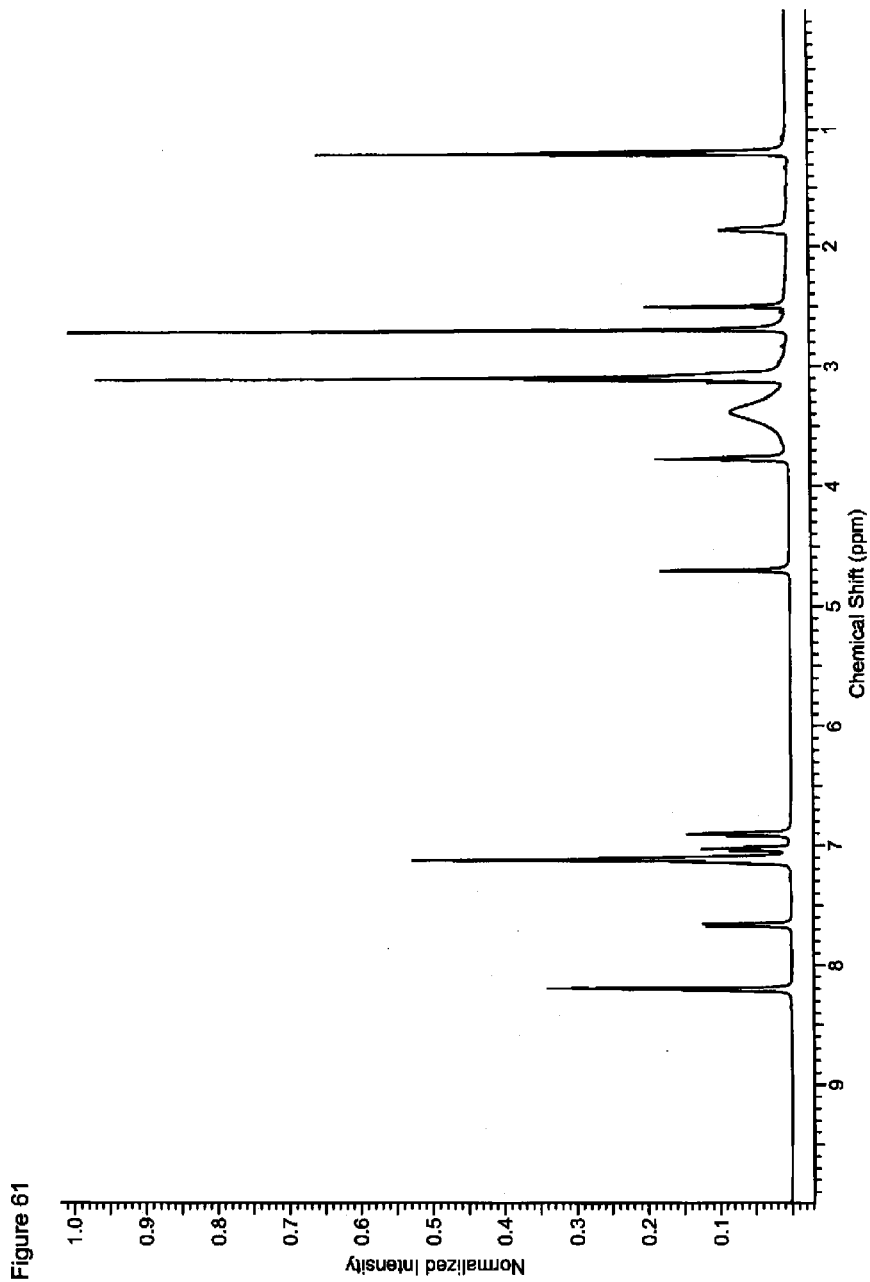
FIG. 61 is the proton nuclear magnetic resonance ($^1$H NMR) spectrum of amorphous imipramine mono-triethylammonium pamoate, 1:1:1 salt.

Method A
To a one liter round-bottom flask equipped with a magnetic stir bar and addition funnel was charged 9.0 g (15.2 mmol) di-triethylammonium pamoate and 192 mL water. The solution was stirred for 5 minutes and then a pre-made solution of 4.83 g (15.2 mmol) imipramine hydrochloride in 93 mL water was added dropwise over 2.75 hours to the above di-triethylammonium pamoate solution. After the addition was complete, the solution was stirred for an additional hour. The water was carefully decanted from the solid/gum that formed and a small aliquot of water added to the residue, which was subsequently collected by filtration, washed with water and dried under vacuum to provide 9.18 g (78%) of an off-white solid (2.2% water). The product was characterized by DSC (FIG. 58), FTIR (FIG. 59), PXRD (FIG. 60), $^1$H NMR (FIG. 61) and HPLC. The PXRD diffractogram indicated the isolated drug substance was amorphous. The relative ratio of imipramine to pamoate was determined to be 1.3/1 by HPLC and the ratio corroborated by $^1$H NMR. The relative ratio of triethylammonium ion to pamoate moiety was approximately ½ by $^1$H NMR.

Method B
To a 100 mL round-bottom flask equipped with a magnetic stir bar and addition funnel was charged 1.23 g (3.16 mmol) pamoic acid, 40 mL water and 769.0 mg (7.6 mmol) triethylamine. A solution of 1.0 g (3.16 mmol) imipramine hydrochloride in 20 mL water was added to the above solution over 3 hours with gum formation. The water was carefully decanted and the gum dried under vacuum to provide 2.1 g (86%) of a tan solid (2.24% water). The relative ratio of imipramine to pamoate was determined to be 1.1/1 by HPLC (and corroborated by $^1$H NMR). The relative ratio of triethylammonium ion to pamoate was ~1/1 by $^1$H NMR.

Example 17

Synthesis of Polymorphic Imipramine Stearylamine Pamoate, (1:1:1) Salt

Figure 62:
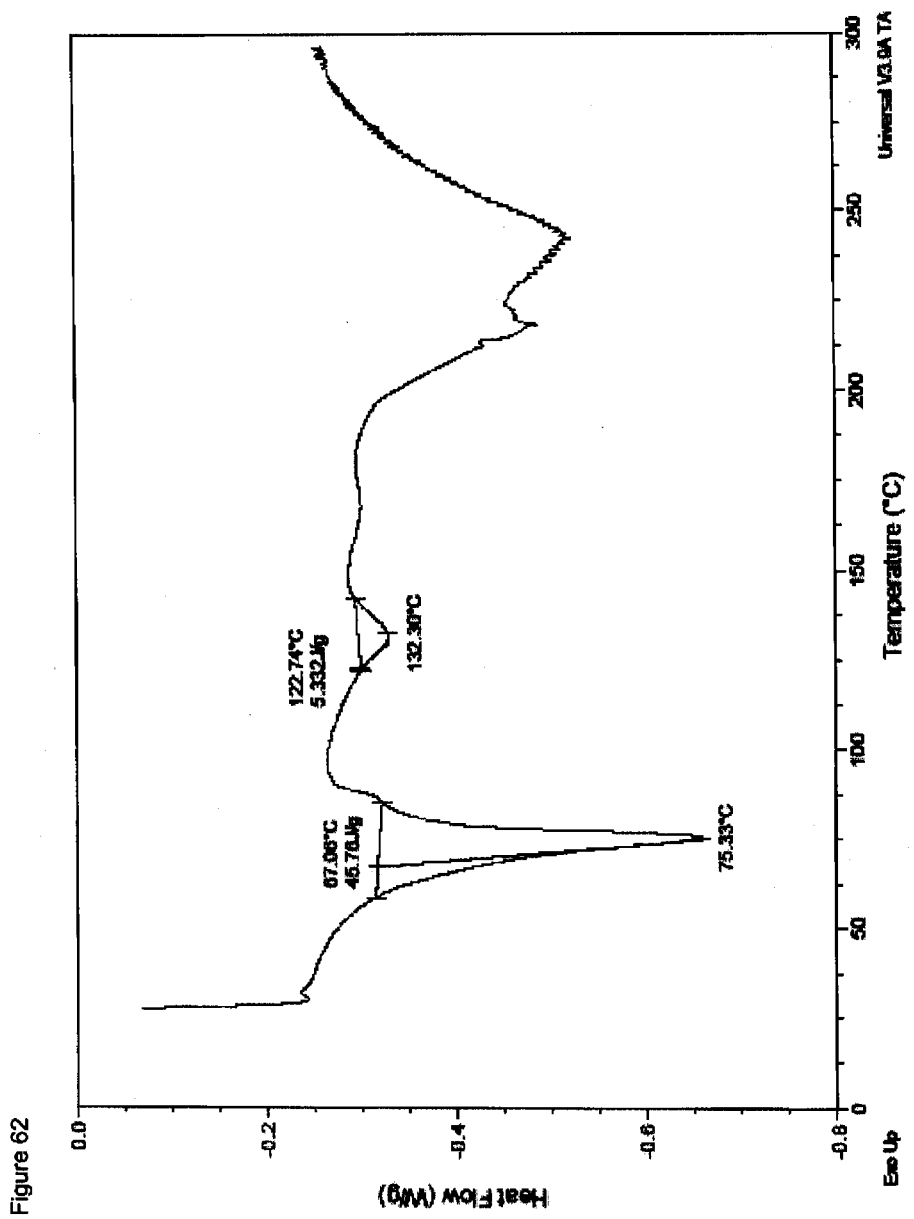
FIG. 62 is the differential scanning calorimetry (DSC) thermogram of polymorphic imipramine stearylamine pamoate, 1:1:1 salt.
Figure 63:
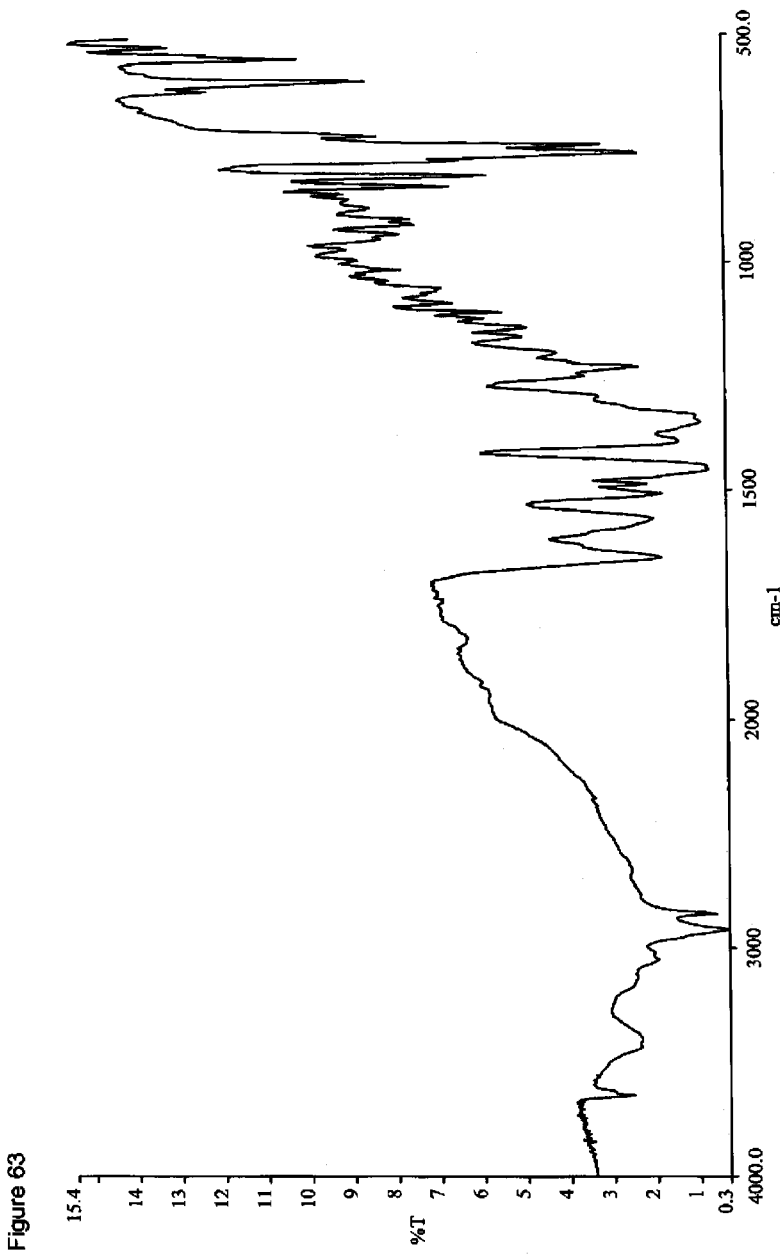
FIG. 63 is the Fourier Transform Infrared (FTIR) spectrum of polymorphic imipramine stearylamine pamoate, 1:1:1 salt.
Figure 64:
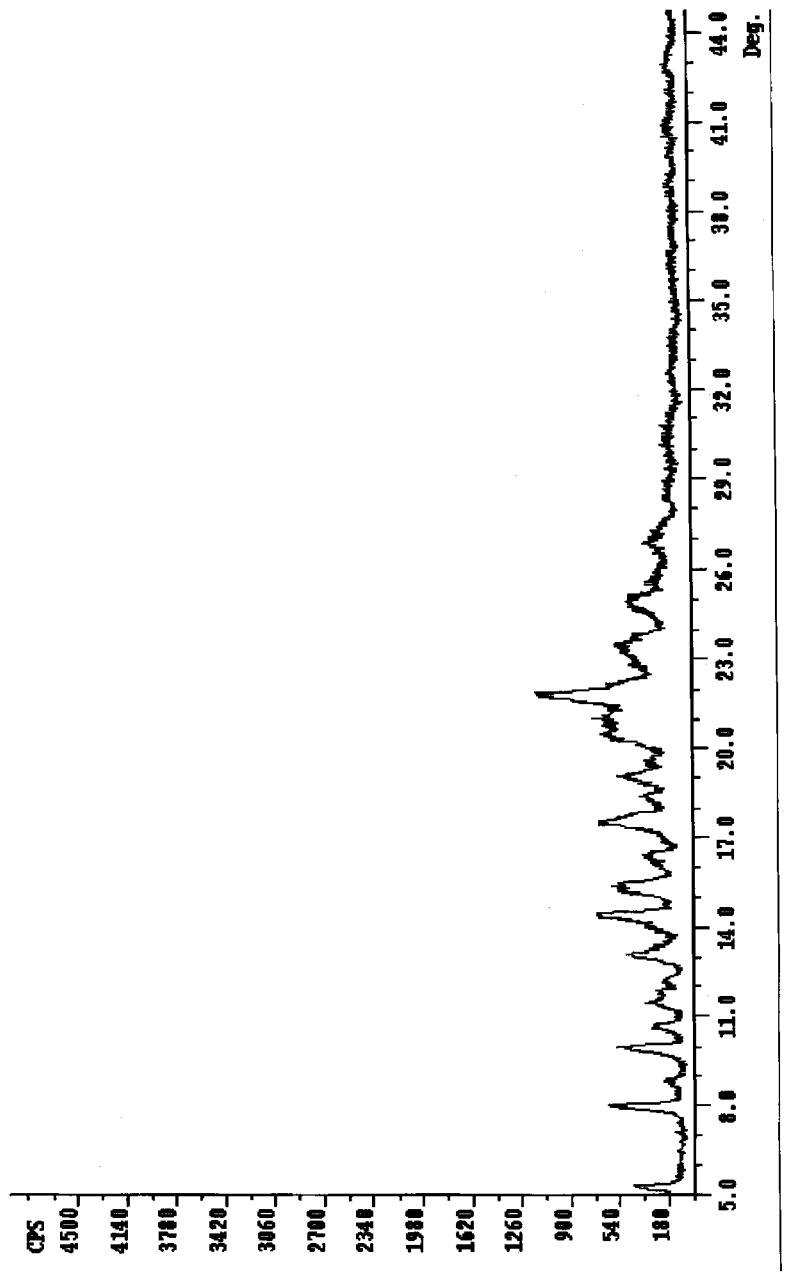
FIG. 64 is the powder X-ray diffraction (PXRD) diffractogram of polymorphic imipramine stearylamine pamoate, 1:1:1 salt.
Figure 65:
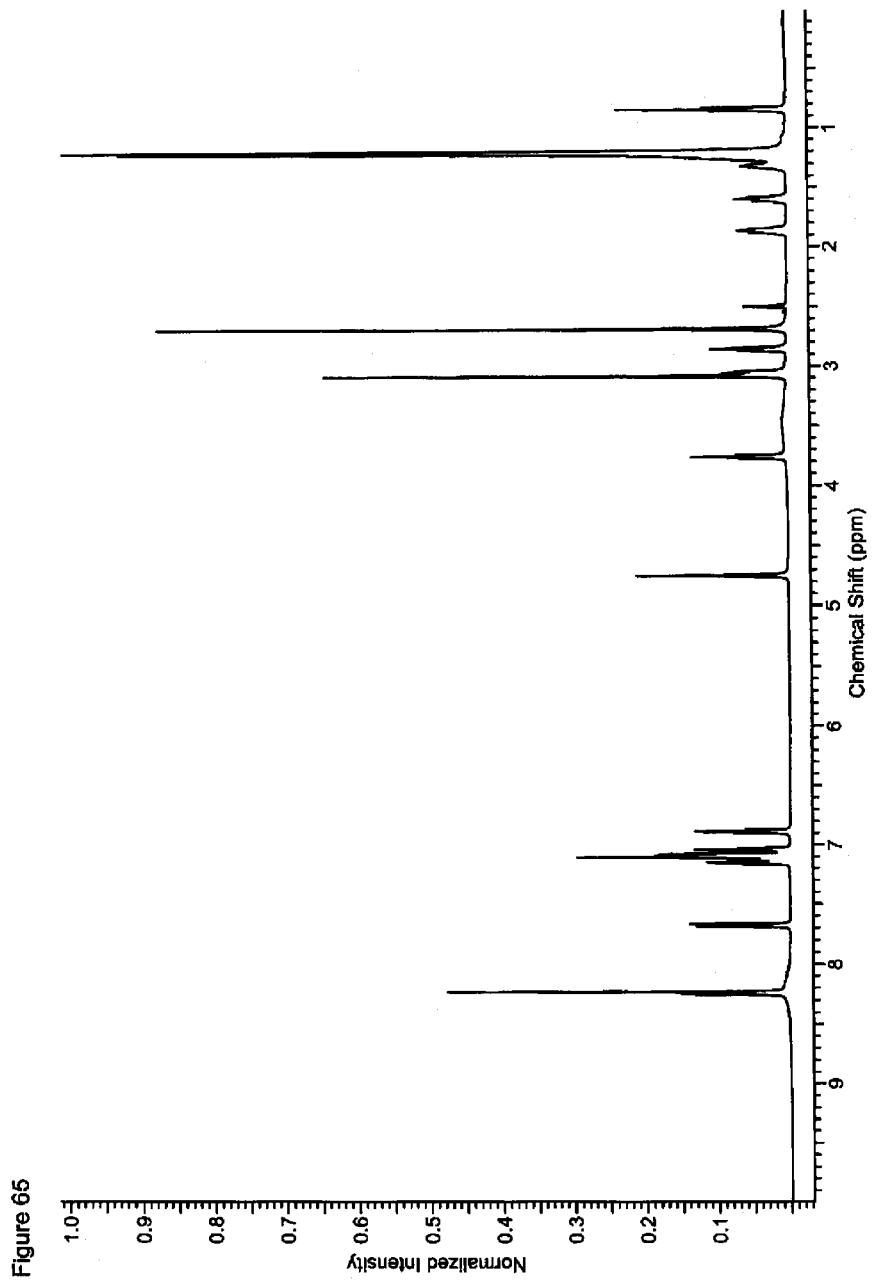
FIG. 65 is the proton nuclear magnetic resonance ($^1$H NMR) spectrum of polymorphic imipramine stearylamine pamoate, 1:1:1 salt.

To a 100 mL round-bottom flask equipped with a magnetic stir bar and addition funnel was charged 730 mg (0.769 mmol) imipramine pamoate, (2:1) salt (prepared as described in King, et al.) in 10.7 g toluene to form a suspension. A solution of 207.3 mg (0.769 mmol) octadecylamine in 12.5 g toluene was prepared and added dropwise to the above suspension over 1 hour. The suspension was stirred for an additional 3 hours and the solids collected by filtration through a medium fritted filter. The product was dried under vacuum to provide 600 mg (83%) of a white solid (2.5% water) which was characterized by DSC, FTIR (FIG. 63), PXRD (FIG. 64), $^1$H NMR (FIG. 65) and HPLC. The PXRD diffractogram indicated the isolated drug product was crystalline. The relative ratio of imipramine/pamoate was determined to be 1.2/1 by HPLC (and corroborated by $^1$H NMR). The relative ratio of stearylamine/pamoate was determined to be about 1/1 by $^1$H NMR. The filtrate from the above work-up was concentrated under reduced pressure and dried under vacuum to give 200 mg of a yellow oil which was characterized by FTIR and $^1$H NMR. The analyses were consistent with those obtained for imipramine free base described in U.S. Pat. No. 5,578,500. The DSC thermogram is provided in FIG. 62 wherein an endothermic phase change of at least 40 J/g is observed at a temperature above 70° C. and an endothermic phase change of at least 1 J/g is observed above 125° C.

Example 18

Synthesis of Amorphous Imipramine Jeffamine® Pamoate, (1:1:1) Salt

Figure 66:
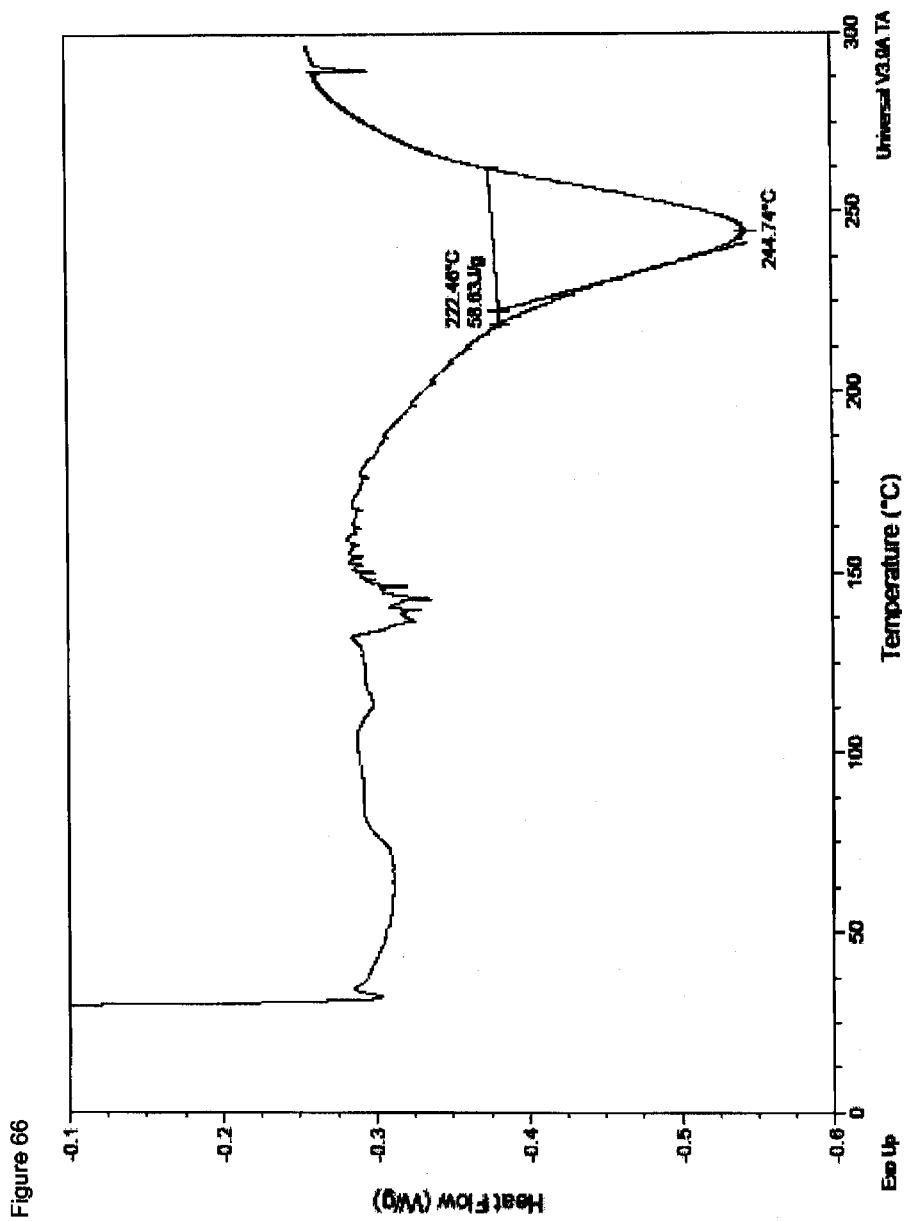
FIG. 66 is the differential scanning calorimetry (DSC) thermogram of amorphous imipramine Jeffamine® pamoate, 1:1:1 salt.
Figure 67:
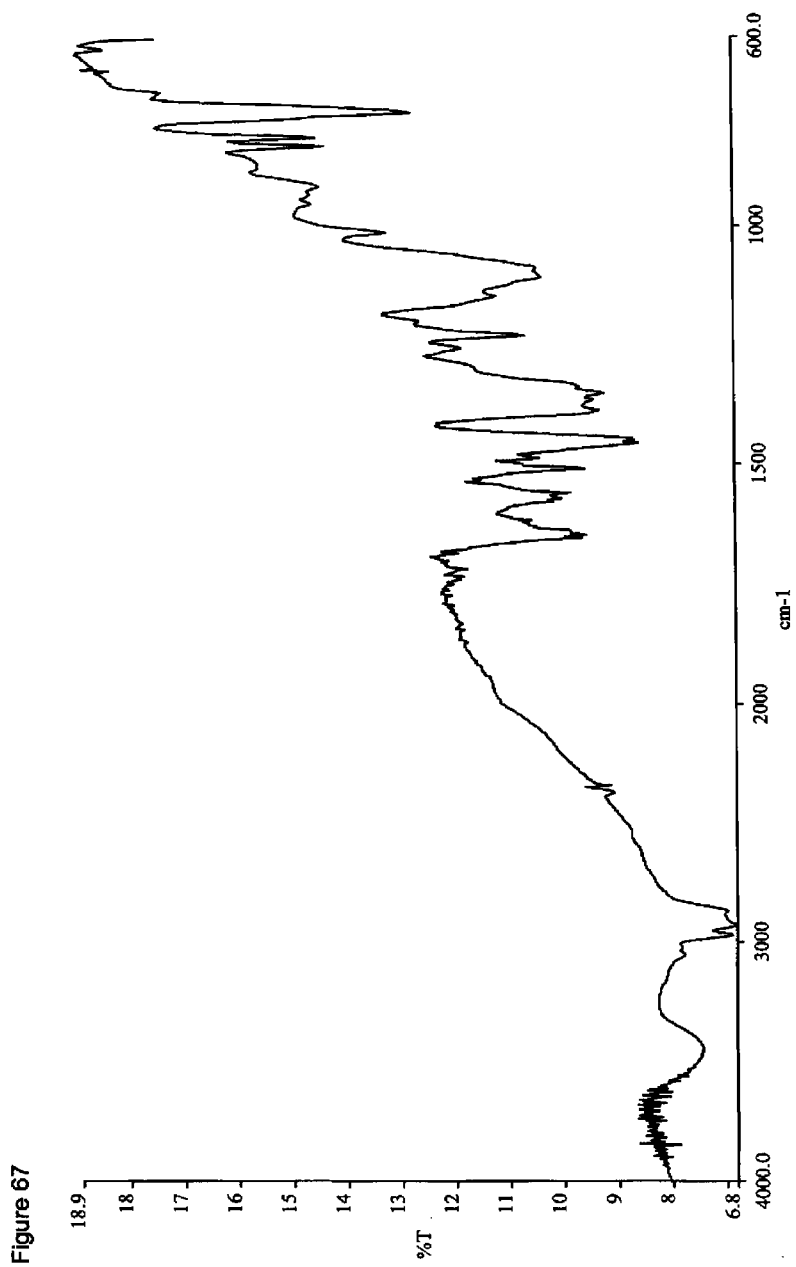
FIG. 67 is the Fourier Transform Infrared (FTIR) spectrum of amorphous imipramine Jeffamine® pamoate, 1:1:1 salt.
Figure 68:
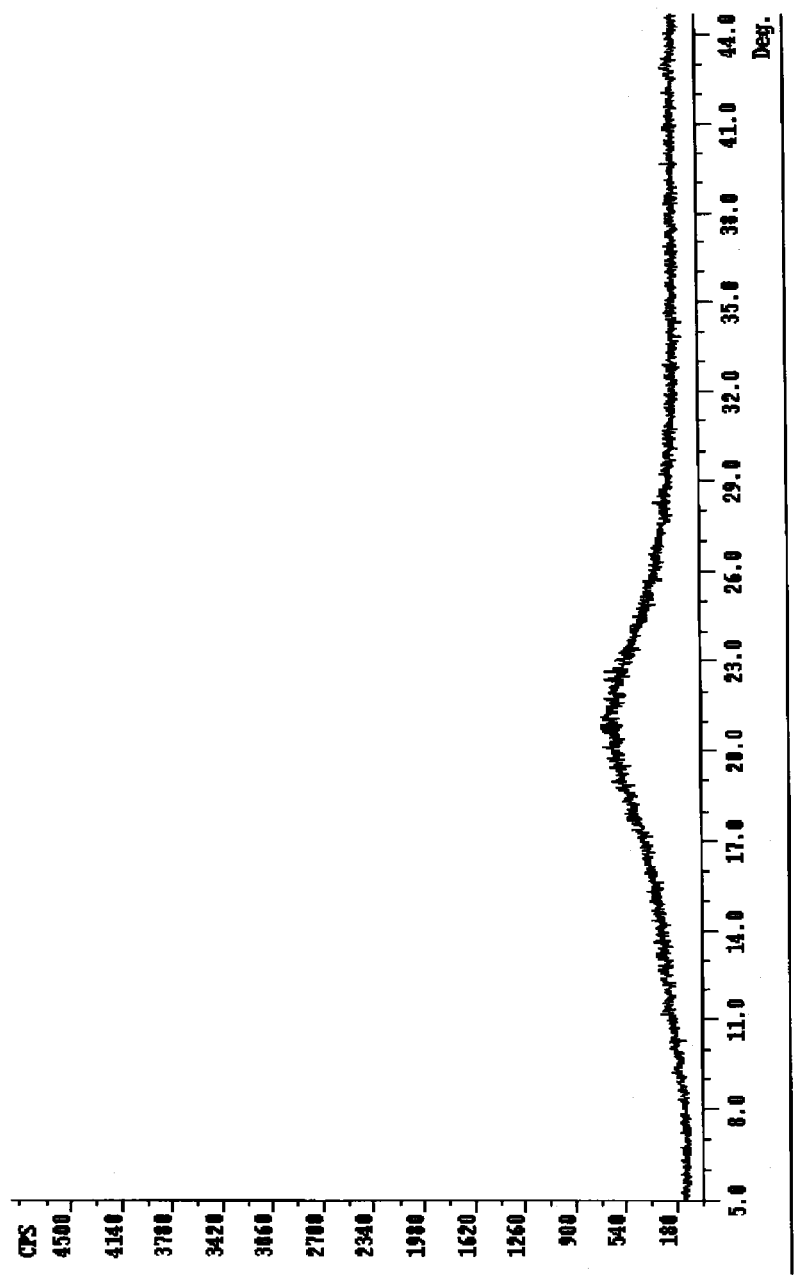
FIG. 68 is the powder X-ray diffraction (PXRD) diffractogram of amorphous imipramine Jeffamine® pamoate, 1:1:1 salt.
Figure 69:
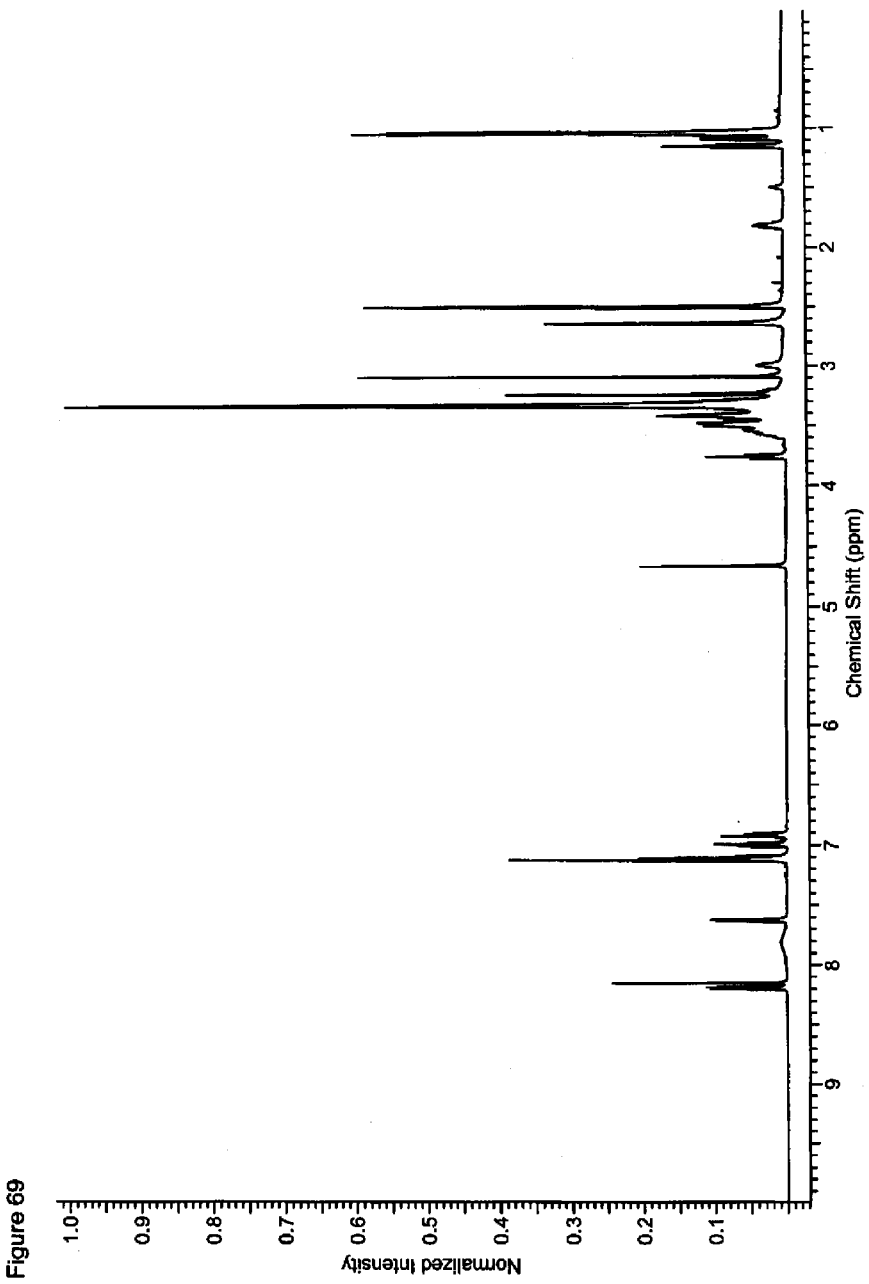
FIG. 69 is the proton nuclear magnetic resonance ($^1$H NMR) spectrum of amorphous imipramine Jeffamine® pamoate, 1:1:1 salt.

To a 500 mL round-bottom flask equipped with a magnetic stir bar and addition funnel was charged 6.82 g (7.18 mmol) imipramine pamoate (2:1) (prepared as described in U.S. Pat. No. 7,718,649 [King et al.] and 135 g toluene to form a suspension. A solution consisting of 4.31 g (7.18 mmol) Jeffamine XTJ-505® available from Huntsman Chemical Company and 91 g toluene was added dropwise to the above suspension over 30 minutes. The contents were allowed to stir overnight at ambient temperature. Solids were collected from the mixture by filtration through a medium fritted filter and dried under vacuum to provide 3.42 g of a light yellow solid which was characterized by DSC, FTIR, $^1$H NMR and HPLC which confirmed the solids consisted of imipramine pamoate (2:1) salt. The toluene filtrate was charged to a one liter round-bottom flask with a magnetic stir bar and to the solution was added 260 mL water and the contents gently mixed but not too vigorously as to avoid forming an emulsion. The two layers were transferred to a separatory funnel and allowed phase with the layers also containing some oil droplets which were not very soluble in either layer. The layers were separated leaving the oily residue behind in the separatory funnel. Concentration of the aqueous layer under reduced pressure at 70° C. followed by drying provided 2.46 g of a yellow oil which was characterized by FTIR, $^1$H NMR and HPLC which was shown to be Jeffamine® pamoate (2:1) salt. Concentration of the toluene layer under reduced pressure at 70° C. followed by drying provided 4.36 g of a semi-solid and from which decanting provided a yellow oil was isolated. The decanted yellow oil (3.39 g) was shown by FTIR and HPLC to be a mixture of mostly imipramine base along with some Jeffamine® pamoate, (2:1) salt. The yellow solid remaining was triturated in toluene and washed with water and dried under vacuum to provide 1.17 g of a soft yellow gum which was characterized by DSC, IR and HPLC and which was found to be 1:1:1 imipramine Jeffamine® pamoate (impure when compared with pure 1:1:1 imipramine Jeffamine® pamoate isolated below) along with some excess imipramine. The oily residue left behind in the separatory funnel above was washed with two portions of toluene and after decanting, the resulting residue dissolved in acetone, transferred to a round-bottom flask and concentrated under reduced pressure at 50° C. The semi-solid obtained was washed by decanting with two portions of water and the resulting extract concentrated under reduced pressure at 70° C. to yield a thick viscous oil which was then dried under vacuum to provide 0.98 g of a light yellow sticky solid (11% yield; 1.0% moisture). The drug substance was characterized by DSC, FTIR (FIG. 67), PXRD (FIG. 68), $^1$H NMR (FIG. 69), and HPLC. The PXRD diffractogram confirmed the drug substance was amorphous. The relative ratio of imipramine/pamoate was determined to be 1.3/1 by HPLC and corroborated by $^1$H NMR. The relative ratio of Jeffamine®/pamoate was determined to be ~1/1 by $^1$H NMR. The DSC thermogram is provided in FIG. 66 wherein observed is an endothermic phase change of at least 50 J/g at a temperature above 240° C.

Example 19

Synthesis of Amorphous Hydrocodone Stearylamine Pamoate, (1:1:1) Salt

Figure 70:
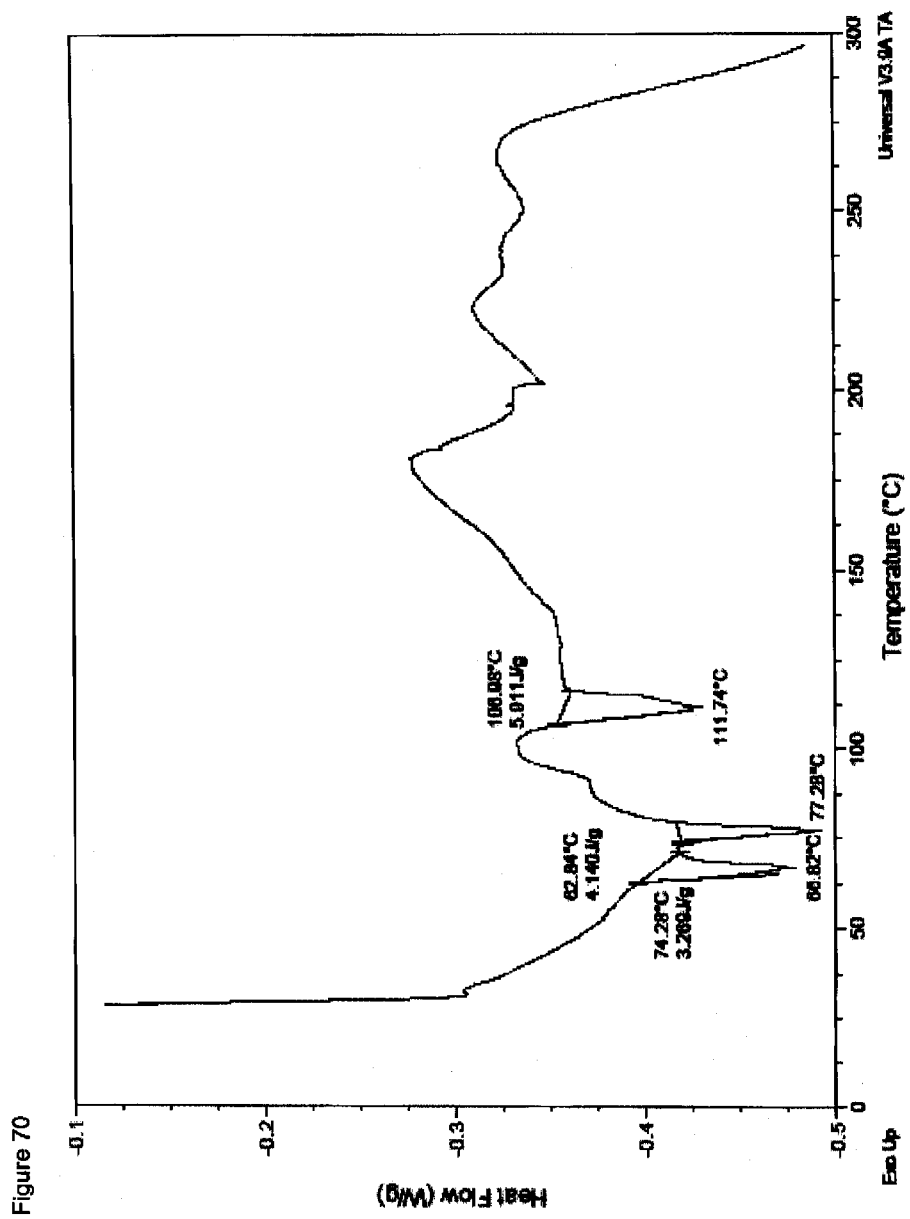
FIG. 70 is the differential scanning calorimetry (DSC) thermogram of amorphous hydrocodone stearylamine pamoate, 1:1:1 salt.
Figure 71:
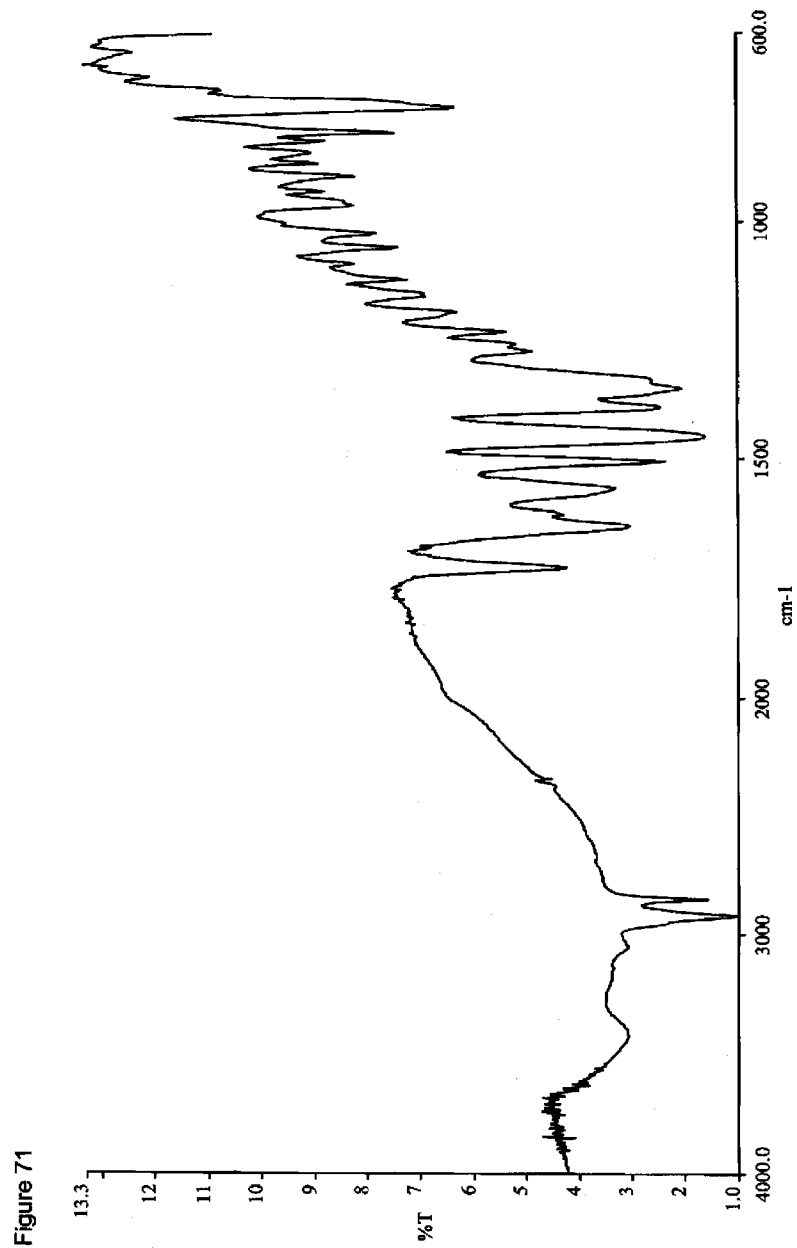
FIG. 71 is the Fourier Transform Infrared (FTIR) spectrum of amorphous hydrocodone stearylamine pamoate, 1:1:1 salt.
Figure 72:
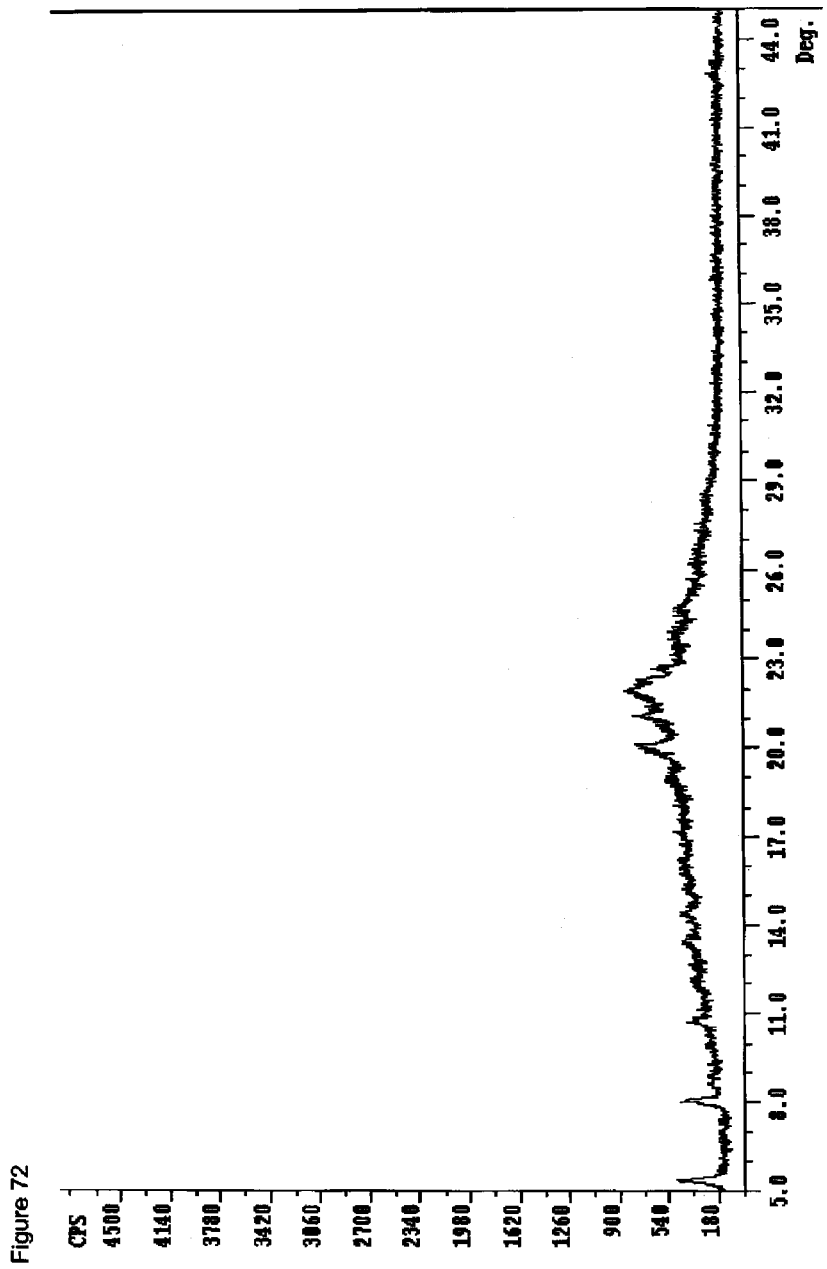
FIG. 72 is the powder X-ray diffraction (PXRD) diffractogram of amorphous hydrocodone stearylamine pamoate, 1:1:1 salt.
Figure 73:
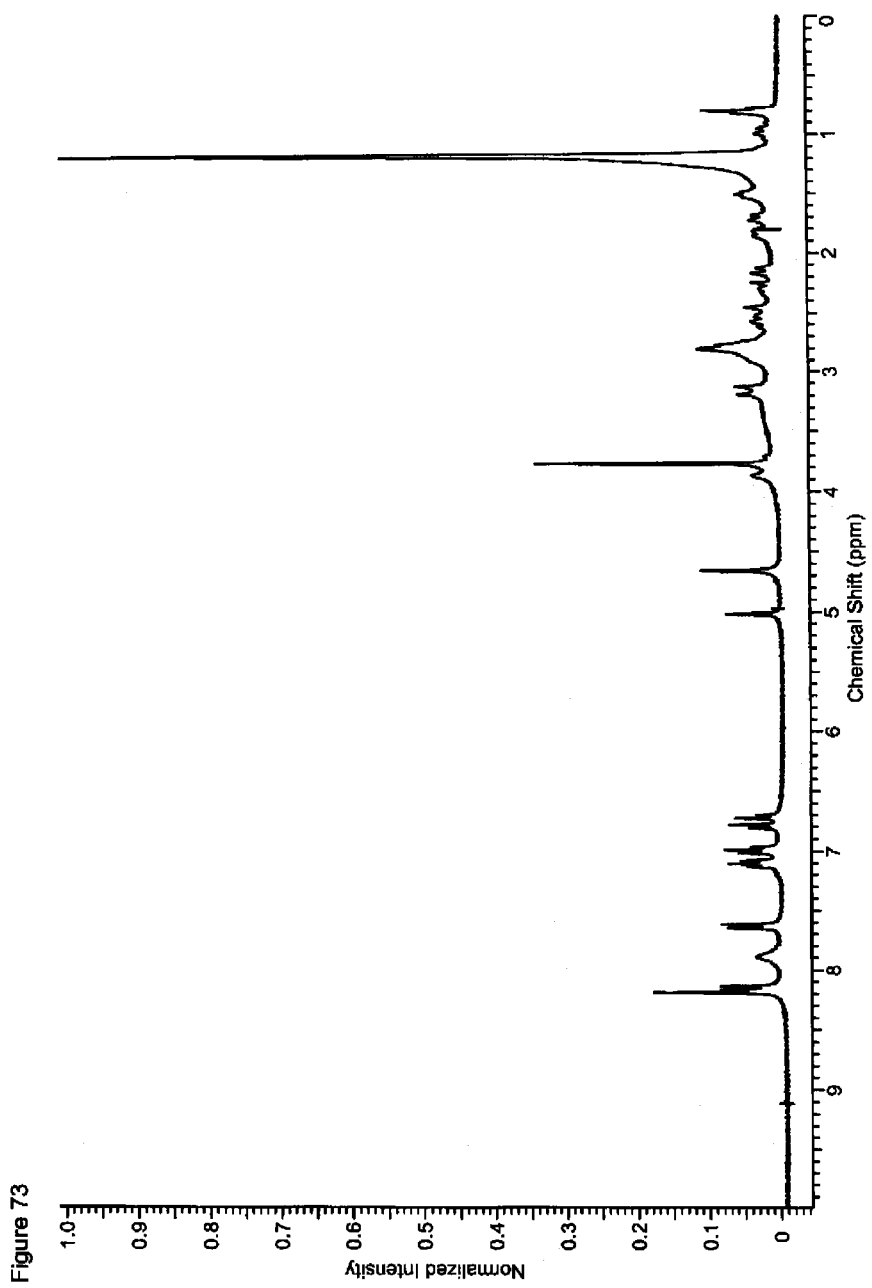
FIG. 73 is the proton nuclear magnetic resonance ($^1$H NMR) spectrum of amorphous hydrocodone stearylamine pamoate, 1:1:1 salt.

To a 100 mL round-bottom flask equipped with a magnetic stir bar and addition funnel was charged 660.0 mg (0.669 mmol) hydrocodone pamoate, (2:1) prepared by the procedure in co-pending patent application, application Ser. No. 12/423,641 entitled, Opioid Salts and Formulation Exhibiting Anti-Abuse and Anti-Dose Dumping Properties, King et al., and 10.0 g toluene to form a suspension. A solution of 180.3 mg (0.669 mmol) octadecylamine in 10.0 g toluene was prepared and added dropwise to the above suspension over a 20 minute period. The suspension was stirred overnight and the solids collected by filtration through a medium fritted filter. The drug substance was dried under vacuum to provide 580 mg (91%) of an off-white solid (4.1% water) which was characterized by DSC, FTIR (FIG. 71), PXRD (FIG. 72), $^1$H NMR (FIG. 73), and HPLC. The PXRD diffractogram indicated the drug substance was predominantly amorphous. The relative ratio of hydrocodone/pamoate was determined to be 1.1/1 by HPLC analysis and was corroborated by $^1$H NMR. The relative ratio of stearylamine/pamoate was determined to be ~1/1 by $^1$H NMR. The DSC thermogram is provided in FIG. 70 wherein an endothermic phase change of at least 1 J/g at a temperature above 65° C.; an endothermic phase change of at least 1 J/g above 70° C. and an endothermic phase change of at least 3 J/g above 105° C. is observed.

The filtrate from the above work-up was concentrated under reduce pressure and dried under vacuum to give ~200 mg of an off-white solid which was characterized by DSC, melting point and IR, and found to match authentic hydrocodone free base.

Example 20

Synthesis of Amorphous Hydrocodone Jeffamine® Pamoate, (1:1:1) Salt

Figure 74:
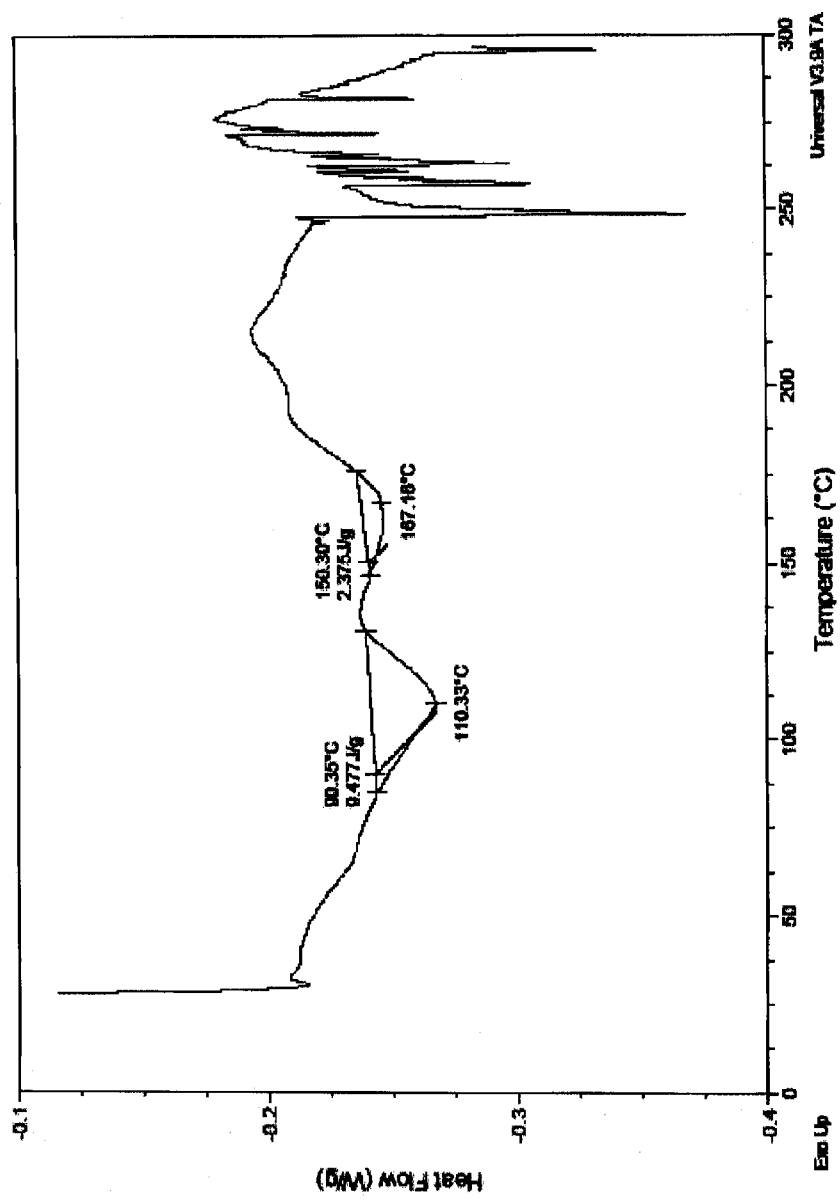
FIG. 74 is the differential scanning calorimetry (DSC) thermogram of amorphous hydrocodone Jeffamine® pamoate, 1:1:1 salt.

To a 250 mL round-bottom flask equipped with a magnetic stir bar and addition funnel was charged 3.00 g (3.04 mmol) hydrocodone pamoate, (2:1) salt as used in Example 19, and 50 g toluene to form a suspension. A solution consisting of 1.82 g (3.04 mmol) Jeffamine XTJ-505® available form Huntsman Chemical Company, and 50 g/toluene was prepared separately and added dropwise to the above suspension over 38 minutes. The contents were allowed to stir overnight. Solids were collected through a medium fritted filter and dried under vacuum to provide 2.6 g (67%) of a light yellow solid (0.6% water) which was characterized by DSC, FTIR (FIG. 75), PXRD (FIG. 76), $^1$H NMR (FIG. 77), and HPLC. The PXRD diffractogram indicated the drug substance was amorphous. HPLC analysis indicated the drug substance contained a ratio of 1.4/1 hydrocodone/pamoate. Proton NMR corroborated the relative ratio of hydrocodone/pamoate to be ~1.3-1.4/1 and the relative ratio of Jeffamine®/pamoate to be ~0.6-0.7/1. The DSC thermogram is provided in FIG. 74 wherein illustrated is an endothermic phase change of at least 5 J/g at a temperature above 105° C. and an endothermic phase change of at least 1 J/g at a temperature above 150° C.

After the above filtration, the toluene filtrate was charged to a one liter round-bottom flask with a magnetic stir bar and to the solution was added 120 mL water and the contents gently mixed to avoid forming an emulsion. The two layers were transferred to a separatory funnel and allowed to phase into two layers and the layers separated.

Concentration of the aqueous layer under reduce pressure at 70° C. followed by drying provided 0.72 g of a yellow oil which was characterized by FTIR, $^1$H NMR and HPLC indicating the isolation of 0.6/1 hydrocodone pamoate salt. The $^1$H NMR spectrum indicated a small amount of hydrocodone relative to pamoate and the presence of excess Jeffamine®.

Concentration of the toluene layer under reduced pressure at 70° C. followed by drying provided 1.36 g of a soft yellow residue which was characterized by DSC, FTIR, PXRD and HPLC which collectively indicated the residue to consists of 22.4/1 hydrocodone pamoate salt, e.g. an excess of hydrocodone base. The $^1$H NMR spectrum of the toluene extract indicated a large excess of hydrocodone and Jeffamine® and the presence of very little pamoate moiety.

Example 21

Synthesis of Amorphous Bis(Triethylammonium) Pamoate

Figure 94:
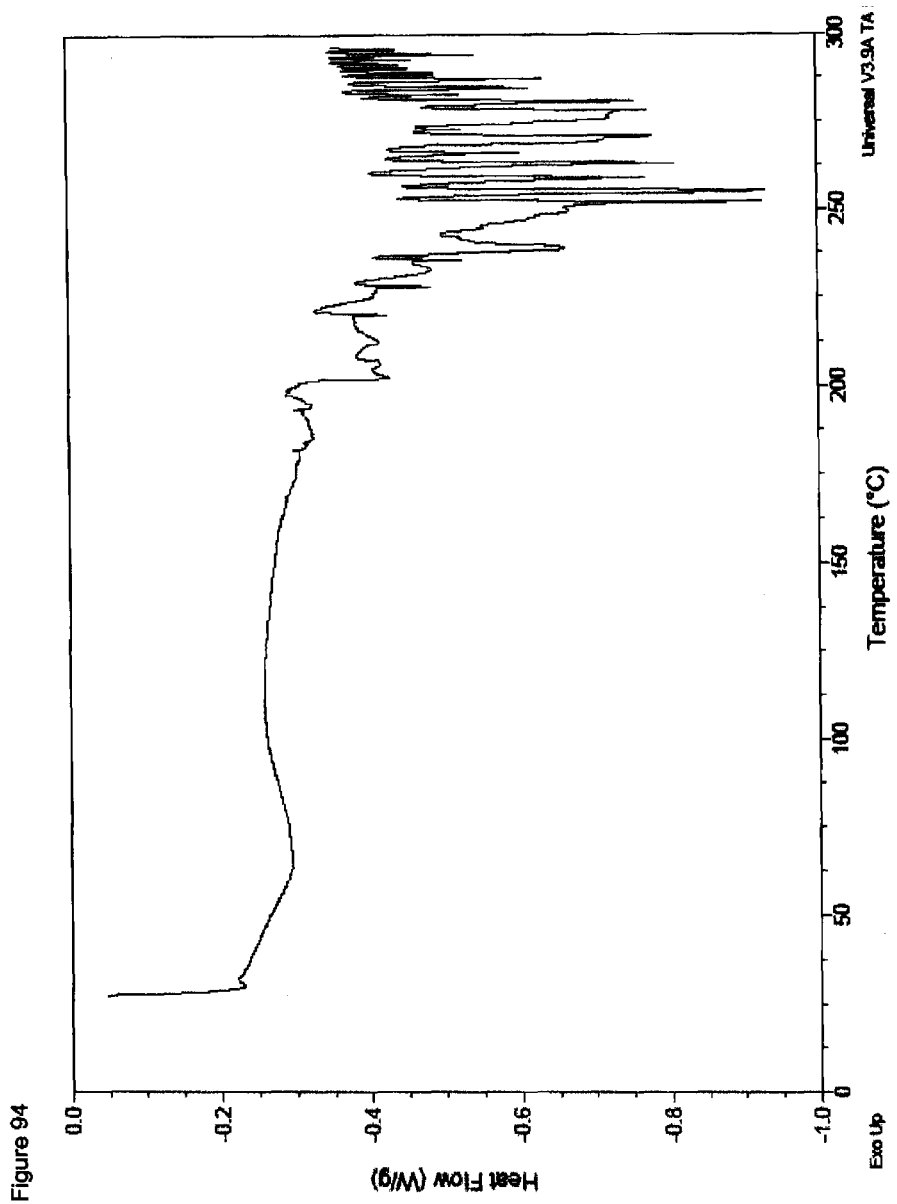
FIG. 94 is the differential scanning calorimetry (DSC) thermogram of amorphous bis(triethylammonium) pamoate.
Figure 95:
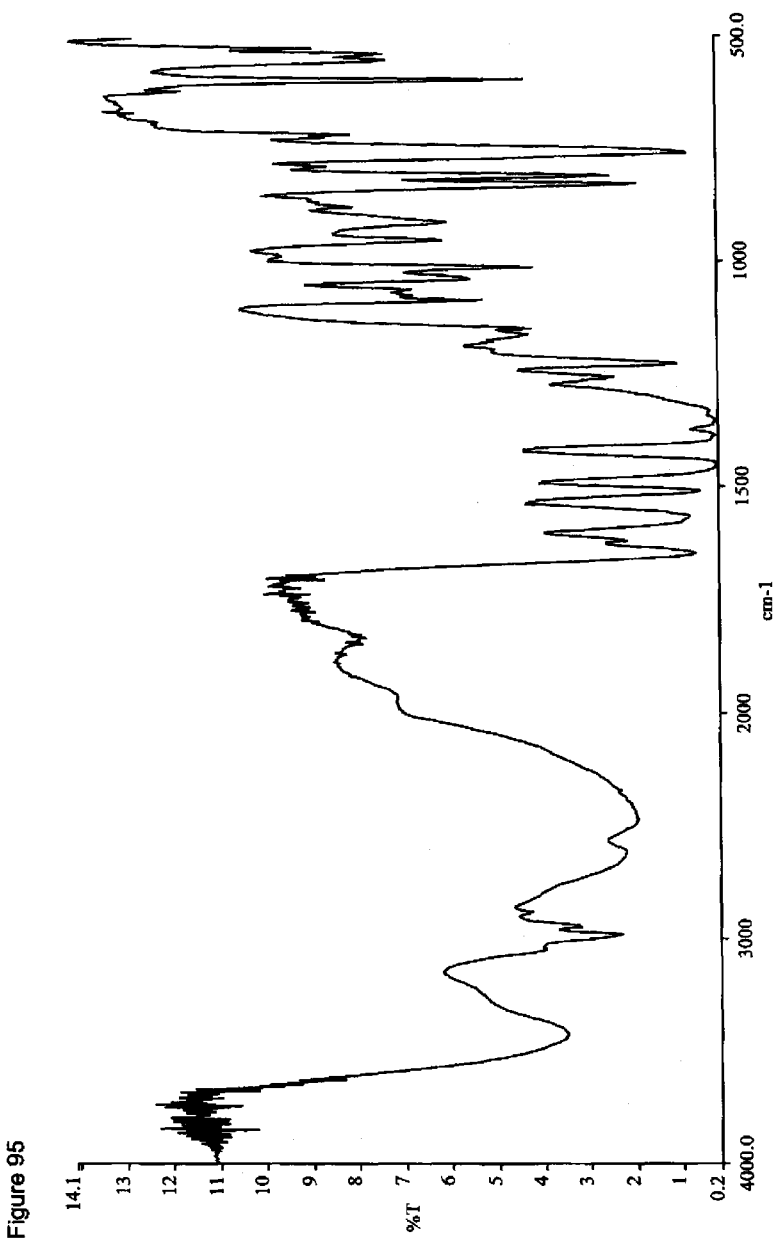
FIG. 95 is the Fourier Transform Infrared (FTIR) spectrum of amorphous bis(triethylammonium) pamoate.
Figure 96:
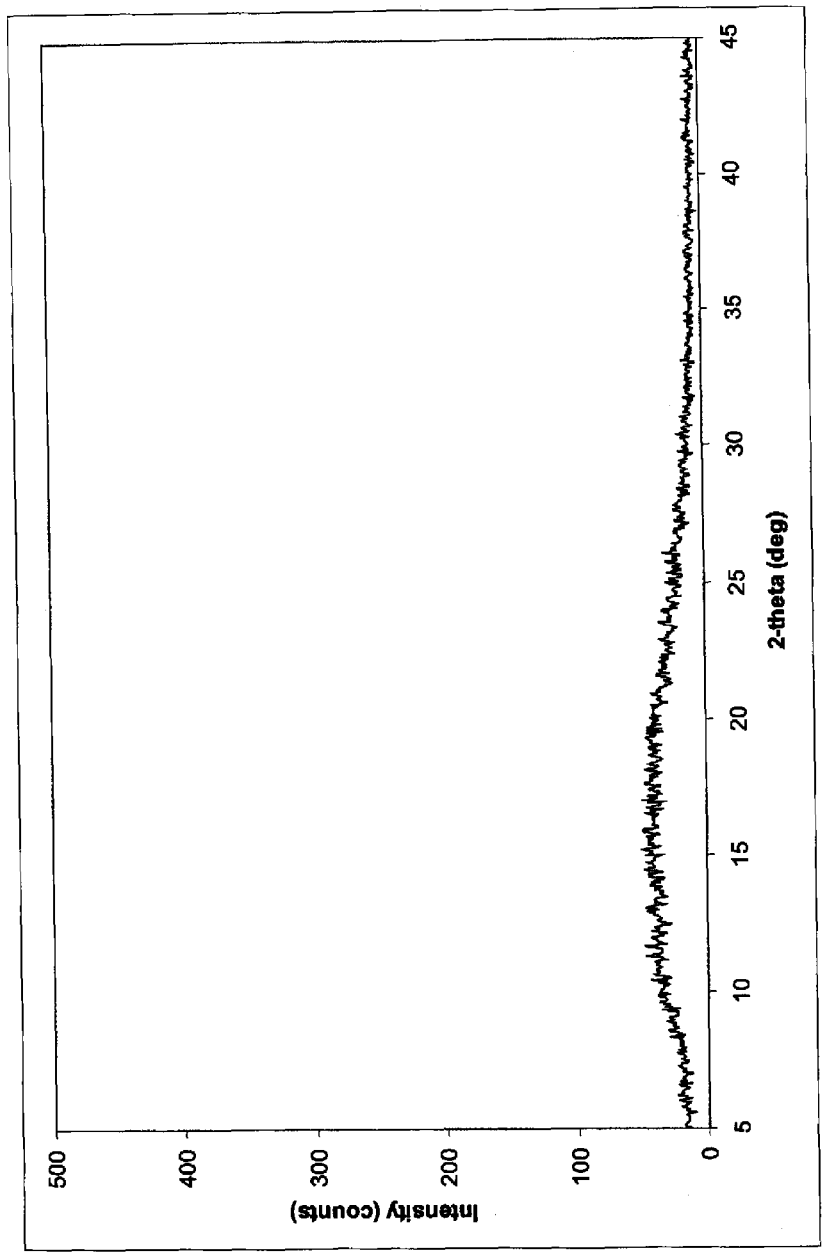
FIG. 96 is the powder X-ray diffraction (PXRD) diffractogram of amorphous bis(triethylammonium) pamoate.
Figure 97:
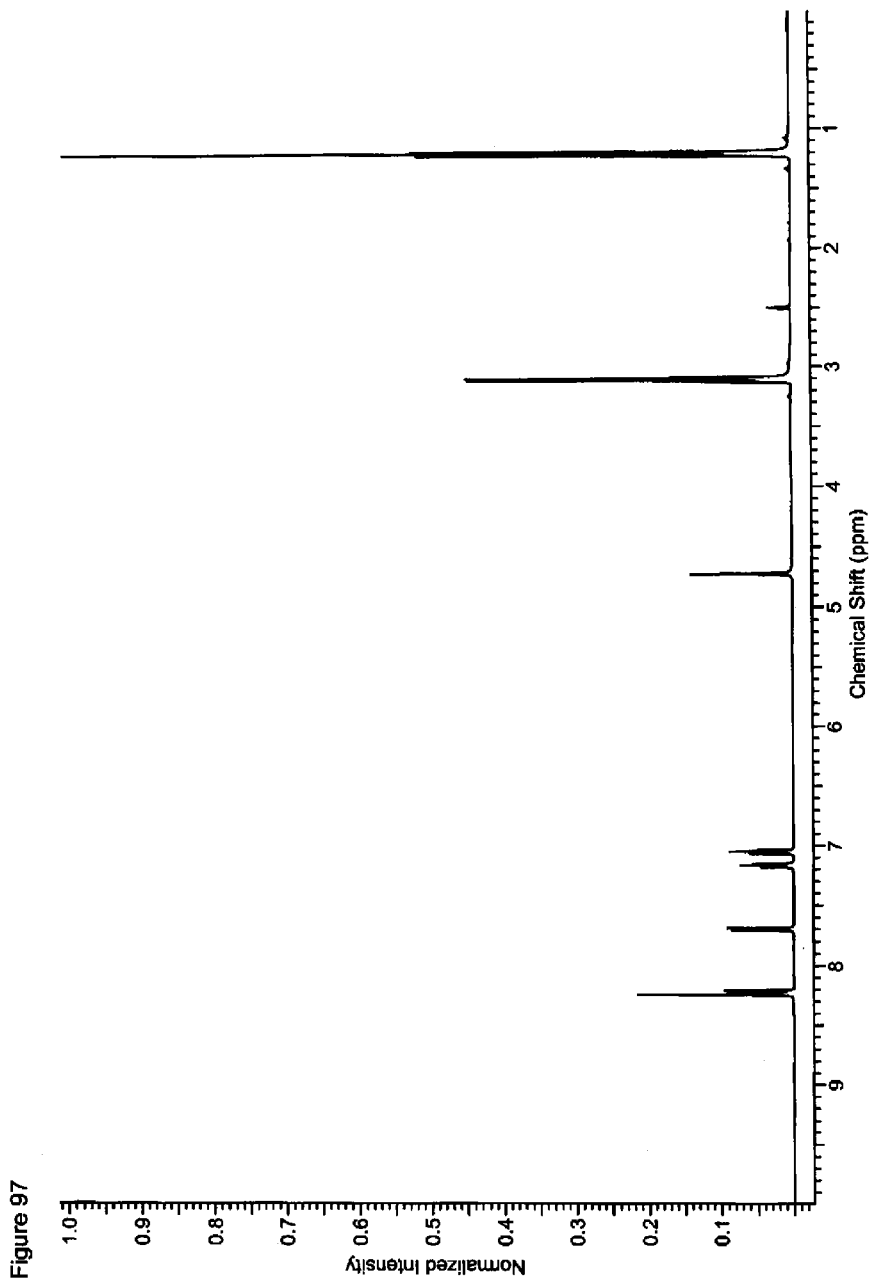
FIG. 97 is the proton nuclear magnetic resonance ($^1$H NMR) spectrum of amorphous bis(triethylammonium) pamoate.

To a one liter round-bottom flask equipped with a magnetic stir bar was charged 20.0 g (51.2 mmol) pamoic acid (0.5% moisture) and 640 mL water. To this suspension was added 11.2 g (110.1 mmol) triethylamine over a period of about 30 seconds which produced a solution with a pH about 8.5-9. The solution was stirred for approximately 1 hour and filtered to remove any particulates. The clear filtrate was concentrated under reduced pressure at 85° C. and dried (under vacuum overnight to provide 29.82 g (99%) of a tan to light brown solid (1.46% moisture) which was characterized by DSC (FIG. 94), FTIR (FIG. 95) PXRD (FIG. 96), and $^1$H NMR (FIG. 97). The results were consistent with the assigned structure and the PXRD diffractogram indicated the material was amorphous.

Example 22

Synthesis of Tetronic® Pamoate, 1:1 Salt

To a 100 mL beaker equipped with a magnetic stir bar was charged 9.98 g (2.77 mmol) Tetronic 701® and 18.7 g water which formed a cloudy mixture. Two equivalents of HCl (relative to Tetronic 701®) were delivered via addition of 5.54 mL 1N hydrochloric acid and stirred for ten minutes upon which the solution became clear.

To a 100 mL round-bottom flask equipped with a magnetic stir bar, thermowell and addition funnel were charged 1.20 g (2.77 mmol) disodium pamoate in 15 g water and the pH adjusted to about 9.5 with a small quantity of 1N sodium hydroxide solution. The Tetronic 701® solution prepared above was added to the disodium pamoate solution via addition funnel over about forty minutes upon which the solution became turbid. The solution was stirred for two hours and was subsequently extracted with diethyl ether (111 g, $1^{st}$ portion; 61 g, $2^{nd}$ extraction). The combined organic layers were concentrated under reduced pressure at ambient temperature to provide 10.5 g of a clear viscous yellow oil (95% yield) which was characterized by IR and proton NMR.

Example 23

Synthesis of Polymorphic Imipramine Pamoate, 1:1 Salt

Figure 104:
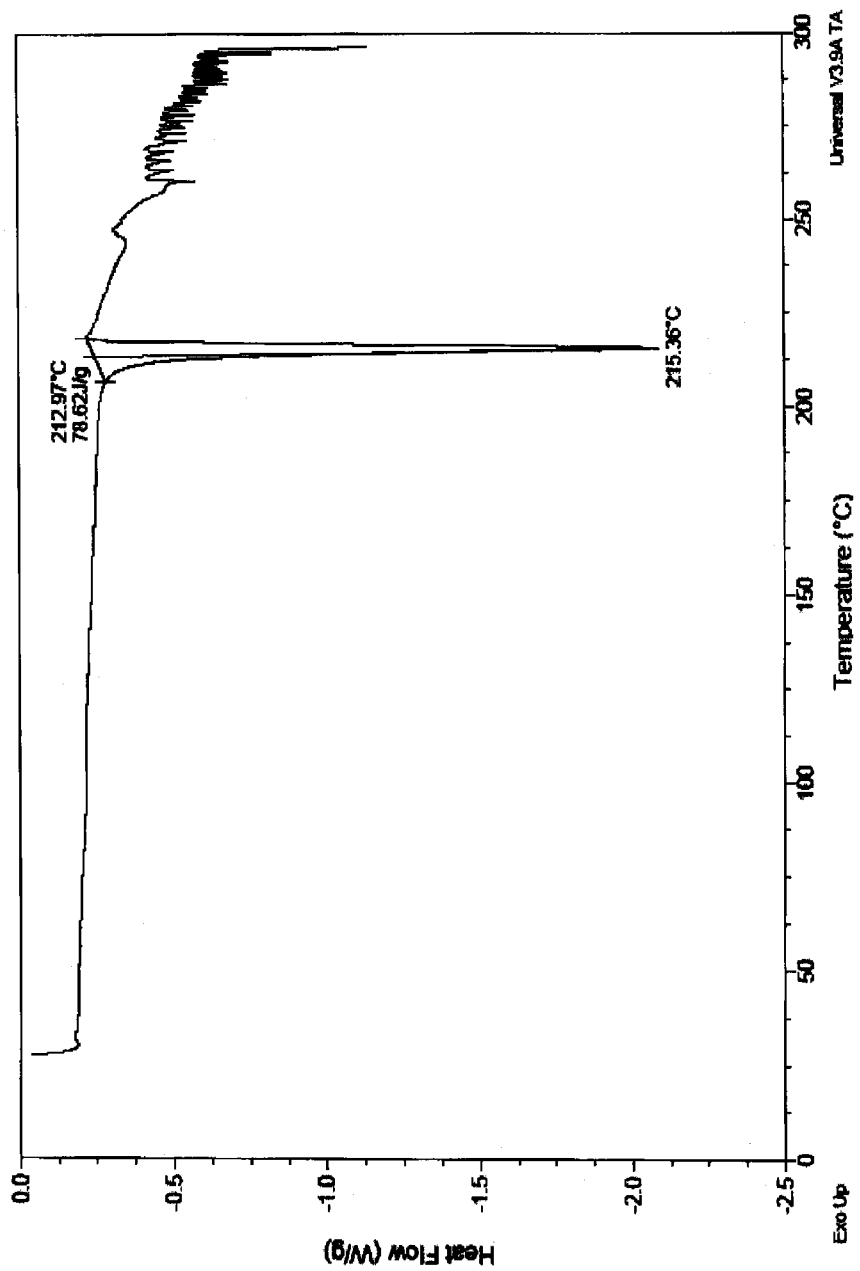
FIG. 104 is the differential scanning calorimetry (DSC) thermogram of polymorphic imipramine pamoate, 1:1 salt.

To a 100 mL round bottom flask equipped with a magnetic stir bar, thermowell, nitrogen inlet and condenser was charged 397.7 mg (0.419 mmol) imipramine pamoate, Form II (2:1) prepared according to King et al. U.S. Pat. No. 7,718,649, 1.67 g (0.419 mmol) Tetronic 701® pamoate (prepared as described above) and about 27.9 g toluene to produce a cloudy yellow suspension. The mixture was heated to about 37-40° C. under nitrogen and stirred overnight at this temperature. The mixture was allowed to cool to ambient temperature, collected by filtration through a medium fritted filter, washed with a small portion of toluene and dried to provide 0.52 g (93%) of a pale yellow-off-white solid (0.277% moisture content) which was characterized by DSC, FTIR (FIG. 105), PXRD (FIG. 106) and $^1$H NMR (FIG. 107). The PXRD analysis indicated isolation of a polymorphic, crystalline material. The relative ratio of imipramine/pamoate was determined to be about 1/1 by HPLC analysis and through structure elucidation by $^1$H NMR. The DSC thermogram is provided in FIG. 104 wherein illustrated is an endothermic phase change of at least 60 J/g at a temperature above 200° C.

The filtrate from above was evaporated to provide about 1.43 g of a yellow oil which was characterized and identified by $^1$H NMR and FTIR to be consistent with Tetronic 701®.

Example 24

Dissolution Procedure

The amine containing organic acid addition salts of the present invention were tested to determine their dissolution profile as a function of pH, and as a function of ethanol concentration in acidic media (dose dumping). To perform these experiments the buffered dissolution media and acidic ethanol solutions were prepared as identified herein, "Preparation of Solutions". The test procedure was derived from the procedures cited in the United States Pharmacopeia and National Formulary (USP), numbers <1087> and <711>. The dose dumping procedure was adopted from the United States Food and Drug Administration's guidance regarding the dose dumping of oxymorphone. The sampling interval and regimen were defined and each sample analyzed by HPLC. Results from the HPLC analyses were plotted as a function of time and dissolution condition (FIG. 28-45, FIGS. 78-93, and FIGS. 98-103). This procedure was used to obtain the pH and dose dumping dissolution profiles disclosed herein. Verb tense within the procedure description does not indicate a prospective condition but was used to facilitate the method's description herein. All activities within the procedure were conducted and executed for each of the compounds reported herein.

Dissolution Procedure

The following is a general procedure for intrinsic dissolution experiments.

Preparation of Solutions:

All reagents are ACS grade or equivalent. All solvents used are a minimal of HPLC grade. Water used in the preparations of all solutions is USP grade. These solution preparations have been taken directly from the USP.

Preparation of 0.1 N HCl:

To prepare 4 L of solution, add 33.3 mL of concentrated HCl to 977.7 mL of water, then add an additional 3000 mL of water.

Preparation of pH 4.5 Acetate Buffer:

To prepare 1 L of solution add 2.99 g of sodium acetate tri-hydrate (NaC$_2$H$_3$O$_2$.3H$_2$O) to a 1000 mL volumetric flask, then add 14.0 mLs of 2N acetic acid solution. Dissolve and dilute to volume with water.

Preparation of pH 6.8 Phosphate Buffer:

To prepare 200 mL of solution first prepare a 0.2 M potassium phosphate solution by adding 27.22 g of monobasic potassium phosphate (KH$_2$PO$_4$) to a 1000 mL volumetric flask, then dissolve and dilute to volume with water. Add 50 mL of this solution to a 200 mL volumetric flask, then add 22.4 mL of 0.2M NaOH and dilute to volume with water.

Preparation of 5% Ethanol Solution for Dose Dumping Dissolution Profiles:

To prepare 900 mL of media combine 45 mL of 200 proof ethanol with 855 mL of 0.1 N HCl (see preparation procedure above).

Preparation of 20% Ethanol Solution for Dose Dumping Dissolution Profiles:

To prepare 900 mL of media combine 180 mL of 200 proof ethanol with 720 mL of 0.1 N HCl (see preparation procedure above).

Preparation of 40% Ethanol Solution for Dose Dumping Dissolution Profiles:

To prepare 900 mL of media combine 360 mL of 200 proof ethanol with 540 mL of 0.1 N HCl (see preparation procedure above).

Preparation of Mobile Phase A (0.1% TFA in H$_2$O):

To prepare 1 L of mobile phase, add 1.0 mL of TFA to 1000 mL of H$_2$O. Mix well and filter this solution through a 0.45 µM nylon filter.

Preparation of Mobile Phase B (0.1% TFA in Acetonitrile):

To prepare 1 L of mobile phase, add 1.0 mL of TFA to 1000 mL acetonitrile. Mix well and filter this solution through a 0.45 µM nylon filter.

Preparation of Mobile Needle/Seal Wash Solution:

To prepare 1 L of solution, add 500 mL H$_2$O to 500 mL acetonitrile and mix well.

Procedure:

Intrinsic Dissolution Profiles:

Note: The following procedures were derived from USP <1087> Intrinsic Dissolution and USP <711> Dissolution methods, as well as manufacturer recommended procedures for use of the International Crystals Laboratories intrinsic dissolution disks.

Preparation of API Pellet for Intrinsic Dissolution:

The material which is to be subjected to dissolution is weighed using an analytical balance. 45.00-55.00 mgs of the analyte was weighed and transferred to an International Crystals Laboratories fixed/static disk 316 stainless die with a 0.8 cm diameter die cavity. A hardened steel punch was then inserted into the cavity and the material was compressed at 2000 psi for 4-5 minutes using a bench top hydraulic press. The punch is then removed to expose the 0.5 cm$^2$ pellet surface. A Viton gasket is then placed around the threaded shoulder of the die and a polypropylene cap is threaded onto the die. This process can be repeated to generate as many pellets as is necessary for the experiment.

Setup of Intrinsic Dissolution Apparatus:

A Distek Dissolution System equipped with a model number TCS0200C temperature control system was filled with water and set to a temperature of 37.3° C. The vessel cavities were then equipped with four 1 L flat-bottomed Distek dissolution vessels. Four vessels were then filled with 500 mL of the following media: 0.1 N HCl, pH 4.5 acetate buffer, pH 6.8 phosphate buffer, and USP grade water. The solutions were allowed to warm in the water bath for approximately 1 hour, but not exceeding 3 hours, or until the temperature of the media matched that of the water bath. Paddles were then mounted to the Distek stirring apparatus above the four dissolution vessels such that the distance between the paddle and the die face is 1 inch. The paddle speed is then set to 50 RPM.

Intrinsic Dissolution Dose Dumping Profiles:

Note: The following procedures were derived from the FDA Draft Guidance for Oxymorphone Hydrochloride (recommended in November, 2007).

Preparation of API Pellet for Intrinsic Dissolution Dose Dumping Profile:

The material which is to be subjected to dissolution is weighed using an analytical balance. 85.00-95.00 mgs of the analyte was weighed and transferred to an International Crystals Laboratories fixed/static disk 316 stainless die with a 0.8 cm diameter die cavity. A hardened steel punch was then inserted into the cavity and the material was compressed at 2000 psi for 4-5 minutes using a bench top hydraulic press. The punch is then removed to expose the 0.5 cm² pellet surface. A Viton gasket is then placed around the threaded shoulder of the die and a polypropylene cap is threaded onto the die. This process can be repeated to generate as many pellets as is necessary for the experiment.

Setup of Intrinsic Dissolution Apparatus for Dose Dumping Profile:

A Distek Dissolution System equipped with a model number TCS0200C temperature control system, was filled with water and set to a temperature of 37.3° C. The vessel cavities were then equipped with four 1 L flat-bottomed Distek dissolution vessels. The vessels were then filled with 900 mL of the following media: 0.1 N HCl, 5% ethanol solution, 20% ethanol Solution, and 40% ethanol solution. The solutions were allowed to warm in the water bath for approximately 1 hour, but not exceeding 3 hours, or until the temperature of the media matched that of the water bath. Paddles were then mounted to the Distek stirring apparatus above the four dissolution vessels such that the distance between the paddle and the die face is 1 inch. The paddle speed is then set to 75 RPM.

Performing an Intrinsic Dissolution Experiment (Dose Dumping or pH Media):

The pellet prepared as described above is submerged into a vessel prepared as described above, with the pellet surface facing up (metal die up, polypropylene cap facing down). Forceps are used to aid this process so that the pellet apparatus can be gently placed into the bottom of the vessel. A timer is used to track the sampling intervals, and is started when the pellet is dropped into the solution. The lid to the dissolution apparatus is then lowered and the stirring apparatus is activated. Some planning is required in spacing out pellet drops such that each vessel can be sampled at the desired time intervals. Sampling is done by aspirating 10 mL of the solution using a Popper® Micro-Mate® Interchangeable Hypodermic Syringe equipped with a Vortex Pharma Group 10 micron cannula porous filter. This filter should be replaced after each use. Although sampling intervals can change from experiment to experiment, the following has been heavily utilized for the experiments described herein. Sampling occurring at t=0, 5, 10, 15, 30, 45, 60, 90, 120, 150, 180 (in minutes).

HPLC Methodology

HPLC Procedure for Analyzing Opioid Pamoates and Xinafoates:

All samples should be analyzed with bracketing standard injections. The standard used should be from a qualified vendor with a known purity. Standard solutions should be prepared to have a concentration that is approximate to that of the samples being analyzed. All samples were ran on a Waters Alliance 2695 Separations Module model number WAT270008 equipped with a Alliance 996 Photodiode Array Detector model number 186000869. The instrument was equipped with an Agilent 300 Extend-C18 5 µm 4.6×250 mm Zorbax column (PN 770995-902). The instrument was then plumbed with the proper solutions mentioned above in the section titled "Preparation of Solutions". The instrument is then set to initial column conditions (see gradient table below):

| Time (minutes) | % A | % B |
| --- | --- | --- |
| 0.00 | 90 | 10 |
| 2.00 | 90 | 10 |
| 8.00 | 25 | 75 |
| 8.01 | 0 | 100 |
| 13.00 | 0 | 100 |
| 13.01 | 90 | 10 |
| 17.00 | 90 | 10 |

This method can be used to analyze samples to plot a dissolution profile or to determine the ratio of drug to organic salt. Due to the significant difference in response factors between pamoate or xinafoate salts, a dilution is sometimes required to quantify the salt portion of the mixture. Typically a solution prepared at roughly 500 µg/mL needs to be diluted by a factor of 20 in order to quantify the pamoate moiety, and the corresponding amine should always be quantified using the stock solution. An exception to this occurs with imipramine pamoate. Imipramine pamoate injections do not require a subsequent dilution when the chromatographic data is extracted at 269 nm. All other injections should be extracted at 254 nm, and even imipramine pamoate can be extracted at this wavelength if the solution is diluted properly (see above) when quantifying the ratio of amine to pamoate.

The sample diluent utilized also has an impact on the chromatography when implementing this method. The following sample diluents were used when analyzing the corresponding pamoate salts for ratio analysis, as well as dissolution profiles. Also, all ratio determinations and ratio plots are determined based on a known standard as identified in the table below.

| Material | Diluent (H₂O:ACN) |
| --- | --- |
| Racemic-Methylphenidate HCl (standard) | 62:38 |
| d-Methylphenidate HCl (standard | 62:38 |
| Dextroamphetamine Sulfate (standard) | 100:0 |
| Racemic-Methylphenidate Pamoate | 62:38 |
| d-Methylphenidate Pamoate | 62:38 |
| Dextroamphetamine Pamoate | 62:38 |
| Imipramine Pamoate | 62:38 |
| Imipramine HCl (standard) | 62:38 |
| Disodium Pamoate (standard) | 62:38 |

In some cases when the typical 62:38 diluent is not sufficient to form a solution, a minimal amount of DMSO can be added to dissolve the material, and then the flask should be diluted to volume with 62:38 (H₂O:ACN).

The present invention has been described with particular reference to the preferred embodiments without limit thereto. One of skill in the art would realize additional embodiments, alterations and improvements which are not specifically set forth but which are within the metes and bounds of the present application as set forth more particularly in the claims appended hereto.

Figure 54:
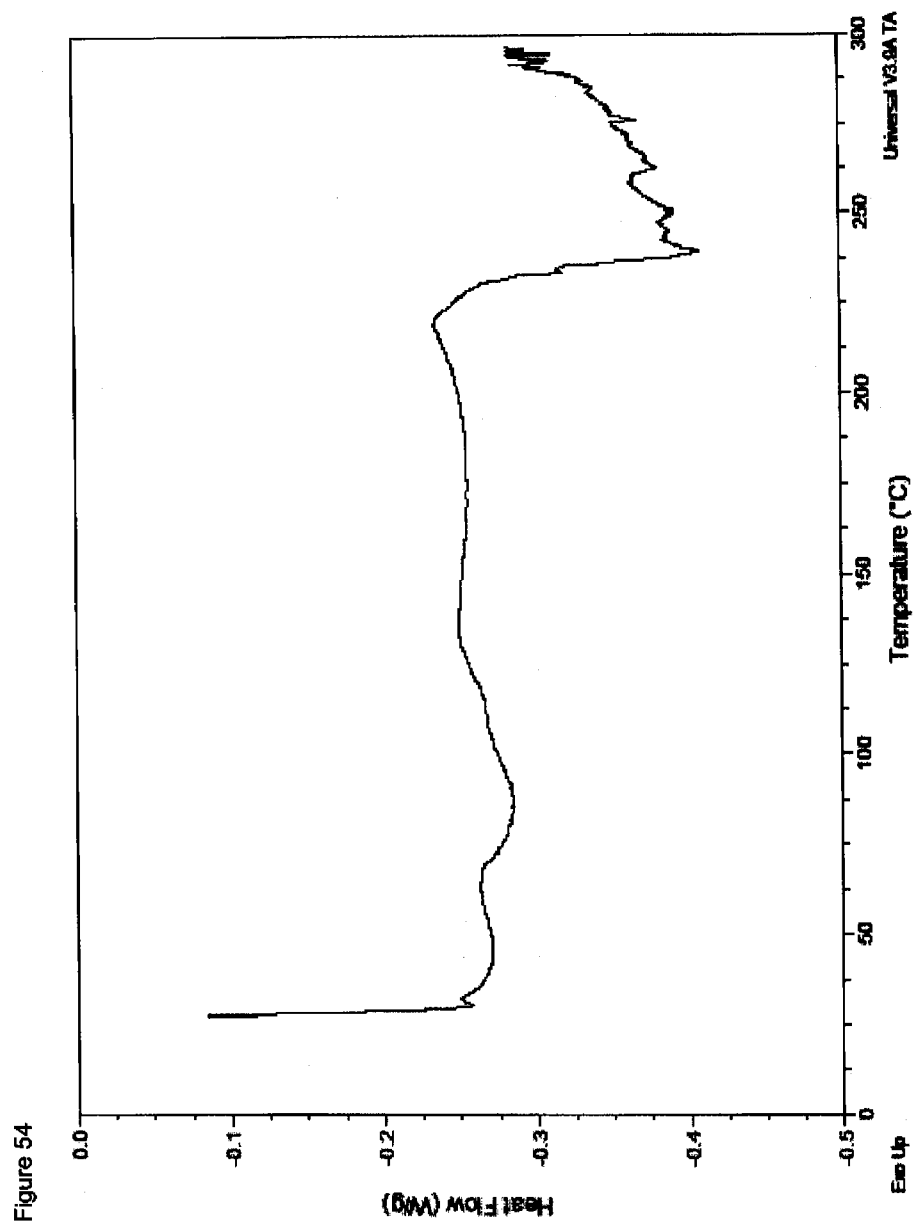
FIG. 54 is the differential scanning calorimetry (DSC) thermogram of amorphous imipramine pamoate, 1:1 salt.
Figure 55:
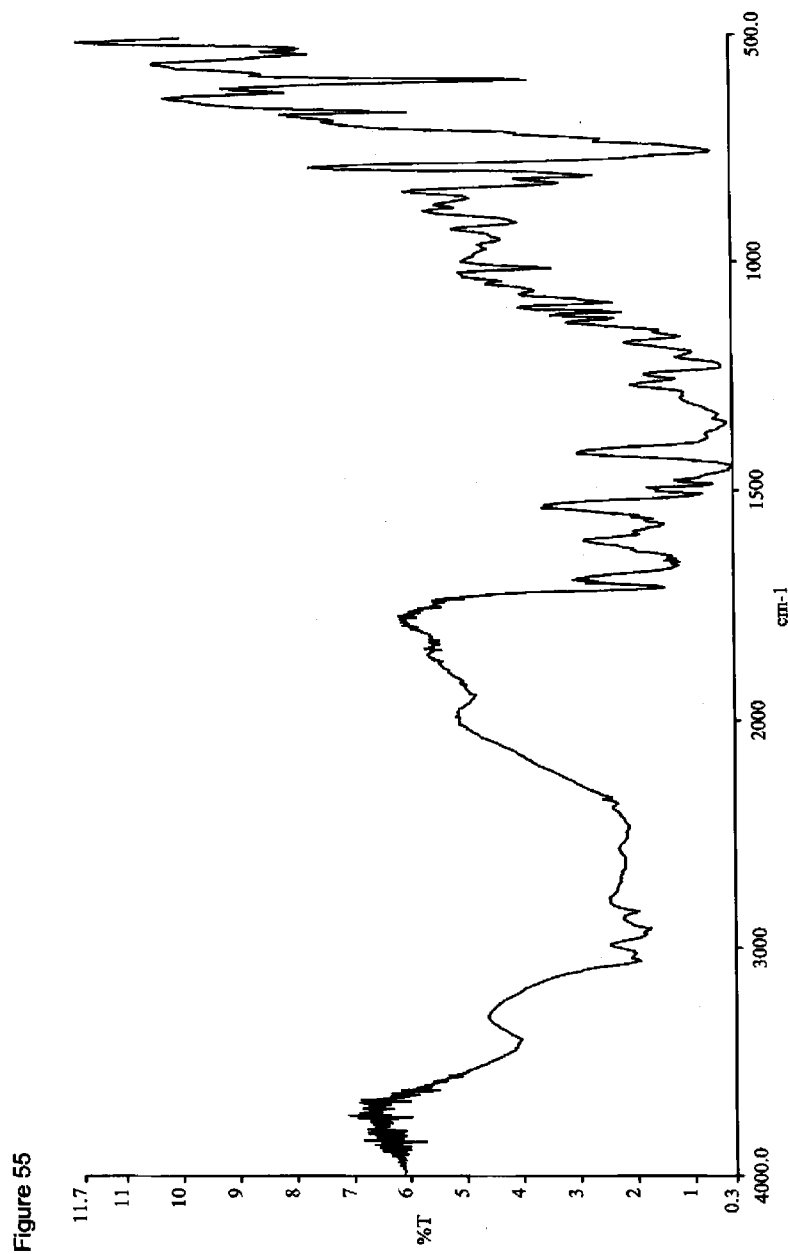
FIG. 55 is the Fourier Transform Infrared (FTIR) spectrum of amorphous imipramine pamoate, 1:1 salt.
Figure 56:
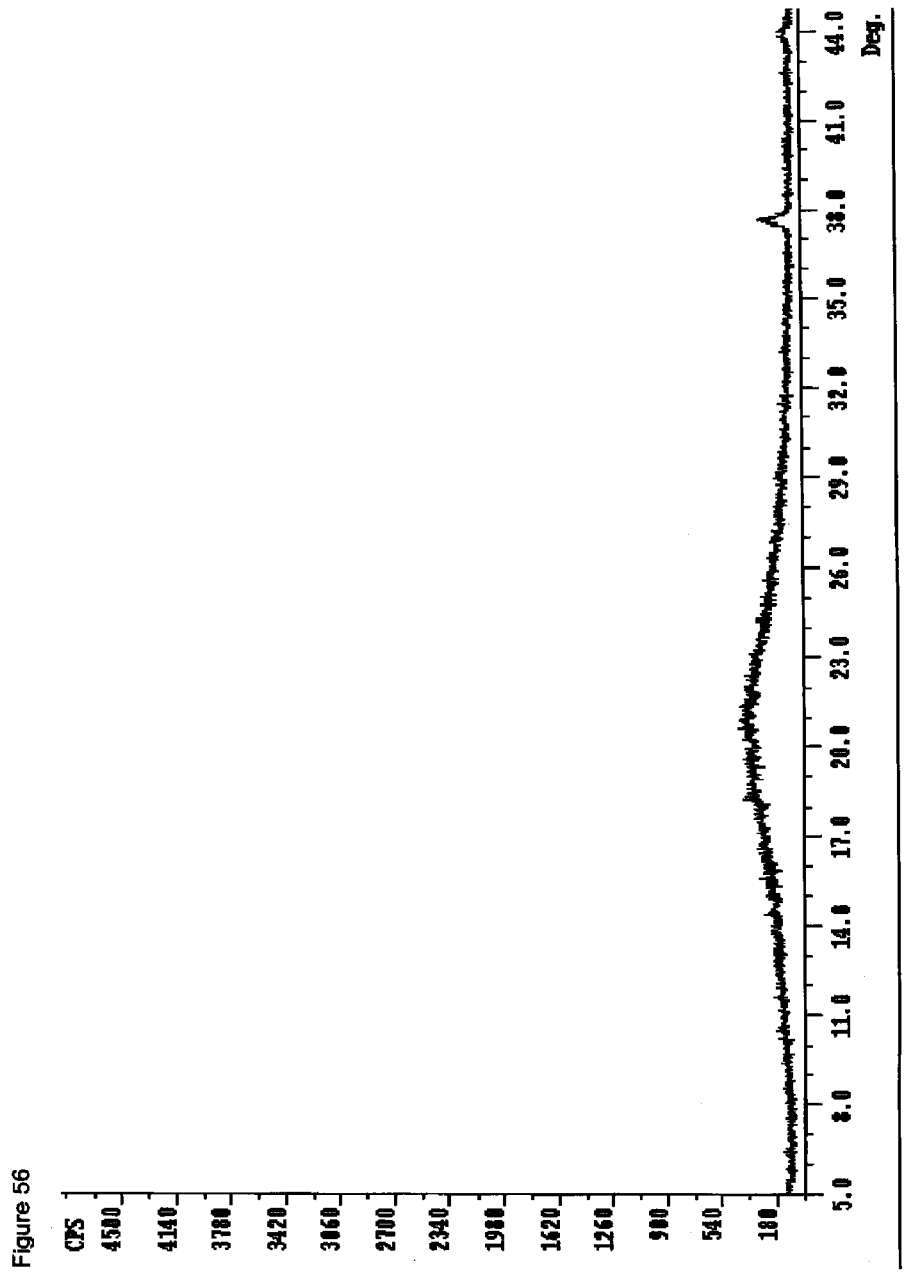
FIG. 56 is the powder X-ray diffraction (PXRD) diffractogram of amorphous imipramine pamoate, 1:1 salt.
Figure 57:
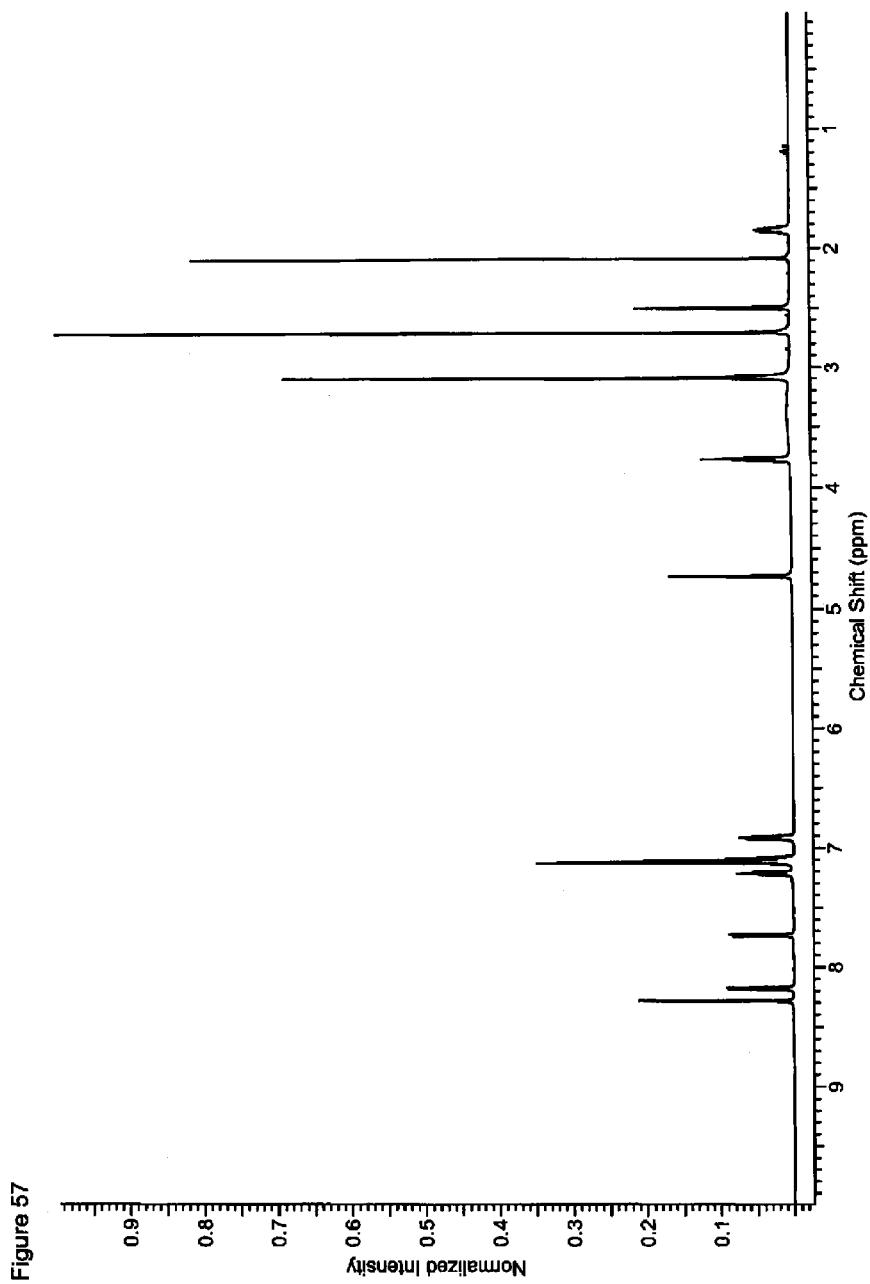
FIG. 57 is the proton nuclear magnetic resonance ($^1$H NMR) spectrum of amorphous imipramine pamoate, 1:1 salt.
Figure 75:
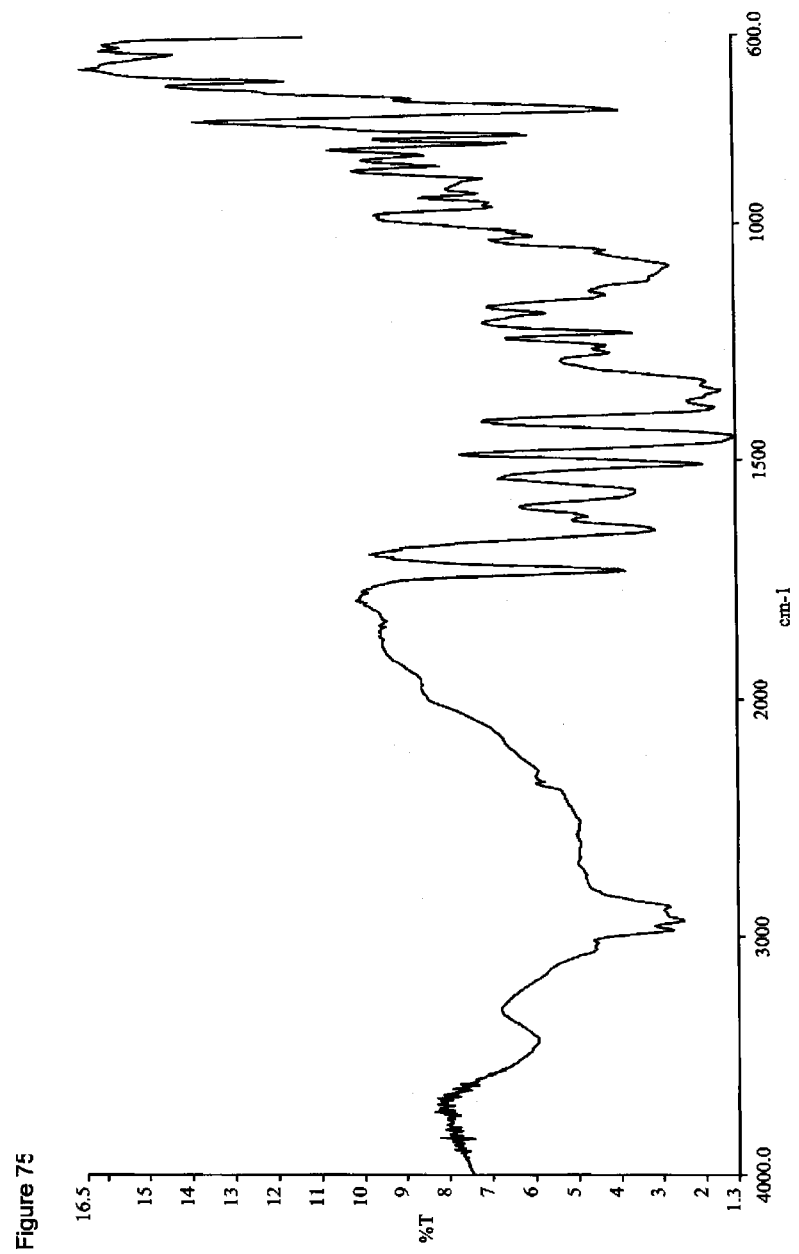
FIG. 75 is the Fourier Transform Infrared (FTIR) spectrum of amorphous hydrocodone Jeffamine® pamoate, 1:1:1 salt.
Figure 76:
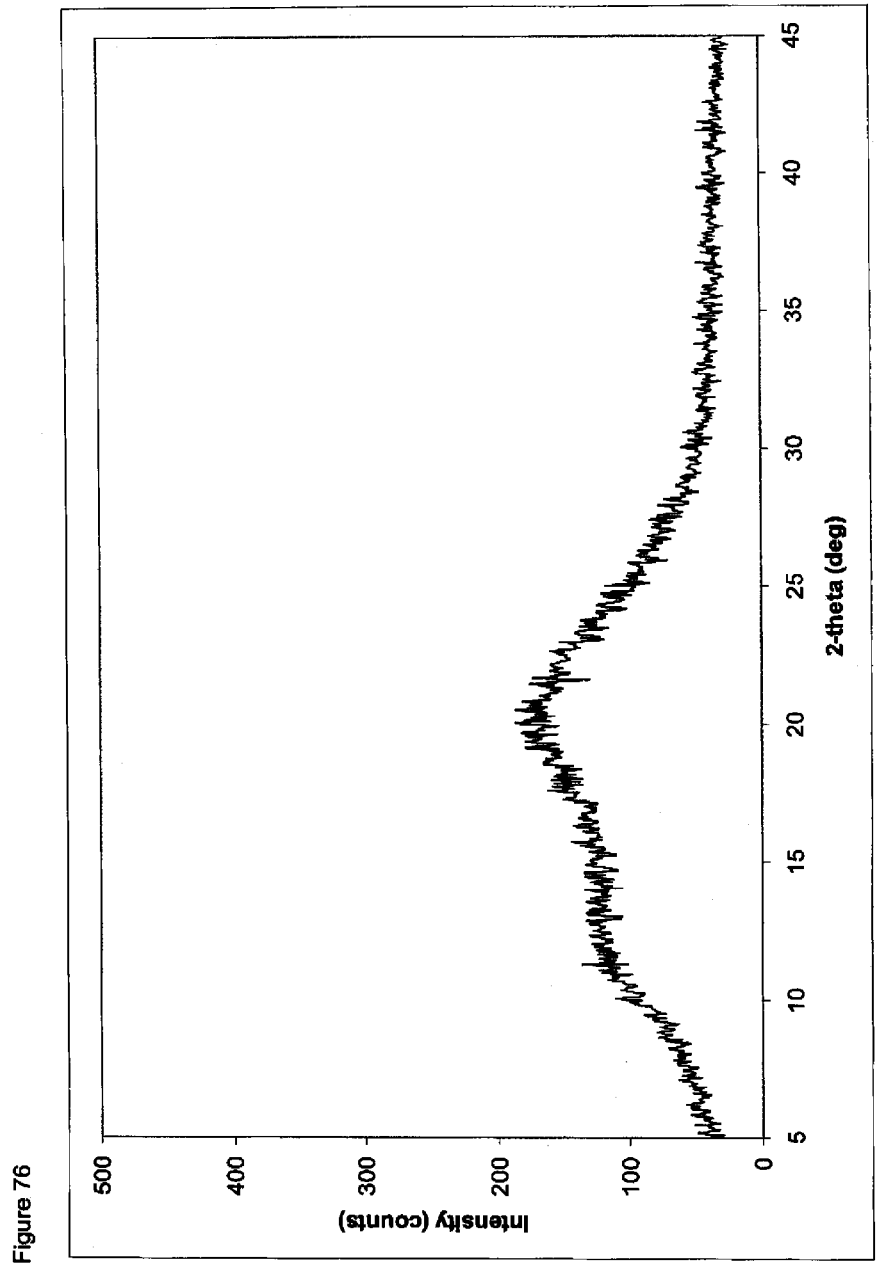
FIG. 76 is the powder X-ray diffraction (PXRD) diffractogram of amorphous hydrocodone Jeffamine® pamoate, 1:1:1 salt.
Figure 77:
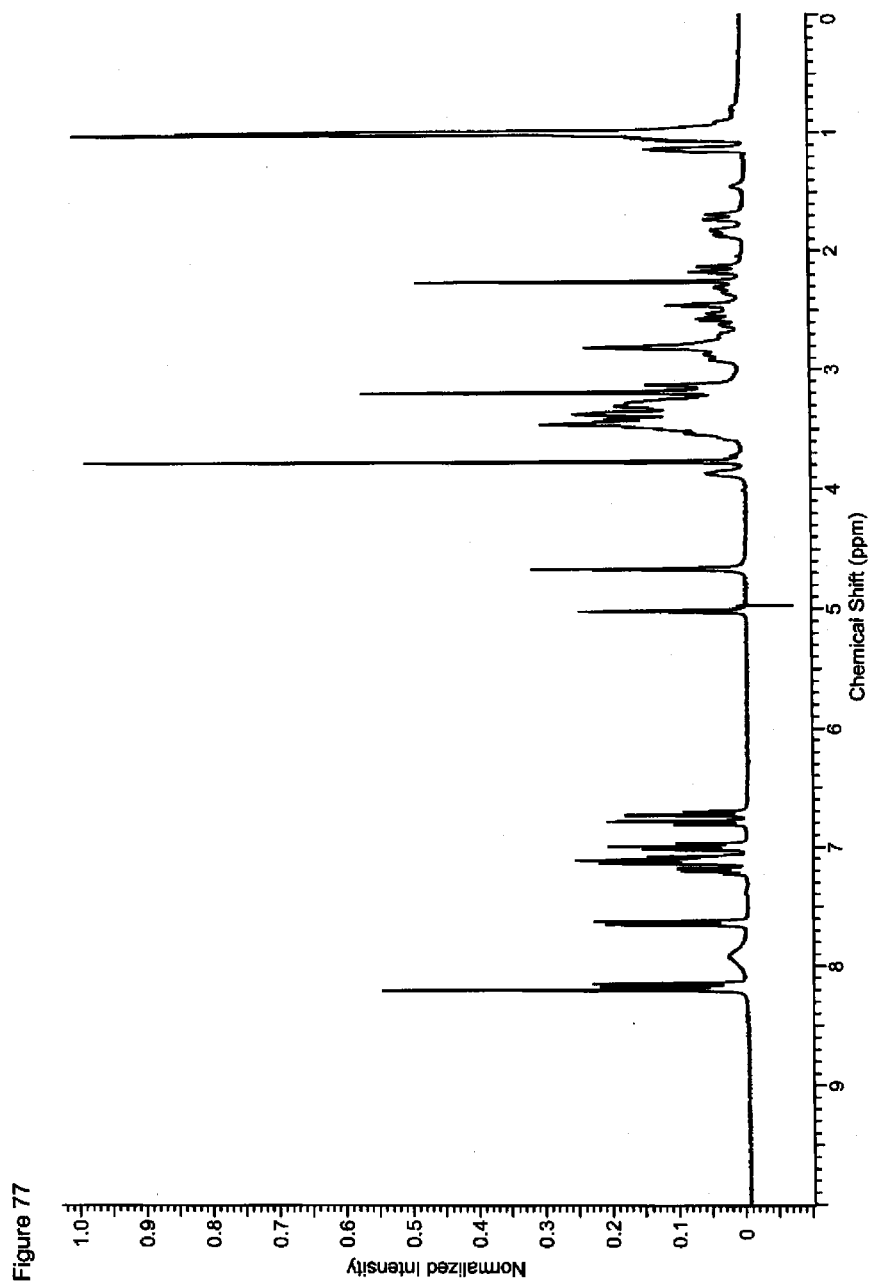
FIG. 77 is the proton nuclear magnetic resonance ($^1$H NMR) spectrum of amorphous hydrocodone Jeffamine® pamoate, 1:1:1 salt.
Figure 105:
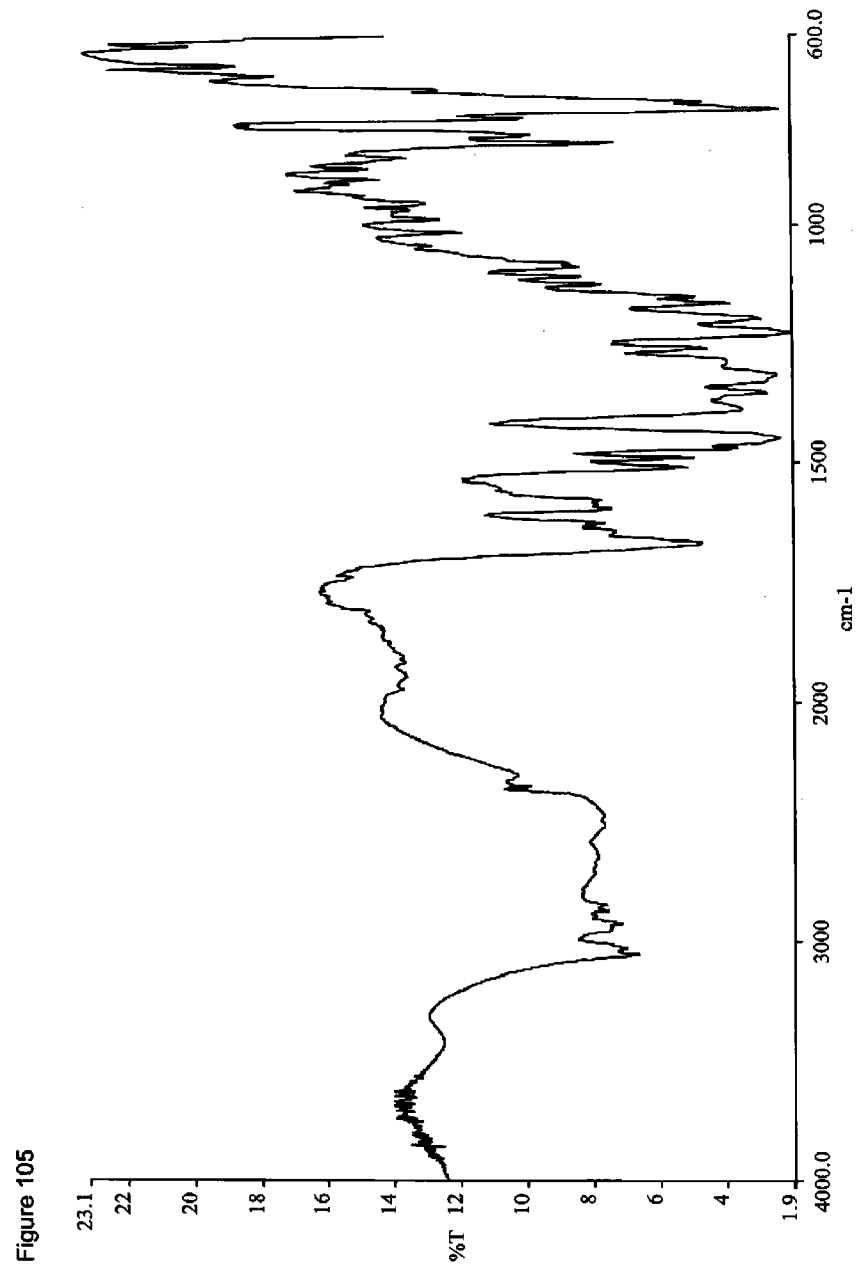
FIG. 105 is the Fourier Transform Infrared (FTIR) spectrum of polymorphic imipramine pamoate, 1:1 salt.
Figure 106:
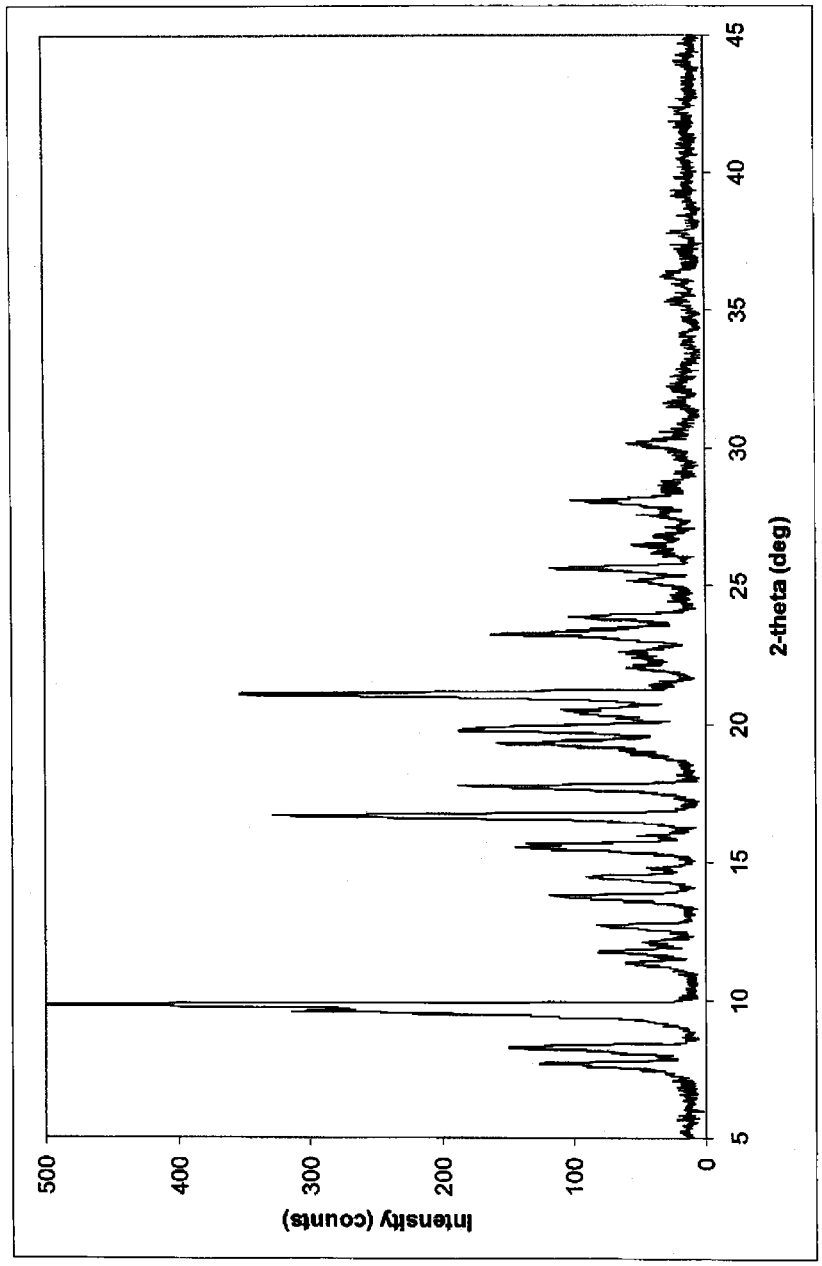
FIG. 106 is the powder X-ray diffraction (PXRD) diffractogram of polymorphic imipramine pamoate, 1:1 salt.
Figure 107:
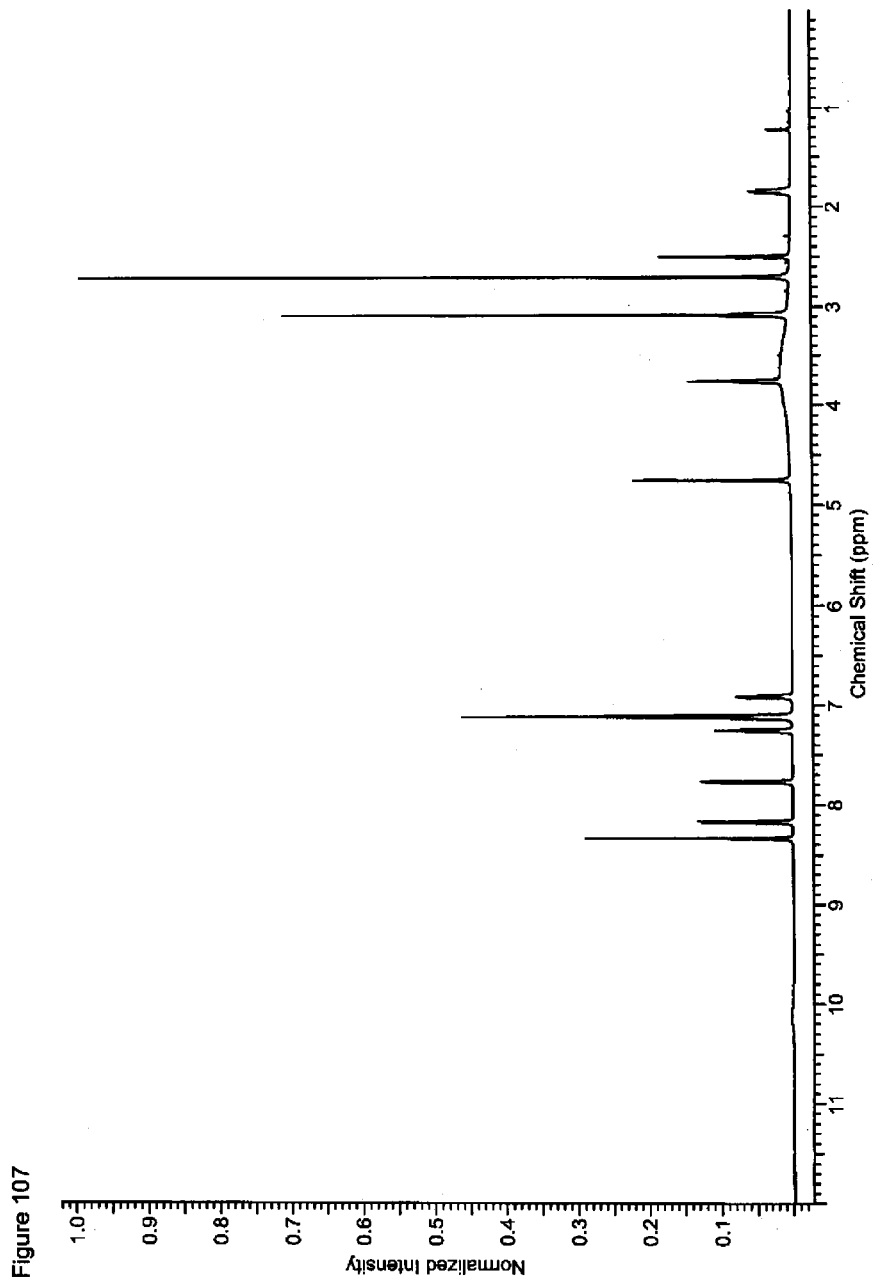
FIG. 107 is the proton nuclear magnetic resonance ($^1$H NMR) spectrum of polymorphic imipramine pamoate, 1:1 salt.

The invention claimed is:

1. A drug product not susceptible to dose dumping wherein said drug product comprises a drug substance wherein said drug substance is selected from the group consisting of:
amorphous racemic-methylphenidate pamoate characterized by at least one method selected from the group consisting of:
an endothermic phase change of at least 70 J/gram at greater than 200° C.;
an FTIR spectrum of FIG. 2; and
a PXRD diffractogram of FIG. 3;
polymorphic racemic-methylphenidate stearylamine pamoate characterized by at least one method selected from the group consisting of:
an endothermic phase change of at least 15 J/g at a temperature above 50° C.; an endothermic phase change of at least 10 J/g at a temperature of above 90° C.; an endothermic phase change of at least 2 J/g at a temperature above 105° C.; an endothermic phase change of at least 4 J/g at above 155° C. and an endothermic phase change of at least 20 J/g above 180° C.; and
a PXRD diffractogram of FIG. 48;
amorphous d-methylphenidate pamoate characterized by at least one method selected from the group consisting of:
an endothermic phase change of at least 45 J/gram at greater than 70° C. and an endothermic phase change of at least 30 J/gram at greater than 180° C.;
an FTIR spectrum of FIG. 11; and
a PXRD diffractogram of FIG. 12;
amorphous d-methylphenidate xinafoate characterized by at least one method selected from the group consisting of:
an endothermic phase change of at least 10 J/gram at greater than 45° C. and an endothermic phase change of at least 50 J/gram at greater than 160° C.;
an FTIR spectrum of FIG. 17; and
a PXRD diffractogram of FIG. 18;
polymorphic dextro-amphetamine xinafoate characterized by at least one method selected from the group consisting of:
an endothermic phase change of at least 60 J/gram at greater than 125° C.;
an FTIR spectrum of FIG. 26; and
a PXRD diffractogram of FIG. 27;
polymorphic d-methylphenidate pamoate characterized by at least one method selected from the group consisting of:
an endothermic phase change of at least 35 J/gram at greater than 185° C.;
an FTIR spectrum of FIG. 14; and
a PXRD diffractogram of FIG. 15;
polymorphic racemic-methylphenidate pamoate characterized by at least one method selected from the group consisting of:
an endothermic phase change of at least 75 J/gram at greater than 200° C.;
an FTIR spectrum of FIG. 5; and
a PXRD diffractogram of FIG. 6;
polymorphic racemic-methylphenidate xinafoate characterized by at least one method selected from the group consisting of:
an endothermic phase change of at least 75 J/gram at greater than 155° C.;
an FTIR spectrum of FIG. 8; and
a PXRD diffractogram of FIG. 9;
amorphous dextro-amphetamine pamoate characterized by at least one method selected from the group consisting of:
endothermic phase change of at least 10 J/gram at greater than 200° C. and an endothermic phase change of at least 75 J/gram at greater than 220° C.;
an FTIR spectrum of FIG. 20; and
a PXRD diffractogram of FIG. 21;
polymorphic dextro-amphetamine pamoate characterized by at least one method selected from the group consisting of:
an endothermic phase change of at least 60 J/gram at greater than 200° C.;
an FTIR spectrum of FIG. 23; and
a PXRD diffractogram of FIG. 24;
amorphous d-methylphenidate mono-triethylammonium pamoate characterized by at least one method selected from the group consisting of:
an endothermic phase change of at least 12 J/g at a temperature above 240° C.
an FTIR spectrum of FIG. 51;
a PXRD diffractogram of FIG. 52; and
$^1$H NMR spectrum of FIG. 53;
amorphous imipramine mono-triethylammonium pamoate characterized by at least one method selected from the group consisting of:
an FTIR spectrum of FIG. 59;
a PXRD diffractogram of FIG. 60; and
$^1$H NMR spectrum of FIG. 61;
polymorphic imipramine stearylamine pamoate characterized by at least one method selected from the group consisting of:
an endothermic phase change of at least 40 J/g at a temperature above 70° C. and an endothermic phase change of at least 1 J/g above 125° C.;
an FTIR spectrum of FIG. 63;
a PXRD diffractogram of FIG. 64; and
$^1$H NMR spectrum of FIG. 65;
amorphous imipramine, CH₃(O(CH₂)₂)$_x$(OCH₂CHCH₃)$_y$NH₂ wherein Y/X is 9:1 with an approximate MW of 600, pamoate characterized by at least one method selected from the group consisting of:
an endothermic phase change of at least 50 J/g at a temperature above 240° C.;
an FTIR spectrum of FIG. 67;
a PXRD diffractogram of FIG. 68; and
$^1$H NMR spectrum of FIG. 69;
amorphous hydrocodone stearylamine pamoate characterized by at least one method selected from the group consisting of:
an endothermic phase change of at least 1 J/g at a temperature above 65° C.; an endothermic phase change of at least 1 J/g above 70° C. and an endothermic phase change of at least 3 J/g above 105° C.;
an FTIR spectrum of FIG. 71;
a PXRD diffractogram of FIG. 72; and
$^1$H NMR spectrum of FIG. 73;

amorphous hydrocodone, $CH_3(O(CH_2)_2)_x(OCH_2CHCH_3)_y NH_2$ wherein Y/X is 9:1 with an approximate MW of 600, pamoate characterized by at least one method selected from the group consisting of:
an endothermic phase change of at least 5 J/g at a temperature above 105° C. and an endothermic phase change of at least 1 J/g at a temperature above 150° C.;
an FTIR spectrum of FIG. 75;
a PXRD diffractogram of FIG. 76; and
$^1$H NMR spectrum of FIG. 77;
polymorphic imipramine pamoate (1:1) characterized by at least one method selected from the group consisting of:
an endothermic phase change of at least 60 J/g at a temperature above 200° C.;
an FTIR spectrum of FIG. 105;
a PXRD diffractogram of FIG. 106; and
$^1$H NMR spectrum of FIG. 107; and
amorphous imipramine pamoate (1:1) characterized by at least one method selected from the group consisting of:
a DSC spectrum of FIG. 54;
an FTIR spectrum of FIG. 55;
a PXRD diffractogram of FIG. 56; and
$^1$H NMR spectrum of FIG. 57;
and said drug substance meets at least one condition in 0.1 N HCl selected from the group consisting of:
no more than 35% of said drug substance is released at 30 minutes with 5 wt % ethanol in said 0.1 N HCl;
the percentage of said drug substance released with at least 5 wt % ethanol in said 0.1 N HCl is no more than a percentage of said drug substance released in said 0.1 N HCl without ethanol; and
the percentage of drug substance released with 40 wt % ethanol in 0.1 N HCl does not exceed 60% while the percentage of drug substance released under the conditions selected from water, 0.1 N HCl, 5 wt % ethanol in 0.1 N HCl and 20 wt % ethanol in 0.1 N HCl does not exceed the drug substance released with 40 wt % ethanol in 0.1 N HCl.

2. The drug product not susceptible to dose dumping of claim 1 wherein no more than 35% of said drug substance is released at 45 minutes with 5 wt % ethanol in said 0.1 N HCl.

3. A drug product not susceptible to dose dumping wherein said drug product comprises a drug substance wherein said drug substance is a pharmaceutically acceptable organic acid salt of an amine containing pharmaceutically active compound selected from the group consisting of amphetamine, methylphenidate, imipramine and hydrocodone and said drug substance meets at least one condition in 0.1 N HCl selected from the group consisting of:
no more than 35% of said drug substance is released at 30 minutes with 5 wt % ethanol in said 0.1 N HCl;
the percentage of said drug substance released with at least 5 wt % ethanol in said 0.1 N HCl is no more than a percentage of said drug substance released in said 0.1 N HCl without ethanol; and
the percentage of drug substance released with 40 wt % ethanol in 0.1 N HCl does not exceed 60% while the percentage of drug substance released under the conditions selected from water, 0.1 N HCl, 5 wt % ethanol in 0.1 N HCl and 20 wt % ethanol in 0.1 N HCl does not exceed the drug substance released with 40 wt % ethanol in 0.1 N HCl wherein said drug substance is amorphous racemic-methylphenidate pamoate has an endothermic phase change of at least 70 J/gram at greater than 200° C.

4. A drug product not susceptible to dose dumping wherein said drug product comprises a drug substance wherein said drug substance is a pharmaceutically acceptable organic acid salt of an amine containing pharmaceutically active compound selected from the group consisting of amphetamine, methylphenidate, imipramine and hydrocodone and said drug substance meets at least one condition in 0.1 N HCl selected from the group consisting of:
no more than 35% of said drug substance is released at 30 minutes with 5 wt % ethanol in said 0.1 N HCl;
the percentage of said drug substance released with at least 5 wt % ethanol in said 0.1 N HCl is no more than a percentage of said drug substance released in said 0.1 N HCl without ethanol; and
the percentage of drug substance released with 40 wt % ethanol in 0.1 N HCl does not exceed 60% while the percentage of drug substance released under the conditions selected from water, 0.1 N HCl, 5 wt % ethanol in 0.1 N HCl and 20 wt % ethanol in 0.1 N HCl does not exceed the drug substance released with 40 wt % ethanol in 0.1 N HCl wherein said drug substance is amorphous racemic-methylphenidate pamoate has an FTIR spectrum of FIG. 2.

5. A drug product not susceptible to dose dumping wherein said drug product comprises a drug substance wherein said drug substance is a pharmaceutically acceptable organic acid salt of an amine containing pharmaceutically active compound selected from the group consisting of amphetamine, methylphenidate, imipramine and hydrocodone and said drug substance meets at least one condition in 0.1 N HCl selected from the group consisting of:
no more than 35% of said drug substance is released at 30 minutes with 5 wt % ethanol in said 0.1 N HCl;
the percentage of said drug substance released with at least 5 wt % ethanol in said 0.1 N HCl is no more than a percentage of said drug substance released in said 0.1 N HCl without ethanol; and
the percentage of drug substance released with 40 wt % ethanol in 0.1 N HCl does not exceed 60% while the percentage of drug substance released under the conditions selected from water, 0.1 N HCl, 5 wt % ethanol in 0.1 N HCl and 20 wt % ethanol in 0.1 N HCl does not exceed the drug substance released with 40 wt % ethanol in 0.1 N HCl wherein said drug substance is amorphous racemic-methylphenidate pamoate has a PXRD diffractogram of FIG. 3.

Figure 5:
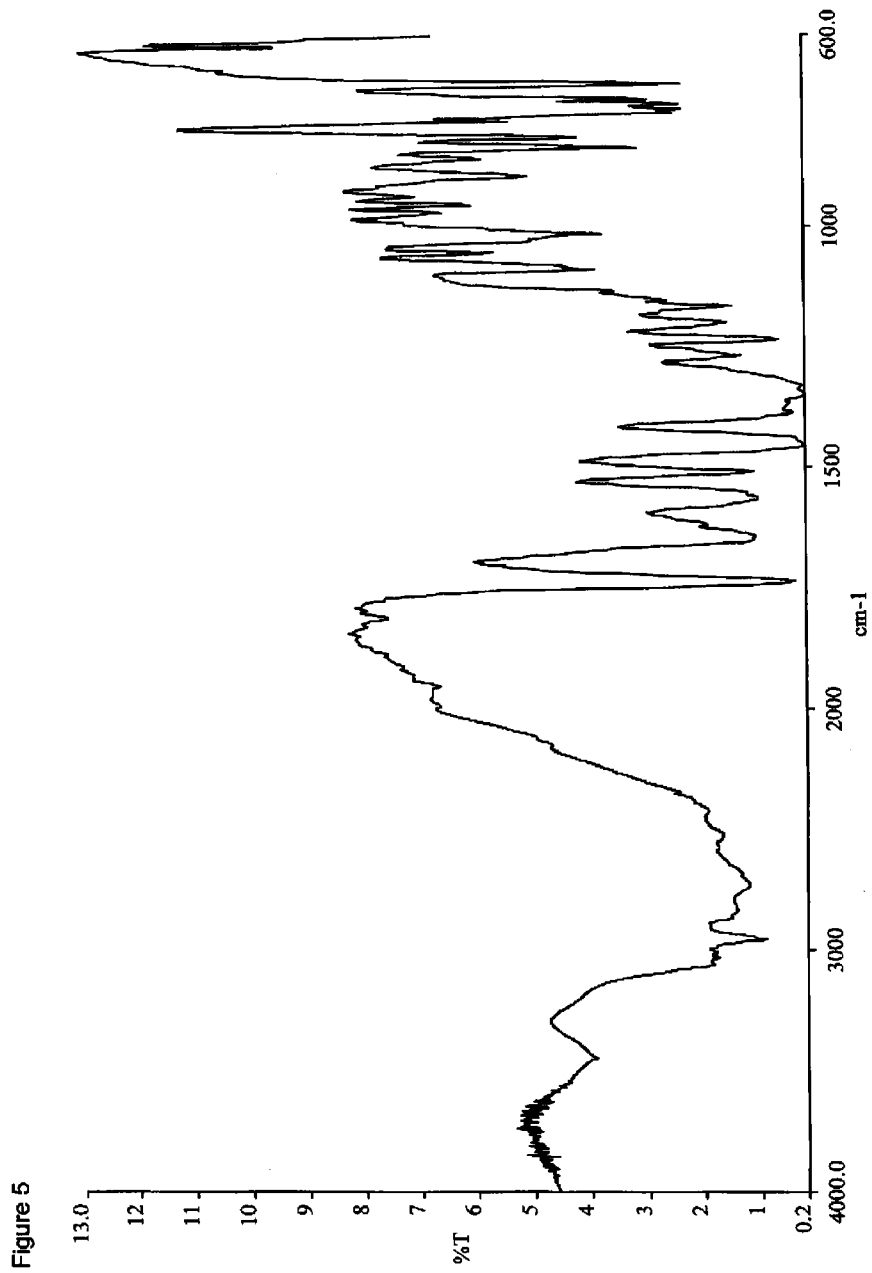
FIG. 5 is the Fourier Transform Infrared (FTIR) spectrum of polymorphic racemic-methylphenidate pamoate.
Figure 6:
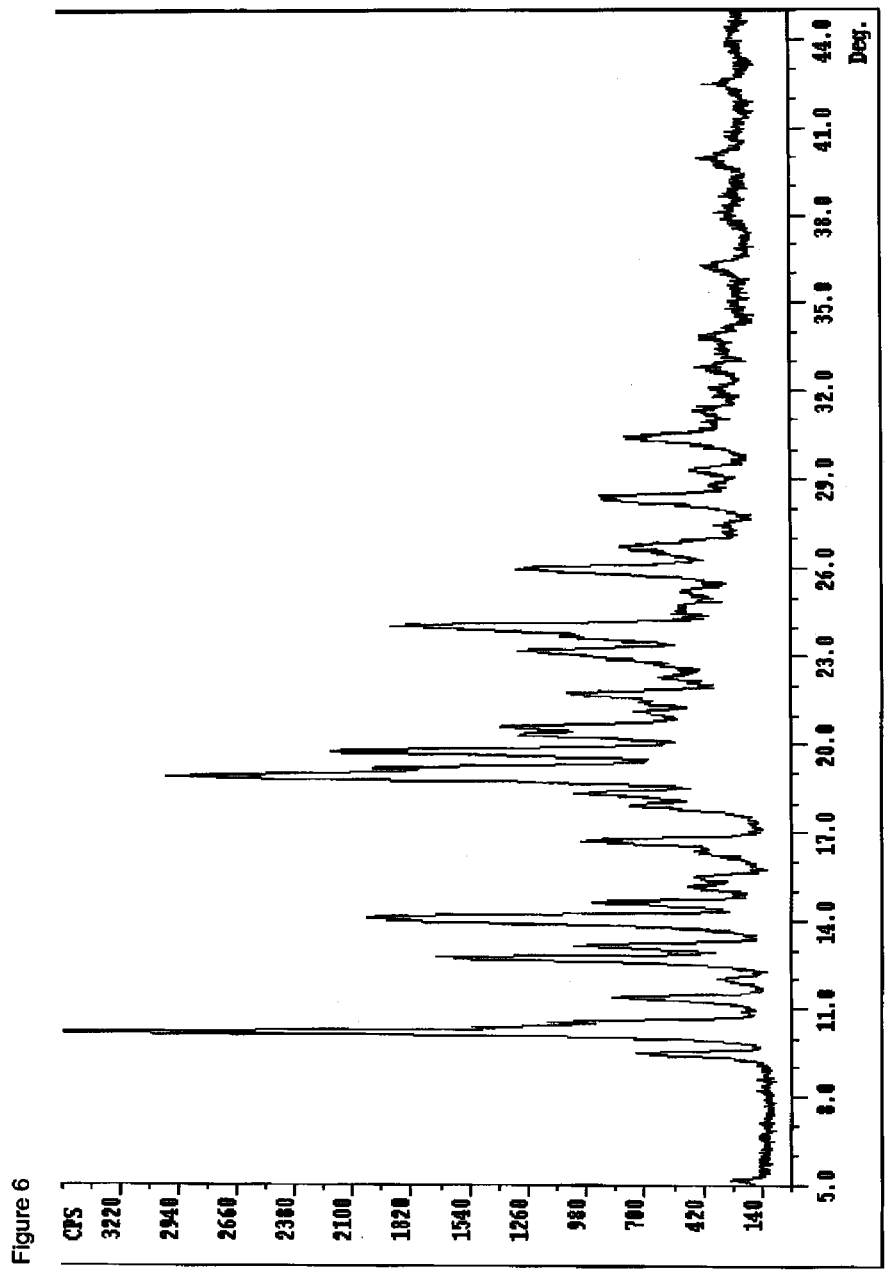
FIG. 6 is the powder X-ray diffraction (PXRD) diffractogram of polymorphic racemic-methylphenidate pamoate.
Figure 8:
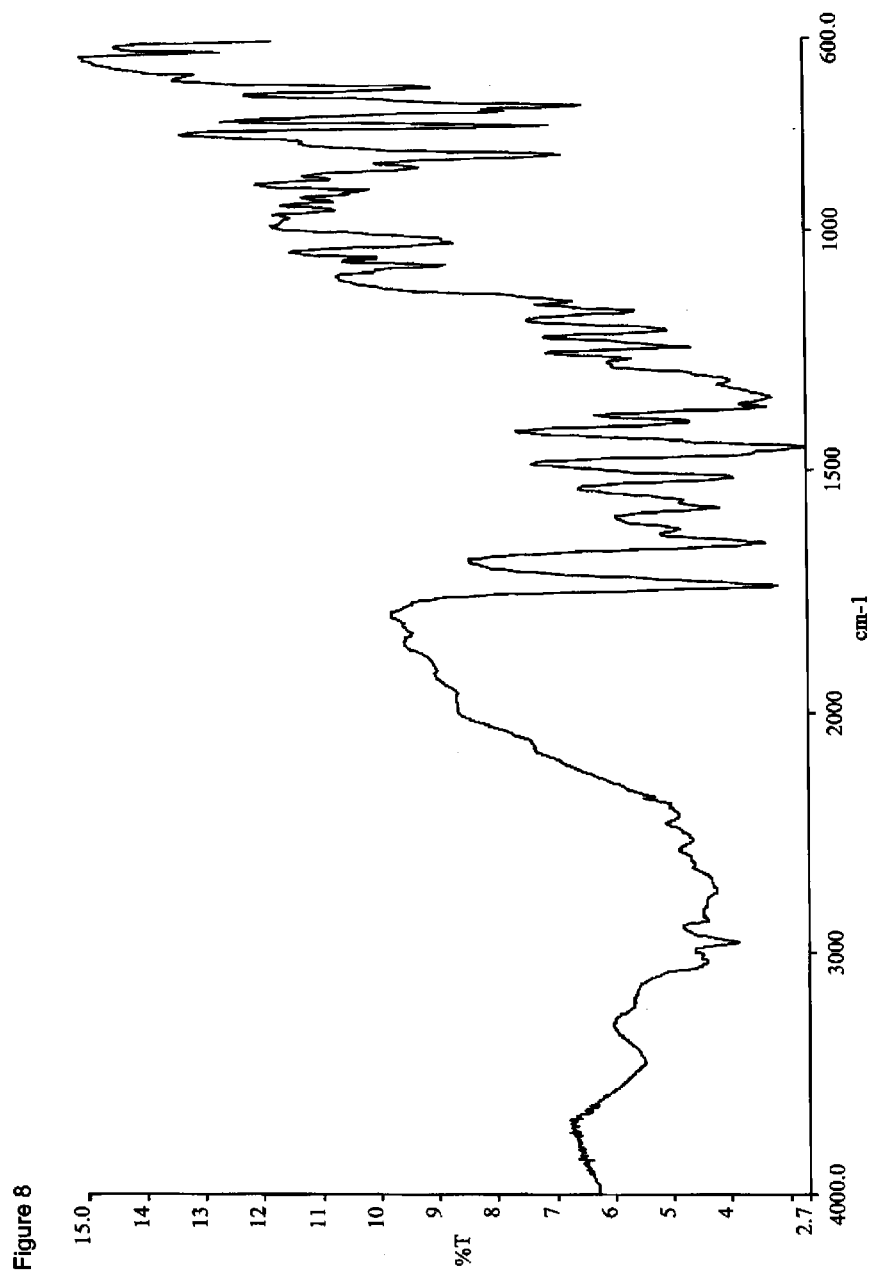
FIG. 8 is the Fourier Transform Infrared (FTIR) spectrum of polymorphic racemic methylphenidate xinafoate.
Figure 9:
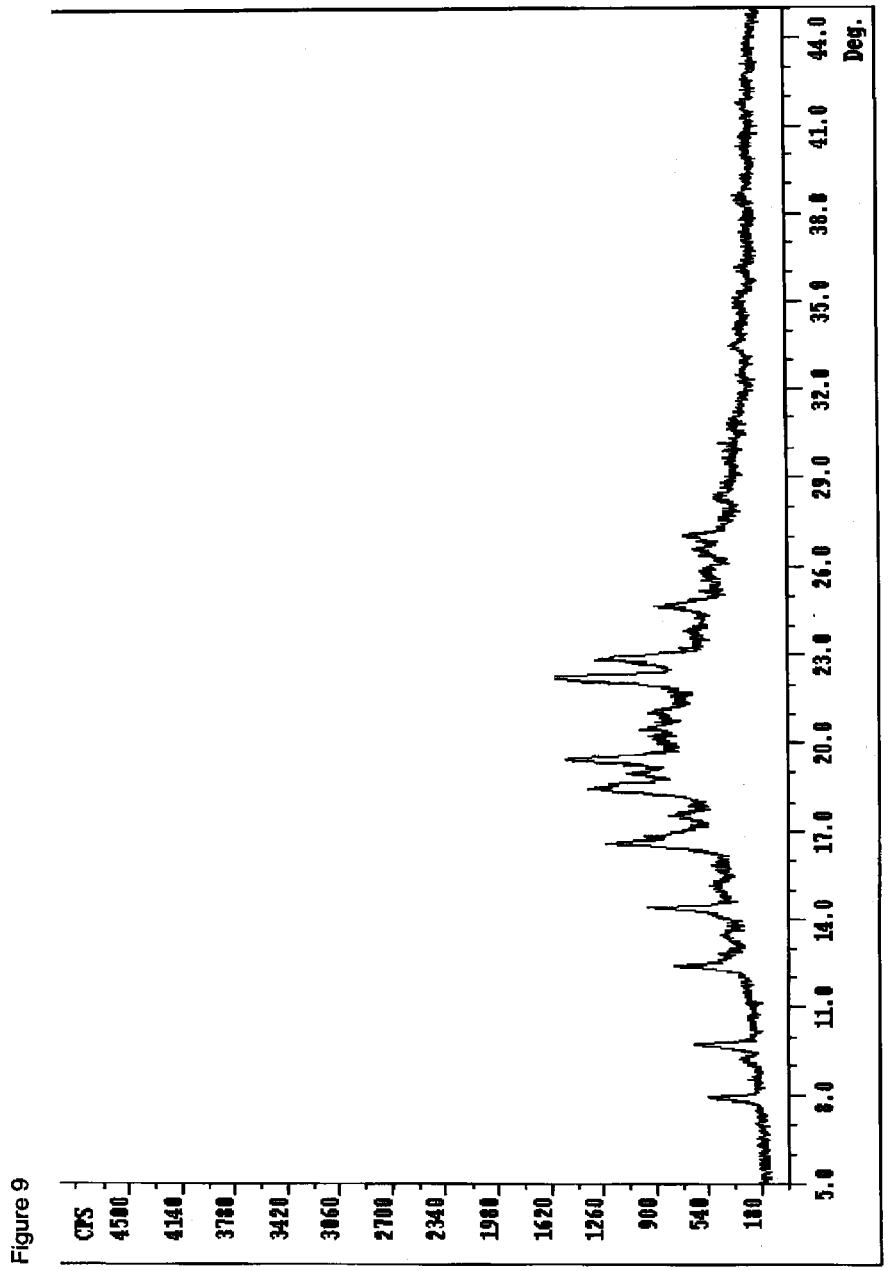
FIG. 9 is the powder X-ray diffraction (PXRD) diffractogram of polymorphic racemic-methylphenidate xinafoate.
Figure 11:
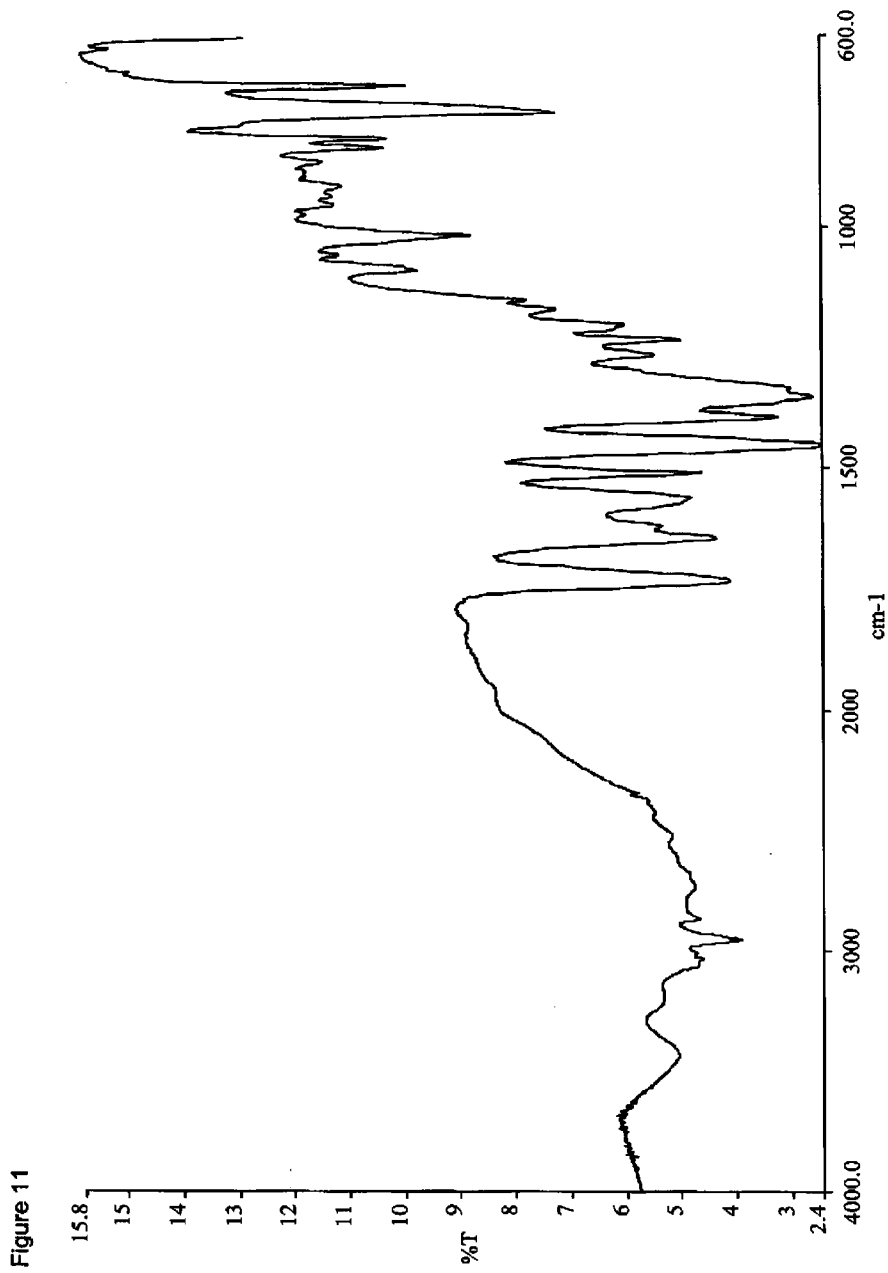
FIG. 11 is the Fourier Transform Infrared (FTIR) spectrum of amorphous d-methylphenidate pamoate.
Figure 12:
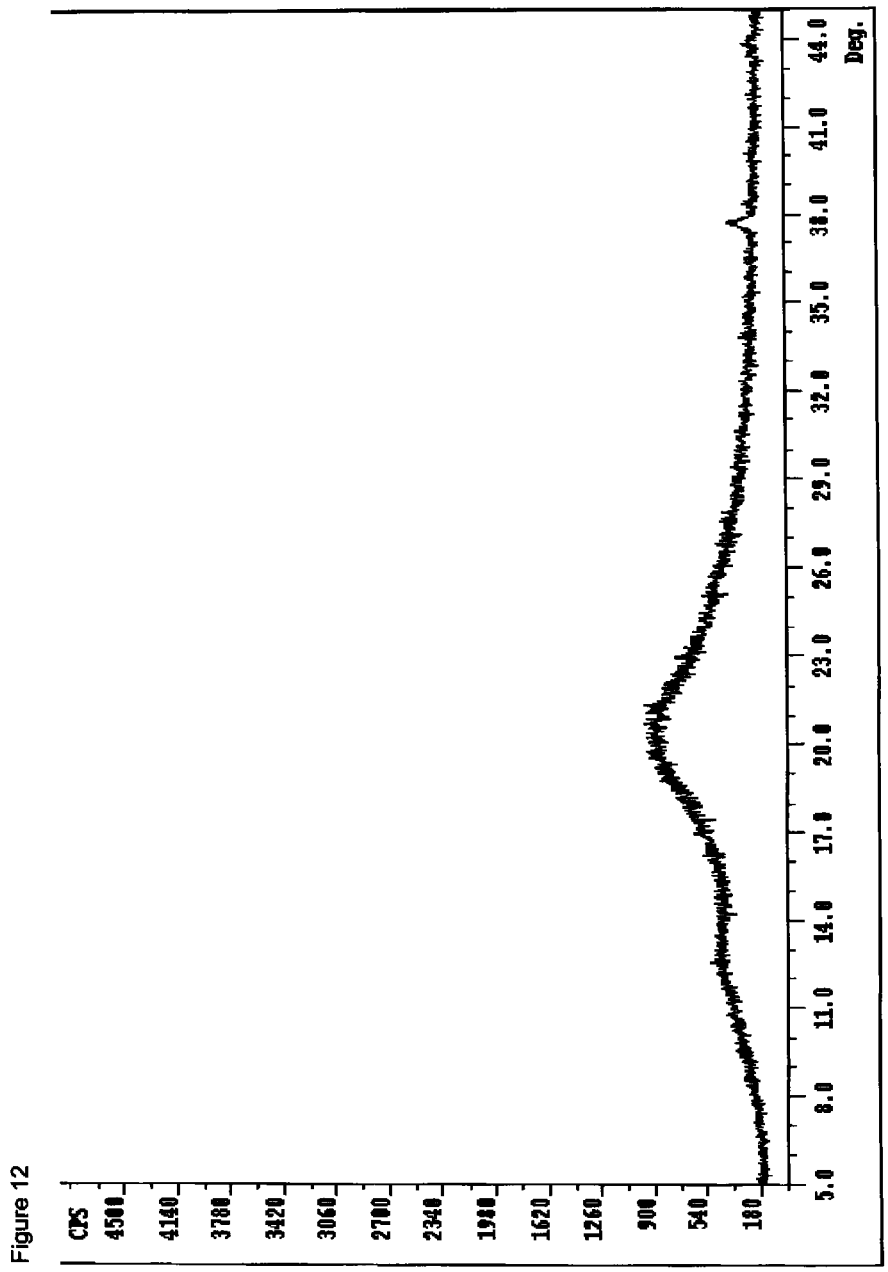
FIG. 12 is the powder X-ray diffraction (PXRD) diffractogram of amorphous d-methylphenidate pamoate.
Figure 14:
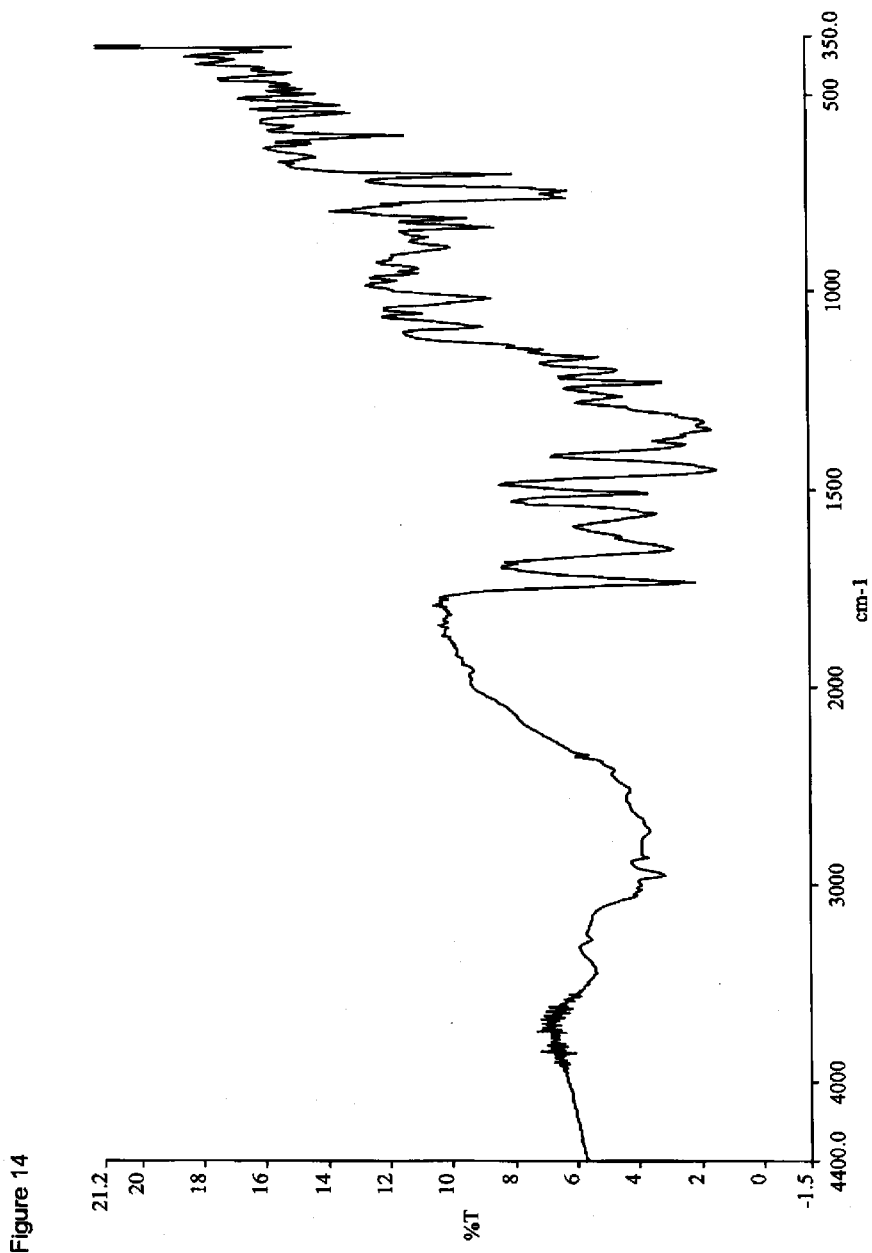
FIG. 14 is the Fourier Transform Infrared (FTIR) spectrum of polymorphic d-methylphenidate pamoate.
Figure 15:
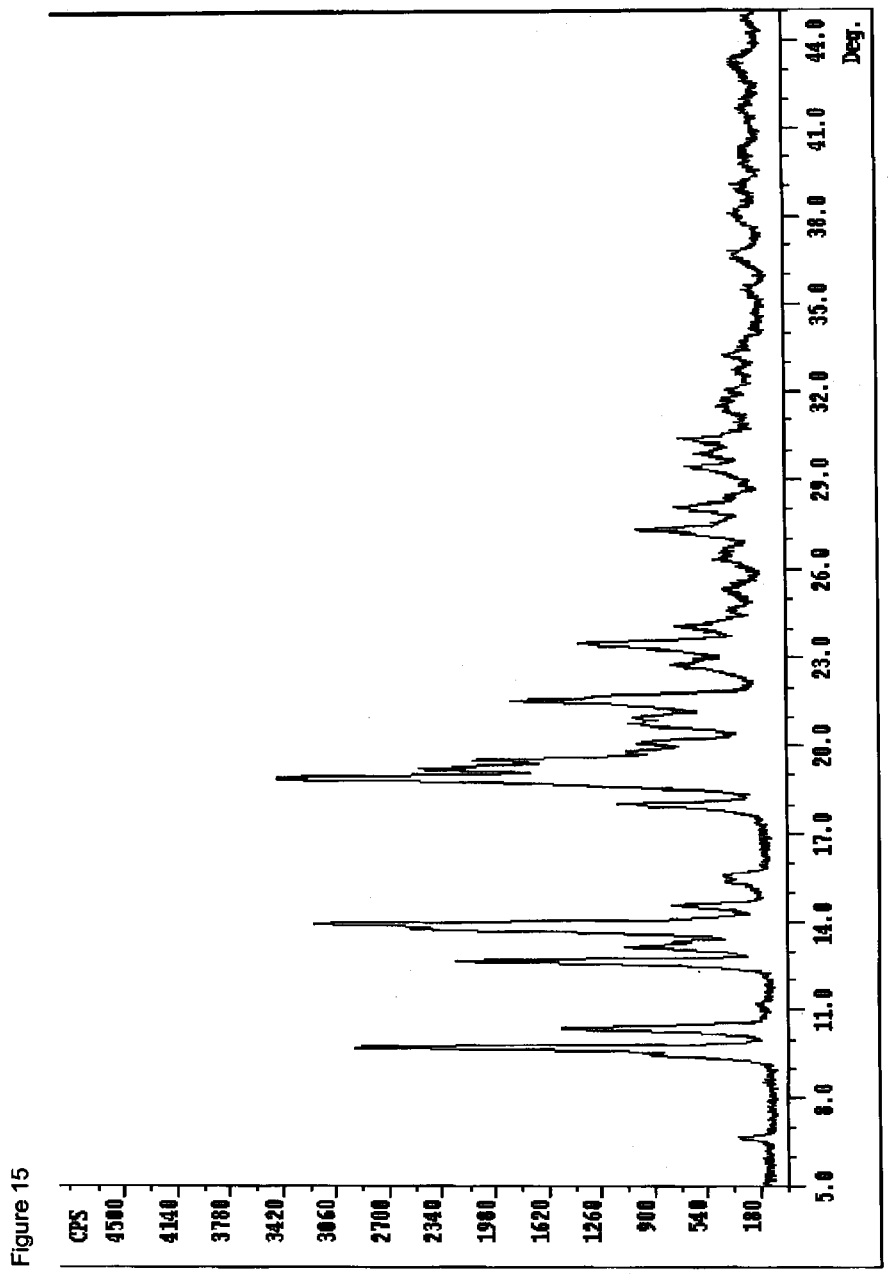
FIG. 15 is the powder X-ray diffraction (PXRD) diffractogram of polymorphic d-methylphenidate pamoate.
Figure 17:
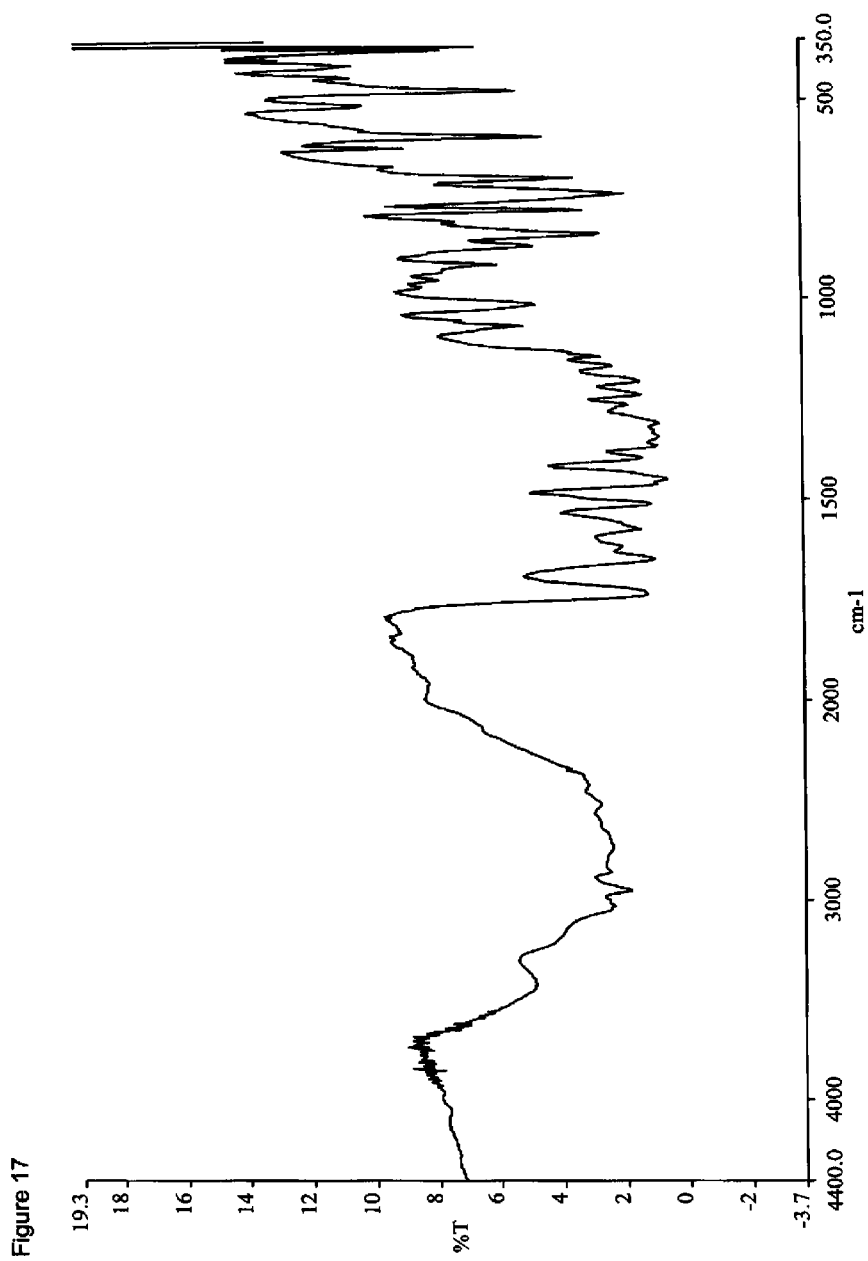
FIG. 17 is the Fourier Transform Infrared (FTIR) spectrum of amorphous d-methylphenidate xinafoate.
Figure 18:
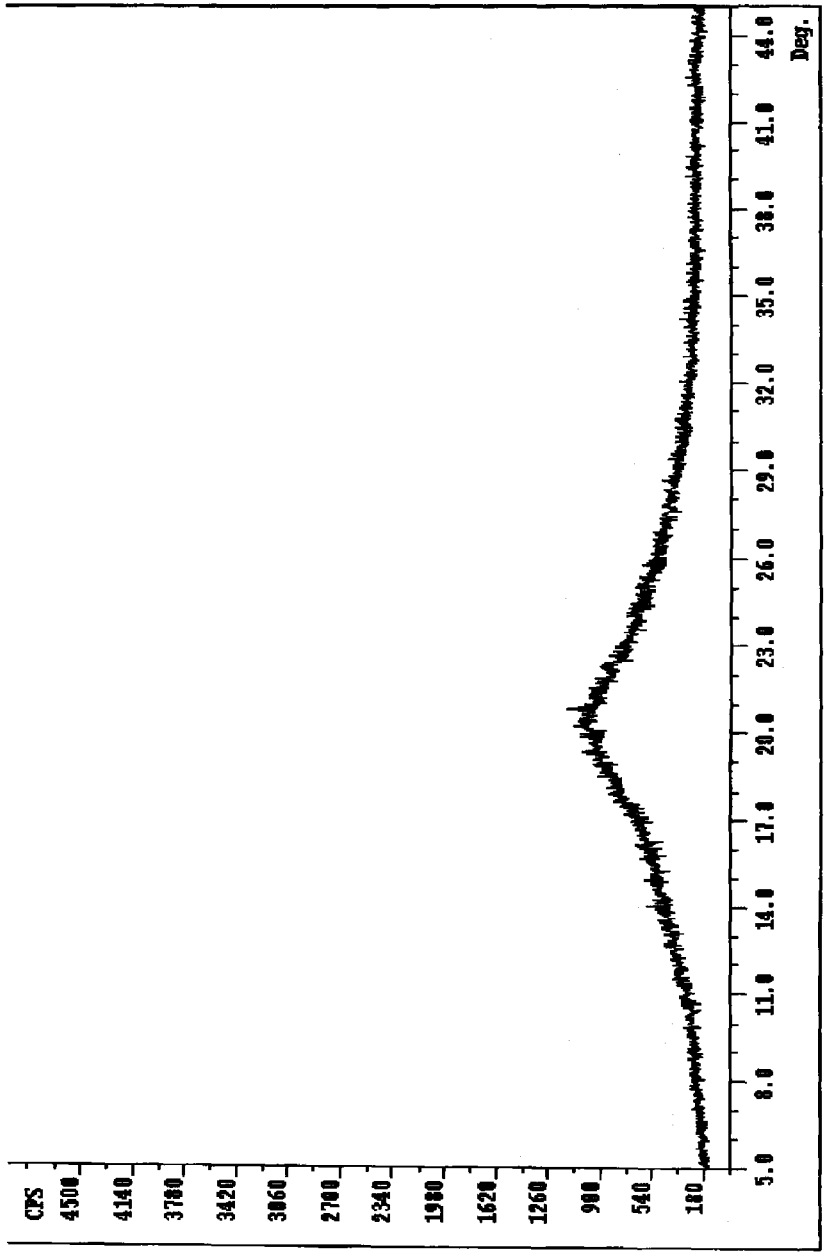
FIG. 18 is the powder X-ray diffraction (PXRD) diffractogram of amorphous d-methylphenidate xinafoate.
Figure 20:
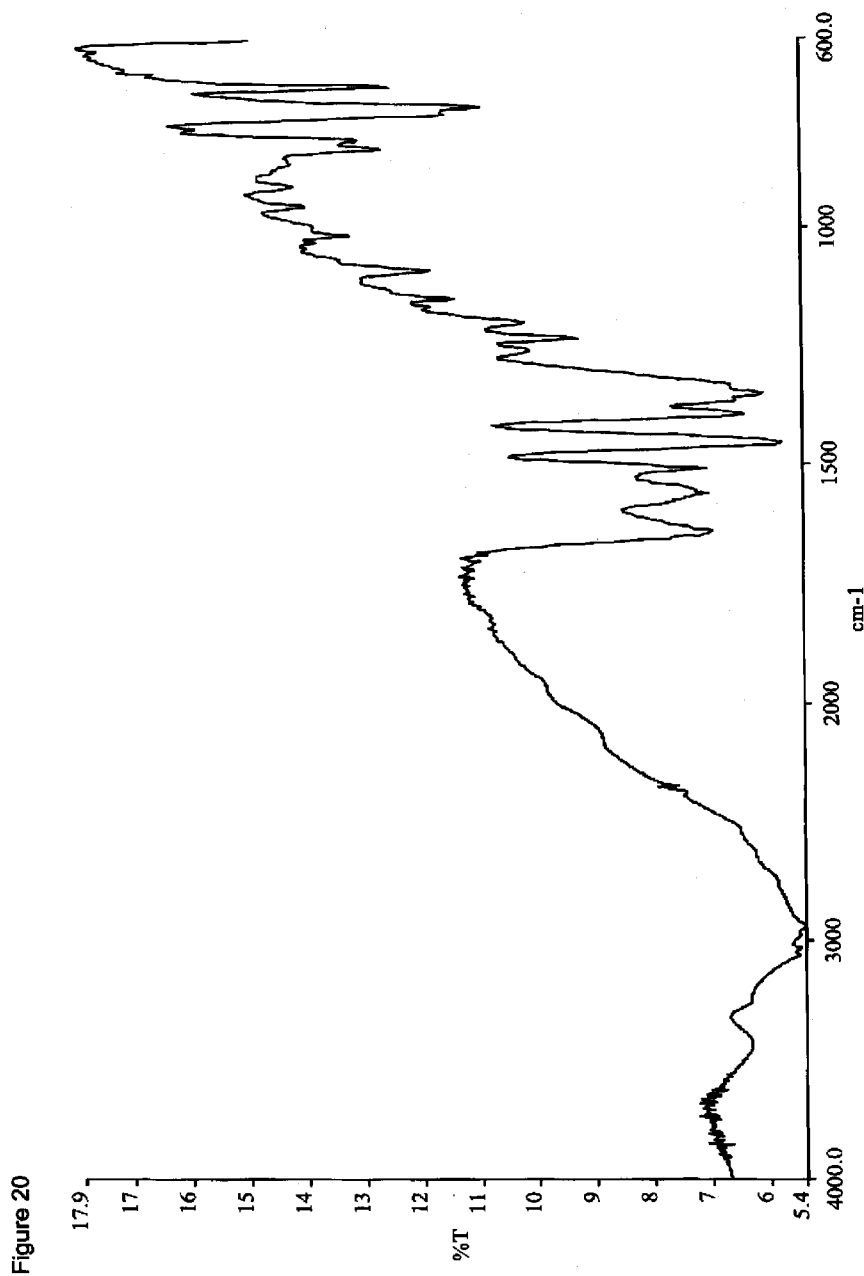
FIG. 20 is the Fourier Transform Infrared (FTIR) spectrum of amorphous dextro-amphetamine pamoate.
Figure 21:
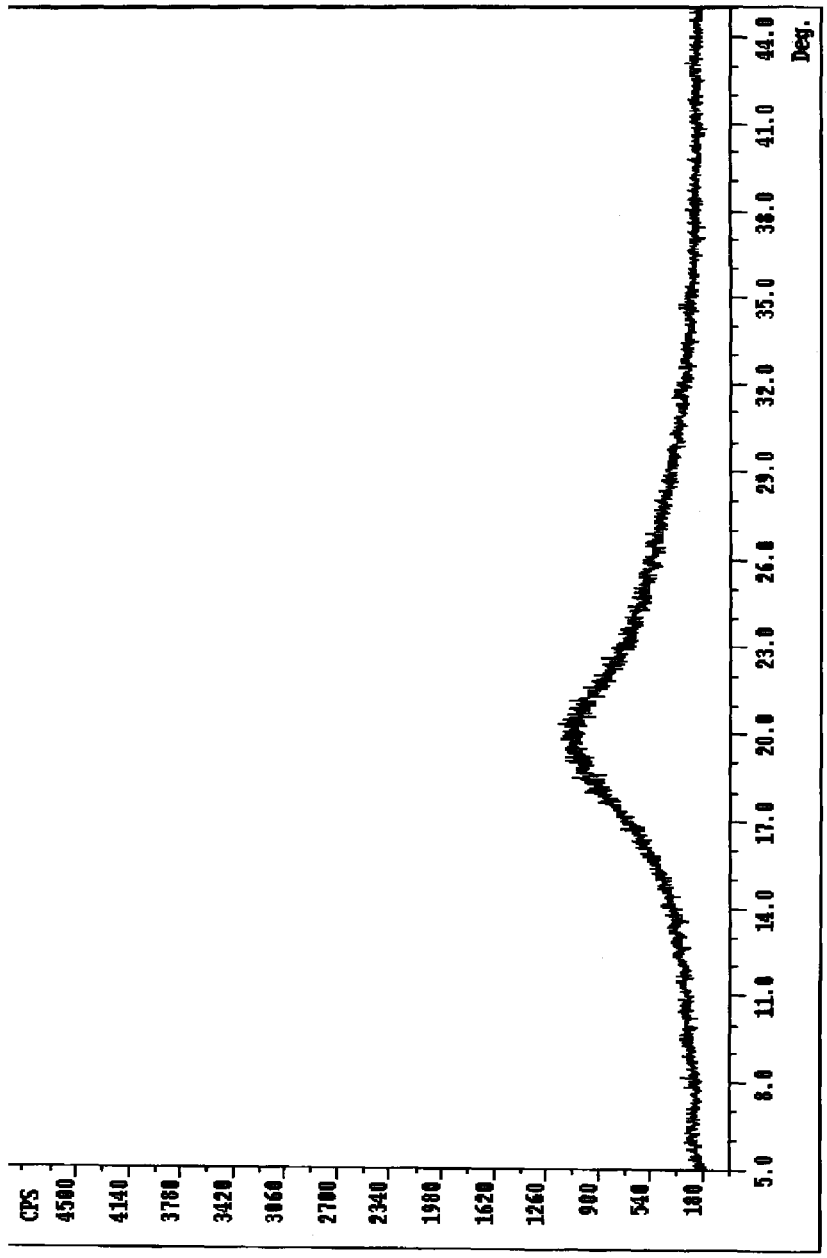
FIG. 21 is the powder X-ray diffraction (PXRD) diffractogram of amorphous dextro-amphetamine pamoate.
Figure 23:
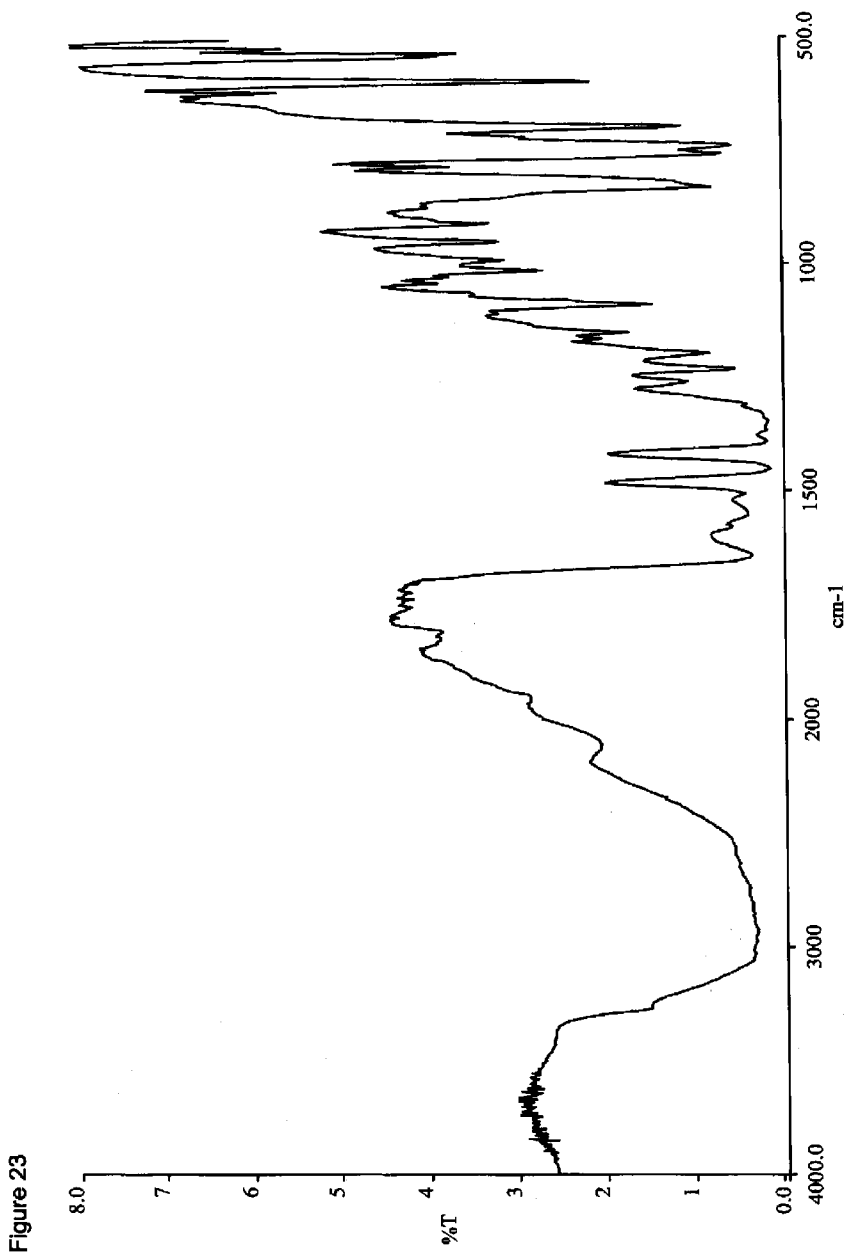
FIG. 23 is the Fourier Transform Infrared (FTIR) spectrum of polymorphic dextro-amphetamine pamoate.
Figure 24:
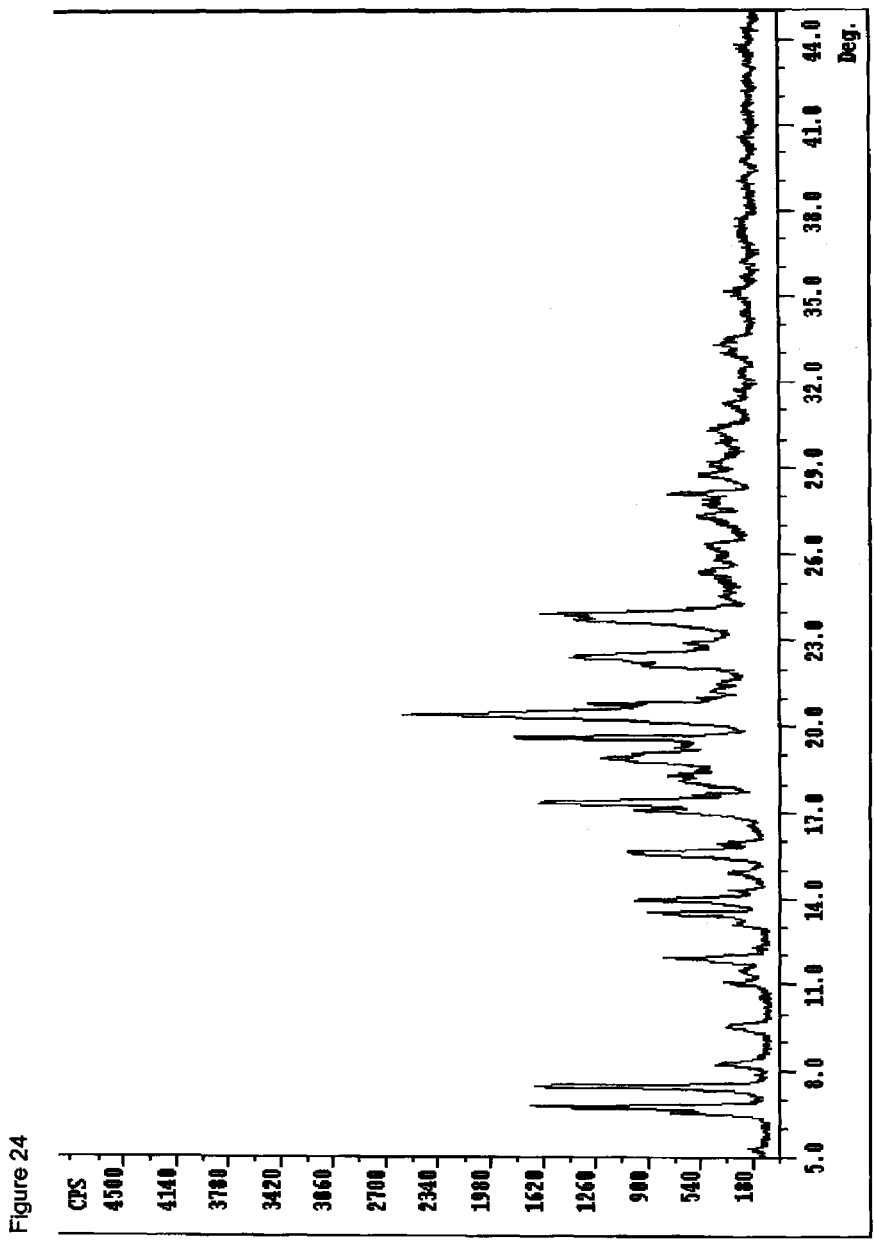
FIG. 24 is the powder X-ray diffraction (PXRD) diffractogram of polymorphic dextro-amphetamine pamoate.
Figure 26:
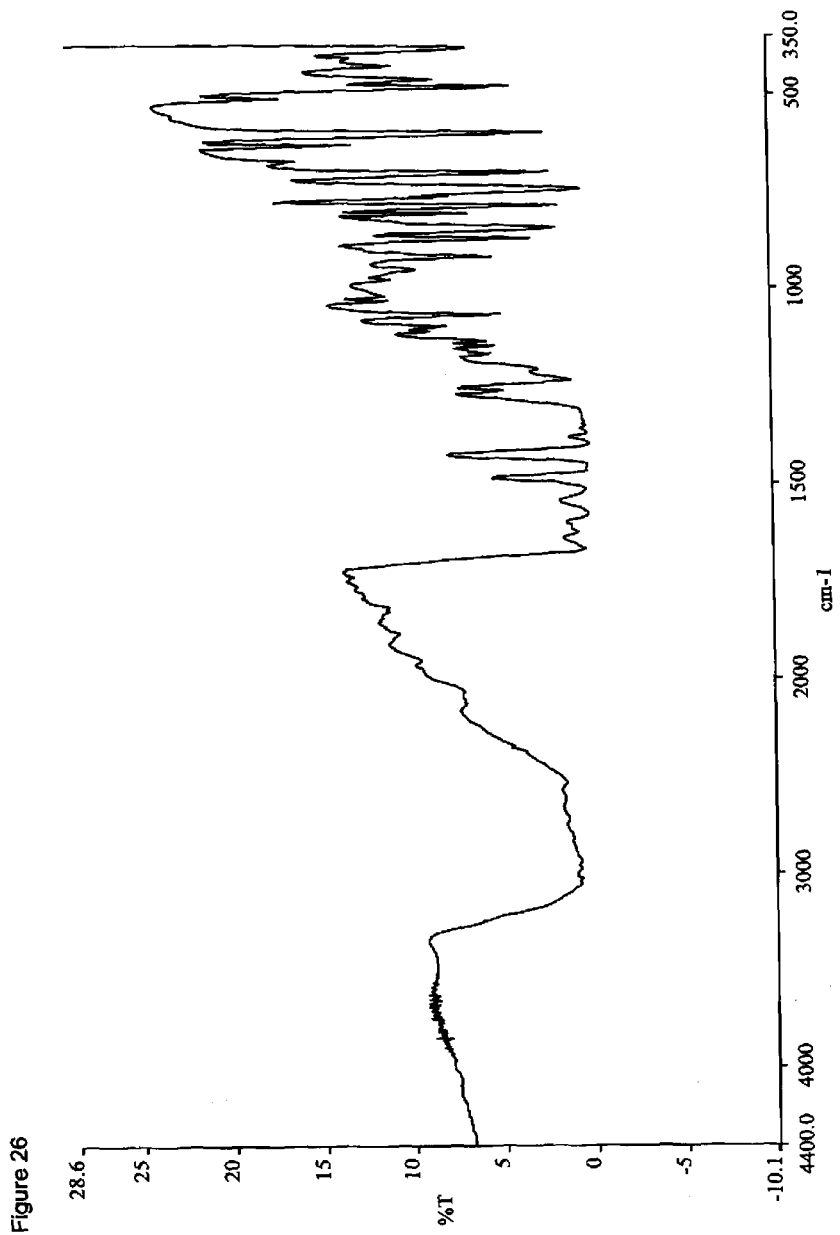
FIG. 26 is the Fourier Transform Infrared (FTIR) spectrum of polymorphic dextro-amphetamine xinafoate.
Figure 27:
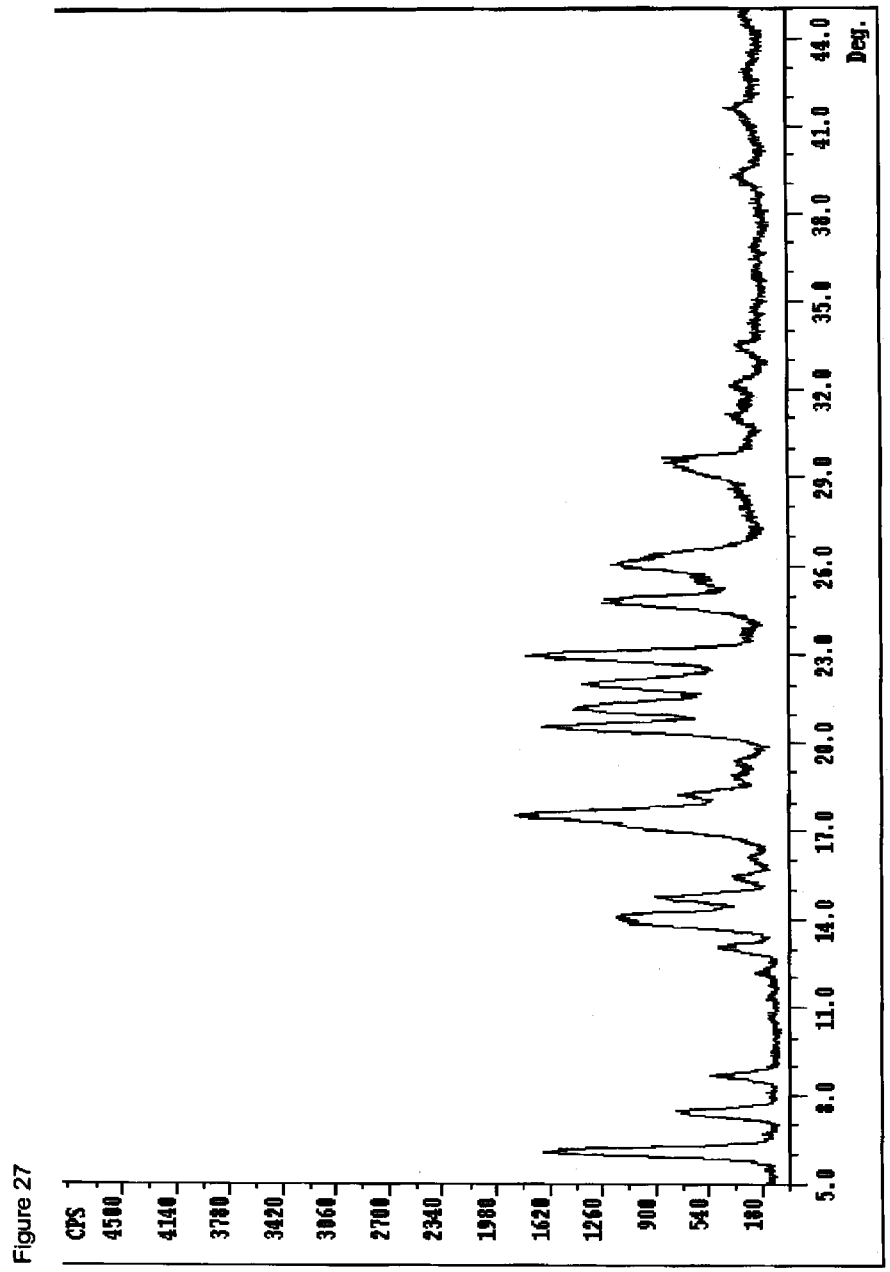
FIG. 27 is the powder X-ray diffraction (PXRD) diffractogram of polymorphic dextro-amphetamine xinafoate.
Figure 51:
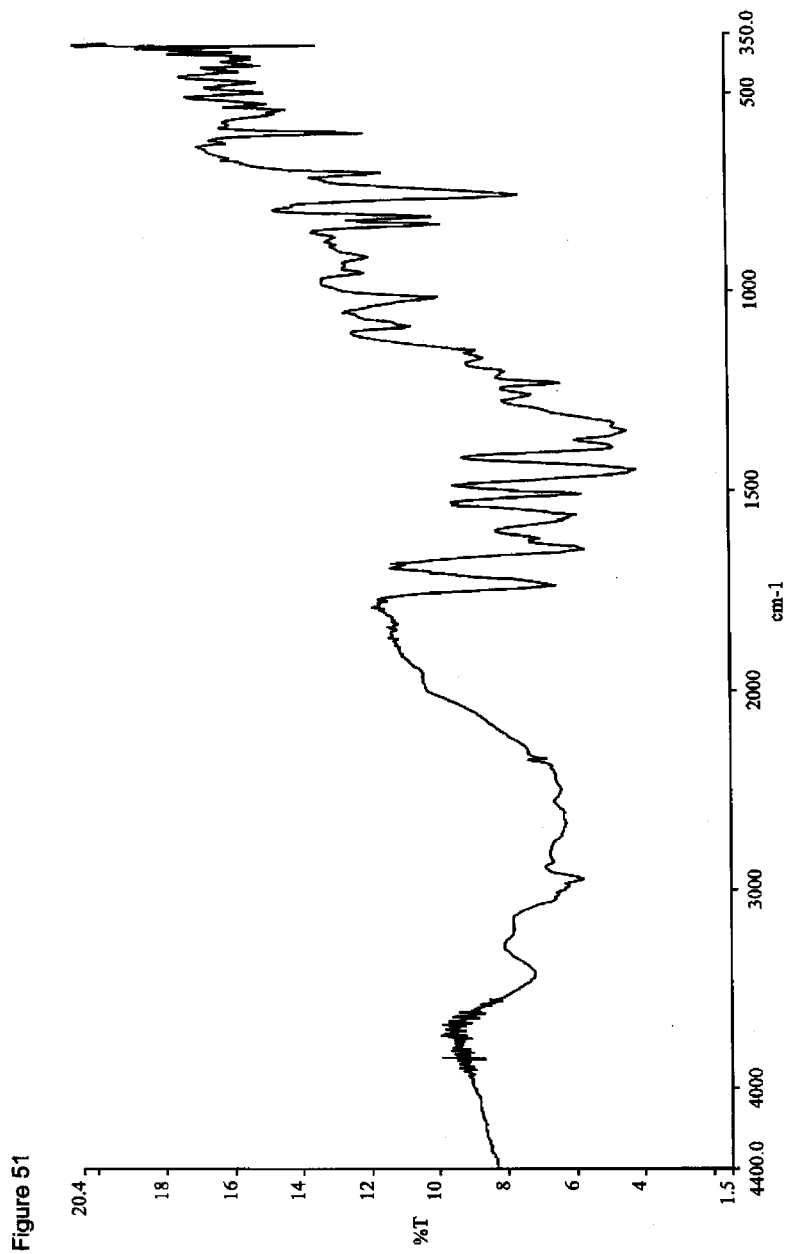
FIG. 51 is the Fourier Transform Infrared (FTIR) spectrum of amorphous d-methylphenidate mono-triethylammonium pamoate, 1:1:1 salt.
Figure 52:
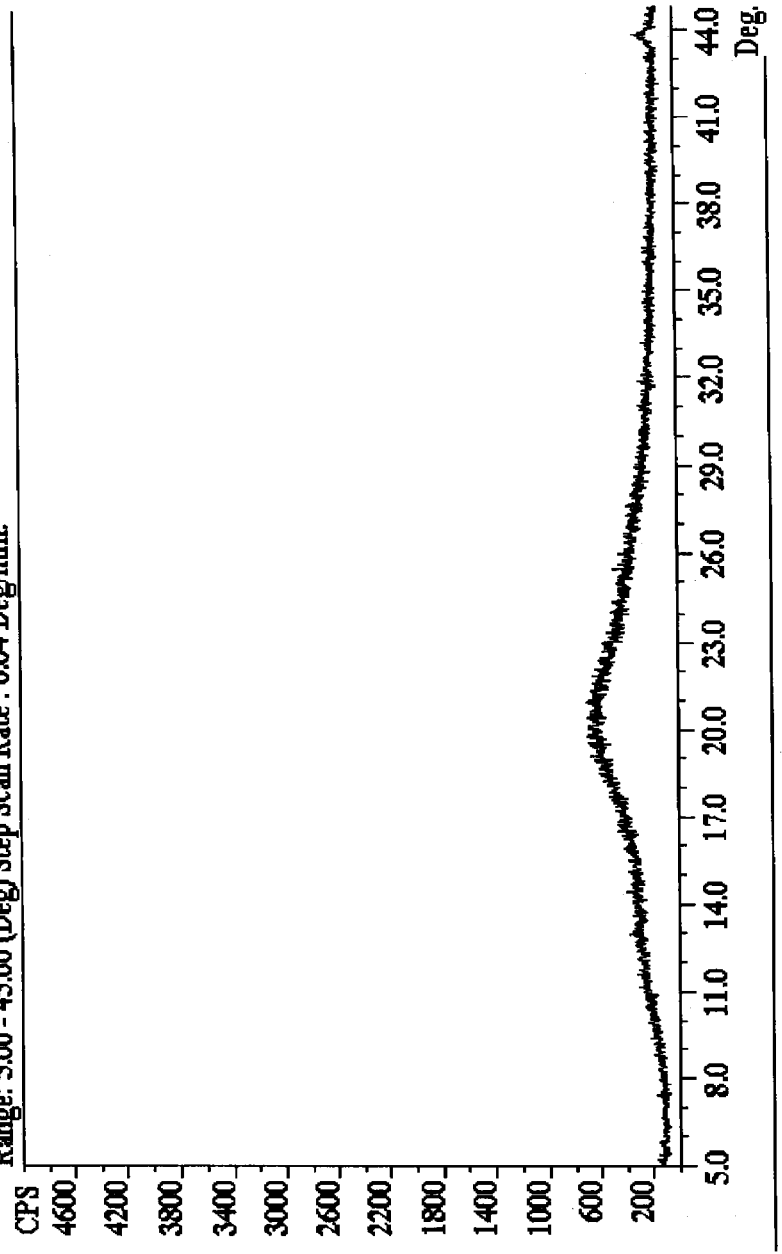
FIG. 52 is the powder X-ray diffraction (PXRD) diffractogram of amorphous d-methylphenidate mono-triethylammonium pamoate, 1:1:1 salt.
Figure 53:
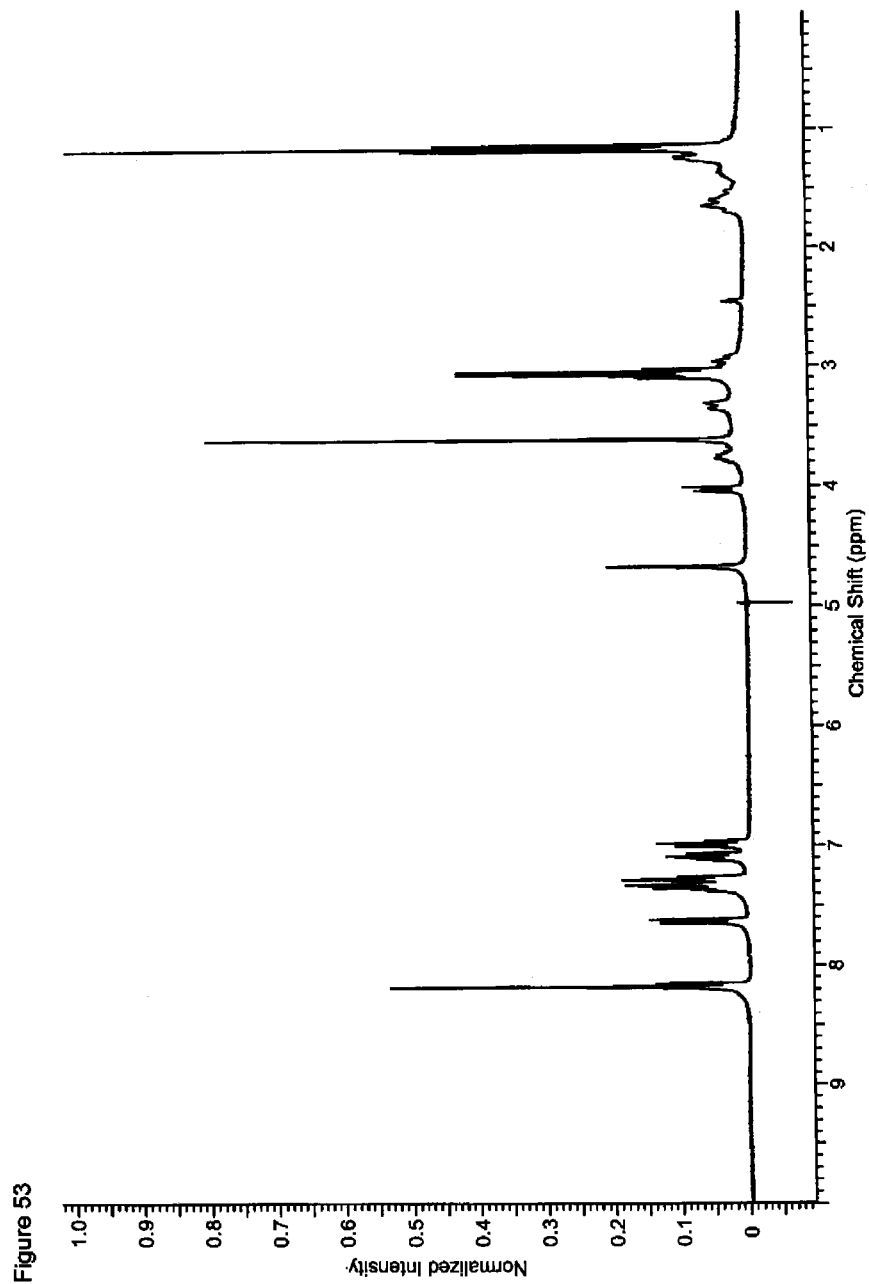
FIG. 53 is the proton nuclear magnetic resonance ($^1$H NMR) spectrum of amorphous d-methylphenidate mono-triethylammonium pamoate, 1:1:1 salt.

6. A drug product not susceptible to dose dumping wherein said drug product comprises a drug substance wherein said drug substance is selected from the group consisting of:
amorphous racemic-methylphenidate pamoate characterized by at least one method selected from the group consisting of:
an endothermic phase change of at least 70 J/gram at greater than 200° C.;
an FTIR spectrum of FIG. 2; and
a PXRD diffractogram of FIG. 3;
polymorphic racemic-methylphenidate stearylamine pamoate characterized by at least one method selected from the group consisting of:
an endothermic phase change of at least 15 J/g at a temperature above 50° C.; an endothermic phase change of at least 10 J/g at a temperature of above 90° C.; an endothermic phase change of at least 2 J/g at a temperature above 105° C.; an endothermic phase change of at least 4 J/g at above 155° C. and an endothermic phase change of at least 20 J/g above 180° C.; and
a PXRD diffractogram of FIG. 48;

amorphous d-methylphenidate pamoate characterized by at least one method selected from the group consisting of:
   an endothermic phase change of at least 45 J/gram at greater than 70° C. and an endothermic phase change of at least 30 J/gram at greater than 180° C.;
   an FTIR spectrum of FIG. 11; and
   a PXRD diffractogram of FIG. 12;
amorphous d-methylphenidate xinafoate characterized by at least one method selected from the group consisting of:
   an endothermic phase change of at least 10 J/gram at greater than 45° C. and an endothermic phase change of at least 50 J/gram at greater than 160° C.;
   an FTIR spectrum of FIG. 17; and
   a PXRD diffractogram of FIG. 18;
polymorphic dextro-amphetamine xinafoate characterized by at least one method selected from the group consisting of:
   an endothermic phase change of at least 60 J/gram at greater than 125° C.;
   an FTIR spectrum of FIG. 26; and
   a PXRD diffractogram of FIG. 27;
polymorphic d-methylphenidate pamoate characterized by at least one method selected from the group consisting of:
   an endothermic phase change of at least 35 J/gram at greater than 185° C.;
   an FTIR spectrum of FIG. 14; and
   a PXRD diffractogram of FIG. 15;
polymorphic racemic-methylphenidate pamoate characterized by at least one method selected from the group consisting of:
   an endothermic phase change of at least 75 J/gram at greater than 200° C.;
   an FTIR spectrum of FIG. 5; and
   a PXRD diffractogram of FIG. 6;
polymorphic racemic-methylphenidate xinafoate characterized by at least one method selected from the group consisting of:
   an endothermic phase change of at least 75 J/gram at greater than 155° C.;
   an FTIR spectrum of FIG. 8; and
   a PXRD diffractogram of FIG. 9;
amorphous dextro-amphetamine pamoate characterized by at least one method selected from the group consisting of:
   endothermic phase change of at least 10 J/gram at greater than 200° C. and an endothermic phase change of at least 75 J/gram at greater than 220° C.;
   an FTIR spectrum of FIG. 20; and
   a PXRD diffractogram of FIG. 21;
polymorphic dextro-amphetamine pamoate characterized by at least one method selected from the group consisting of:
   an endothermic phase change of at least 60 J/gram at greater than 200° C.;
   an FTIR spectrum of FIG. 23; and
   a PXRD diffractogram of FIG. 24; and
amorphous d-methylphenidate mono-triethylammonium pamoate characterized by at least one method selected from the group consisting of:
   an endothermic phase change of at least 12 J/g at a temperature above 240° C.
   an FTIR spectrum of FIG. 51;
   a PXRD diffractogram of FIG. 52; and
   $^1$H NMR spectrum of FIG. 53;
and said drug substance meets at least one condition in 0.1 N HCl selected from the group consisting of:
   no more than 35% of said drug substance is released at 30 minutes with 5 wt % ethanol in said 0.1 N HCl;
   the percentage of said drug substance released with at least 5 wt % ethanol in said 0.1 N HCl is no more than a percentage of said drug substance released in said 0.1 N HCl without ethanol; and
   the percentage of drug substance released with 40 wt % ethanol in 0.1 N HCl does not exceed 60% while the percentage of drug substance released under the conditions selected from water, 0.1 N HCl, 5 wt % ethanol in 0.1 N HCl and 20 wt % ethanol in 0.1 N HCl does not exceed the drug substance released with 40 wt % ethanol in 0.1 N HCl.

7. The drug product not susceptible to dose dumping of claim 6 wherein drug substance is selected from the group consisting of:
   polymorphic dextro-amphetamine xinafoate characterized by at least one method selected from the group consisting of:
      an endothermic phase change of at least 60 J/gram at greater than 125° C.;
      an FTIR spectrum of FIG. 26; and
      a PXRD diffractogram of FIG. 27;
   amorphous dextro-amphetamine pamoate characterized by at least one method selected from the group consisting of:
      endothermic phase change of at least 10 J/gram at greater than 200° C. and an endothermic phase change of at least 75 J/gram at greater than 220° C.;
      an FTIR spectrum of FIG. 20; and
      a PXRD diffractogram of FIG. 21; and
   polymorphic dextro-amphetamine pamoate characterized by at least one method selected from the group consisting of:
      an endothermic phase change of at least 60 J/gram at greater than 200° C.;
      an FTIR spectrum of FIG. 23; and
      a PXRD diffractogram of FIG. 24;
   and said drug substance meets at least one condition in 0.1 N HCl selected from the group consisting of:
   no more than 35% of said drug substance is released at 30 minutes with 5 wt % ethanol in said 0.1 N HCl;
   the percentage of said drug substance released with at least 5 wt % ethanol in said 0.1 N HCl is no more than a percentage of said drug substance released in said 0.1 N HCl without ethanol; and
   the percentage of drug substance released with 40 wt % ethanol in 0.1 N HCl does not exceed 60% while the percentage of drug substance released under the conditions selected from water, 0.1 N HCl, 5 wt % ethanol in 0.1 N HCl and 20 wt % ethanol in 0.1 N HCl does not exceed the drug substance released with 40 wt % ethanol in 0.1 N HCl.

Figure 48:
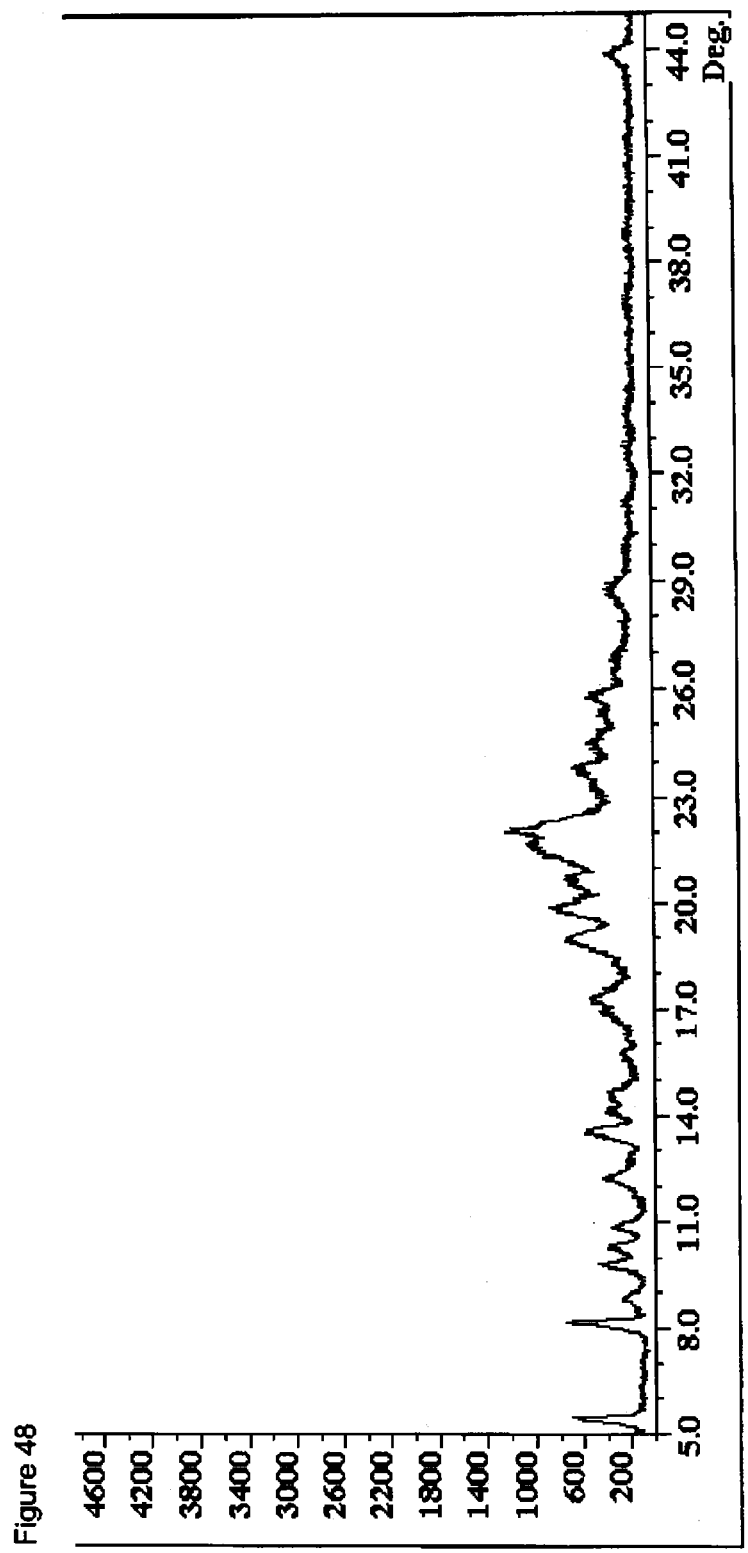
FIG. 48 is the powder X-ray diffraction (PXRD) diffractogram of polymorphic racemic-methylphenidate stearylamine pamoate, 1:1:1 salt.
Figure 49:
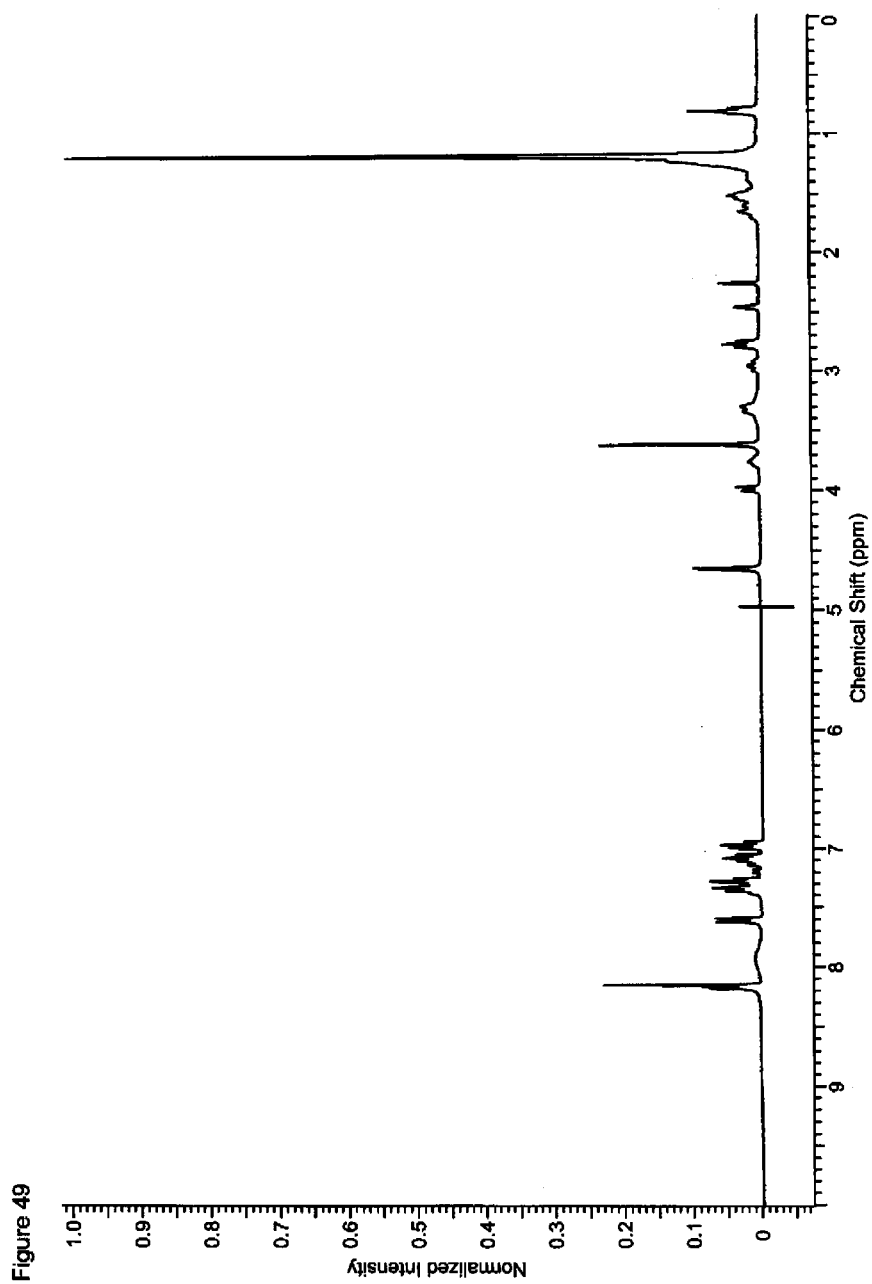
FIG. 49 is the proton nuclear magnetic resonance ($^1$H NMR) spectrum of polymorphic racemic-methylphenidate stearylamine pamoate, 1:1:1 salt.

8. The drug product not susceptible to dose dumping of claim 6 wherein said drug substance is selected from the group consisting of:
   amorphous racemic-methylphenidate pamoate characterized by at least one method selected from the group consisting of:
      an endothermic phase change of at least 70 J/gram at greater than 200° C.;
      an FTIR spectrum of FIG. 2; and
      a PXRD diffractogram of FIG. 3;

polymorphic racemic-methylphenidate stearylamine pamoate characterized by at least one method selected from the group consisting of:
  an endothermic phase change of at least 15 J/g at a temperature above 50° C.; an endothermic phase change of at least 10 J/g at a temperature of above 90° C.; an endothermic phase change of at least 2 J/g at a temperature above 105° C.; an endothermic phase change of at least 4 J/g at above 155° C. and an endothermic phase change of at least 20 J/g above 180° C.; and
  a PXRD diffractogram of FIG. 48;
amorphous d-methylphenidate pamoate characterized by at least one method selected from the group consisting of:
  an endothermic phase change of at least 45 J/gram at greater than 70° C. and an endothermic phase change of at least 30 J/gram at greater than 180° C.;
  an FTIR spectrum of FIG. 11; and
  a PXRD diffractogram of FIG. 12;
amorphous d-methylphenidate xinafoate characterized by at least one method selected from the group consisting of:
  an endothermic phase change of at least 10 J/gram at greater than 45° C. and an endothermic phase change of at least 50 J/gram at greater than 160° C.;
  an FTIR spectrum of FIG. 17; and
  a PXRD diffractogram of FIG. 18;
polymorphic d-methylphenidate pamoate characterized by at least one method selected from the group consisting of:
  an endothermic phase change of at least 35 J/gram at greater than 185° C.;
  an FTIR spectrum of FIG. 14; and
  a PXRD diffractogram of FIG. 15;
polymorphic racemic-methylphenidate pamoate characterized by at least one method selected from the group consisting of:
  an endothermic phase change of at least 75 J/gram at greater than 200° C.;
  an FTIR spectrum of FIG. 5; and
  a PXRD diffractogram of FIG. 6;
polymorphic racemic-methylphenidate xinafoate characterized by at least one method selected from the group consisting of:
  an endothermic phase change of at least 75 J/gram at greater than 155° C.;
  an FTIR spectrum of FIG. 8; and
  a PXRD diffractogram of FIG. 9; and
amorphous d-methylphenidate mono-triethylammonium pamoate characterized by at least one method selected from the group consisting of:
  an endothermic phase change of at least 12 J/g at a temperature above 240° C.
  an FTIR spectrum of FIG. 51;
  a PXRD diffractogram of FIG. 52; and
  $^1$H NMR spectrum of FIG. 53;
and said drug substance meets at least one condition in 0.1 N HCl selected from the group consisting of:
no more than 35% of said drug substance is released at 30 minutes with 5 wt % ethanol in said 0.1 N HCl;
the percentage of said drug substance released with at least 5 wt % ethanol in said 0.1 N HCl is no more than a percentage of said drug substance released in said 0.1 N HCl without ethanol; and
the percentage of drug substance released with 40 wt % ethanol in 0.1 N HCl does not exceed 60% while the percentage of drug substance released under the conditions selected from water, 0.1 N HCl, 5 wt % ethanol in 0.1 N HCl and 20 wt % ethanol in 0.1 N HCl does not exceed the drug substance released with 40 wt % ethanol in 0.1 N HCl.

9. The drug product not susceptible to dose dumping of claim 1 wherein said substance is selected from the group consisting of:
amorphous imipramine mono-triethylammonium pamoate characterized by at least one method selected from the group consisting of:
  an FTIR spectrum of FIG. 59;
  a PXRD diffractogram of FIG. 60; and
  $^1$H NMR spectrum of FIG. 61;
polymorphic imipramine stearylamine pamoate characterized by at least one method selected from the group consisting of:
  an endothermic phase change of at least 40 J/g at a temperature above 70° C. and an endothermic phase change of at least 1 J/g above 125° C.;
  an FTIR spectrum of FIG. 63;
  a PXRD diffractogram of FIG. 64; and
  $^1$H NMR spectrum of FIG. 65;
amorphous imipramine, $CH_3(O(CH_2)_2)_x(OCH_2CHCH_3)_y$ $NH_2$ wherein Y/X is 9:1 with an approximate MW of 600, pamoate characterized by at least one method selected from the group consisting of:
  an endothermic phase change of at least 50 J/g at a temperature above 240° C.;
  an FTIR spectrum of FIG. 67;
  a PXRD diffractogram of FIG. 68; and
  $^1$H NMR spectrum of FIG. 69;
amorphous hydrocodone stearylamine pamoate characterized by at least one method selected from the group consisting of:
  an endothermic phase change of at least 1 J/g at a temperature above 65° C.; an endothermic phase change of at least 1 J/g above 70° C. and an endothermic phase change of at least 3 J/g above 105° C.;
  an FTIR spectrum of FIG. 71;
  a PXRD diffractogram of FIG. 72; and
  $^1$H NMR spectrum of FIG. 73;
amorphous hydrocodone, $CH_3(O(CH_2)_2)_x(OCH_2CHCH_3)_y$ $NH_2$ wherein Y/X is 9:1 with an approximate MW of 600, pamoate characterized by at least one method selected from the group consisting of:
  an endothermic phase change of at least 5 J/g at a temperature above 105° C. and an endothermic phase change of at least 1 J/g at a temperature above 150° C.;
  an FTIR spectrum of FIG. 75;
  a PXRD diffractogram of FIG. 76; and
  $^1$H NMR spectrum of FIG. 77;
polymorphic imipramine pamoate (1:1) characterized by at least one method selected from the group consisting of:
  an endothermic phase change of at least 60 J/g at a temperature above 200° C.;
  an FTIR spectrum of FIG. 105;
  a PXRD diffractogram of FIG. 106; and
  $^1$H NMR spectrum of FIG. 107; and
amorphous imipramine pamoate (1:1) characterized by at least one method selected from the group consisting of:
  a DSC spectrum of FIG. 54;
  an FTIR spectrum of FIG. 55;
  a PXRD diffractogram of FIG. 56; and
  $^1$H NMR spectrum of FIG. 57;
and said drug substance meets at least one condition in 0.1 N HCl selected from the group consisting of:

no more than 35% of said drug substance is released at 30 minutes with 5 wt % ethanol in said 0.1 N HCl;

the percentage of said drug substance released with at least 5 wt % ethanol in said 0.1 N HCl is no more than a percentage of said drug substance released in said 0.1 N HCl without ethanol; and the percentage of drug substance released with 40 wt % ethanol in 0.1 N HCl does not exceed 60% while the percentage of drug substance released under the conditions selected from water, 0.1 N HCl, 5 wt % ethanol in 0.1 N HCl and 20 wt % ethanol in 0.1 N HCl does not exceed the drug substance released with 40 wt % ethanol in 0.1 N HCl.

* * * * *